(12) United States Patent
Hurrey et al.

(10) Patent No.: US 11,020,384 B2
(45) Date of Patent: *Jun. 1, 2021

(54) ANTIARRHYTHMIC FORMULATION

(71) Applicant: InCarda Therapeutics, Inc., Newark, CA (US)

(72) Inventors: Michael Laird Hurrey, San Ramon, CA (US); Luiz Belardinelli, Palo Alto, CA (US); Prashanti Madhavapeddi, Fremont, CA (US); Carlos Schuler, Kensington, CA (US)

(73) Assignee: InCarda Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/901,941

(22) Filed: Jun. 15, 2020

(65) Prior Publication Data

US 2021/0030732 A1 Feb. 4, 2021

Related U.S. Application Data

(60) Provisional application No. 62/881,689, filed on Aug. 1, 2019.

(51) Int. Cl.
| | |
|---|---|
| *A61K 47/40* | (2006.01) |
| *A61K 9/00* | (2006.01) |
| *A61K 9/08* | (2006.01) |
| *A61K 31/4458* | (2006.01) |
| *A61K 47/12* | (2006.01) |

(52) U.S. Cl.
CPC ........ *A61K 31/4458* (2013.01); *A61K 9/0078* (2013.01); *A61K 47/12* (2013.01); *A61K 47/40* (2013.01); *A61K 9/008* (2013.01); *A61K 9/08* (2013.01)

(58) Field of Classification Search
None
See application file for complete search history.

(56) References Cited

U.S. PATENT DOCUMENTS

| | | |
|---|---|---|
| 3,991,761 A | 11/1976 | Cocozza |
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,962,095 A | 10/1990 | Grover et al. |
| 4,995,385 A | 2/1991 | Valentini et al. |
| 5,364,880 A | 11/1994 | Druzgala |
| 5,458,135 A | 10/1995 | Patton et al. |
| 5,619,985 A | 4/1997 | Ohki et al. |
| 5,785,049 A | 7/1998 | Smith et al. |
| 5,855,913 A | 1/1999 | Hanes et al. |
| 5,874,064 A | 2/1999 | Edwards et al. |
| 5,922,675 A | 7/1999 | Baker et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |
| 6,077,543 A | 6/2000 | Gordon et al. |
| 6,132,766 A | 10/2000 | Sankaram et al. |
| 6,257,233 B1 | 7/2001 | Burr et al. |
| 6,357,490 B1 | 3/2002 | Johnston et al. |
| 6,358,530 B1 | 3/2002 | Eljamal et al. |
| 6,372,258 B1 | 4/2002 | Platz et al. |
| 6,503,480 B1 | 1/2003 | Edwards et al. |
| 6,546,929 B2 | 4/2003 | Burr et al. |
| 6,968,226 B2 | 11/2005 | Mehra et al. |
| 7,302,295 B2 | 11/2007 | Stahmann et al. |
| 7,473,433 B2 | 1/2009 | Weikert et al. |
| 8,394,813 B2 | 3/2013 | Mickle et al. |
| 8,641,631 B2 | 2/2014 | Sierra et al. |
| 8,974,828 B2 | 3/2015 | Schuler et al. |
| 9,549,912 B2 | 1/2017 | Milner et al. |
| 10,010,294 B2 | 7/2018 | Narasimhan et al. |
| 10,045,939 B2 | 8/2018 | Schuler et al. |
| 2002/0017295 A1 | 2/2002 | Weers et al. |
| 2002/0065473 A1 | 5/2002 | Wang et al. |
| 2002/0115655 A1 | 8/2002 | Mehanna et al. |
| 2003/0005924 A1 | 1/2003 | Rabinowitz et al. |
| 2003/0077229 A1 | 4/2003 | Dugger, III |

(Continued)

FOREIGN PATENT DOCUMENTS

| | | |
|---|---|---|
| AU | 2013248242 A1 | 11/2013 |
| CN | 101467968 A | 7/2009 |

(Continued)

OTHER PUBLICATIONS

Aliot, "Twenty-five years in the making: flecainide is safe and effective for the management of atrial fibrillation", Europace, 13, 161-173, 2011 (Year: 2011).*
2015 ACC/AHA/HRS Guideline for the Management of Adult Patients With Supraventricular Tachycardia—Table 9 (accessed Dec. 2019): http://www.onlinejacc.org/content/67/13/e27/T9.
Abarbanell, et al. Prehospital management of rapid atrial fibrillation: recommendations for treatment protocols. Am J Emerg Med. Jan. 2001;19(1):6-9.
Alp, N J et al., Randomised double blind trial of oral versus intravenous flecainide for the cardioversion of acute atrial fibrillation, Heart, 2000;84:37-40.
Anderson JL et al., Oral Flecainide Acetate for the Treatment of Ventricular Arrhythmias, (1981). NEJM. 305: 473-477.
Approved Pharmaceutical Products Containing Cyclodextrins, Cyclodextrin News, Feb. 2013, vol. 26, No. 12, 1-16.

(Continued)

*Primary Examiner* — Robert T. Crow
*Assistant Examiner* — John P Nguyen
(74) *Attorney, Agent, or Firm* — Wilson Sonsini Goodrich & Rosati

(57) ABSTRACT

Pharmaceutical compositions comprising an antiarrhythmic agent for treatment of a heart condition via inhalation. Methods of treating a heart condition include administering by inhalation an effective amount of at least one antiarrhythmic pharmaceutical agent to a patient in need thereof. Nebulized drug product and kits are also disclosed.

28 Claims, 34 Drawing Sheets

(56) References Cited

U.S. PATENT DOCUMENTS

| | | |
|---|---|---|
| 2003/0079742 A1 | 5/2003 | Giroux |
| 2003/0144701 A1 | 7/2003 | Mehra et al. |
| 2004/0011358 A1 | 1/2004 | Smaldone et al. |
| 2004/0035413 A1 | 2/2004 | Smaldone et al. |
| 2004/0045546 A1 | 3/2004 | Hirsh et al. |
| 2004/0077995 A1 | 4/2004 | Ferek-Petric et al. |
| 2004/0099269 A1 | 5/2004 | Hale et al. |
| 2004/0105820 A1 | 6/2004 | Weers et al. |
| 2004/0109826 A1 | 6/2004 | Malladi et al. |
| 2004/0156792 A1 | 8/2004 | Tarara et al. |
| 2004/0167228 A1 | 8/2004 | Rabinowitz et al. |
| 2005/0009776 A1 | 1/2005 | Gadgil et al. |
| 2005/0070552 A1 | 3/2005 | Fedida et al. |
| 2005/0142070 A1 | 6/2005 | Hartley et al. |
| 2005/0211245 A1 | 9/2005 | Smaldone et al. |
| 2005/0211253 A1 | 9/2005 | Smaldone et al. |
| 2005/0235987 A1 | 10/2005 | Smaldone et al. |
| 2005/0272810 A1 | 12/2005 | Davis et al. |
| 2006/0034847 A1 | 2/2006 | Yun et al. |
| 2006/0034906 A1 | 2/2006 | Boni et al. |
| 2006/0052333 A1 | 3/2006 | Belardinelli et al. |
| 2006/0105045 A1 | 5/2006 | Buchanan et al. |
| 2006/0120962 A1 | 6/2006 | Rabinowitz et al. |
| 2007/0014733 A1 | 1/2007 | O'Donnell et al. |
| 2007/0014734 A1 | 1/2007 | O'Donnell et al. |
| 2007/0122352 A1 | 5/2007 | Kunka et al. |
| 2007/0122353 A1 | 5/2007 | Hale et al. |
| 2007/0178050 A1* | 8/2007 | Hill ................. A61K 31/573 424/45 |
| 2007/0282177 A1 | 12/2007 | Pilz |
| 2008/0038363 A1 | 2/2008 | Zaffaroni et al. |
| 2008/0066741 A1 | 3/2008 | Lemahieu et al. |
| 2008/0161296 A1 | 7/2008 | Davis et al. |
| 2008/0226736 A1 | 9/2008 | Caponetti et al. |
| 2008/0269625 A1 | 10/2008 | Halperin et al. |
| 2008/0275036 A1 | 11/2008 | Cross et al. |
| 2009/0264783 A1 | 10/2009 | Xi et al. |
| 2010/0086606 A1 | 4/2010 | Ogawa et al. |
| 2011/0224232 A1 | 9/2011 | Williams, III et al. |
| 2012/0003318 A1 | 1/2012 | Schuler et al. |
| 2014/0290647 A1 | 10/2014 | Salvinelli et al. |
| 2015/0044288 A1 | 2/2015 | Surber |
| 2015/0164871 A1 | 6/2015 | Grunnet et al. |
| 2015/0313842 A1 | 11/2015 | Schuler et al. |
| 2018/0296480 A1 | 10/2018 | Schuler et al. |
| 2018/0303435 A1 | 10/2018 | Narasimhan et al. |
| 2018/0318213 A1 | 11/2018 | Schuler et al. |
| 2018/0325818 A1 | 11/2018 | Schuler |
| 2019/0060230 A1 | 2/2019 | Schuler et al. |

FOREIGN PATENT DOCUMENTS

| | | |
|---|---|---|
| DE | 102004045796 A1 | 3/2006 |
| DE | 202013105420 U1 | 4/2014 |
| DE | 102013009114 A1 | 12/2014 |
| EP | 1276474 B1 | 6/2007 |
| EP | 1911481 A2 | 4/2008 |
| EP | 1982711 A1 | 10/2008 |
| EP | 2081547 B1 | 5/2012 |
| EP | 2533766 B1 | 5/2013 |
| EP | 2808015 A1 | 12/2014 |
| EP | 1848424 B1 | 4/2017 |
| EP | 1866323 B1 | 5/2017 |
| EP | 3238708 A1 | 11/2017 |
| EP | 3024458 B1 | 1/2018 |
| EP | 3308785 A2 | 4/2018 |
| EP | 3485881 A1 | 5/2019 |
| GB | 2564444 A | 1/2019 |
| JP | 2002529393 A | 9/2002 |
| RU | 38570 U1 | 7/2004 |
| RU | 2003107672 A | 8/2004 |
| WO | WO-9003144 A1 | 4/1990 |
| WO | WO-9524183 A1 | 9/1995 |
| WO | WO-9531479 A1 | 11/1995 |
| WO | WO-9632096 A1 | 10/1996 |
| WO | WO-9632149 A1 | 10/1996 |
| WO | WO-9916419 A1 | 4/1999 |
| WO | WO-9916420 A1 | 4/1999 |
| WO | WO-9916421 A1 | 4/1999 |
| WO | WO-9916422 A1 | 4/1999 |
| WO | WO-0007572 A2 | 2/2000 |
| WO | WO-0027359 A1 | 5/2000 |
| WO | WO-0072904 A1 | 12/2000 |
| WO | WO-0185136 A2 | 11/2001 |
| WO | WO-0185137 A2 | 11/2001 |
| WO | WO-0228377 A1 | 4/2002 |
| WO | WO-02083220 A2 | 10/2002 |
| WO | WO-02094236 A1 | 11/2002 |
| WO | WO-03030979 A1 | 4/2003 |
| WO | WO-03105020 A2 | 12/2003 |
| WO | WO-2004071368 A2 | 8/2004 |
| WO | WO-2005018635 A2 | 3/2005 |
| WO | WO-2005065435 A2 | 7/2005 |
| WO | WO-2005065649 A1 | 7/2005 |
| WO | WO-2005079897 A1 | 9/2005 |
| WO | WO-2005117858 A2 | 12/2005 |
| WO | WO-2006083779 A2 | 8/2006 |
| WO | WO-2006083780 A2 | 8/2006 |
| WO | WO-2007042467 A1 | 4/2007 |
| WO | WO-2007050075 A1 | 5/2007 |
| WO | WO-2007050347 A1 | 5/2007 |
| WO | WO-2007052108 A2 | 5/2007 |
| WO | WO-2008036247 A1 | 3/2008 |
| WO | WO-2008039242 A1 | 4/2008 |
| WO | WO-2008051621 A2 | 5/2008 |
| WO | WO-2008066745 A1 | 6/2008 |
| WO | WO-2008072190 A2 | 6/2008 |
| WO | WO-2008116165 A2 | 9/2008 |
| WO | WO-2008134630 A1 | 11/2008 |
| WO | WO-2010019914 A2 | 2/2010 |
| WO | WO-2010022259 A1 | 2/2010 |
| WO | WO-2010042658 A1 | 4/2010 |
| WO | WO-2010107964 A1 | 9/2010 |
| WO | WO-2012024106 A2 | 2/2012 |
| WO | WO-2014191837 A2 | 12/2014 |
| WO | WO-2015021954 A1 | 2/2015 |
| WO | WO-2015079197 A1 | 6/2015 |
| WO | WO-2016090009 A1 | 6/2016 |
| WO | WO-2017136421 A1 | 8/2017 |
| WO | WO-2021022058 A2 | 2/2021 |

OTHER PUBLICATIONS

Barbato, et al. Role of beta2 adrenergic receptors in human atherosclerotic coronary arteries. Circulation. 2005, 111:288-294.

Bollman A. et al, Importance of Left Atrial Diameter and Atrial Fibrillatory Frequency for Conversion of Persistent Atrial Fibrillation With Oral Flecainide (2002), Am. J. Cardiol. 90:1011-1014.

Boriani G. etal., Flecainide Acetate: Concentration-Response Relationships for Antiarrhythmic and Electrocardiographic Effects, (1993), Int. J. Clin. Pharm.Res. XII1(4) 211-219.

Borlak, et al. Metabolism of verapamil in cultures of rat alveolar epithelial cells and pharmacokinetics after administration by intravenous and inhalation routes. Drug Metab Dispos. Aug. 2005;33(8):1108-14. Epub May 10, 2005.

Chen LY, Chung MK, Allen LA, et al. Atrial Fibrillation Burden: Moving Beyond Atrial Fibrillation as a Binary Entity: A Scientific Statement From the American Heart Association. Circulation. 2018;137(20):e623-e644. doi:10.1161/CIR.0000000000000568.

Combined Search and Examination Report dated Jun. 1, 2020 for Application Serial No. GB2007515.6 (7 pages).

Conard GJ, Ober RE. Metabolism of flecainide. Am J Cardiol. 1984;53(5):41B-51B. doi:10.1016/0002-9149(84)90501-0.

Cosio, Francisco G. et al., Delayed rhythm control of atrial fibrillation may be a cause of failure to prevent recurrences: reasons for change to active antiarrhythmic treatment at the time of the first detected episode, Europace,2008, 10, 21-27, doi:10.1093/europace/eum276.

Crijns HJGM. Et al Acute conversion of atrial fibrillation to sinus rhythm: clinical efficacy of flecainide acetate. Comparison of two regimens (1988), Eur. Heart. J.; 9:634-638.

(56) References Cited

OTHER PUBLICATIONS

De Antonio BS, Victor Z. et al., Pulmonary delivery off lecainide causes a rate-dependent predominant effect on atrial compared with ventricular depolarization duration revealed by intracardiac recordings in an intact porcine model, J Cardiovasc Electro physiol. Nov. 2018;29(11):1563-1569. doi: 10.1111/jce.13708.Epub Sep. 14, 2018. PMID: 30106207.
Dell'orfano, et al. Drugs for Conversion of Atrial Fibrillation. Am. Fam. Physician. 58(2); 471-480, Aug. 1, 1998. 6 pages.
Deneer, et al. Absorption kinetics and pharmacodynamics of two oral dosage forms of flecainide in patients with an episode of paroxysmal atrial fibrillation. Eur J Clin Pharmacol. Dec. 2004;60(10):693-701.
Deneer VHM et al, Absorption kinetics and pharmacodynamics of two oral dosage forms of flecainide in patients with an episode of paroxysmal atrial fibrillation, (2004),Eur J Clin Pharmacol, 60:693-701.
Duff, MD, Henry J. et al., Suppression of Resistant Ventricular Arrhythmias by Twice Daily Dosing With Flecainide, (1981). Am J Cardiol; 48: 1133-1140.
Engdahl, MD, PhD, Johan et al., Stepwise Screening of Atrial Fibrillation in a 75-Year-Old Population, Implications for Stroke Prevention, Circulation, 2013;127:930-937.
European Office Action dated Nov. 16, 2017 for European Patent Application No. EP10754091.6.
European search report and search opinion dated Jan. 21, 2014 for EP Application No. 10754091.6.
European Search Report dated Sep. 2, 2019 for EP Application No. 19176305.1.
European Search Report dated Sep. 4, 2019 for EP Application No. 19176272.3.
Evrarda, B et al., Cyclodextrins as a potential carrier in drug nebulization, Journal of Controlled Release (2004), vol. 96, iss.3, pp. 403-410.
Falk MD, Rodney H. et al., Flecainide, Journal of Cardiovascular Electrophysiology, Nov. 1994, vol. 5, No. 11, 964-981.
Feldman, et al. Analysis of Coronary Response to Various Doses of Intracoronary Nitroglycerin. Circulation. 1982, 66:321-327.
"Flecainide" entry in Chem Spider website online retrieved on May 11, 2020 from URL:www.chemspider.com/Chemical-Structure.3239.html.
Gaglione, et al. Is There Coronary Vasoconstriction after Intracoronary Beta-adrenergic Blockade in Patients with Coronary Artery Disease. J Am Coll Cardiol. 1987, 10:299-310.
Go, MD, Alan S. et al., Association of Burden of Atrial Fibrillation With Risk of Ischemic Stroke in Adults With Paroxysmal Atrial Fibrillation The KP-Rhythm Study, JAMA Cardiol. 2018;3(7):601-608.doi:10.1001/jamacardio.2018.1176.
Gordan, Richard et al, Autonomic and endocrine control of cardiovascular function, World J Cardiol Apr. 26, 2015; 7(4): 204-214.
Gould, Sarah et al., 2-Hydroxypropyl-J3-cyclodextrin(HP-J3-CD): A toxicology review, Food and Chemical Toxicology 43(2005) 1451-1459.
Harrison, et al. Effect of Single Doses of Inhaled Lignocaine on FEV1 and Bronchial Reactivity in Asthma. Respir Med. Dec. 1992, 12:1359-635.
Hellestrand, K J et al., Acute electrophysiological effects of flecainide acetate on cardiac conduction and refractorinessin man, Br Heart j 1982; 48: 140-8.
Hellestrand, Kevin J.et al., Response of an Abnormal Sinus Node to Intravenous Flecainide Acetate, PACE, 1984, vol. 7, 436-439.
Ikeda, "Effects of Flecainide on the Electrophysiologic Properties of Isolated Canine and Rabbit Myocardial Fibers", JACC vol. 5, No. 2, pp. 303-310, Feb. 1985.
International Search Report and Written Opinion dated Apr. 18, 2017 for International PCT Patent Application No. PCT/US2017/016018.
International search report and written opinion dated Jul. 12, 2010 for PCT Application No. PCT/US2010/027740.

Jensen, Paul N. et al., Incidence of and Risk Factors for Sick Sinus Syndrome in the General Population, Journal of the American College of Cardiology, 2014, vol. 64, No. 6, 531-538.
Juan Tamargo et al., "Narrow therapeutic index drugs: a clinical pharmacological consideration to flecainide", Eur J Clin Pharmacol, vol. 71, 549-567, 2015.
Kim Y, Oksanen DA, Massefski W Jr, Blake JF, Duffy EM, Chrunyk B. Inclusion complexation of ziprasidone mesylate with beta-cyclodextrin sulfobutyl ether. J Pharm Sci. 1998;87(12):1560-1567. doi:10.1021/js980109t.
Kowey, MD, Peter R. et al., Acute Treatment of Atrial Fibrillation, Am J Cardiol, 1998;81(5A):16C-22C.
Kroemer, "Flecainide enantiomers: Disposition i human subjects and electrophysiologic actions in vitro", Clinical Pharmacology & Therapeutics, vol. 46, Issue 5, pp. 584-590, Nov. 1989.
Loftsson, Thorsteinn, Drug solubilization by complexation, International Journal of Pharmaceutics 531 (2017) 276-280.
Loftsson, Thorsteinn et al., Cyclodextrins as Functional Excipients: Methods to Enhance Complexation Efficiency, Journal of Pharmaceutical Sciences, vol. 101, No. 9, Sep. 2012,3019-3032.
Lopez-Vidriero, M.T. Issues relating to safety and efficacy in nebulizer use. Eur. Respir. Rev., 2000, 10:72, 210-212.
Malanga, Milo et al., "Back to the Future": A New Look at Hydroxypropyl Beta-Cyclodextrins, Journal of Pharmaceutical Sciences 105 (2016) 2921-2931.
Markey, Gerard C. et al., Intravenous Flecainide for Emergency Department Management of Acute Atrial Fibrillation, The Journal of Emergency Medicine, 2018, vol. 54, No. 3, pp. 320-327.
Marum AA, Araujo Silva B, Bortolotto AL, et al. Pulmonary Delivery of Metoprolol Reduces Ventricular Rate During Atrial Fibrillation and Accelerates Conversion to Sinus Rhythm. J Cardiovasc Pharmacol.2020;75(2):135-140. doi:10.1097/FJC.0000000000000780.
Marum AA, Silva BA, Bortolotto AL, et al. Optimizing flecainide plasma concentration profile for atrial fibrillation conversion while minimizing adverse ventricular effects by rapid, low-dose intratracheal or intravenous administration. Int J Cardiol. 2019;274:170-174. doi:10.1016/j.ijcard.2018.09.029.
Nasser, MD, Mohammad et al., Flecainide-induced Torsades de Pointes: Case Report and Review of Literature, Rev Cardiovasc Med. 2015;16(3):214-220 doi: 10.3909/ricm0761.
Nattel, Stanley et al., Early management of atrial fibrillation to prevent cardiovascular complications, European Heart Journal, 2014, 35, 1448-1456, doi:10.1093/eurheartj/ehu028.
Noguchi, et al. Effects of Intracoronary Propranolol on Coronary Blood Flow and Regional Myocardial Function in Dogs. Eur J Pharmacol. 1987, 144(2):201-10.
Notice of allowance dated Jan. 21, 2015 for U.S. Appl. No. 13/257,249.
Office action dated Jan. 3, 2013 for U.S. Appl. No. 13/257,249.
Office Action dated Apr. 17, 2017 for U.S. Appl. No. 14/632,252.
Office Action dated Apr. 27, 2016 for U.S. Appl. No. 14/632,252.
Office action dated Jun. 20, 2014 for U.S. Appl. No. 13/257,249.
Office Action dated Jul. 24, 2017 for U.S. Appl. No. 15/422,053.
Office action dated Sep. 9, 2015 for U.S. Appl. No. 14/632,252.
Office action dated Sep. 26, 2013 for U.S. Appl. No. 13/257,249.
Office Action dated Dec. 1, 2016 for U.S. Appl. No. 14/632,252.
Office Action dated Dec. 28, 2018 for U.S. Appl. No. 16/172,456.
Ottinger, Elizabeth et al., Collaborative Development of 2-Hydroxypropyl-B-Cyclodextrin for the Treatment of Niemann-Pick Type C1 Disease, Curr Top Med Chem, (2014); 14(3),330-339.
Paul Dorian, MD, Antiarrhythmic Action of n-Blockers: Potential Mechanisms, J Cardiovasc Pharmacol Therapeut 10 (Supplement I): 2005, S15-S22.
PCT/US2018/032092 International Search Report and Written Opinion dated Aug. 1, 2018.
Proietti R, Hadjis A, AlTurki A, et al. A Systematic Review on the Progression of Paroxysmal to Persistent Atrial Fibrillation: Shedding New Light on the Effects of Catheter Ablation. JACC Clin Electrophysiol. 2015;1(3):105-115. doi:10.1016/j.jacep.2015.04.010.
Rabinowitz, et al. Ultra-fast absorption of amorphous pure drug aerosols via deep lung inhalation. J Pharm Sci. Nov. 2006;95(11):2438-51.

(56) References Cited

OTHER PUBLICATIONS

Razavi, M. Safe and effective pharmacologic management of arrhythmias. Tex Heart Inst J. 2005;32(2):209-11.
Reisinger, Johann et al., Flecainide versus ibutilide forimmediate cardioversion of atrial fibrillation of recent onset, European Heart Journal, 2004, 25, 1318-1324.
Ryzhakov, Alexey et al., Self-Assembly of Cyclodextrins and Their Complexes in Aqueous Solutions, Journal of Pharmaceutical Sciences 105 (2016) 2556-2569.
Safety Data Sheet, 2-Hydroxypropyl-.beta.-cyclodextrin,pp. 1-5, according to Regulation (EC) No. 1907/2006 as amended by (EC) No. 1272/2008, Revision: Apr. 20, 2018 Supersedes Revision: Feb. 2, 2015.
Salerno DM, Granrud G, Sharkey P, et al. Pharmacodynamics and side effects of flecainide acetate. Clin Pharmacol Ther. 1986;40(1):101-107. doi:10.1038/clpt.1986.145.
Saokham, Phennapha et al., Solubility of Cyclodextrins and Drug/Cyclodextrin Complexes, Molecules (2018), 23, 1161, 1-15.
Search Report dated May 12, 2020 for Russian Application Serial No. 2018131232, (4 pages).
Search Report dated Nov. 22, 2019 for Application No. 11201805788W, (2 pages).
Stella, Valentino J. et al., Cyclodextrins, Toxicologic Pathology, (2008) 36:30-42, ISSN: 0192-6233, print / 1533-1601 online, DOI: 10.1177/0192623307310945.
Stocco FG, Evaristo E, Silva AC, et al. Comparative Pharmacokinetic and Electrocardiographic Effects of Intratracheal and Intravenous Administration of Flecainide in Anesthetized Pigs. Journal of Cardiovascular Pharmacology. Sep. 2018;72(3):129-135. DOI: 10.1097/fjc.0000000000000605.
Supplementary European Search Report dated Aug. 6, 2019 for EP Application No. 17748062.1.
Suttorp MJ., et al. Intravenous Flecainide Versus Verapamil for Acute Conversion of Paroxysmal Atrial Fibrillation or Flutter to Sinus Rhythm, (1989), Am. J. Cardiol. 63:693-696.
Suttorp, et al. The value of class IC antiarrhythmic drugs for acute conversion of paroxysmal atrial fibrillation or flutter to sinus rhythm. J Am Coll Cardiol. Dec. 1990;16(7):1722-7.
Suttorp MJ., et al., The Valueof Class IC Antiarrhythmic Drugs for Acute Conversion of Paroxysmal Atrial Fibrillation or Flutter to Sinus Rhythm, (1990), JACC, 16:1722-1727.
Svennberg, MD, Emma et al., Mass Screening for Untreated Atrial Fibrillation, The Strokestop Study, Circulation,2015, 2177-2184,DOI:10.1161/CIRCULATIONHA.114.014343.
Tessarolo Silva F, Pedreira GC, Medeiros SA, et al. Multimodal mechanisms and enhanced efficiency of atrial fibrillation cardioversion by pulmonary delivery of a novel flecainide formulation. Journal of Cardiovascular Electrophysiology. Jan. 2020;31(1):205-213. DOI:10.1111/jce.14289.
Tiwari, Gaurav et al., Cyclodextrins in delivery systems: Applications, J Pharm Bioallied Sci. (2010) Apr.-Jun.; 2(2): 72-79.
Twiss, et al. Efficacy of Calcium Channel Blockers as Maintenance Therapy for Asthma. British J of Clinical Pharmacology. Nov. 2001.
U.S. Appl. No. 14/632,252 Notice of Allowance dated Mar. 29, 2018.
U.S. Appl. No. 15/422,053 Notice of Allowance dated Mar. 5, 2018.
U.S. Appl. No. 15/976,516 Office Action dated Mar. 19, 2019.
U.S. Appl. No. 16/013,165 Final Office Action dated May 9, 2019.
U.S. Appl. No. 16/013,178 Final Office Action dated May 10, 2019.
U.S. Appl. No. 16/172,456 Final Office Action dated Sep. 27, 2019.
U.S. Appl. No. 16/192,337 Non-Final Office Action dated Dec. 12, 2019.
U.S. Appl. No. 15/928,851 Office Action dated Oct. 9, 2018.
U.S. Appl. No. 16/013,165 Office Acton dated Aug. 28, 2018.
U.S. Appl. No. 16/013,178 Office Action dated Sep. 18, 2018.
U.S. Appl. No. 16/172,456 Non-Final Office Action dated May 11, 2020.
U.S. Appl. No. 16/789,151 Non-Final Office Action dated May 19, 2020.
U.S. Appl. No. 16/789,156 Non-Final Office Action dated May 22, 2020.
U.S. Appl. No. 16/789,151 Final Office Action dated Jul. 6, 2020.
Verrier, PhD, Richard L. et al., Accelerated conversion of atrial fibrillation to normal sinus rhythm by pulmonary delivery of flecainide acetatein a porcine model, Heart Rhythm. Dec. 2018;15(12):1882-1888. doi:10.1016/j.hrthm.2018.06.036. Epub Jun. 26, 2018. PMID: 29958990.
Verrier, Richard L, and Luiz Belardinelli. "Pulmonary Delivery of Antiarrhythmic Drugs for Rapid Conversion of New-Onset Atrial Fibrillation." Journal of cardiovascular pharmacology vol. 75,4 (2020): 276-283. doi:10.1097/FJC.0000000000000804.
Verrier RL, Fuller H, Justo F, Nearing BD, Rajamani S, Belardinelli L. Unmasking atrial repolarization to assess alternans, spatiotemporal heterogeneity, and susceptibility to atrial fibrillation. Heart Rhythm. 2016;13(4):953-961. doi:10.1016/j.hrthm.2015.11.019.
Wijffels MC, Kirchhof CJ, Dorland R, Allessie MA. Atrial fibrillation begets atrial fibrillation. A study in awake chronically instrumented goats. Circulation. 1995;92(7):1954-1968. doi:10.1161/01.cir.92.7.1954.
Written Opinion dated Nov. 29, 2019 for Application No. 11201805788W, (6 pages).
Zalewski, et al. Myocardial Protection during Transient Coronary Artery Occlusion in Man: Beneficial Effects of Regional Beta-adrenergic Blockade. Circulation. 1986, 73:734-73.
U.S. Appl. No. 16/901,909 Non-Final Office Action dated Sep. 18, 2020.
Allen LV Jr, Erickson MA 3rd. Stability of baclofen, captopril, diltiazem hydrochloride, dipyridamole, and flecainide acetate in extemporaneously compounded oral liquids. Am J Health Syst Pharm. Sep. 15, 1996;53(18):2179-84. doi: 10.1093/ajhp/53.18.2179. PMID: 8879325.
Arzu Ari, "Jet, Ultrasonic, and Mesh Nebulizers: An Evaluation of Nebulizers for Better Clinical Outcomes" [online], (2014), retrieved on Nov. 21, 2020 from URL https://scholarworks.gsu.edu/cgi/viewcontent.cgi?referer=http://scholargoogle.conn/&httpsredir=1&article =1001&context=rt facpub.
Farncombe M, Chater S. Clinical application of nebulized opioids for treatment of dyspnoea in patients with malignant disease. Support Care Cancer. May 1994;2(3):184-7. doi: 10.1007/BF00417478. PMID: 7518312.
Hopson JR, et al., "Safety and utility of flecainide acetate in the routine care of patients with supraventricular tachyarrhythmias: results of a multicenter trial. The Flecainide Supraventricular Tachycardia Study Group.", Am J Cardiol. Jan. 25, 1996;77(3):72A-82A. doi:10.1016/s0002-9149(97)89121-7. PMID: 8607395.
Lie-A-Huen L, van den Akker J, den Hertog A, Meijer DK. The action of flecainide acetate and its enantiomers on mammalian non-myelinated nerve fibres. Pharm Weekbl Sci. Jun. 23, 1989;11(3):92-4. doi: 10.1007/BF02110256. Erratum in: Pharm Weekbl Sci Aug. 25, 1989;11(4):136. PMID: 2505226.
U.S. Appl. No. 16/192,337 Office Action dated Sep. 4, 2020.
Shiga, Tsuyoshi, et al. "Pharnnacokineticsof intravenous amiodarone and its electrocardiographic effects on healthyJapanese subjects." Heart and vessels 26.3 (2011): 274-281.
U.S. Appl. No. 16/789,151 Non-Final Office Action dated Nov. 30, 2020.
U.S. Appl. No. 16/789,156 Non-Final Office Action dated Dec. 17, 2020.
International Search Report and Written Opinion dated Feb. 24, 2021 for International Application Serial No. PCT/US2020/044291, (13 pages).
Loftsson T, and Brewster ME, Pharmaceutical applications of cyclodextrins: effects on drug permeation through biological membranes, Journal of Pharmacy and Pharmacology, Sep. 2011;63(9):1119-35. doi:10.1111/j.2042-7158.2011.01279.x. Epub Apr. 4, 2011 PMID: 21827484.

\* cited by examiner

ANTIARRHYTHMIC FORMULATION

CROSS-REFERENCE

This application claims benefit of U.S. Provisional Application No. 62/881,689, filed Aug. 1, 2019, which application is incorporated herein by reference in its entirety.

BACKGROUND

Cardiac arrhythmia (also dysrhythmia) is a term for any of a large and heterogeneous group of conditions in which there is abnormal electrical activity in the heart. The heart beat may be too fast or too slow and may be regular or irregular.

Atrial arrhythmia therapy is afield with a high level of unmet clinical need. Many drugs used today have been on the market since the early 1980s and 1990s and are mostly inadequate due to either lack of efficacy or a side-effect profile that is often cardiac related, that necessitates extensive monitoring of the patient.

What is needed for fast and safe cardioversion (resolution of arrhythmia) is therapy that:
  (a) causes little to no risk of acceleration of ventricular rate before cardioversion;
  (b) slows atrio-ventricular (AV) conduction so that there is ventricular rate control and cardioversion at the same time;
  (c) causes minimal to no effect in prolonging the QRS interval above the upper range of normal value (about 120 milliseconds) and should have a low risk of torsade de pointes; and
  (d) causes minimal to no negative inotropic effect; it should have only mild negative chronotropic effect, without the risk of severe bradycardia when the patient reverts to sinus rhythm.
  (e) causes minimal to no hypotension.
  (f) causes no adverse event other than one that is mild, is transient (i.e. lasting no more than several minutes), does not require treatment, and has no sequelae.

None of the current approved drug products exhibit these characteristics. High oral and intravenous (IV) doses required to compensate for absorption, metabolism, and dilution result in blood high blood concentrations for an extended period of time that can cause the dangerous adverse cardiac events like pro-arrhythmias, QT prolongation, and torsade de pointes. FELDMAN et al., "Analysis of Coronary Response to Various Doses of Intracoronary Nitroglycerin," Circulation, 66:321-327 (1982); and BARBATO et al., "Adrenergic Receptors in Human Atherosclerotic Coronary Arteries," Circulation, 111:288-294 (2005). Comorbid conditions also limit use of ideal drugs in some patients, for example the case with intravenous adenosine. GAGLIONE et al., "Is There Coronary Vasoconstriction after Intracoronary Beta-adrenergic Blockade in Patients with Coronary Artery Disease," J Am Coll Cardiol, 10:299-310 (1987). Drugs like verapamil and diltiazem injections are second line of therapy requiring close monitoring of patients. NOGUCHI et al., "Effects of Intracoronary Propranolol on Coronary Blood Flow and Regional Myocardial Function in Dogs," Eur J Pharmacol., 144(2):201-10 (1987); and ZALEWSKI et al., "Myocardial Protection during Transient Coronary Artery Occlusion in Man: Beneficial Effects of Regional Beta-adrenergic Blockade," Circulation, 73:734-73 (1986).

Paroxysmal atrial fibrillation (PAF) is a subset of the overall atrial fibrillation (AF) population and is estimated to be 25-30% of the overall AF population. About 2.5 million patients are affected by AF in the United States. The population of PAF patients is estimated to be 900,000 to 1.5 million worldwide.

Paroxysmal supraventricular tachycardia (PSVT) is a type of arrhythmia that affects about 500,000 to 600,000 patients in the United States.

Ablation techniques, e.g., RF ablation, are often used to treat arrhythmias. But ablation is expensive with the cost typically ranging from about $25,000 to $36,000 per procedure. Despite the high expense, ablation may not completely correct the arrhythmia. Often, multiple ablation procedures are required to achieve a satisfactory therapeutic result.

Oral medications, e.g., pills, tend to require high doses and long time for onset of action. The oral dose for heart medications generally tends to be well over 1 mg. High doses increase the likelihood of side effects and drug-drug interactions as these patients typically take multiple medications. The time for onset for oral cardiovascular medications tends to be around 60 minutes. Oral antiarrhythmic medications have been predominantly developed for prevention whereas treatment being given intravenously.

Intravenous injection usually requires a hospital setting for administering a medicine and typically involves a visit to the emergency room (ER). These overheads result in this therapy being expensive compared to therapies where the patients can self-administer their medicines. Intravenous injection requires a dose that is higher than what is actually needed in the heart to compensate for dilution and metabolism. Drug injected by IV passes through the right side of the heart and then the lungs before reaching the left side of the heart. The drug remains in the blood stream at a high concentration bathing all the organs and tissues with this drug in a high concentration, until the drug gets excreted through the kidneys or through other metabolic routes (e.g., hepatic). As a result, IV drugs may cause unwanted side effects. Drugs administered via the IV route are significantly diluted in the venous blood volume and lungs before reaching the cardiac circulation.

Injecting a drug to the heart directly is usually a last-resort taken by a cardiologist as a life saving measure in an emergency. The doses of the drugs injected directly into the heart in this manner are usually less than their IV and/or oral doses.

In some cases, an unplanned surgery is necessary to save the patient's life. Of course, unplanned surgeries are expensive and risky to the patient.

Cardiac arrhythmias are associated with disabling symptoms like tightness around the chest, palpitations, feeling tired, shortness of breath, and sometimes chest pain.

In view of the above, arrhythmias frequently result in emergency room (ER) visits, where intravenous drugs are administered, sometimes necessitating an extended stay in the hospital and in some cases also leading to unplanned invasive procedures. Pipeline Insights: Antiarrhythmics, Datamonitor (06/2006); and TWISS et al., "Efficacy of Calcium Channel Blockers as Maintenance Therapy for Asthma," British J of Clinical Pharmacology (November 2001).

There remains, however, a need for improved compositions and methods for treating heart conditions. Accordingly, there also remains a need for methods of making these compositions.

SUMMARY

Described herein, in some aspects, is a pharmaceutical composition, comprising: a therapeutically effective amount of a salt of flecainide, wherein the pharmaceutical composition is in the form of a liquid solution that has the salt of flecainide at a concentration above 60 mg/mL.

In some cases, the pharmaceutical composition further comprises a cyclodextrin. In some cases, a pH of the solution is above 5.5 when the pH is measured at room temperature. In some cases, a pH of the solution is from about 5.5 to about 6.5 when the pH is measured at room temperature. In some cases, the pharmaceutical composition further comprises a cyclodextrin, and wherein a pH of the solution is above 5.5 when the pH is measured at room temperature. In some cases, the cyclodextrin is selected from the group consisting of: α-cyclodextrin, β-cyclodextrin, γ-cyclodextrin, derivatized α-cyclodextrins, derivatized β-cyclodextrins, and derivatized γ-cyclodextrins. In some cases, the cyclodextrin is selected from the group consisting of: α-cyclodextrin, β-cyclodextrin, γ-cyclodextrin, hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, succinyl-β-cyclodextrin, 6A-amino-6A-deoxy-N-(3-hydroxypropyl)-β-cyclodextrin, sulfobutylether-β-cyclodextrin, sulfobutylether-γ-cyclodextrin, sulfoalkylether-β-cyclodextrins, and sulfoalkylether-γ-cyclodextrins. In some cases, the cyclodextrin comprises hydroxypropyl-β-cyclodextrin. In some cases, a concentration of the cyclodextrin in the pharmaceutical composition is about 1% (w/v) to about 80% (w/v) of the solution. In some cases, the concentration of the cyclodextrin is at least about 5% (w/v) of the solution. In some cases, in the concentration of the cyclodextrin is at least about 10% (w/v) of the solution. In some cases, the concentration of the cyclodextrin is about 20% (w/v) of the solution. In some cases, the concentration of the cyclodextrin is at most about 20% (w/v) of the solution. In some cases, the concentration of the cyclodextrin is about 25% (w/v) of the solution. In some cases, the concentration of the cyclodextrin is at most about 25% (w/v) of the solution. In some cases, the concentration of the cyclodextrin is from about 10% (w/v) to about 30% (w/v) of the solution. In some cases, the concentration of the salt of flecainide is at most about 200 mg/mL. In some cases, the concentration of the salt of flecainide is from about 65 mg/mL to about 130 mg/mL. In some cases, the concentration of the salt of flecainide is from about 70 mg/mL to about 115 mg/mL. In some cases, the concentration of the salt of flecainide is about 100 mg/mL. In some cases, the concentration of the salt of flecainide is about 75 mg/mL. In some cases, the salt of flecainide is selected from the group consisting of: flecainide acetate, flecainide hydrochloride, flecainide citrate, flecainide phosphate, and flecainide nitrate. In some cases, the salt of flecainide comprises flecainide acetate. In some cases, the salt of flecainide comprises flecainide hydrochloride.

In some cases, the pharmaceutical composition further comprises an acid. In some cases, the acid is selected from the group consisting of: acetic acid, citric acid, nitric acid, hydrochloric acid, sulfuric acid, maleic acid, tartaric acid, phosphoric acid, aconitic acid, adipic acid, ascorbic acid, benzoic acid, caprylic acid, cholic acid, formic acid, glutamic acid, lactic acid, propionic acid, sorbic acid, stearic acid, and succinic acid. In some cases, a concentration of the acid in the pharmaceutical composition is from about 2 mM to about 200 mM. In some cases, the concentration of the acid is at most about 50 mM. In some cases, the concentration of the acid is about 20 mM. In some cases, the concentration of the acid is about 5 mM. In some cases, the acid comprises acetic acid. In some cases, the concentration of acetic acid is about 5 mM. In some cases, the acid comprises a mixture of acids selected from the group consisting of: acetic acid, citric acid, nitric acid, hydrochloric acid, and sulfuric acid. In some cases, the acid comprises hydrochloric acid.

In some cases, the salt of flecainide comprises flecainide acetate, and wherein the acid comprises acetic acid. In some cases, the pH of the solution is at most about 6.5. In some cases, the pH of the solution is about 5.9.

In some cases, the pharmaceutical composition further comprises an artificial sweetener configured to improve organoleptic properties of the pharmaceutical composition. In some cases, the artificial sweetener is selected from the group consisting of: acesulfame potassium, aspartame, cyclamate, mogrosides, saccharin, stevia, sucralose, neotame, mannitol, sorbitol, xylitol, lactitol, isomalt, maltitol, and pharmaceutically acceptable salts thereof. In some cases, the artificial sweetener comprises saccharin. In some cases, the artificial sweetener comprises a salt of saccharin. In some cases, the artificial sweetener comprises saccharin sodium.

In some cases, the pharmaceutical composition is formulated for administration via inhalation. In some cases, the pharmaceutical composition comprises nebulized droplets having a mass median aerodynamic diameter of less than 10 µm.

Described herein, in some aspects, is a unit dose of any pharmaceutical composition provided herein, comprising from about 50 mg to about 350 mg of the salt of flecainide.

In some cases, the unit dose comprises from about 250 mg to about 350 mg of the salt of flecainide. In some cases, the unit dose comprises from about 100 mg to about 250 mg of the salt of flecainide. In some cases, the unit dose comprises about 315 mg of the salt of flecainide. In some cases, the unit dose comprises about 260 mg of the salt of flecainide. In some cases, the unit dose comprises about 230 mg of the salt of flecainide. In some cases, the unit dose comprises about 200 mg of the salt of flecainide. In some cases, the unit dose further comprises a container containing the pharmaceutical composition. In some cases, the container is selected from the group consisting of: a vial, a syringe, a capsule, a blow fill seal, a blister, a cartridge, and an ampoule.

Described herein, in some aspects, is a kit, comprising: any pharmaceutical composition or any unit dose described herein and instructions for use of the pharmaceutical composition for treatment of a heart condition. In some cases, the heart condition comprises atrial fibrillation. In some cases, the atrial fibrillation comprises tachycardia. In some cases, the atrial arrhythmia is selected from the group consisting of: supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, or lone atrial fibrillation.

Described herein, in some aspects, is a kit, comprising: any pharmaceutical composition provided herein and a nebulizer. In some cases, the kit further comprises instructions for use of the nebulizer and the pharmaceutical composition for treatment of a heart condition. In some cases, the kit further comprises instructions for use of the nebulizer and the pharmaceutical composition for treatment of atrial arrhythmia. In some cases, the kit further comprises instructions for use of a nebulizer to inhalationally administer a dose of the pharmaceutical composition in aerosol to a subject. In some cases, the atrial arrhythmia comprises tachycardia. In some cases, the atrial arrhythmia is selected from the group consisting of: supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, or lone atrial fibrillation. In some cases, the nebulizer is configured to deliver the dose of the pharmaceutical composition in aerosol, wherein the aerosol of the pharmaceutical composition has droplets that have a mass median aerodynamic diameter of less than 10 μm. In some cases, the nebulizer is a breath-actuated nebulizer. In some cases, the nebulizer is a jet nebulizer. In some cases, the instructions contain instructions for use of the nebulizer to inhalationally administer the dose of the pharmaceutical composition in aerosol to a subject, wherein the dose contains from about 50 mg to about 150 mg of the salt of flecainide. In some cases, the pharmaceutical composition is in the form of a liquid solution that has: (i) the salt of flecainide at a concentration of from about 65 mg/mL to about 95 mg/mL; (ii) the cyclodextrin at a concentration of from about 10% (w/v) to about 30% (w/v) of the solution; and (iii) a pH of from about 5.5 to about 6.5 when said pH is measured at room temperature. In some cases, the concentration of the salt of flecainide is from about 65 mg/mL to about 95 mg/mL. In some cases, the concentration of the salt of flecainide is from about 70 mg/mL to about 80 mg/mL. In some cases, the instructions contain instructions for use of the nebulizer to deliver the pharmaceutical composition in an aerosolized dose that contains about 90 mg of the salt of flecainide. In some cases, the instructions contain instructions for use of the nebulizer to deliver the pharmaceutical composition in an aerosolized dose that contains about 120 mg of the salt of flecainide.

Described herein, in some aspects, is a kit, comprising: a pharmaceutical composition that comprises a salt of flecainide, a cyclodextrin, and an acid; a nebulizer configured to deliver the pharmaceutical composition as droplets having a mass median aerodynamic diameter of less than 10 μm; and instructions for use of the nebulizer to deliver the pharmaceutical composition in an aerosolized dose that contains from about 50 mg to about 250 mg of the salt of flecainide, wherein the pharmaceutical composition is in the form of a liquid solution that has (i) the salt of flecainide at a concentration of between 65 mg/mL and 100 mg/mL, (ii) the cyclodextrin at a concentration of from about 10% (w/v) to about 30% (w/v) of the solution; and (iii) a pH of from about 5.5 to about 6.5 when the pH is measured at room temperature. In some embodiments, the kit further comprises a nose clip. A nose clip can be used to hinder passage of air through a nose of a subject during inhalation and increase the proportion of a total inhaled volume that is the aerosol issued by the nebulizer. In some embodiments, the dose contains from about 150 mg to about 250 mg of the salt of flecainide. In some embodiments, the dose contains about 200 mg of the salt of flecainide.

Described herein, in some aspects, is a method of treating a subject suffering from a heart condition, comprising: administering to the subject via inhalation a pharmaceutical composition in the form of a liquid solution, wherein the pharmaceutical composition comprises a therapeutically effective amount of a salt of flecainide, and wherein a concentration of the salt of flecainide in the pharmaceutical composition is above 60 mg/mL. In some cases, the pharmaceutical composition further comprises a cyclodextrin. In some cases, a pH of the solution is above 5.5 when the pH is measured at room temperature.

Described herein, in some aspects, is a method of treating a human subject suffering from a heart condition, comprising administering to the subject via inhalation within about 10 min a pharmaceutical composition in the form of a liquid solution, wherein the pharmaceutical composition comprises a therapeutically effective amount of a salt of flecainide, and wherein the administration results in a peak plasma concentration ($C_{max}$) of the salt of flecainide in the subject that is at least 200 ng/mL. In some cases, a concentration of the salt of flecainide in the pharmaceutical composition is above 60 mg/mL of the solution. In some cases, the pharmaceutical composition further comprises a cyclodextrin. In some cases, the administration of the pharmaceutical composition results in a peak plasma concentration ($C_{max}$) of the salt of flecainide in the subject that is at least 200 ng/mL. In some cases, the administration of the pharmaceutical composition results in a peak plasma concentration ($C_{max}$) of the salt of flecainide in the subject that is at least 250 ng/mL. In some cases, the $C_{max}$ is between about 250 ng/mL and about 1000 ng/mL. In some cases, the $C_{max}$ is between about 300 ng/mL and about 700 ng/mL. In some cases, the $C_{max}$ is between about 400 ng/mL and about 600 ng/mL. In some cases, the administration of the pharmaceutical composition is performed within about 10 min. In some cases, the administration of the pharmaceutical composition is performed within about 5 min. In some cases, the administration is performed via a nebulizer. In some cases, the nebulizer is a breath-actuated nebulizer. In some cases, the nebulizer is a jet nebulizer. In some cases, from about 50 mg to about 150 mg of the salt of flecainide is administered to the subject via inhalation. In some cases, from about 75 mg to about 125 mg of the salt of flecainide is administered to the subject via inhalation. In some cases, from about 50 mg to about 250 mg of the salt of flecainide is administered to the subject via inhalation. In some cases, from about 150 mg to about 250 mg of the salt of flecainide is administered to the subject via inhalation. In some cases, about 90 mg of the salt of flecainide is administered to the subject via inhalation. In some cases, about 120 mg of the salt of flecainide is administered to the subject via inhalation. In some cases, about 150 mg of the salt of flecainide is administered to the subject via inhalation. In some cases, about 200 mg of the salt of flecainide is administered to the subject via inhalation. In some cases, the heart condition comprises atrial arrhythmia. In some cases, the atrial arrhythmia comprises tachycardia. In some cases, the atrial arrhythmia the atrial arrhythmia is selected from the group consisting of: supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, or lone atrial fibrillation. In some cases, the method comprises aerosolizing the pharmaceutical composition by forming droplets having a mass median aerodynamic diameter of less than 10 m. In some cases, the method comprises acute treatment after detection of the atrial arrhythmia. In some cases, the subject has normal sinus rhythm within 10 minutes after the administering. In some cases, the subject has normal sinus rhythm within 8 minutes after the administering. In some cases, the subject has normal sinus rhythm within 5 minutes after the administering. In some cases, the cyclodextrin is selected from the group consisting of: α-cyclodextrin, β-cyclodextrin, γ-cyclodextrin, derivatized α-cyclodextrins, derivatized β-cyclodextrins, and derivatized γ-cyclodextrins. In some cases, the cyclodextrin is selected from the group consisting of: α-cyclodextrin, β-cyclodextrin, γ-cyclodextrin, hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin dimaltosyl-β-cyclodextrin, succinyl-β-cyclodextrin, 6A-amino-6A-deoxy-N-(3-hydroxypropyl)-β-cyclodextrin, sulfobutylether-β-cyclodextrin, sulfobutylether-γ-cyclodextrin, sulfoalkylether-β-cyclodextrins, and sulfoalkylether-γ-cyclodextrins. In some cases, the cyclodextrin comprises hydroxypropyl-β-cyclodextrin. In some cases, a concentration of the cyclodextrin in the pharmaceutical composition is about 1% (w/v) to about 80% (w/v) of the solution. In some cases, the concentration of the cyclodextrin is at least about 5% (w/v) of the solution. In some cases, the concentration of the cyclodextrin is at least about 10% (w/v) of the solution. In some cases, the concentration of the cyclodextrin is about 20% (w/v) of the solution. In some cases, the concentration of the cyclodextrin is about 22.5% (w/v) of the solution. In some cases, the concentration of the cyclodextrin is at most about 20% (w/v) of the solution. In some cases, the concentration of the cyclodextrin is at most about 25% (w/v) of the solution. In some cases, the concentration of the cyclodextrin is at most about 23% (w/v) of the solution. In some cases, the concentration of the cyclodextrin is at most about 22.5% (w/v) of the solution. In some cases, the concentration of the salt of flecainide is at most about 200 mg/mL. In some cases, the concentration of the salt of flecainide is from about 65 mg/mL to about 130 mg/mL. In some cases, the concentration of the salt of flecainide is from about 70 mg/mL to about 115 mg/mL. In some cases, the concentration of the salt of flecainide is about 100 mg/mL. In some cases, the concentration of the salt of flecainide is about 75 mg/mL. In some cases, the salt of flecainide is selected from the group consisting of: flecainide acetate, flecainide hydrochloride, flecainide citrate, flecainide phosphate, and flecainide nitrate. In some cases, the salt of flecainide comprises flecainide acetate. In some cases, the salt of flecainide comprises flecainide hydrochloride. In some cases, the pharmaceutical composition further comprises an acid. In some cases, the acid is selected from the group consisting of: acetic acid, citric acid, nitric acid, hydrochloric acid, and sulfuric acid. In some cases, a concentration of the acid in the pharmaceutical composition is from about 2 mM to about 200 mM. In some cases, the concentration of the acid is at most about 50 mM. In some cases, the concentration of the acid is about 20 mM. In some cases, the concentration of the acid is about 5 mM. In some cases, the acid comprises acetic acid. In some cases, the concentration of acetic acid is about 5 mM. In some embodiments, the concentration of citric acid is 3.5 mM. In some cases, the acid comprises a mixture of acids selected from the group consisting of: acetic acid, citric acid, nitric acid, hydrochloric acid, and sulfuric acid. In some cases, the acid comprises hydrochloric acid. In some cases, the salt of flecainide comprises flecainide acetate, and wherein the acid comprises acetic acid. In some cases, the pH of the solution is from about 4.5 to about 6.5, from about 5 to about 6.5, from about 5 to about 6.2, or from about 5.2 to about 5.9. In some cases, the pH of the solution is at most about 6.5. In some cases, the pH of the solution is about 5.9. In some cases, the pH of the solution is about 5.2. In some cases, the salt of flecainide comprises flecainide acetate. In some cases, the pharmaceutical composition further comprises an artificial sweetener configured to improve organoleptic properties of the pharmaceutical composition. In some cases, the artificial sweetener is selected from the group consisting of: acesulfame potassium, aspartame, cyclamate, mogrosides, saccharin, *stevia*, sucralose, neotame, and sugar alcohols. In some cases, the artificial sweetener comprises saccharin. In some cases, the artificial sweetener comprises a salt of saccharin. In some cases, the artificial sweetener comprises saccharin sodium.

Described herein, in some aspects, is a method of manufacturing a liquid formulation for the treatment of a heart condition comprising a therapeutically effective amount of a salt of flecainide for treating the heart condition, wherein a concentration of the salt of flecainide in the formulation is above 60 mg/mL.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which.

DETAILED DESCRIPTION

Figure 1:
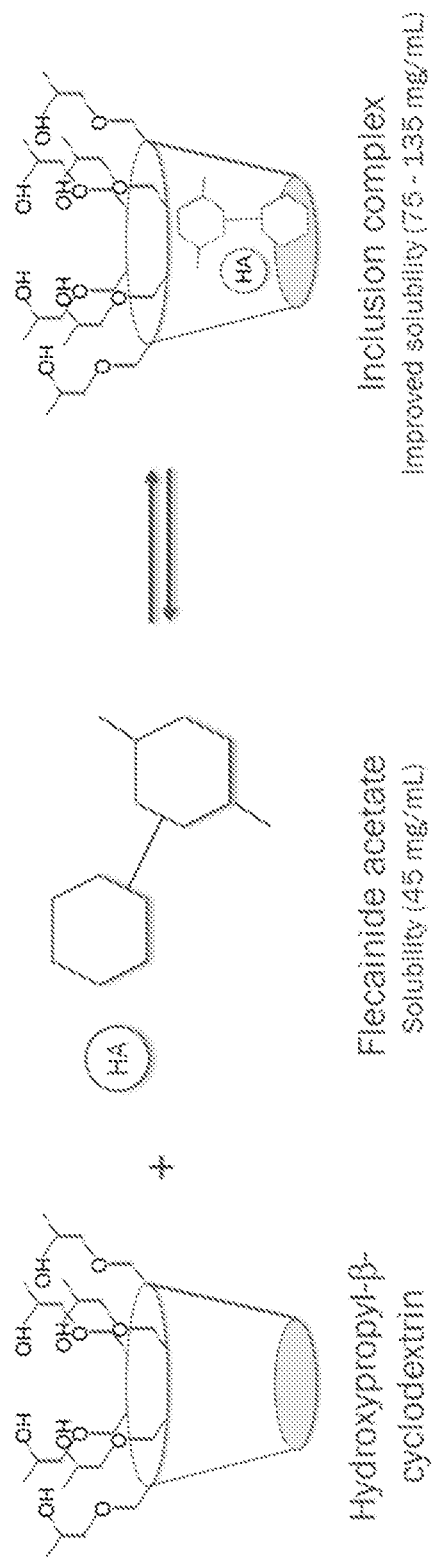
FIG. 1 is a schematic demonstrating the complexation between hydroxypropyl-β-cyclodextrin and flecainide acetate in an exemplary pharmaceutical formulation.

As an overview, the present disclosure relates to a novel formulation comprising a relatively high concentration of flecainide to treat a heart condition (e.g., cardiac arrhythmic) in a subject in need thereof. In some aspects, provided herein are methods of treatment comprising administering a novel formulation comprising a relatively high concentration of flecainide to treat a heart condition (e.g., cardiac arrhythmic) in a subject in need thereof.

In some embodiments, the pharmaceutical composition and the method of treatment provided herein are advantageous in offering fast, efficient, and safe therapeutic solution to heart conditions, such as cardiac arrhythmia, such as atrial arrhythmia. In some embodiments, the present disclosure relates to inhalation administration of a pharmaceutical composition in the form of a solution that comprises a salt of flecainide.

In some embodiments, the drug mass nebulization rate contributes to the efficiency of the inhalation therapy, as demonstrated in studies in human subjects for the pharmacokinetics and pharmacodynamics of inhalation administration of flecainide acetate (e.g., clinical studies FLE-001, FLE-003 (in healthy subjects) and FLE-002 (patients) sponsored by InCarda Therapeutics, Inc.). In some embodiments, human subjects cannot be expected to inhale the nebulized drug solution continuously for longer than approximately 4.5 minutes without a break. Long inhalation duration (e.g., longer than 5 minutes) can result in fatigue, inadequate or poor compliance with proper inhalation maneuver in some subjects, which can lead to insufficient delivery of drug to the lung, and stress. In some cases, stress in some subjects, e.g., stress induced by long inhalation duration or other discomfort, can lead to a rise in sympathetic tone, which can render cardioversion more difficult.

In some cases, a fast drug mass nebulization rate minimizes inhalation time for an effective dose. The drug mass nebulization rate can be strongly influenced by the drug concentration in the nebulization solution. In a nebulized product, the drug delivery rate can be constrained by the ability of the device to produce a nebulized cloud with an appropriate droplet size for inhalation (e.g., less than 5 microns). On the other hand, when the aerosolization rate is too high and the cloud too dense, the small nebulized droplets can coalesce into larger droplets which tend to deposit in the mouth and throat and do not reach the lungs.

In one aspect, the present disclosure provides a pharmaceutical composition, comprising: a therapeutically effective amount of a salt of flecainide, wherein the pharmaceutical composition is in the form of a liquid solution that has the salt of flecainide at a concentration above 60 mg/mL. In some embodiments, the pharmaceutical composition further comprises a cyclodextrin. In some embodiments, the presence of cyclodextrin increases the solubility of the salt of flecainide as compared to a corresponding formulation without the cyclodextrin. In some embodiments, the solution has pH above 5.5 when the pH is measured at room temperature. In some embodiments, the pharmaceutical composition further comprises a cyclodextrin, and the pH of the solution is above 5.5 when the pH is measured at room temperature. In some embodiments, the presence of cyclodextrin renders it possible to increase pH of the solution without compromising the solubility of the salt of flecainide, as compared to a corresponding solution without the cyclodextrin.

In some embodiments, the pharmaceutical composition or formulation provided herein enables delivery of more pharmaceutically active ingredient, e.g., flecainide, to the subject. In some embodiments, the subject pharmaceutical composition or formulation has an increased flecainide concentration as compared to a corresponding flecainide formulation (e.g., flecainide acetate water solution which has a solubility around 60 mg/mL). In some cases, the increased flecainide concentration increases the delivery speed when the composition is nebulized and administered via inhalation. In some embodiments, the increased flecainide concentration shortens the inhalation duration as a given dose can be delivered at a higher speed as compared to a corresponding formulation with a lower concentration of flecainide. Shorter inhalation duration can improve subject compliance, which can further increase the delivery efficiency of the drug.

In some embodiments, the pharmaceutical composition or formulation provided herein reduces adverse cough of the subject while inhaling, has improved organoleptic properties, and improves overall patient experience of inhalation. In some embodiments, the improved overall inhalation experience results in better compliance with the full inhalation program. In some embodiments, more effective drug delivery is achieved when the subject has better inhalation compliance, and thus more drug is delivered.

In some embodiments, the subject pharmaceutical composition or formulation has improved pharmacokinetics or pharmacodynamics parameter(s), for instance, the peak plasma level of flecainide ($C_{max}$) can be higher with the subject pharmaceutical composition as compared to a corresponding pharmaceutical composition in which the concentration of the salt of flecainide is lower. In some embodiments, the $C_{max}$ achieved with the subject pharmaceutical composition is at least 10%, 20%, 30%, 40%, 50%, 60%, 70%, 80%, 90%, or 100%, or 1.1, 1.2, 1.3, 1.4, 1.5, 1.6, 1.7, 1.8, 1.9, 2.0 or greater fold higher as compared to a corresponding pharmaceutical composition in which the concentration of the salt of flecainide is lower.

In some embodiments, a pharmaceutical composition with a low concentration of acid or a high pH, e.g., at most about 10 mM acetic acid, e.g., about 5 mM acetic acid, or e.g. a pH of higher than 5.5, e.g., a pH of 5.9 when the pH is measured at room temperature, has a higher $C_m$a as compared to a corresponding pharmaceutical composition in which the concentration of the acid is higher or the pH is lower, e.g., at least about 50 mM acetic acid, e.g., about 90 mM acetic acid, or e.g., a pH of at most 5.5, e.g., a pH of about 5.2 when the pH is measured at room temperature. In some embodiments, the $C_{max}$ achieved with the subject pharmaceutical composition that has a low concentration of acid or a high pH is at least 10%, 20%, 30%, 40%, 50%, 60%, 70%, 80%, 90%, or 100%, or 1.1, 1.2, 1.3, 1.4, 1.5, 1.6, 1.7, 1.8, 1.9, 2.0 or greater fold higher as compared to a corresponding pharmaceutical composition in which the concentration of the acid is higher or the pH is lower. In some embodiments, the $C_{max}$ achieved with the subject pharmaceutical composition that has at most about 10 mM acetic acid, e.g., about 5 mM acetic acid, or a pH of higher than 5.5, e.g., a pH of 5.9 when the pH is measured at room temperature is at least 10%, 20%, 30%, 40%, 50%, 60%, 70%, 80%, 90%, or 100%, or 1.1, 1.2, 1.3, 1.4, 1.5, 1.6, 1.7, 1.8, 1.9, 2.0 or greater fold higher as compared to a corresponding pharmaceutical composition in which the concentration of the acetic acid is about 90 mM, or the pH is about 5.2.

In one aspect of the present disclosure, provided herein is a unit dose of a pharmaceutical composition provided herein. In some embodiments, the unit dose comprises about 50 mg to about 350 mg of the salt of flecainide. In another aspect, provided herein are kits comprising the pharmaceutical composition or the unit dose provided herein and instructions for use of the pharmaceutical composition for treatment of a heart condition (e.g., cardiac arrhythmia, e.g., atrial arrhythmia).

In one aspect of the present disclosure, provided is a system comprising a pharmaceutical composition provided herein and a nebulizer. In some embodiments, the system further comprises instructions for use of the nebulizer and the pharmaceutical composition for treatment of a heart condition. In some embodiments, the system comprises: a pharmaceutical composition that comprises a salt of flecainide, a cyclodextrin, and an acid; a nebulizer configured to inhalationally administer the pharmaceutical composition as droplets having a mass median aerodynamic diameter of less than 10 μm; and instructions for use of the nebulizer to inhalationally administer the pharmaceutical composition in an aerosolized dose that contains from about 50 mg to about 150 mg of the salt of flecainide, wherein the pharmaceutical composition is in the form of a liquid solution that has (i) the salt of flecainide at a concentration of from about 65 mg/mL to about 95 mg/mL, (ii) the cyclodextrin at a concentration of from about 10% (w/v) to about 30% (w/v) of the solution; and (iii) a pH of from about 5.5 to about 6.5 when the pH is measured at room temperature.

In one aspect of the present disclosure, provided is a method of treating a subject suffering from a heart condition. In some embodiments, the method comprises: administering to the subject via inhalation a pharmaceutical composition in the form of a liquid solution, wherein the pharmaceutical composition comprises a therapeutically effective amount of a salt of flecainide, and wherein a concentration of the salt of flecainide in the pharmaceutical composition is above 60 mg/mL.

As used herein, "heart condition" can refer to a condition where heart has an abnormal function and/or structure, for example, heart is beating in an irregular rhythm, experiencing arrhythmia, atrial fibrillation, and/or tachycardia, there is myocardial infarction, and/or coronary heart disease. As used herein, "atrial arrhythmia" can refer to an arrhythmia that affects at least one atrium and does not include bradycardia. For instance, atrial arrhythmia may originate in and affect at least one atrium. As used herein, "tachycardia" can refer to an arrhythmia in which the heart beat is too fast. For instance, tachycardia may involve a resting heart rate of over 100 beats per minute, such as greater than 110, greater than 120, or greater than 130 beats minute. In some cases, tachycardia can comprise sinus tachycardia, atrial fibrillation, atrial flutter, AV nodal reentrant tachycardia, accessory pathway mediated tachycardia, atrial tachycardia, multifocal atrial tachycardia, junctional tachycardia, ventricular tachycardia, supraventricular tachycardia, or any combination thereof.

As used herein, the phrase "heart rhythm arrhythmia" can refer to an arrhythmia in which the heart beat is irregular. As used herein, the term "atrial fibrillation" can refer to an abnormal heart rhythm characterized by rapid and irregular beating of the atria. As used herein, the term "cardioversion" can refer to a process by which an abnormally fast heart rate (tachycardia) or other cardiac arrhythmia is converted to a normal sinus rhythm. Cardioversion can be induced by electricity, drugs, or both.

As used herein, the singular forms "a," "an," and "the" can include plural referents unless the context clearly dictates otherwise. Thus, for example, reference to "an antiarrhythmic agent" can include not only a single active agent but also a combination or mixture of two or more different active agents.

Reference herein to "one embodiment," "one version," or "one aspect" can include one or more such embodiments, versions or aspects, unless otherwise clear from the context.

As used herein, the term "pharmaceutically acceptable solvate" can refer to a solvate that retains one or more of the biological activities and/or properties of the antiarrhythmic pharmaceutical agent and that is not biologically or otherwise undesirable. Examples of pharmaceutically acceptable solvates include, but are not limited to, antiarrhythmic pharmaceutical agents in combination with water, isopropanol, ethanol, methanol, DMSO, ethyl acetate, acetic acid, ethanolamine, or combinations thereof.

As used herein, the term "salt" is equivalent to the term "pharmaceutically acceptable salt," and can refer to those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, di nitrobenzoates, hydroxybenzoates, methoxybenzoates, phthalates, sulfonates, xylenesulfonates, phenylacetates, phenyipropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, "atrial arrhythmia" can refer to an arrhythmia that affects at least one atrium and does not include bradycardia. For instance, atrial arrhythmia can originate in and affect at least one atrium.

As used herein, "tachycardia" can mean an arrhythmia in which the heart beat is too fast, e.g., faster than normal. For instance, tachycardia may involve a resting heart rate of over 100 beats per minute, such as greater than 110, greater than 120, or greater than 130 beats minute.

As used herein, the phrase "heart rhythm arrhythmia" can refer to an arrhythmia in which the heart beat is irregular.

As used herein, the amount of an agent as described herein in the coronary circulation of the heart" can be measured by extracting a sample from any vascular region of the coronary circulation of the heart (e.g., arteries, veins, including coronary sinus) by using a cannula. The amount of the agent in the sample can then be determined by known means, such as bioanalytical techniques that employ analytical equipment such as LC-MS/MS. Thus, the amount of the agent in the blood in the heart can be measured for any particular time.

As used herein, the terms "treating" and "treatment" can refer to reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein can include prevention of a particular condition, disease, or disorder in a susceptible individual as well as treatment of a clinically symptomatic individual.

As used herein, "nominal amount" can refer to the amount contained within the unit dose receptacle(s) that are administered.

As used herein, "effective amount" can refer to an amount covering both therapeutically effective amounts and prophylactically effective amounts.

As used herein, a "therapeutically effective amount" of an active agent can refer to an amount that is effective to achieve a desired therapeutic result. A therapeutically effective amount of a given active agent can vary with respect to factors such as the type and severity of the disorder or disease being treated and the age, gender, and weight of the patient. In some cases, "inhalation" (e.g., "oral inhalation" or "nasal inhalation") refers to inhalation delivery of a therapeutically effective amount of a pharmaceutical agent contained in one unit dose receptacle, which, in some instance, can require one or more breaths, like 1, 2, 3, 4, 5, 6, 7, 8, 9, or more breaths. For example, if the effective amount is 90 mg, and each unit dose receptacle contains 30 mg, the delivery of the effective amount can require 3 inhalations.

Unless otherwise specified, the term "therapeutically effective amount" can include a "prophylactically effective amount," e.g., an amount of active agent that is effective to prevent the onset or recurrence of a particular condition, disease, or disorder in a susceptible individual.

As used herein, the phrase "minimum effective amount" can mean the minimum amount of a pharmaceutical agent necessary to achieve an effective amount.

As used herein, "mass median diameter" or "MMD" can refer to the median diameter of a plurality of particles, typically in a polydisperse particle population, e.g., consisting of a range of particle sizes. MMD values as reported herein are determined by laser diffraction (Sympatec Helos, Clausthal-Zellerfeld, Germany), unless the context indicates otherwise. For instance, for powders the samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" can refer to the diameter of a single particle, as determined by microscopy, unless the context indicates otherwise.

As used herein, "mass median aerodynamic diameter" or "MMAD" can refer to the median aerodynamic size of a plurality of particles or particles, typically in a polydisperse population. The "aerodynamic diameter" can be the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

By a "pharmaceutically acceptable" component is meant a component that is not biologically or otherwise undesirable, e.g., the component may be incorporated into a pharmaceutical formulation of the disclosure and administered to a patient as described herein without causing any significant undesirable biological effects or interacting in a deleterious manner with any of the other components of the formulation in which it is contained. When the term "pharmaceutically acceptable" is used to refer to an excipient, it can imply that the component has met the required standards of toxicological and manufacturing testing or that it is included on the Inactive Ingredient Guide prepared by the U.S. Food and Drug Administration.

As used herein, "P wave" can represent the wave generated by the electrical depolarization of the atria (right and left) and is usually 0.08 to 0.1 seconds (80-100 ms) in duration.

As used herein, "room temperature" can refer to a temperature that is from 18° C. to 25° C.

Cyclodextrins

In some aspects of the present disclosure, a cyclodextrin is used as a solubility enhancer of a salt of flecainide. Cyclodextrins are cyclic carbohydrates derived from starch. The unmodified cyclodextrins differ by the number of glucopyranose units joined together in the cylindrical structure. The parent cyclodextrins contain 6, 7, or 8 glucopyranose units and are referred to as α-, β-, and γ-cyclodextrin respectively. Each cyclodextrin subunit can have secondary hydroxyl groups at the 2 and 3 positions and a primary hydroxyl group at the 6-position. The cyclodextrins can be pictured as hollow truncated cones with hydrophilic exterior surfaces and hydrophobic interior cavities. In aqueous solutions, these hydrophobic cavities can provide a haven for hydrophobic organic compounds that can fit all or part of their structure into these cavities. This process, known as inclusion complexation, can result in increased apparent aqueous solubility and stability for the complexed drug.

The cyclodextrin in a pharmaceutical composition provided herein can include, but not limited to, α-cyclodextrin, β-cyclodextrin, γ-cyclodextrin, derivatized α-cyclodextrins, derivatized β-cyclodextrins, and derivatized γ-cyclodextrins. Non-limiting examples of cyclodextrin that can be used in the subject pharmaceutical composition include α-cyclodextrin, β-cyclodextrin, γ-cyclodextrin, hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin dimaltosyl-β-cyclodextrin, succinyl-β-cyclodextrin, 6A-amino-6A-deoxy-N-(3-hydroxypropyl)-β-cyclodextrin, sulfobutylether-β-cyclodextrin, sulfobutylether-γ-cyclodextrin, sulfoalkylether-β-cyclodextrins, and sulfoalkylether-γ-cyclodextrins. In some embodiments, the pharmaceutical composition comprises hydroxypropyl-β-cyclodextrin (HPβCD). In some embodiments, the pharmaceutical composition comprises more than one species of cyclodextrins, such as, 2, 3, 4, 5, 6, 7, 8, 9, 10 or more different species of cyclodextrins. In some embodiments, the pharmaceutical composition comprises HPPCD and one or more other cyclodextrins, such as, 1, 2, 3, 4, 5, 6, 7, 8, 9, 10 or more other different species of cyclodextrins.

The subject pharmaceutical composition can comprise a cyclodextrin at a concentration of at least about 1% (w/v) of the solution, such as at least about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 28%, 30%, 35%, 40%, 45%, 50%, 55%, 60%, 65%, 70%, 75%, 80%, 85%, 90%, 100%, or more (w/v) of the solution. In some embodiments, the pharmaceutical composition comprises a cyclodextrin at a concentration of from about 1% (w/v) to about 80% (w/v) of the solution, such as from about 2% (w/v) to about 70% (w/v), from about 2% (w/v) to about 60% (w/v), from about 2% (w/v) to about 50% (w/v), from about 2% (w/v) to about 40% (w/v), from about 2% (w/v) to about 30% (w/v), from about 2% (w/v) to about 20% (w/v), from about 2% (w/v) to about 15% (w/v), from about 2% (w/v) to about 10% (w/v), from about 2% (w/v) to about 8% (w/v), from about 2% (w/v) to about 5% (w/v), from about 5% (w/v) to about 80% (w/v), from about 5% (w/v) to about 70% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 5% (w/v) to about 15% (w/v), from about 5% (w/v) to about 12% (w/v), from about 5% (w/v) to about 10% (w/v), from about 10% (w/v) to about 60% (w/v), from about 10% (w/v) to about 50% (w/v), from about 10% (w/v) to about 40% (w/v), from about 10% (w/v) to about 30% (w/v), from about 20% (w/v) to about 30% (w/v), from about 10% (w/v) to about 25% (w/v), from about 19% (w/v) to about 25% (w/v), from about 19.5% (w/v) to about 25% (w/v), from about 20% (w/v) to about 25% (w/v), from about 20.5% (w/v) to about 25% (w/v), from about 21% (w/v) to about 25% (w/v), from about 21.5% (w/v) to about 25% (w/v), from about 22% (w/v) to about 25% (w/v), from about 22.5% (w/v) to about 25% (w/v), from about 23% (w/v) to about 25% (w/v), from about 10% (w/v) to about 20% (w/v), or from about 10% (w/v) to about 15% (w/v) of the solution. In some embodiments, the pharmaceutical composition comprises a cyclodextrin at a concentration of about 2%, 3%, 4%, 5%, 6%, 7%, 8%, 9%, 10%, 11%, 12%, 13%, 14%, 15%, 16%, 17%, 18%, 19%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 31%, 32%, 33%, 34%, 35%, 38%, 40%, 45%, 50%, 55%, 60%, 65%, 70%, 75%, or 80% (w/v) of the solution.

In some embodiments, the concentration of the cyclodextrin contributes to the viscosity of the solution, which can reduce the nebulization efficiency (or rate) of the solution. For instance, in some cases, the higher the concentration of the cyclodextrin is, the higher viscosity of the solution is. In some cases, the concentration of the cyclodextrin in the pharmaceutical composition is controlled so that the viscosity of the solution is not higher than a reference value, such as about 3.1 cP, 3.2 cP, 3.3 cP, 3.4 cP, 3.5 cP, 3.6 cP, 3.7 cP, 3.8 cP, 3.9 cP, 4.0 cP, 4.1 cP, 4.2 cP, 4.3 cP, 4.4 cP, 4.5 cP, 4.6 cP, 4.7 cP, 4.8 cP, 4.9 cP, or 5.0 cP. In some cases, the concentration of the cyclodextrin in the pharmaceutical composition is at most about 2%, 5%, 8%, 10%, 12%, 15%, 18%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 31%, 32%, 33%, 34%, 35%, 38%, 40%, 45%, 50%, 55%, 60%, 65%, 70%, 75%, or 80% (w/v) of the solution.

In some embodiments, the pharmaceutical composition comprises HPPCD at a concentration of about 20% (w/v) of the solution. In some embodiments, the pharmaceutical composition comprises HPPCD at a concentration of about 22.5% (w/v) of the solution. In some embodiments, the pharmaceutical composition comprises HPPCD at a concentration of about 20% (w/v) of the solution.

Acids

Some aspects of the present disclosure relate to use of one or more acids in the pharmaceutical composition. In some cases, the acid enhances solubility of flecainide. In some cases, flecainide freebase has a low solubility, e.g., in water. In some cases, certain salts of flecainide have higher solubility as compared to other salts of flecainide and flecainide freebase. For instance, flecainide acetate can have a higher solubility as compared to some other flecainide salts, as demonstrated in Example 1. In some cases, acid is provided in the pharmaceutical composition to provide anion for flecainide salt formation and sufficiently low pH to ensure the solubility of the flecainide salt.

In some cases, a mixture of more than one acid can increase flecainide solubility as compared to a single acid. In some instances, the pharmaceutical composition comprises acetic acid as the single acid. In some instances, the pharmaceutical composition comprises citric acid as the single acid. In some cases, the pharmaceutical composition comprises a mixture of different acids. In some cases, the pharmaceutical composition comprises lactic acid. In some cases, the pharmaceutical composition comprises L-(+)-lactic acid. In some cases, the pharmaceutical composition comprises D-(−)-lactic acid. In some cases, the pharmaceutical composition comprises a mixture of D-(−)-lactic acid and L-(+)-lactic acid, i.e. the pharmaceutical composition comprises DL-lactic acid. In some cases, there are equal amounts of D-(−)-lactic acid and L-(+)-lactic acid in the pharmaceutical composition. In some cases, the pharmaceutical composition comprises ascorbic acid. Non-limiting examples of the acids that can be used in the subject pharmaceutical compositions and methods of treatment include any suitable organic or inorganic acid, such as any GRAS (Generally Recognized As Safe) listed acid, e.g., acetic acid, aconitic acid, adipic acid, alginic acid, benzoic acid, caprylic acid, citric acid, cholic acid, formic acid, lactic acid (e.g., D-(−)-lactic acid or L-(+)-lactic acid), linoleic acid, malic acid, maleic acid, propionic acid, stearic acid, succinic acid, sulfuric acid, tannic acid, tartaric acid, glutamic acid, hydrochloric acid, phosphoric acid, ascorbic acid, erythorbic acid, sorbic acid, or thiodipropionic acid, or any other acid that is not listed in GRAS but is pharmaceutically acceptable in the subject pharmaceutical composition.

In some cases, the pharmaceutical composition comprises a mixture of different acids, such as 2, 3, 4, 5, 6, 7, 8, 9, 10 or more different acids. In some cases, the pharmaceutical composition comprises one of the following: acetic acid and nitric acid; acetic acid and sulfuric acid; acetic acid and citric acid; acetic acid, nitric acid, and sulfuric acid; acetic acid, nitric acid, and citric acid; acetic acid, citric acid, and sulfuric acid; or acetic acid, nitric acid, citric acid, and sulfuric acid.

In some embodiments, the pharmaceutical composition has a pH that is above 5.5 when the pH is measured at room temperature, such as above 5.6, above 5.7, above 5.8, above 5.9, above 6.0, above 6.1, above 6.2, above 6.3, above 6.4, above 6.5, above 6.6, above 6.7, or above 6.8 when the pH is measured at room temperature. In some cases, the pharmaceutical composition is acidic at room temperature, e.g., having a pH at most 6.9, at most 6.8, at most 6.7, at most 6.6, at most 6.5, at most 6.4, at most 6.3, at most 6.2, at most 6.1, at most 6.0, at most 5.9, at most 5.8, at most 5.7, or at most 5.6 when the pH is measured at room temperature. In some cases, the pharmaceutical composition has a pH that is between about 5.5 and about 6.5 when the pH is measured at room temperature, such as between about 5.6 and about 6.4, between about 5.7 and about 6.3, between about 5.8 and about 6.2, or between about 5.9 and about 6.1 when the pH is measured at room temperature. In some instances, the pharmaceutical composition has a pH of about 5.5, 5.6, 5.7, 5.8, 5.9, 6.0, 6.1, 6.2, 6.3, or 6.4 when the pH is measured at room temperature. In some examples, the pharmaceutical composition has a pH of about 5.5 when the pH is measured at room temperature. In some embodiments, the pH of the pharmaceutical composition is titrated by a pH buffer as described herein.

In some embodiments, the concentration of the acid in the pharmaceutical composition is about 2 mM to about 200 mM, such as about 2 mM to about 180 mM, from about 2 mM to about 150 mM, from about 2 mM to about 120 mM, from about 2 mM to about 100 mM, from about 2 mM to about 80 mM, from about 2 mM to about 60 mM, from about 2 mM to about 50 mM, from about 2 mM to about 40 mM, from about 2 mM to about 30 mM, from about 2 mM to about 20 mM, from about 2 mM to about 10 mM, from about 2 mM to about 8 mM, 2 mM to about 6 mM, from about 5 mM to about 200 mM, from about 5 mM to about 150 mM, from about 5 mM to about 120 mM, from about 5 mM to about 100 mM, from about 5 mM to about 80 mM, from about 5 mM to about 60 mM, from about 5 mM to about 50 mM, from about 5 mM to about 40 mM, from about 5 mM to about 30 mM, from about 5 mM to about 20 mM, from about 5 mM to about 10 mM, from about 5 mM to about 8 mM, from about 10 mM to about 200 mM, from about 10 mM to about 150 mM, from about 10 mM to about 120 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 200 mM, from about 20 mM to about 150 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 40 mM to about 200 mM, from about 40 mM to about 150 mM, from about 40 mM to about 120 mM, from about 40 mM to about 100 mM, from about 40 mM to about 90 mM, from about 40 mM to about 80 mM, from about 40 mM to about 70 mM, from about 40 mM to about 60 mM, or about 40 mM to about 50 mM. In some embodiments, the concentration of the acid in the pharmaceutical composition is at most about 200 mM, such as at most about 180 mM, at most about 160 mM, at most about 150 mM, at most about 140 mM, at most about 120 mM, at most about 100 mM, at most about 90 mM, at most about 80 mM, at most about 70 mM, at most about 60 mM, at most about 50 mM, at most about 40 mM, at most about 30 mM, at most about 20 mM, at most about 10 mM, at most about 9 mM, at most about 8 mM, at most about 7 mM, at most about 6 mM, at most about 5 mM, at most about 4 mM, at most about 3 mM, at most about 2 mM, or at most about 1 mM. In some embodiments, the concentration of the acid in the pharmaceutical composition is about 100 mM, about 90 mM, about 80 mM, about 70 mM, about 60 mM, about 50 mM, about 40 mM, about 30 mM, about 20 mM, about 10 mM, about 9 mM, about 8 mM, about 7 mM, about 6 mM, about 5 mM, about 4 mM, about 3 mM, about 2 mM, or about 1 mM. In some embodiments, the concentration of the acid in the pharmaceutical composition is about 20 mM. In some embodiments, the concentration of the acid in the pharmaceutical composition is about 5 mM.

Without wishing to be bound to a particular theory, the concentration of the acid in the pharmaceutical composition can contribute to the pharmaceutical application of the composition. In some embodiments, the acid concentration and thus the pH of the solution can influence solubility of the flecainide salt in the formulation, therefore affecting the concentration of the flecainide salt. As discussed above, the concentration of the flecainide salt can contribute to the delivery efficiency and rate of the pharmaceutical composition. In some embodiments, the acid concentration can influence the organoleptic properties of the pharmaceutical composition. For instance, the lower the pH of the solution is, the more irritating the solution can be to the mouth, the nose, the pharynx, or other parts of the respiratory system, particularly the upper respiratory system. Irritation of the solution can induce cough or other adverse reactions, or reduced compliance of the subject, therefore adversely affecting the delivery efficiency of the pharmaceutical composition.

In some embodiments, the pharmaceutical composition provided herein does not induce coughing reflex when being inhaled by a subject. In some embodiments, the pharmaceutical composition provided herein induces coughing reflex less frequently when being inhaled by a subject as compared to a corresponding pharmaceutical composition that has a higher acid concentration or lower pH, such as about 10%, 20%, 30%, 50%, 60%, 70%, 80%, 90%, or 100%, or 1.1, 1.2, 1.3, 1.4, 1.5, 1.6, 1.7, 1.8, 1.9, 2.0 or greater fold lower as compared to the corresponding pharmaceutical composition. In some embodiments, a subject receiving inhalation administration of the pharmaceutical composition reports less severe discomfort when inhaling the composition, or has lower incidence of reporting discomfort when inhaling the composition, as compared to a corresponding pharmaceutical composition that has a higher acid concentration or lower pH, such as about 10%, 20%, 30%, 50%, 60%, 70%, 80%, 90%, or 100%, or 1.1, 1.2, 1.3, 1.4, 1.5, 1.6, 1.7, 1.8, 1.9, 2.0 or greater fold lower as compared to the corresponding pharmaceutical composition.

Without wishing to be bound by a certain theory, the presence of a cyclodextrin in the pharmaceutical composition can reduce the concentration of acid that is required to achieve a desirable concentration of flecainide salt according to some aspects of the present disclosure. In some embodiments, the presence of a cyclodextrin (e.g., HPβCD) increases flecainide solubility, e.g., through inclusion complexation that "dissolves" flecainide salt (e.g., flecainide acetate) inside the cavity of the cyclodextrin. The inclusion complexation, on the other hand, can reduce the reliability of flecainide salt on the acid (or the low pH) to be dissolved in the solution. Therefore, as a result, the introduction of cyclodextrin (e.g., HPβCD) can lead to reduction of acid concentration in the solution, both of which synergistically lead to increased flecainide concentration in the solution, improved organoleptic properties, increased delivery speed, and improved delivery efficiency.

Sweeteners and Organoleptic Properties

In some embodiments, the pharmaceutical composition provided herein comprises a sweetener to improve the organoleptic properties of the composition. The sweetener can be a natural sweet substance, e.g. certain sugars, or an artificial sweetener. Without wishing to be bound to a certain theory, the presence of the sweetener in the pharmaceutical composition can improve the organoleptic properties of the composition. In some cases, the presence of the sweetener in the pharmaceutical composition can improve the compliance of the subject. presence of the sweetener in the pharmaceutical composition can increase the delivery efficiency of the composition. In some embodiments, the presence of the sweetener in the pharmaceutical composition can enhance the therapeutic effects of the composition.

Non-limiting examples of artificial sweeteners that can be used in the pharmaceutical composition include acesulfame potassium, aspartame, cyclamate, mogrosides, saccharin, *stevia*, sucralose, neotame, and sugar alcohols (e.g., erythritol, hydrogenated starch hydrolysates, isomalt, lactitol, maltitol, mannitol, sorbitol, and xylitol), such as those used in commercial products, like Sweet n'low powder sweetener, Truvia powder sweetener, Equal (aspartame), *Stevia* powder sachet, Aspen Naturals liquid *stevia*, Now Better *Stevia* liquid sweetener, Sweet N'Low liquid sweetener, Quick Sweet: Neotame liquid sweetener, or Splenda powder sachet, or pharmaceutically acceptable salts thereof. In some embodiments, the pharmaceutical composition comprises saccharin. In some embodiments, the pharmaceutical composition comprises a salt of saccharin. In some embodiments, the pharmaceutical composition comprises saccharin sodium.

Natural sweet substances that can be used in the pharmaceutical composition include, but not limited to, sucrose, agave, brown sugar, confectioner's (powdered) sugar, corn syrup, dextrose, fructose, fruit juice concentrate, glucose, high-fructose corn syrup, honey, invert sugar, lactose, malt sugar, maltose, maple syrup, molasses, nectars, raw sugar, and syrup. Sugars can increase the viscosity of the liquid solution, thus the concentration of any sugar added into the pharmaceutical composition, in some embodiments, is tightly controlled below a certain threshold value.

In some embodiments, the concentration of the sweetener, e.g., artificial sweetener, in the pharmaceutical composition is between about 0.001% (w/v) to about 1% (w/v) of the solution, such as 0.002% to 1%, 0.005% to 1%, 0.01% to 1%, 0.02% to 1%, 0.05% to 1%, 0.08% to 1%, 0.1% to 1%, 0.2% to 1%, 0.5% to 1%, 0.8 to 1%, 0.002% to 0.5%, 0.005% to 0.5%, 0.01% to 0.5%, 0.02% to 0.5%, 0.05% to 0.5%, 0.08% to 0.5%, 0.1% to 0.5%, 0.2% to 0.5%, 0.005% to 0.1%, 0.01% to 0.1%, 0.02% to 0.1%, 0.05% to 0.1%, 0.08% to 0.1%, 0.005% to 0.05%, 0.01% to 0.05%, or 0.02% to 0.05% (w/v) of the solution. In some embodiments, the concentration of the sweetener, e.g., artificial sweetener, in the pharmaceutical composition is at least about 0.001%, at least about 0.002%, at least about 0.005%, at least about 0.01%, at least about 0.02%, at least about 0.05%, at least about 0.08%, at least about 0.1%, at least about 0.2%, at least about 0.5%, or at least about 0.8, or at least about 1% (w/v) of the solution. In some embodiments, the concentration of the sweetener, e.g., artificial sweetener, in the pharmaceutical composition is at most about 0.001%, at most about 0.002%, at most about 0.005%, at most about 0.01%, at most about 0.02%, at most about 0.05%, at most about 0.08%, at most about 0.1%, at most about 0.2%, at most about 0.5%, or at most about 0.8, or at most about 1% (w/v) of the solution.

Pharmaceutical Compositions, Formulations, and Kits

In one aspect, provided herein are pharmaceutical composition for treatment of a heart condition, e.g., cardiac arrhythmia, e.g., atrial arrhythmia.

The pharmaceutical composition can include a therapeutically effective amount of a salt of flecainide. The therapeutically effective amount of flecainide can be effective for treatment of a heart condition, e.g., cardiac arrhythmia, e.g., atrial arrhythmia, when it is administered to a subject in need thereof via inhalation. In some cases, the therapeutically effective amount of flecainide salt is effective for treatment of atrial arrhythmia by inducing cardioversion when it is administered to a subject in need thereof via inhalation.

In some cases, provided herein are pharmaceutical composition including a therapeutically effective amount of a salt of flecainide. As described herein, in some embodiments, the pharmaceutical composition is in the form of a liquid solution. In some cases, the concentration of flecainide or the salt of flecainide (e.g., flecainide acetate or flecainide hydrochloride) in the pharmaceutical compositions or formulations is about 60 mg/mL to about 200 mg/mL, such as 60 mg/mL to 195 mg/mL, 60 mg/mL to 190 mg/mL, 60 mg/mL to 185 mg/mL, 60 mg/mL to 175 mg/mL, 60 mg/mL to 170 mg/mL, 60 mg/mL to 165 mg/mL, 60 mg/mL to 160 mg/mL, 60 mg/mL to 155 mg/mL, 60 mg/mL to 150 mg/mL, 60 mg/mL to 145 mg/mL, 60 mg/mL to 140 mg/mL, 60 mg/mL to 135 mg/mL, 60 mg/mL to 130 mg/mL, 60 mg/mL to 125 mg/mL, 60 mg/mL to 120 mg/mL, 60 mg/mL to 118 mg/mL, 60 mg/mL to 115 mg/mL, 60 mg/mL to 112 mg/mL, 60 mg/mL to 110 mg/mL, 60 mg/mL to 108 mg/mL, 60 mg/mL to 105 mg/mL, 60 mg/mL to 102 mg/mL, 60 mg/mL to 100 mg/mL, 60 mg/mL to 98 mg/mL, 60 mg/mL to 95 mg/mL, 60 mg/mL to 92 mg/mL, 60 mg/mL to 90 mg/mL, 60 mg/mL to 88 mg/mL, 60 mg/mL to 85 mg/mL, 60 mg/mL to 82 mg/mL 60 mg/mL to 80 mg/mL, 60 mg/mL to 78 mg/mL, 60 mg/mL to 75 mg/mL, 60 mg/mL to 72 mg/mL, 60 mg/mL to 70 mg/mL, 70 mg/mL to 195 mg/mL, 70 mg/mL to 190 mg/mL, 70 mg/mL to 185 mg/mL, 70 mg/mL to 175 mg/mL, 70 mg/mL to 170 mg/mL, 70 mg/mL to 165 mg/mL, 70 mg/mL to 160 mg/mL, 70 mg/mL to 155 mg/mL, 70 mg/mL to 150 mg/mL, 70 mg/mL to 145 mg/mL, 70 mg/mL to 140 mg/mL, 70 mg/mL to 135 mg/mL, 70 mg/mL to 130 mg/mL, 70 mg/mL to 125 mg/mL, 70 mg/mL to 120 mg/mL, 70 mg/mL to 118 mg/mL, 70 mg/mL to 115 mg/mL, 70 mg/mL to 112 mg/mL, 70 mg/mL to 110 mg/mL, 70 mg/mL to 108 mg/mL, 70 mg/mL to 105 mg/mL, 70 mg/mL to 102 mg/mL, 70 mg/mL to 100 mg/mL, 70 mg/mL to 98 mg/mL, 70 mg/mL to 95 mg/mL, 70 mg/mL to 92 mg/mL, 70 mg/mL to 90 mg/mL, 70 mg/mL to 88 mg/mL, 70 mg/mL to 85 mg/mL, 70 mg/mL to 82 mg/mL 70 mg/mL to 80 mg/mL, 70 mg/mL to 78 mg/mL, 70 mg/mL to 75 mg/mL, 80 mg/mL to 195 mg/mL, 80 mg/mL to 190 mg/mL, 80 mg/mL to 185 mg/mL, 80 mg/mL to 175 mg/mL, 80 mg/mL to 170 mg/mL, 80 mg/mL to 165 mg/mL, 80 mg/mL to 160 mg/mL, 80 mg/mL to 155 mg/mL, 80 mg/mL to 150 mg/mL, 80 mg/mL to 145 mg/mL, 80 mg/mL to 140 mg/mL, 80 mg/mL to 135 mg/mL, 80 mg/mL to 130 mg/mL, 80 mg/mL to 125 mg/mL, 80 mg/mL to 120 mg/mL, 80 mg/mL to 118 mg/mL, 80 mg/mL to 115 mg/mL, 80 mg/mL to 112 mg/mL, 80 mg/mL to 110 mg/mL, 80 mg/mL to 108 mg/mL, 80 mg/mL to 105 mg/mL, 80 mg/mL to 102 mg/mL, 80 mg/mL to 100 mg/mL, 80 mg/mL to 98 mg/mL, 80 mg/mL to 95 mg/mL, 80 mg/mL to 92 mg/mL, 80 mg/mL to 90 mg/mL, 80 mg/mL to 88 mg/mL, 80 mg/mL to 85 mg/mL, 90 mg/mL to 195 mg/mL, 90 mg/mL to 190 mg/mL, 90 mg/mL to 185 mg/mL, 90 mg/mL to 175 mg/mL, 90 mg/mL to 170 mg/mL, 90 mg/mL to 165 mg/mL, 90 mg/mL to 160 mg/mL, 90 mg/mL to 155 mg/mL, 90 mg/mL to 150 mg/mL, 90 mg/mL to 145 mg/mL, 90 mg/mL to 140 mg/mL, 90 mg/mL to 135 mg/mL, 90 mg/mL to 130 mg/mL, 90 mg/mL to 125 mg/mL, 90 mg/mL to 120 mg/mL, 90 mg/mL to 118 mg/mL, 90 mg/mL to 115 mg/mL, 90 mg/mL to 112 mg/mL, 90 mg/mL to 110 mg/mL, 90 mg/mL to 108 mg/mL, 90 mg/mL to 105 mg/mL, 90 mg/mL to 102 mg/mL, 90 mg/mL to 100 mg/mL, 90 mg/mL to 98 mg/mL, 90 mg/mL to 95 mg/mL, 100 mg/mL to 195 mg/mL, 100 mg/mL to 190 mg/mL, 100 mg/mL to 185 mg/mL, 100 mg/mL to 175 mg/mL, 100 mg/mL to 170 mg/mL, 100 mg/mL to 165 mg/mL, 100 mg/mL to 160 mg/mL, 100 mg/mL to 155 mg/mL, 100 mg/mL to 150 mg/mL, 100 mg/mL to 145 mg/mL, 100 mg/mL to 140 mg/mL, 100 mg/mL to 135 mg/mL, 100 mg/mL to 130 mg/mL, 100 mg/mL to 125 mg/mL, 100 mg/mL to 120 mg/mL, 100 mg/mL to 118 mg/mL, or 100 mg/mL to 115 mg/mL.

In some cases, the concentration of flecainide or the salt of flecainide (e.g., flecainide acetate or flecainide hydrochloride) in the pharmaceutical compositions or formulations is at least about 115 mg/mL, at least about 112 mg/mL, at least about 110 mg/mL, at least about 109 mg/mL, at least about 108 mg/mL, at least about 107 mg/mL, at least about 106 mg/mL, at least about 105 mg/mL, at least about 104 mg/mL, at least about 103 mg/mL, at least about 102 mg/mL, at least about 101 mg/mL, at least about 100 mg/mL, at least about 99 mg/mL, at least about 98 mg/mL, at least about 97 mg/mL, at least about 96 mg/mL, at least about 95 mg/mL, at least about 94 mg/mL, at least about 93 mg/mL, at least about 92 mg/mL, at least about 91 mg/mL, at least about 90 mg/mL, at least about 89 mg/mL, at least about 88 mg/mL, at least about 87 mg/mL, at least about 86 mg/mL, at least about 85 mg/mL, at least about 84 mg/mL, at least about 83 mg/mL, at least about 82 mg/mL, at least about 81 mg/mL, at least about 80 mg/mL, at least about 79 mg/mL, at least about 78 mg/mL, at least about 77 mg/mL, at least about 76 mg/mL, at least about 75 mg/mL, at least about 74 mg/mL, at least about 73 mg/mL, at least about 72 mg/mL, at least about 71 mg/mL, at least about 70 mg/mL, at least about 69 mg/mL, at least about 68 mg/mL, at least about 67 mg/mL, at least about 66 mg/mL, at least about 65 mg/mL, at least about 64 mg/mL, at least about 63 mg/mL, at least about 62 mg/mL, at least about 61 mg/mL, or at least about 60 mg/mL.

In some cases, the concentration of flecainide or the salt of flecainide (e.g., flecainide acetate or flecainide hydrochloride) in the pharmaceutical compositions or formulations is about 195 mg/mL, about 190 mg/mL, about 185 mg/mL, about 175 mg/mL, about 170 mg/mL, about 165 mg/mL, about 160 mg/mL, about 155 mg/mL, about 150 mg/mL, about 145 mg/mL, about 140 mg/mL, about 135 mg/mL, about 130 mg/mL, about 125 mg/mL, about 120 mg/mL, about 118 mg/mL, about 115 mg/mL, about 112 mg/mL, about 110 mg/mL, about 109 mg/mL, about 108 mg/mL, about 107 mg/mL, about 106 mg/mL, about 105 mg/mL, about 104 mg/mL, about 103 mg/mL, about 102 mg/mL, about 101 mg/mL, about 100 mg/mL, about 99 mg/mL, about 98 mg/mL, about 97 mg/mL, about 96 mg/mL, about 95 mg/mL, about 94 mg/mL, about 93 mg/mL, about 92 mg/mL, about 91 mg/mL, about 90 mg/mL, about 89 mg/mL, about 88 mg/mL, about 87 mg/mL, about 86 mg/mL, about 85 mg/mL, about 84 mg/mL, about 83 mg/mL, about 82 mg/mL, about 81 mg/mL, about 80 mg/mL, about 79 mg/mL, about 78 mg/mL, about 77 mg/mL, about 76 mg/mL, about 75 mg/mL, about 74 mg/mL, about 73 mg/mL, about 72 mg/mL, about 71 mg/mL, about 70 mg/mL, about 69 mg/mL, about 68 mg/mL, about 67 mg/mL, about 66 mg/mL, about 65 mg/mL, about 64 mg/mL, about 63 mg/mL, about 62 mg/mL, or about 61 mg/mL.

In some cases, the nominal concentration of flecainide or the salt of flecainide (e.g., flecainide acetate or flecainide hydrochloride) in the pharmaceutical compositions or formulations is about 125 mM to about 430 mM, such as 125 mM to 420 mM, 125 mM to 400 mM, 125 mM to 390 mM, 125 mM to 380 mM, 125 mM to 370 mM, 125 mM to 360 mM, 125 mM to 350 mM, 125 mM to 340 mM, 125 mM to 330 mM, 125 mM to 320 mM, 125 mM to 310 mM, 125 mM to 300 mM, 125 mM to 290 mM, 125 mM to 280 mM, 125 mM to 270 mM, 125 mM to 260 mM, 125 mM to 250 mM, 125 mM to 240 mM, 125 mM to 230 mM, 125 mM to 220 mM, 125 mM to 210 mM, 125 mM to 200 mM, 125 mM to 190 mM, 125 mM to 180 mM, 125 mM to 170 mM, 125 mM to 160 mM, 125 mM to 155 mM, 125 mM to 150 mM, 125 mM to 145 mM, 125 mM to 140 mM, 125 mM to 135 mM, 125 mM to 130 mM, 140 mM to 420 mM, 140 mM to 400 mM, 140 mM to 390 mM, 140 mM to 380 mM, 140 mM to 370 mM, 140 mM to 360 mM, 140 mM to 350 mM, 140 mM to 340 mM, 140 mM to 330 mM, 140 mM to 320 mM, 140 mM to 310 mM, 140 mM to 300 mM, 140 mM to 290 mM, 140 mM to 280 mM, 140 mM to 270 mM, 140 mM to 260 mM, 140 mM to 250 mM, 140 mM to 240 mM, 140 mM to 230 mM, 140 mM to 220 mM, 140 mM to 210 mM, 140 mM to 200 mM, 140 mM to 190 mM, 140 mM to 180 mM, 140 mM to 170 mM, 140 mM to 160 mM, 140 mM to 155 mM, 140 mM to 150 mM, 140 mM to 145 mM, 160 mM to 420 mM, 160 mM to 400 mM, 160 mM to 390 mM, 160 mM to 380 mM, 160 mM to 370 mM, 160 mM to 360 mM, 160 mM to 350 mM, 160 mM to 340 mM, 160 mM to 330 mM, 160 mM to 320 mM, 160 mM to 310 mM, 160 mM to 300 mM, 160 mM to 290 mM, 160 mM to 280 mM, 160 mM to 270 mM, 160 mM to 260 mM, 160 mM to 250 mM, 160 mM to 240 mM, 160 mM to 230 mM, 160 mM to 220 mM, 160 mM to 210 mM, 160 mM to 200 mM, 16 mM to 9 mM, 6 mM to 180 mM, 160 mM to 170 mM, 180 mM to 420 mM, 180 mM to 400 mM, 180 mM to 390 mM, 180 mM to 380 mM, 180 mM to 370 mM, 180 mM to 360 mM, 180 mM to 350 mM, 180 mM to 340 mM, 180 mM to 330 mM, 180 mM to 320 mM, 180 mM to 310 mM, 180 mM to 300 mM, 180 mM to 290 mM, 180 mM to 280 mM, 180 mM to 270 mM, 180 mM to 260 mM, 180 mM to 250 mM, 180 mM to 240 mM, 180 mM to 230 mM, 180 mM to 220 mM, 180 mM to 210 mM, 180 mM to 200 mM, 180 mM to 190 mM, 200 mM to 420 mM, 200 mM to 400 mM, 200 mM to 390 mM, 200 mM to 380 mM, 200 mM to 370 mM, 200 mM to 360 mM, 200 mM to 350 mM, 200 mM to 340 mM, 200 mM to 330 mM, 200 mM to 320 mM, 200 mM to 310 mM, 200 mM to 300 mM, 200 mM to 290 mM, 200 mM to 280 mM, 200 mM to 270 mM, 200 mM to 260 mM, 200 mM to 250 mM, 200 mM to 240 mM, 200 mM to 230 mM, 200 mM to 220 mM, or 200 mM to 210 mM.

In some cases, the nominal concentration of flecainide or the salt of flecainide (e.g., flecainide acetate or flecainide hydrochloride) in the pharmaceutical compositions or formulations is at least about 400 mM, at least about 390 mM, at least about 380 mM, at least about 370 mM, at least about 360 mM, at least about 350 mM, at least about 340 mM, at least about 330 mM, at least about 320 mM, at least about 310 mM, at least about 300 mM, at least about 290 mM, at least about 280 mM, at least about 270 mM, at least about 260 mM, at least about 255 mM, at least about 250 mM, at least about 245 mM, at least about 240 mM, at least about 235 mM, at least about 230 mM, at least about 225 mM, at least about 220 mM, at least about 215 mM, at least about 210 mM, at least about 200 mM, at least about 190 mM, at least about 180 mM, at least about 170 mM, at least about 160 mM, at least about 155 mM, at least about 150 mM, at least about 145 mM, at least about 140 mM, at least about 135 mM, at least about 130 mM, or at least about 125 mM.

In some cases, the concentration of flecainide or the salt of flecainide (e.g., flecainide acetate or flecainide hydrochloride) in the pharmaceutical compositions or formulations is about 420 mM, about 400 mM, about 390 mM, about 380 mM, about 370 mM, about 360 mM, about 350 mM, about 340 mM, about 330 mM, about 320 mM, about 310 mM, about 300 mM, about 290 mM, about 280 mM, about 270 mM, about 260 mM, about 255 mM, about 250 mM, about 245 mM, about 240 mM, about 235 mM, about 230 mM, about 225 mM, about 220 mM, about 215 mM, about 210 mM, about 200 mM, about 190 mM, about 180 mM, about 170 mM, about 160 mM, about 155 mM, about 150 mM, about 145 mM, about 140 mM, about 135 mM, about 130 mM, or about 125 mM.

In some aspects, also provided herein are unit doses of pharmaceutical compositions described herein for treatment of heart condition, e.g., cardiac arrhythmia, e.g., atrial arrhythmia, via oral or nasal inhalation.

In one version, a unit dose of the pharmaceutical composition provided herein includes at least about 50 mg, such as at least about 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 450 mg, 500 mg or more of flecainide or a flecainide salt, e.g., flecainide acetate or flecainide hydrochloride. A unit dose of the pharmaceutical composition provided herein can include flecainide or the flecainide salt in the range of about 50 mg to about 500 mg, such as 50 mg to 60 mg, 50 mg to 70 mg, 50 mg to 80 mg, 50 mg to 90 mg, 50 mg to 100 mg, 50 mg to 110 mg, 50 mg to 120 mg, 50 mg to 130 mg, 50 mg to 140 mg, 50 mg to 150 mg, 50 mg to 160 mg, 50 mg to 170 mg, 50 mg to 180 mg, 50 mg to 190 mg, 50 mg to 200 mg, 50 mg to 210 mg, 50 mg to 220 mg, 50 mg to 230 mg, 50 mg to 240 mg, 50 mg to 250 mg, 50 mg to 260 mg, 50 mg to 270 mg, 50 mg to 280 mg, 50 mg to 290 mg, 50 mg to 300 mg, 50 mg to 310 mg, 50 mg to 320 mg, 50 mg to 330 mg, 50 mg to 340 mg, 50 mg to 350 mg, 50 mg to 360 mg, 50 mg to 370 mg, 50 mg to 380 mg, 50 mg to 390 mg, 50 mg to 400 mg, 50 mg to 450 mg, 50 mg to 500 mg, 80 mg to 90 mg, 80 mg to 100 mg, 80 mg to 110 mg, 80 mg to 120 mg, 80 mg to 130 mg, 80 mg to 140 mg, 80 mg to 150 mg, 80 mg to 160 mg, 80 mg to 170 mg, 80 mg to 180 mg, 80 mg to 190 mg, 80 mg to 200 mg, 80 mg to 210 mg, 80 mg to 220 mg, 80 mg to 230 mg, 80 mg to 240 mg, 80 mg to 250 mg, 80 mg to 260 mg, 80 mg to 270 mg, 80 mg to 280 mg, 80 mg to 290 mg, 80 mg to 300 mg, 80 mg to 310 mg, 80 mg to 320 mg, 80 mg to 330 mg, 80 mg to 340 mg, 80 mg to 350 mg, 80 mg to 360 mg, 80 mg to 370 mg, 80 mg to 380 mg, 80 mg to 390 mg, 80 mg to 400 mg, 80 mg to 450 mg, 80 mg to 500 mg, 120 mg to 140 mg, 120 mg to 150 mg, 120 mg to 160 mg, 120 mg to 170 mg, 120 mg to 180 mg, 120 mg to 190 mg, 120 mg to 200 mg, 120 mg to 210 mg, 120 mg to 220 mg, 120 mg to 230 mg, 120 mg to 240 mg, 120 mg to 250 mg, 120 mg to 260 mg, 120 mg to 270 mg, 120 mg to 280 mg, 120 mg to 290 mg, 120 mg to 300 mg, 120 mg to 310 mg, 120 mg to 320 mg, 120 mg to 330 mg, 120 mg to 340 mg, 120 mg to 350 mg, 120 mg to 360 mg, 120 mg to 370 mg, 120 mg to 380 mg, 120 mg to 390 mg, 120 mg to 400 mg, 120 mg to 450 mg, 120 mg to 500 mg, 150 mg to 160 mg, 150 mg to 170 mg, 150 mg to 180 mg, 150 mg to 190 mg, 150 mg to 200 mg, 150 mg to 210 mg, 150 mg to 220 mg, 150 mg to 230 mg, 150 mg to 240 mg, 150 mg to 250 mg, 150 mg to 260 mg, 150 mg to 270 mg, 150 mg to 280 mg, 150 mg to 290 mg, 150 mg to 300 mg, 150 mg to 310 mg, 150 mg to 320 mg, 150 mg to 330 mg, 150 mg to 340 mg, 150 mg to 350 mg, 150 mg to 360 mg, 150 mg to 370 mg, 150 mg to 380 mg, 150 mg to 390 mg, 150 mg to 400 mg, 150 mg to 450 mg, 150 mg to 500 mg, 180 mg to 200 mg, 180 mg to 210 mg, 180 mg to 220 mg, 180 mg to 230 mg, 180 mg to 240 mg, 180 mg to 250 mg, 180 mg to 260 mg, 180 mg to 270 mg, 180 mg to 280 mg, 180 mg to 290 mg, 180 mg to 300 mg, 180 mg to 310 mg, 180 mg to 320 mg, 180 mg to 330 mg, 180 mg to 340 mg, 180 mg to 350 mg, 180 mg to 360 mg, 180 mg to 370 mg, 180 mg to 380 mg, 180 mg to 390 mg, 180 mg to 400 mg, 180 mg to 450 mg, 180 mg to 500 mg, 200 mg to 220 mg, 200 mg to 230 mg, 200 mg to 240 mg, 200 mg to 250 mg, 200 mg to 260 mg, 200 mg to 270 mg, 200 mg to 280 mg, 200 mg to 290 mg, 200 mg to 300 mg, 200 mg to 310 mg, 200 mg to 320 mg, 200 mg to 330 mg, 200 mg to 340 mg, 200 mg to 350 mg, 200 mg to 360 mg, 200 mg to 370 mg, 200 mg to 380 mg, 200 mg to 390 mg, 200 mg to 400 mg, 200 mg to 450 mg, 200 mg to 500 mg, 220 mg to 240 mg, 220 mg to 250 mg, 220 mg to 260 mg, 220 mg to 270 mg, 220 mg to 280 mg, 220 mg to 290 mg, 220 mg to 300 mg, 220 mg to 310 mg, 220 mg to 320 mg, 220 mg to 330 mg, 220 mg to 340 mg, 220 mg to 350 mg, 220 mg to 360 mg, 220 mg to 370 mg, 220 mg to 380 mg, 220 mg to 390 mg, 220 mg to 400 mg, 220 mg to 450 mg, 220 mg to 500 mg, 250 mg to 260 mg, 250 mg to 270 mg, 250 mg to 280 mg, 250 mg to 290 mg, 250 mg to 300 mg, 250 mg to 310 mg, 250 mg to 320 mg, 250 mg to 330 mg, 250 mg to 340 mg, 250 mg to 350 mg, 250 mg to 360 mg, 250 mg to 370 mg, 250 mg to 380 mg, 250 mg to 390 mg, 250 mg to 400 mg, 250 mg to 450 mg, 250 mg to 500 mg, 280 mg to 260 mg, 280 mg to 270 mg, 280 mg to 280 mg, 280 mg to 290 mg, 280 mg to 300 mg, 280 mg to 310 mg, 280 mg to 320 mg, 280 mg to 330 mg, 280 mg to 340 mg, 280 mg to 350 mg, 280 mg to 360 mg, 280 mg to 370 mg, 280 mg to 380 mg, 280 mg to 390 mg, 280 mg to 400 mg, 280 mg to 450 mg, 280 mg to 500 mg, 300 mg to 320 mg, 300 mg to 330 mg, 300 mg to 340 mg, 300 mg to 350 mg, 300 mg to 360 mg, 300 mg to 370 mg, 300 mg to 380 mg, 300 mg to 390 mg, 300 mg to 400 mg, 300 mg to 450 mg, 300 mg to 500 mg, 320 mg to 330 mg, 320 mg to 340 mg, 320 mg to 350 mg, 320 mg to 360 mg, 320 mg to 370 mg, 320 mg to 380 mg, 320 mg to 390 mg, 320 mg to 400 mg, 320 mg to 450 mg, 320 mg to 500 mg, 340 mg to 360 mg, 340 mg to 370 mg, 340 mg to 380 mg, 340 mg to 390 mg, 340 mg to 400 mg, 340 mg to 450 mg, or 340 mg to 500 mg.

In one version, a unit dose as provided herein includes flecainide or a flecainide salt of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 450 mg, or about 500 mg.

In one aspect, provided herein are formulations for treatment of a heart condition, e.g., cardiac arrhythmia, e.g., atrial arrhythmia. The formulations can include the pharmaceutical compositions provided herein and a pharmaceutically acceptable carrier, excipient, diluent, or any other suitable component for the intended administration routes, such as oral or nasal inhalation. Examples of pharmaceutically acceptable excipients include, but are not limited to, lipids, metal ions, surfactants, amino acids, carbohydrates, buffers, salts, polymers, and the like, and combinations thereof.

The pharmaceutical formulation according to one or more embodiments of the disclosure may comprise a salt of flecainide and, optionally, one or more other active ingredients and, optionally, one or more pharmaceutically acceptable excipients. For example, the pharmaceutical formulation can comprise particles of the flecainide salt with no other ingredients added (neat particles), may comprise neat particles of antiarrhythmic pharmaceutical agent together with other particles, and/or may comprise particles comprising antiarrhythmic pharmaceutical agent and one or more active ingredients and/or one or more pharmaceutically acceptable excipients.

In one aspect, also provided herein are kits for treatment of heart conditions via inhalation. The kits can include one or more pharmaceutical agents, for instance, a salt of flecainide, or some additional active agent(s) as described herein. In some cases, the kits include container for the pharmaceutical agents or compositions. In some cases, unit doses of the pharmaceutical agents as discussed above are provided in the kits. In some cases, the kits also include containers/receptacles for containing the pharmaceutical agents.

In some cases, the kits include separate containers/receptacles for containing the pharmaceutical composition as described herein. In some cases, the kits include an aerosolization device for forming an aerosol of the pharmaceutical compositions. The aerosolization device can be any device as provided herein, and in some cases, used for inhalation of the pharmaceutical compositions. In some cases, the kits include nasal spray device as provided herein. In some cases, the pharmaceutical composition(s) is/are present in aerosol form in the kits. In some other cases, the kits include a single container for containing the pharmaceutical composition. The kits can further include instructions for methods of using the kit. The instructions can be presented in the form of a data sheet, a manual, in a piece of paper, printed on one or more containers or devices of the kit. Alternatively, the instructions can be provided in electronic form, for instance, available in a disc or online with a weblink available from the kit. The instructions for use of the kit can comprise instructions for use of the pharmaceutical composition and the aerosolization device (e.g., a nebulizer) to treat any applicable indication, e.g., a heart condition, e.g., cardiac arrhythmia, e.g., atrial arrhythmia. The instructions for use of the kit can comprise instructions for use of the pharmaceutical composition and the aerosolization device (e.g., a nebulizer) to treat atrial fibrillation. In some cases, the kits include a nose clip. A nose clip can be used to hinder passage of air through a nose of a subject during inhalation and increase the proportion of a total inhaled volume that is the aerosol issued by the nebulizer.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), and maltodextrins.

Non-limiting examples of lipids include phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In some cases, the phospholipid comprises a saturated phospholipid, such as one or more phosphatidylcholines. Exemplary acyl chain lengths are 16:0 and 18:0 (e.g., palmitoyl and stearoyl). The phospholipid content can be determined by the active agent activity, the mode of delivery, and other factors.

Phospholipids from both natural and synthetic sources can be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids can comprise those that have a gel to liquid crystal phase transition greater than about 40° C., such as greater than about 60° C., or greater than about 80° C. The incorporated phospholipids can be relatively long chain (e.g., $C_{16}$-$C_{22}$) saturated lipids. Exemplary phospholipids useful in the present disclosure include, but are not limited to, phosphoglycerides such as dipalmitoylphosphatidylcholine, distearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition can also comprise a polyvalent cation, as disclosed in WO 01/85136 and WO 01/85137, which are incorporated herein by reference in their entireties. The polyvalent cation can be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C. The molar ratio of polyvalent cation to phospholipid can be at least about 0.05:1, such as about 0.05:1 to about 2.0:1 or about 0.25:1 to about 1.0:1. An example of the molar ratio of polyvalent cation: phospholipid is about 0.50:1. When the polyvalent cation is calcium, it can be in the form of calcium chloride. Although metal ion, such as calcium, is often included with phospholipid, none is required.

The pharmaceutical composition can include one or more surfactants. For instance, one or more surfactants can be in the liquid phase with one or more being associated with solid particles or particles of the composition. By "associated with" it is meant that the pharmaceutical compositions can incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and can be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated herein by reference in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338. Examples of ionic surfactants include, but are not limited to, sodium sulfosuccinate, and fatty acid soaps. Examples of amino acids include, but are not limited to hydrophobic amino acids. Use of amino acids as pharmaceutically acceptable excipients is known in the art as disclosed in WO 95/31479, WO 96/32096, and WO 96/32149, which are incorporated herein by reference in their entireties.

Examples of buffers include, but are not limited to, acetate, tris, or citrate. Examples of acids include, but are not limited to, carboxylic acids. Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like. Examples of organic solids include, but are not limited to, camphor, and the like. The pharmaceutical composition of one or more embodiments of the present disclosure can also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions can be tailored to optimize the effectiveness of the antiarrhythmic pharmaceutical agent(s).

For solutions, the compositions can include one or more osmolality adjuster, such as sodium chloride. For instance, sodium chloride can be added to solutions to adjust the osmolality of the solution. In one or more embodiments, an aqueous composition consists essentially of the antiarrhythmic pharmaceutical agent, the osmolality adjuster, and water.

Solutions can also comprise a buffer or a pH adjusting agent, typically a salt prepared from an organic acid or base. Representative buffers comprise organic acid salts of citric acid, lactic acid, ascorbic acid, gluconic acid, carbonic acid, tartaric acid, succinic acid, acetic acid, or phthalic acid, Tris, tromethamine hydrochloride, or phosphate buffers. Thus, the buffers include citrates, phosphates, phthalates, and lactates.

Besides the above mentioned pharmaceutically acceptable excipients, it can be desirable to add other pharmaceutically acceptable excipients to the pharmaceutical composition to improve particle rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients can be used to provide structure and form to the particle compositions (e.g., latex particles). In this regard, it will be appreciated that the rigidifying components can be removed using a post-production technique such as selective solvent extraction.

The pharmaceutical compositions of one or more embodiments of the present disclosure can lack taste. In this regard, although taste masking agents are optionally included within the composition, the compositions in some embodiments do not include a taste masking agent other than a cyclodextrin and lack taste even without a taste masking agent.

The pharmaceutical compositions can also include mixtures of pharmaceutically acceptable excipients. For instance, mixtures of carbohydrates and amino acids are within the scope of the present disclosure.

The compositions of one or more embodiments of the present disclosure can take various forms, such as solutions, dry powders, reconstituted powders, suspensions, or dispersions comprising a non-aqueous phase, such as propellants (e.g., chlorofluorocarbon, hydrofluoroalkane).

The solutions of the present disclosure are typically clear. In this regard, many of the antiarrhythmic pharmaceutical agents of the present disclosure are water soluble.

In some embodiments, the isotonicity of the solution ranges from isotonic to physiologic isotonicity. Physiologic isotonicity is the isotonicity of physiological fluids.

In some versions, the pharmaceutical composition is a nebulized aerosol and comprises liquid droplets having a mass median diameter less than about 20 μm, such as less than about 10 μm, less than about 7 μm, or less than about 5 μm. The droplets can have a mass median aerodynamic diameter ranging from about 1 μm to about 6 μm, such as about 1.5 μm to about 5 μm, or about 2 μm to about 4 μm. If the droplets are too large, a larger percentage of the particles cannot reach the lungs. If the droplets are too small, a larger percentage of the droplets can be exhaled.

Unit doses of the pharmaceutical compositions can be placed in a container. Examples of containers include, but are not limited to, syringes, capsules, blow fill seal, blisters, vials, ampoules, cartridges, or container closure systems made of metal, polymer (e.g., plastic, elastomer), glass, or the like. For instance, the vial can be a colorless Type I borosilicate glass ISO 4R 6 mL vial with a chlorobutyl rubber siliconized stopper, and flip-off type aluminum cap with colored plastic cover. In some embodiments, the vial can be a colorless Type I borosilicate glass ISO 6R 10 mL vial with a chlorobutyl rubber siliconized stopper, and flip-off type aluminum cap with colored plastic cover.

The container can be inserted into an aerosolization device. The container can be of a suitable shape, size, and material to contain the pharmaceutical composition and to provide the pharmaceutical composition in a usable condition. For example, the capsule or blister can comprise a wall which comprises a material that does not adversely react with the pharmaceutical composition. In addition, the wall can comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule can comprise telescopically adjoining sections, as described for example in U.S. Pat. No. 4,247,066 which is incorporated herein by reference in its entirety. The size of the capsule can be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.10 ml to about 1.37 mL, respectively. Suitable capsules are available commercially from, for example, Shionogi Qualicaps Co. in Nara, Japan and Capsugel in Greenwood, S.C. After filling, a top portion can be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

For solutions, the amount of the composition in the unit dose can range from about 0.5 mL to about 15 mL, such as 1 mL to 15 mL, 2 mL to 15 mL, 3 mL to 15 mL, 4 mL to 15 mL, 5 mL to 15 mL, 6 mL to 15 mL, 7 mL to 15 mL, 8 mL to 15 mL, 9 mL to 15 mL, 10 mL to 15 mL, 11 mL to 15 mL, 12 mL to 15 mL, 10 mL to 15 mL, 14 mL to 15 mL, 1 mL to 13 mL, 2 mL to 13 mL, 3 mL to 13 mL, 4 mL to 13 mL, 5 mL to 13 mL, 6 mL to 13 mL, 7 mL to 13 mL, 8 mL to 13 mL, 9 mL to 13 mL, 10 mL to 13 mL, 11 mL to 13 mL, 12 mL to 13 mL, 1 mL to 10 mL, 2 mL to 10 mL, 3 mL to 10 mL, 4 mL to 10 mL, 5 mL to 10 mL, 6 mL to 10 mL, 7 mL to 10 mL, 8 mL to 10 mL, 9 mL to 10 mL, 1 mL to 8 mL, 2 mL to 8 mL, 3 mL to 8 mL, 4 mL to 8 mL, 5 mL to 8 mL, 6 mL to 8 mL, 7 mL to 8 mL, 1 mL to 5 mL, 2 mL to 5 mL, 3 mL to 5 mL, 4 mL to 5 mL, or 1 mL to 3 mL. In some embodiments, the amount of the composition in a unit dose is about 1 mL, about 2 mL, about 3 mL, about 4 mL, about 5 mL, about 6 mL, about 7 mL, about 8 mL, about 9 mL, about 10 mL, about 11 mL, about 12 mL, about 10 mL, about 14 mL, or about 15 mL. In some embodiments, the amount of the composition in a unit dose is at most about 2 mL, at most about 3 mL, at most about 4 mL, at most about 5 mL, at most about 6 mL, at most about 7 mL, at most about 8 mL, at most about 9 mL, at most about 10 mL, at most about 11 mL, at most about 12 mL, at most about 10 mL, at most about 14 mL, or at most about 15 mL.

The compositions of the present disclosure can be made by any of the various methods and techniques known and available to those skilled in the art.

For instance, a solution of antiarrhythmic pharmaceutical agent can be made using the following procedure. Typically, manufacturing equipment is sterilized before use. A portion of the final volume, e.g., 70%, of solvent, e.g., water for injection, can be added into a suitable container. Some or all of other additional pharmaceutically acceptable carrier or excipient, solubilizer, or other additional ingredients of the pharmaceutical composition (e.g., cyclodextrin, e.g., HPβCD; e.g., acids, e.g., acetic acid, hydrochloric acid, nitric acid, or citric acid; e.g., saccharin, e.g., saccharin sodium) can be added either before or after addition of the antiarrhythmic agent, e.g., the flecainide salt, e.g., flecainide acetate. Antiarrhythmic pharmaceutical agent, e.g., a salt of flecainide can then be added. The antiarrhythmic pharmaceutical agent can be mixed until dissolved. Additional solvent can be added to make up the final batch volume. The batch can be filtered, e.g., through a 0.2 μm filter into a sterilized receiving vessel. Filling components can be sterilized before use in filling the batch into vials, e.g., 10 mL vials.

As an example, the above-noted sterilizing can include the following. A 5 liter type 1 glass bottle and lid can be placed in an autoclave bag and sterilized at elevated temperature, e.g., 121° C. for 15 minutes, using an autoclave. Similarly, vials can be placed into suitable racks, inserted into an autoclave bag, and sterilized at elevated temperature, e.g., 121° C. for 15 minutes, using an autoclave. Also, similarly, stoppers can be placed in an autoclave bag and sterilized at elevated temperature, e.g., 121° C. for 15 minutes, using an autoclave. Before sterilization, sterilizing filters can be attached to tubing, e.g., a 2 mm length of 7 mm×13 mm silicone tubing. A filling line can be prepared by placed in an autoclave bag and sterilized at elevated temperature, e.g., 121° C. for 15 minutes, using an autoclave.

The above-noted filtration can involve filtration into a laminar flow work area. The receiving bottle and filters can be set up in the laminar flow work area.

The above-noted filling can also be conducted under laminar flow protection. The filling line can be unwrapped and placed into the receiving bottle. The sterilized vials and stoppers can be unwrapped under laminar flow protection. Each vial can be filled, e.g., to a target fill of 5 g, and stoppered. A flip off collar can be applied to each vial. The sealed vials can be inspected for vial leakage, correct overseals, and cracks.

The pharmaceutical composition according to one or more embodiments of the disclosure may, if desired, contain a combination of antiarrhythmic pharmaceutical agent (e.g., flecainide salt) and one or more additional active agents. Examples of additional active agents include, but are not limited to, agents that may be delivered through the lungs.

Additional active agents may comprise, for example, hypnotics and sedatives, psychic energizers, tranquilizers, respiratory drugs, anticonvulsants, muscle relaxants, anti-parkinson agents (dopamine antagonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, antiepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitic, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation, may act locally or systemically.

The additional active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of additional active agents suitable for use in this disclosure include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFFR) gene, deoxyribonuclease (DNase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the disclosure is intended to encompass synthetic, native, glycosylated, unglycosylated, pegylated forms, and biologically active fragments, derivatives, and analogs thereof.

Additional active agents for use in the disclosure can further include nucleic acids, as bare nucleic acid molecules, vectors, associated viral particles, plasmid DNA or RNA or other nucleic acid constructions of a type suitable for transfection or transformation of cells, e.g., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

When a combination of active agents is used, the agents may be provided in combination in a single species of pharmaceutical composition or individually in separate species of pharmaceutical compositions.

Methods of Treatment

The methods, compositions, and kits provided herein can include administration of the pharmaceutical composition via inhalation, e.g., oral or nasal inhalation.

The therapy provided herein can comprise or be suitable for inhalation, e.g., oral or nasal inhalation. In some cases, during administration via oral inhalation, the pharmaceutical agent is inhaled by the patient through the mouth and absorbed by the lungs. In some cases, during administration via nasal inhalation, the pharmaceutical agent is inhaled by the patient through the nose and absorbed by the nasal mucous and/or the lungs.

The inhalation route can avoid first-pass hepatic metabolism, hence dosing variability can be eliminated. Unlike the case for oral tablets or pills, the patient's metabolic rates may not matter as the administration is independent of the metabolic paths experienced when a drug is administered via oral route through gastrointestinal tract, e.g., as tablets, pills, solution, or suspension. A fast onset of action, a potential improvement in efficacy, and/or a reduction in dose can be achieved with the fast absorption of drugs from the nasal mucosa and/or lungs.

The fast absorption rate of drugs through the lungs can be achieved because of the large surface area available in the lungs for aerosols small enough to penetrate central and peripheral lung regions. Consequently, the rate and extent of absorption of drugs delivered via inhalation can yield plasma concentrations vs. time profiles that are comparable with the IV route of administration.

The time for onset of action can be short. For instance, the patient may have normal sinus rhythm within 20 minutes of initiating the administering, such as within 15 minutes, within 10 minutes, or within 5 minutes of initiating the administering. In some cases, the rapid onset of action is advantageous because the longer a patient remains in arrhythmia (i.e. atrial fibrillation), the more difficult it will be to restore normal sinus rhythm.

In some embodiments, the method of the present disclosure allows the patient to avoid other therapies, such as ablation and/or electrical cardioversion. In other embodiments, the method of the present disclosure is used in combination with other therapies, such as before or after electrical cardioversion and/or ablation therapy.

In some aspects of the present disclosure, the compositions or formulations of the pharmaceutical composition via inhalation. The pharmaceutical compositions can be aerosolized prior to administration or can be presented to a user in the form of an aerosol.

The pharmaceutical compositions can be administered using an aerosolization device. The aerosolization device can be a nebulizer, a metered dose inhaler, or a liquid dose instillation device. The aerosolization device can comprise the extrusion of the pharmaceutical preparation through micron or submicron-sized holes with subsequent Rayleigh break-up into fine droplets. The pharmaceutical composition can be delivered by a nebulizer as described in WO 99/16420, by a metered dose inhaler as described in WO 99/16422, by a liquid dose instillation apparatus as described in WO 99/16421, and by a dry powder inhaler as described in U.S. Published Application Nos. 20020017295 and 20040105820, WO 99/16419, WO 02/83220, and U.S. Pat. No. 6,546,929, which are incorporated herein by reference in their entireties. As such, an inhaler can comprise a canister containing the particles or particles and propellant, and wherein the inhaler comprises a metering valve in communication with an interior of the canister. The propellant can be a hydrofluoroalkane.

For instance, the pharmaceutical formulation can be in liquid solution, and can be administered with nebulizers, such as that disclosed in PCT WO 99/16420, the disclosure of which is hereby incorporated in its entirety by reference, in order to provide an aerosolized medicament that can be administered to the pulmonary air passages of a patient in need thereof. Nebulizers known in the art can easily be employed for administration of the claimed formulations. Breath-activated or breath-actuated nebulizers, as well as those comprising other types of improvements which have been, or will be, developed are also compatible with the formulations of the present disclosure and are contemplated as being within the scope thereof.

In some cases, the nebulizer is a breath activated or breath-actuated nebulizer. In some cases, the nebulizer is a hand-held inhaler device (e.g., AeroEclipse® II Breath Actuated Nebulizer (BAN)). In some cases, the nebulizer has a compressed air source. In some cases, the nebulizer converts liquid medication into an aerosol. In some cases, the nebulizer converts liquid medication into an aerosol by extruding the pharmaceutical preparation through micron or submicron-sized holes. In some cases, the nebulizer converts liquid medication into an aerosol so it can be inhaled into the lungs. In some cases, the nebulizer is a small volume nebulizer. In some cases, the nebulizer is a small volume jet nebulizer. In some cases, aerosolized medication is only produced when inhaled through the device. In some cases, the medication is contained in the cup between breaths or during breaks in treatment. In some cases, the medication is contained in the cup until ready to be inhaled.

Nebulizers can impart energy into a liquid pharmaceutical formulation to aerosolize the liquid, and to allow delivery to the pulmonary system, e.g., the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium.

In one type of nebulizer that can be used in the subject methods and kits, generally referred to as a jet nebulizer, compressed gas is forced through an orifice in the container. The compressed gas forces liquid to be withdrawn through a nozzle, and the withdrawn liquid can mix with the flowing gas to form aerosol droplets. A cloud of droplets can then be administered to the patients respiratory tract.

In another type of nebulizer that can be used in the subject methods and kits, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs. In another type of nebulizer that can be used in the subject methods and kits, the nebulizing comprises extrusion through micron or submicron-sized holes followed by Rayleigh break-up into fine droplets.

Alternatively or additionally, the pharmaceutical formulation may be in a liquid form and may be aerosolized using a nebulizer as described in WO 2004/071368, which is herein incorporated by reference in its entirety, as well as U.S. Published application Nos. 2004/0011358 and 2004/0035413, which are both herein incorporated by reference in their entireties. Other examples of nebulizers include, but are not limited to, the Aeroneb®Go or Aeroneb®Pro nebulizers, available from Aerogen Ltd. of Galway, Ireland; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan. Other examples of nebulizers include devices produced by Medspray (Enschede, The Netherlands).

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using a nebulizer of this type are introduced at a low velocity, thereby decreasing the likelihood of the droplets being driven to an undesired region. It has been found that when using a nebulizer of the extrusion/Rayleigh jet breakup type, the generated droplets are also introduced at a low velocity, thereby decreasing the likelihood of the droplets being driven to an undesired region.

In some cases, the nebulizer that can be used in the subject methods and kits is of the vibrating mesh type. In some cases, the nebulizer that can be used in the subject methods and kits is of the pressurizedjet type. In some cases, the nebulizer that can be used in the subject methods and kits is of the extrusion/Rayleigh breakup type. In some cases, the nebulizer is lightweight (at most 60 g, at most 100 g, at most 200 g, at most 250 g) and nearly silent. In some cases, the nebulizer has a sound level less than 35 A-weighted decibels (dBA) at 1 meter. In some cases, the nebulizer has a medication cup capacity of 6 mL. In some cases, the nebulizer has a residual volume of less than 0.3 mL. In some cases, the nebulizer generates an average flow rate of 0.4 mL/min. In some cases, the nebulizer generates an average flow rate of 0.5 mL/min. In some cases, the nebulizer generates an average flow rate of 0.6 mL/min. In some cases, the nebulizer generates an average flow rate of 0.7 mL/min. In some cases, the nebulizer generates an average flow rate of 0.8 mL/min. In some cases, the nebulizer generates an average flow rate of 0.9 mL/min. In some cases, the nebulizer generates an average flow rate of 1.0 mL/min. In some cases, the nebulizer generates an average flow rate of 1.1 mL/min. In some cases, the nebulizer generates an average flow rate of 1.2 mL/min. In some cases, the nebulizer generates an average particle size of 3.0 m MMAD. In some cases, the nebulizer generates an average particle size between 3.0 m MMAD and 4.0 m MMAD. In some cases, the nebulizer generates an average particle size of 3.0 m MMAD. In some cases, the nebulizer generates an average particle size between 3.0 m MMAD and 5.0 m MMAD. In some cases, the nebulizer generates an average particle size of 3.0 m MMAD. In some cases, the nebulizer generates an average particle size between 3.0 m MMAD and 6.0 m MMAD.

In still another type of nebulizer that can be used in the subject methods and kits, ultrasonic waves are generated to directly vibrate and aerosolize the pharmaceutical formulation.

The pharmaceutical formulations disclosed herein can also be administered to the lungs of a patient via aerosolization, such as with a metered dose inhaler. The use of such formulations provides for superior dose reproducibility and improved lung deposition as disclosed in WO 99/16422, hereby incorporated in its entirety by reference. Metered dose inhalers (MDIs) known in the art can be employed for administration of the claimed pharmaceutical compositions. Breath-activated or breath-actuated MDIs and pressurized MDIs (pMDIs), as well as those comprising other types of improvements which have been, or will be, developed are also compatible with the formulations of the present disclosure and, as such, are contemplated as being within the scope thereof.

Along with MDIs and nebulizers, it will be appreciated that the formulations of one or more embodiments of the present disclosure can be used in conjunction with liquid dose instillation or LDI techniques as disclosed in, for example, WO 99/16421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present disclosure may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present disclosure can have improved emitted dose efficiency. Accordingly, high doses of the pharmaceutical composition can be delivered using a variety of aerosolization devices and techniques.

The emitted dose (ED) of the particles of the present disclosure may be greater than about 30%, such as greater than about 40%, greater than about 50%, greater than about 60%, or greater than about 70%.

The pharmaceutical composition can be administered to the patient on an as-needed basis. For instance, the methods, kits, and compositions can find particular use in treating a subject experiencing a heart condition, e.g., cardiac arrhythmia, e.g., atrial arrhythmia. In some cases, a subject is administered with the therapy described herein when he/she is experiencing atrial arrhythmia. In some cases, the pharmaceutical composition is administered to a subject after the onset of an episode of cardiac arrhythmia. In other cases, the subject is treated between episodes of cardiac arrhythmias.

The dose of the antiarrhythmic agent, e.g., flecainide salt, e.g., flecainide acetate, can be administered during a single inhalation or can be administered during several inhalations. The fluctuations of antiarrhythmic pharmaceutical agent concentration can be reduced by administering the pharmaceutical composition more often or can be increased by administering the pharmaceutical composition less often. Therefore, the pharmaceutical composition provided herein can be administered from about four times daily to about once a month, such as about once daily to about once every two weeks, about once every two days to about once a week, and about once per week.

In one version, the antiarrhythmic can be administered daily. In this case, the daily dosage of the flecainide acetate ranges from about 0.1 mg to about 600 mg, such as about 0.5 mg to about 500 mg, about 1 mg to about 400 mg, about 2 mg to about 300 mg, and about 3 mg to about 200 mg.

In some cases, the therapy provided herein is provided to a subject for more than once on an as-needed basis. For instance, the present disclosure may involve a follow-up inhalation if no cardioversion occurs after an initial inhalation. In some instances, if no cardioversion occurs within 30 minutes of the initial inhalation, the follow-up dosage is higher or the same as the initial dosage.

The dosing can be guided by how the patient feels. Additionally or alternatively, dosing can be guided by using a portable/mobile ECG device. For instance, the dosing may be guided by using a Holter monitor.

In another version, the pharmaceutical composition is administered prophylactically to a subject who is likely to develop an arrhythmia. For example, a patient who has a history of arrhythmias can be prophylactically treated with a pharmaceutical composition comprising antiarrhythmic pharmaceutical agent to reduce the likelihood of developing an arrhythmia.

The pharmaceutical composition can be administered to a patient in any regimen which is effective to prevent an arrhythmia. Illustrative prophylactic regimes include administering an antiarrhythmic pharmaceutical agent as described herein 1 to 21 times per week.

In some cases, patient receiving administration of pharmaceutical composition according to the method described herein needs to meet one or more of the following ECG criteria: P waves not seen on the ECG; fibrillatory waves are coarse; there are varying RR intervals; there are irregular-irregular QRS complexes; or there is an elevated ventricular rate. In some cases, method of treatment disclosed herein comprises confirming a patient in atrial fibrillation episode via ECG. In some cases, the method comprises confirming a patient having the following ECG features before administering the pharmaceutical composition as described herein: P waves not seen on the ECG; fibrillatory waves are coarse; there are varying RR intervals; there are irregular-irregular QRS complexes; and there is an elevated ventricular rate. In some cases, a patient receiving administration of pharmaceutical composition according to the method described herein has a medical history that is current within predetermined time period and qualifies the patient to receive flecainide safely. In some cases, the patient's current AF episode has had a duration of less than 48 hours. In some cases, total flecainide exposure the patient receives within past 24 hour period does not exceed 320 mg.

The amount of the flecainide salt that is delivered to the subject (e.g., approximately the amount of the flecainide salt exiting a mouthpiece when being inhaled by the subject) for the treatment of arrhythmia, e.g., atrial arrhythmia, e.g., atrial fibrillation, can be between about 50 mg to about 300 mg, such as 50 mg to 60 mg, 50 mg to 70 mg, 50 mg to 80 mg, 50 mg to 90 mg, 50 mg to 100 mg, 50 mg to 110 mg, 50 mg to 120 mg, 50 mg to 130 mg, 50 mg to 140 mg, 50 mg to 150 mg, 50 mg to 160 mg, 50 mg to 170 mg, 50 mg to 180 mg, 50 mg to 190 mg, 50 mg to 200 mg, 50 mg to 210 mg, 50 mg to 220 mg, 50 mg to 230 mg, 50 mg to 240 mg, 50 mg to 250 mg, 50 mg to 260 mg, 50 mg to 270 mg, 50 mg to 280 mg, 50 mg to 290 mg, 70 mg to 80 mg, 70 mg to 90 mg, 70 mg to 100 mg, 70 mg to 110 mg, 70 mg to 120 mg, 70 mg to 130 mg, 70 mg to 140 mg, 70 mg to 170 mg, 70 mg to 160 mg, 70 mg to 170 mg, 70 mg to 180 mg, 70 mg to 190 mg, 70 mg to 200 mg, 70 mg to 210 mg, 70 mg to 220 mg, 70 mg to 230 mg, 70 mg to 240 mg, 70 mg to 270 mg, 70 mg to 260 mg, 70 mg to 270 mg, 70 mg to 280 mg, 70 mg to 290 mg, 70 mg to 300 mg, 80 mg to 90 mg, 80 mg to 100 mg, 80 mg to 110 mg, 80 mg to 120 mg, 80 mg to 130 mg, 80 mg to 140 mg, 80 mg to 150 mg, 80 mg to 160 mg, 80 mg to 170 mg, 80 mg to 180 mg, 80 mg to 190 mg, 80 mg to 200 mg, 80 mg to 210 mg, 80 mg to 220 mg, 80 mg to 230 mg, 80 mg to 240 mg, 80 mg to 250 mg, 80 mg to 260 mg, 80 mg to 270 mg, 80 mg to 280 mg, 80 mg to 290 mg, 80 mg to 300 mg, 100 mg to 110 mg, 100 mg to 120 mg, 100 mg to 130 mg, 100 mg to 140 mg, 100 mg to 150 mg, 100 mg to 160 mg, 100 mg to 170 mg, 100 mg to 180 mg, 100 mg to 190 mg, 100 mg to 200 mg, 100 mg to 210 mg, 100 mg to 220 mg, 100 mg to 230 mg, 100 mg to 240 mg, 100 mg to 250 mg, 100 mg to 260 mg, 100 mg to 270 mg, 100 mg to 280 mg, 100 mg to 290 mg, 100 mg to 300 mg, 120 mg to 140 mg, 120 mg to 150 mg, 120 mg to 160 mg, 120 mg to 170 mg, 120 mg to 180 mg, 120 mg to 190 mg, 120 mg to 200 mg, 120 mg to 210 mg, 120 mg to 220 mg, 120 mg to 230 mg, 120 mg to 240 mg, 120 mg to 250 mg, 120 mg to 260 mg, 120 mg to 270 mg, 120 mg to 280 mg, 120 mg to 290 mg, 120 mg to 300 mg, 150 mg to 160 mg, 150 mg to 170 mg, 150 mg to 180 mg, 150 mg to 190 mg, 150 mg to 200 mg, 150 mg to 210 mg, 150 mg to 220 mg, 150 mg to 230 mg, 150 mg to 240 mg, 150 mg to 250 mg, 150 mg to 260 mg, 150 mg to 270 mg, 150 mg to 280 mg, 150 mg to 290 mg, 150 mg to 300 mg, 180 mg to 200 mg, 180 mg to 210 mg, 180 mg to 220 mg, 180 mg to 230 mg, 180 mg to 240 mg, 180 mg to 250 mg, 180 mg to 260 mg, 180 mg to 270 mg, 180 mg to 280 mg, 180 mg to 290 mg, 180 mg to 300 mg, 200 mg to 220 mg, 200 mg to 230 mg, 200 mg to 240 mg, 200 mg to 250 mg, 200 mg to 260 mg, 200 mg to 270 mg, 200 mg to 280 mg, 200 mg to 290 mg, 200 mg to 300 mg, 220 mg to 240 mg, 220 mg to 250 mg, 220 mg to 260 mg, 220 mg to 270 mg, 220 mg to 280 mg, 220 mg to 290 mg, 220 mg to 300 mg, 250 mg to 260 mg, 250 mg to 270 mg, 250 mg to 280 mg, 250 mg to 290 mg, 250 mg to 300 mg, 280 mg to 260 mg, 280 mg to 270 mg, 280 mg to 280 mg, 280 mg to 290 mg, or 280 mg to 300 mg.

In one version, the amount of the flecainide salt that is delivered to the subject (e.g., approximately the amount of the flecainide salt exiting the aerosolization device when being inhaled by the subject) for the treatment of arrhythmia, e.g., atrial arrhythmia, e.g., atrial fibrillation, is at least about 50 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, at least about 200 mg, at least about 210 mg, at least about 220 mg, at least about 230 mg, at least about 240 mg, at least about 250 mg, at least about 260 mg, at least about 270 mg, at least about 280 mg, or at least about 290 mg.

In one version, the amount of the flecainide salt that is delivered to the subject (e.g., approximately the amount of the flecainide salt exiting a mouthpiece when being inhaled by the subject) for the treatment of arrhythmia, e.g., atrial arrhythmia, e.g., atrial fibrillation, is at most about 100 mg, at most about 110 mg, at most about 120 mg, at most about 130 mg, at most about 140 mg, at most about 150 mg, at most about 160 mg, at most about 170 mg, at most about 180 mg, at most about 190 mg, at most about 200 mg, at most about 210 mg, at most about 220 mg, at most about 230 mg, at most about 240 mg, at most about 250 mg, at most about 260 mg, at most about 270 mg, at most about 280 mg, or at most about 290 mg.

In some cases, the amount of the flecainide salt that is delivered to the subject (e.g., approximately the amount of the flecainide salt exiting a mouthpiece when being inhaled by the subject) for the treatment of arrhythmia, e.g., atrial arrhythmia, e.g., atrial fibrillation, is about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, or about 290 mg.

There can be loss of a pharmaceutical composition along the respiratory pathway when the pharmaceutical composition is inhaled by a subject, so that not all the pharmaceutical composition reaches the lung for absorption into the systemic circulation. In some embodiments, the estimated total lung dose (eTLD, e.g., a theoretical value that measures the dose of the pharmaceutical active ingredient that reaches the lung, e.g., about 70% of the dose exiting the aerosolization device) of the flecainide acetate that is delivered according to the methods provided herein is between about 40 mg to about 180 mg, such as 40 mg to 60 mg, 40 mg to 70 mg, 40 mg to 80 mg, 40 mg to 90 mg, 40 mg to 100 mg, 40 mg to 110 mg, 40 mg to 120 mg, 40 mg to 130 mg, 40 mg to 140 mg, 40 mg to 150 mg, 40 mg to 160 mg, 40 mg to 170 mg, 40 mg to 180 mg, 50 mg to 60 mg, 50 mg to 70 mg, 50 mg to 80 mg, 50 mg to 90 mg, 50 mg to 100 mg, 50 mg to 110 mg, 50 mg to 120 mg, 50 mg to 130 mg, 50 mg to 140 mg, 50 mg to 150 mg, 50 mg to 160 mg, 50 mg to 170 mg, 50 mg to 180 mg, 70 mg to 80 mg, 70 mg to 90 mg, 70 mg to 100 mg, 70 mg to 110 mg, 70 mg to 120 mg, 70 mg to 130 mg, 70 mg to 140 mg, 70 mg to 170 mg, 70 mg to 160 mg, 70 mg to 170 mg, 70 mg to 180 mg, 80 mg to 90 mg, 80 mg to 100 mg, 80 mg to 110 mg, 80 mg to 120 mg, 80 mg to 130 mg, 80 mg to 140 mg, 80 mg to 150 mg, 80 mg to 160 mg, 80 mg to 170 mg, 80 mg to 180 mg, 90 mg to 100 mg, 90 mg to 110 mg, 90 mg to 120 mg, 90 mg to 130 mg, 90 mg to 140 mg, 90 mg to 150 mg, 90 mg to 160 mg, 90 mg to 170 mg, 90 mg to 180 mg, 100 mg to 110 mg, 100 mg to 120 mg, 100 mg to 130 mg, 100 mg to 140 mg, 100 mg to 150 mg, 100 mg to 160 mg, 100 mg to 170 mg, 100 mg to 180 mg, 120 mg to 140 mg, 120 mg to 150 mg, 120 mg to 160 mg, 120 mg to 170 mg, 120 mg to 180 mg, 150 mg to 160 mg, 150 mg to 170 mg, or 150 mg to 180 mg.

In some cases, the eTLD of the flecainide acetate that is delivered according to the methods provided herein is at least about 40 mg, at least about 60 mg, at least about 70 mg, at least about 80 mg, at least about 90 mg, at least about 100 mg, at least about 110 mg, at least about 120 mg, at least about 130 mg, at least about 140 mg, at least about 150 mg, at least about 160 mg, or at least about 170 mg. In some cases, the eTLD of the flecainide acetate that is delivered according to the methods provided herein is at most about 60 mg, at most about 70 mg, at most about 80 mg, at most about 90 mg, at most about 100 mg, at most about 110 mg, at most about 120 mg, at most about 130 mg, at most about 140 mg, at most about 150 mg, at most about 160 mg, at most about 170 mg, or at most about 180 mg. In some cases, the eTLD of the flecainide acetate that is delivered according to the methods provided herein is about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 160 mg, about 170 mg, or about 180 mg.

This method of treatment results in a pulsatile pharmacokinetic profile and transient pharmacodynamic effect mimicking the effect of an IV. This method delivers high drug concentrations that are safe and effective to the heart, while the distribution to the rest of the body results in the drug being diluted to sub-therapeutic levels. This method is the shortest route of delivery to the heart next to intra-cardial injection. This provides the convenience of self-administration like the “pill-in-the-pocket” approach, but the effectiveness and fast onset of action of an IV. Although the delivery of medications through the lung for systemic effect is not new, it was thought it wouldn’t be effective to the heart, because of the fast passage of drug through it. The animal and human PK/PD data in this study show that the drug exposure is sufficient for therapeutic effect at a much lower dose compared to other routes of administration. This method ensures dug concentrations in overall plasma are much lower than what is achieved by oral/IV hence minimizing drug-drug interactions and side effects.

In some cases, the $T_{max}$ of the antiarrhythmic pharmaceutical agent administered via inhalation can be from about 0.1 minute to about 30 minutes, such as 0.1-0.5, 0.1-1, 0.1-1.5, 0.1-2, 0.1-2.5, 0.1-3, 0.1-3.5, 0.1-4, 0.1-4.5, 0.1-5, 0.1-6, 0.1-8, 0.1-10, 0.1-15, 0.1-20, 0.1-25, 0.1-30, 0.2-0.5, 0.2-1, 0.2-1.5, 0.2-2, 0.2-2.5, 0.2-3, 0.2-3.5, 0.2-4, 0.2-4.5, 0.2-5, 0.2-6, 0.2-8, 0.2-10, 0.2-15, 0.2-20, 0.2-25, 0.2-30, 0.3-0.5, 0.3-1, 0.3-1.5, 0.3-2, 0.3-2.5, 0.3-3, 0.3-3.5, 0.3-4, 0.3-4.5, 0.3-5, 0.3-6, 0.3-8, 0.3-10, 0.3-15, 0.3-20, 0.3-25, 0.3-30, 0.5-1, 0.5-1.5, 0.5-2, 0.5-2.5, 0.5-3, 0.5-3.5, 0.5-4, 0.5-4.5, 0.5-5, 0.5-6, 0.5-8, 0.5-10, 0.5-15, 0.5-20, 0.5-25, 0.5-30, 1-1.5, 1-2, 1-2.5, 1-3, 1-3.5, 1-4, 1-4.5, 1-5, 1-6, 1-8, 1-10, 1-15, 1-20, 1-25, 1-30, 1.5-2, 1.5-2.5, 1.5-3, 1.5-3.5, 1.5-4, 1.5-4.5, 1.5-5, 1.5-6, 1.5-8, 1.5-10, 1.5-15, 1.5-20, 1.5-25, 1.5-30, 2-2.5, 2-3, 2-3.5, 2-4, 2-4.5, 2-5, 2-6, 2-8, 2-10, 2-15, 2-20, 2-25, 2-30, 2.5-3, 2.5-3.5, 2.5-4, 2.5-4.5, 2.5-5, 2.5-6, 2.5-8, 2.5-10, 2.5-15, 2.5-20, 2.5-25, 2.5-30, 3-3.5, 3-4, 3-4.5, 3-5, 3-6, 3-8, 3-10, 3-15, 3-20, 3-25, 3-30, 3.5-4, 3.5-4.5, 3.5-5, 3.5-6, 3.5-8, 3.5-10, 3.5-15, 3.5-20, 3.5-25, 3.5-30, 4-4.5, 4-5, 4-6, 4-8, 4-10, 4-15, 4-20, 4-25, 4-30, 4.5-5, 4.5-6, 4.5-8, 4.5-10, 4.5-15, 4.5-20, 4.5-25, 4.5-30, 5-6, 5-8, 5-10, 5-15, 5-20, 5-25, 5-30, 5.5-6, 5.5-8, 5.5-10, 5.5-15, 5.5-20, 5.5-25, 5.5-30, 6-8, 6-10, 6-15, 6-20, 6-25, 6-30, 8-10, 8-15, 8-20, 8-25, 8-30, 10-15, 10-20, 10-25, 10-30, 15-20, 15-25, 15-30, 20-25, 20-30, or 25-30 min. A range given out in the present disclosure can be a range between two accurate numerical values, in some cases, a range in the present disclosure can also refer to a range between two approximate numerical values. For instance, “1-10” can refer to “from 1 to 10” in some cases, while in other case, “1-10” can refer to “from about 1 to about 10”. In some cases, the $T_{max}$ of the antiarrhythmic pharmaceutical agent administered via inhalation can be 0.01-5, 0.02-5, 0.03-5, 0.04-5, 0.05-5, 0.06-5, 0.07-5, 0.08-5, 0.09-5, 0.12-5, 0.14-5, 0.15-5, 0.16-5, 0.18-5, 0.2-5, 0.24-5, 0.26-5, 0.28-5, 0.3-5, 0.35-5, 0.4-5, 0.5-5, 0.6-5, 0.7-5, 0.8-5, 0.9-5, or 1-5 min. In some cases, the $T_{max}$ of the antiarrhythmic pharmaceutical agent administered via inhalation can be from about 0.1 to about 3 min. In some cases, the $T_{max}$ of the antiarrhythmic pharmaceutical agent administered via inhalation can be from about 0.1 to about 5 min. In some cases, the $T_{max}$ of the antiarrhythmic pharmaceutical agent (e.g., flecainide) administered via inhalation can be from about 0.2 to about 5 min. In one or more embodiments, the antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $T_{max}$ can be calculated as the amount of time at which the maximum plasma concentration of the antiarrhythmic pharmaceutical agent is observed. In some cases, the $T_{max}$ can be calculated as the amount of time after administration of the antiarrhythmic pharmaceutical agent when the maximum plasma concentration is reached. In some cases, the $T_{max}$ can be calculated as the amount of time after the initiation of the administration of the antiarrhythmic pharmaceutical agent when the maximum plasma concentration is reached. In some cases, the $T_{max}$ can be calculated as the amount of time after the completion of the administration of the antiarrhythmic pharmaceutical agent when the maximum plasma concentration is reached. In some cases, the $T_{max}$ can be calculated from plasma concentration of the antiarrhythmic pharmaceutical agent measured in the left ventricular chamber. In some cases, the $T_{max}$ can be calculated from plasma concentration of the antiarrhythmic pharmaceutical agent measured in the pulmonary artery. In some cases, the $T_{max}$ can be calculated from plasma concentration of the antiarrhythmic pharmaceutical agent measured in the vein (e.g., femoral vein). In some cases, the $T_{max}$ can be measured in a human PK/PD study. The term "human PK/PD study" as used herein can refer to any settings where a human subject receives administration of a single dose of the antiarrhythmic agent as provided herein and a pharmacokinetic (PK) or pharmacodynamic (PD) parameter is measured from the human subject after the administration of the antiarrhythmic agent. In some cases, a human PK/PD study as provided herein can refer to a clinical study performed in a clinic or hospital settings. In some cases, the human PK/PD study can be a single center or multi-center study. A human PK/PD study can be performed on healthy human subjects or human cardiovascular patients. In some cases, the patients with cardiovascular disease experience arrhythmia as described herein. In some cases, a human PK/PD study can be a single-dose study, in other cases, a human PK/PD study can be a multi-dose (e.g. escalating doses) study.

In some cases, the $C_{max}$ of the antiarrhythmic pharmaceutical agent administered via inhalation can be from about 10 ng/mL to about 5000 ng/mL, such as from about 10-30, 10-50, 10-70, 10-80, 10-90, 10-100, 10-110, 10-120, 10-130, 10-140, 10-150, 10-160, 10-170, 10-180, 10-190, 10-200, 10-250, 10-300, 10-350, 10-400, 10-450, 10-500, 10-550, 10-600, 10-650, 10-700, 10-800, 10-900, 10-1000, 10-1500, 10-2000, 10-3000, 10-4000, 10-5000, 20-30, 20-50, 20-70, 20-80, 20-90, 20-100, 20-110, 20-120, 20-130, 20-140, 20-150, 20-160, 20-170, 20-180, 20-190, 20-200, 20-250, 20-300, 20-350, 20-400, 20-450, 20-500, 20-550, 20-600, 20-650, 20-700, 20-800, 20-900, 20-1000, 20-1500, 20-2000, 20-3000, 20-4000, 20-5000, 30-50, 30-70, 30-80, 30-90, 30-100, 30-110, 30-120, 30-130, 30-140, 30-150, 30-160, 30-170, 30-180, 30-190, 30-200, 30-250, 30-300, 30-350, 30-400, 30-450, 30-500, 30-550, 30-600, 30-650, 30-700, 30-800, 30-900, 30-1000, 30-1500, 30-2000, 30-3000, 30-4000, 30-5000, 50-70, 50-80, 50-90, 50-100, 50-110, 50-120, 50-130, 50-140, 50-150, 50-160, 50-170, 50-180, 50-190, 50-200, 50-250, 50-300, 50-350, 50-400, 50-450, 50-500, 50-550, 50-600, 50-650, 50-700, 50-800, 50-900, 50-1000, 50-1500, 50-2000, 50-3000, 50-4000, 50-5000, 70-80, 70-90, 70-100, 70-110, 70-120, 70-130, 70-140, 70-150, 70-160, 70-170, 70-180, 70-190, 70-200, 70-250, 70-300, 70-350, 70-400, 70-450, 70-500, 70-550, 70-600, 70-650, 70-700, 70-800, 70-900, 70-1000, 70-1500, 70-2000, 70-3000, 70-4000, 70-5000, 80-90, 80-100, 80-110, 80-120, 80-130, 80-140, 80-150, 80-160, 80-170, 80-180, 80-190, 80-200, 80-250, 80-300, 80-350, 80-400, 80-450, 80-500, 80-550, 80-600, 80-650, 80-700, 80-800, 80-900, 80-1000, 80-1500, 80-2000, 80-3000, 80-4000, 80-5000, 90-100, 90-110, 90-120, 90-130, 90-140, 90-150, 90-160, 90-170, 90-180, 90-190, 90-200, 90-250, 90-300, 90-350, 90-400, 90-450, 90-500, 90-550, 90-600, 90-650, 90-700, 90-800, 90-900, 90-1000, 90-1500, 90-2000, 90-3000, 90-4000, 90-5000, 100-110, 100-120, 100-130, 100-140, 100-150, 100-160, 100-170, 100-180, 100-190, 100-200, 100-250, 100-300, 100-350, 100-400, 100-450, 100-500, 100-550, 100-600, 100-650, 100-700, 100-800, 100-900, 100-1000, 100-1500, 100-2000, 100-3000, 100-4000, 100-5000, 110-120, 110-130, 110-140, 110-150, 110-160, 110-170, 110-180, 110-190, 110-200, 110-250, 110-300, 110-350, 110-400, 110-450, 110-500, 110-550, 110-600, 110-650, 110-700, 110-800, 110-900, 110-1000, 110-1500, 110-2000, 110-3000, 110-4000, 110-5000, 120-130, 120-140, 120-150, 120-160, 120-170, 120-180, 120-190, 120-200, 120-250, 120-300, 120-350, 120-400, 120-450, 120-500, 120-550, 120-600, 120-650, 120-700, 120-800, 120-900, 120-1000, 120-1500, 120-2000, 120-3000, 120-4000, 120-5000, 130-140, 130-150, 130-160, 130-170, 130-180, 130-190, 130-200, 130-250, 130-300, 130-350, 130-400, 130-450, 130-500, 130-550, 130-600, 130-650, 130-700, 130-800, 130-900, 130-1000, 130-1500, 130-2000, 130-3000, 130-4000, 130-5000, 140-150, 140-160, 140-170, 140-180, 140-190, 140-200, 140-250, 140-300, 140-350, 140-400, 140-450, 140-500, 140-550, 140-600, 140-650, 140-700, 140-800, 140-900, 140-1000, 140-1500, 140-2000, 140-3000, 140-4000, 140-5000, 150-160, 150-170, 150-180, 150-190, 150-200, 150-250, 150-300, 150-350, 150-400, 150-450, 150-500, 150-550, 150-600, 150-650, 150-700, 150-800, 150-900, 150-1000, 150-1500, 150-2000, 150-3000, 150-4000, 150-5000, 160-170, 160-180, 160-190, 160-200, 160-250, 160-300, 160-350, 160-400, 160-450, 160-500, 160-550, 160-600, 160-650, 160-700, 160-800, 160-900, 160-1000, 160-1500, 160-2000, 160-3000, 160-4000, 160-5000, 170-180, 170-190, 170-200, 170-250, 170-300, 170-350, 170-400, 170-450, 170-500, 170-550, 170-600, 170-650, 170-700, 170-800, 170-900, 170-1000, 170-1500, 170-2000, 170-3000, 170-4000, 170-5000, 180-190, 180-200, 180-250, 180-300, 180-350, 180-400, 180-450, 180-500, 180-550, 180-600, 180-650, 180-700, 180-800, 180-900, 180-1000, 180-1500, 180-2000, 180-3000, 180-4000, 180-5000, 190-200, 190-250, 190-300, 190-350, 190-400, 190-450, 190-500, 190-550, 190-600, 190-650, 190-700, 190-800, 190-900, 190-1000, 190-1500, 190-2000, 190-3000, 190-4000, 190-5000, 200-250, 200-300, 200-350, 200-400, 200-450, 200-500, 200-550, 200-600, 200-650, 200-700, 200-800, 200-900, 200-1000, 200-1500, 200-2000, 200-3000, 200-4000, 200-5000, 250-300, 250-350, 250-400, 250-450, 250-500, 250-550, 250-600, 250-650, 250-700, 250-800, 250-900, 250-1000, 250-1500, 250-2000, 250-3000, 250-4000, 250-5000, 300-350, 300-400, 300-450, 300-500, 300-550, 300-600, 300-650, 300-700, 300-800, 300-900, 300-1000, 300-1500, 300-2000, 300-3000, 300-4000, 300-5000, 350-400, 350-450, 350-500, 350-550, 350-600, 350-650, 350-700, 350-800, 350-900, 350-1000, 350-1500, 350-2000, 350-3000, 350-4000, 350-5000, 400-450, 400-500, 400-550, 400-600, 400-650, 400-700, 400-800, 400-900, 400-1000, 400-1500, 400-2000, 400-3000, 400-4000, 400-5000, 450-500, 450-550, 450-600, 450-650, 450-700, 450-800, 450-900, 450-1000, 450-1500, 450-2000, 450-3000, 450-4000, 450-5000, 500-550, 500-600, 500-650, 500-700, 500-800, 500-900, 500-1000, 500-1500, 500-2000, 500-3000, 500-4000, 500-5000, 550-600, 550-650, 550-700, 550-800, 550-900, 550-1000, 550-1500, 550-2000, 550-3000, 550-4000, 550-5000, 600-650, 600-700, 600-800, 600-900, 600-1000, 600-1500, 600-2000, 600-3000, 600-4000, 600-5000, 650-700, 650-800, 650-900, 650-1000, 650-1500, 650-2000, 650-3000, 650-4000, 650-5000, 700-800, 700-900, 700-1000, 700-1500, 700-2000, 700-3000, 700-4000, 700-5000, 800-900, 800-1000, 800-1500, 800-2000, 800-3000, 800-4000, 800-5000, 900-1000, 900-1500, 900-2000, 900-3000, 900-4000, 900-5000, 1000-1500, 1000-2000, 1000-3000, 1000-4000, 1000-5000, 1500-2000, 1500-3000, 1500-4000, 1500-5000, 2000-3000, 2000-

4000, 2000-5000, 3000-4000, 3000-5000, or 4000-5000 ng/mL. In some cases, the $C_{max}$ of the antiarrhythmic pharmaceutical agent administered via inhalation can be from about 20 ng/mL to about 500 ng/mL, such as 20-500, 30-500, 40-500, 50-500, 60-500, 70-500, 80-500, 90-500, 100-500, 150-500, 200-500, or 250-500 ng/mL. In some cases, the $C_{max}$ of the antiarrhythmic pharmaceutical agent administered via inhalation can be from about 50 to about 500 ng/mL. In some cases, the $C_{max}$ of the antiarrhythmic pharmaceutical agent administered via inhalation can be from about 200 to about 500 ng/mL. In some cases, the $C_{max}$ of the antiarrhythmic pharmaceutical agent administered via inhalation is at least about 200 ng/mL. In some cases, the $C_{max}$ of the antiarrhythmic pharmaceutical agent administered via inhalation is at least about 250 ng/mL. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $C_{max}$ can be calculated as the maximum plasma concentration of the antiarrhythmic pharmaceutical agent observed. In some cases, the $C_{max}$ can be calculated as the peak plasma concentration that the antiarrhythmic pharmaceutical agent achieves after the drug has been administrated. In some cases, the $C_{max}$ can be calculated from plasma concentration of the antiarrhythmic pharmaceutical agent measured in the left ventricular chamber. In some cases, the $C_{max}$ can be calculated from plasma concentration of the antiarrhythmic pharmaceutical agent measured in the pulmonary artery. In some cases, the $C_{max}$ can be calculated from plasma concentration of the antiarrhythmic pharmaceutical agent measured in the vein (e.g., femoral vein). In some cases, the $C_{max}$ can be measured in a human PK/PD study.

In some cases, the $AUC_{Last}$ of the antiarrhythmic pharmaceutical agent administered via inhalation can be from about 100 hr*ng/mL to about 10000 hr*ng/mL, such as from 100-200, 100-300, 100-400, 100-420, 100-440, 100-460, 100-480, 100-500, 100-520, 100-540, 100-560, 100-580, 100-600, 100-620, 100-640, 100-660, 100-680, 100-700, 100-800, 100-900, 100-1000, 100-1500, 100-2000, 100-3000, 100-3500, 100-4000, 100-4500, 100-5000, 100-5500, 100-6000, 100-6500, 100-7000, 100-8000, 100-9000, 100-10000, 200-300, 200-400, 200-420, 200-440, 200-460, 200-480, 200-500, 200-520, 200-540, 200-560, 200-580, 200-600, 200-620, 200-640, 200-660, 200-680, 200-700, 200-800, 200-900, 200-1000, 200-1500, 200-2000, 200-3000, 200-3500, 200-4000, 200-4500, 200-5000, 200-5500, 200-6000, 200-6500, 200-7000, 200-8000, 200-9000, 200-10000, 300-400, 300-420, 300-440, 300-460, 300-480, 300-500, 300-520, 300-540, 300-560, 300-580, 300-600, 300-620, 300-640, 300-660, 300-680, 300-700, 300-800, 300-900, 300-1000, 300-1500, 300-2000, 300-3000, 300-3500, 300-4000, 300-4500, 300-5000, 300-5500, 300-6000, 300-6500, 300-7000, 300-8000, 300-9000, 300-10000, 400-420, 400-440, 400-460, 400-480, 400-500, 400-520, 400-540, 400-560, 400-580, 400-600, 400-620, 400-640, 400-660, 400-680, 400-700, 400-800, 400-900, 400-1000, 400-1500, 400-2000, 400-3000, 400-3500, 400-4000, 400-4500, 400-5000, 400-5500, 400-6000, 400-6500, 400-7000, 400-8000, 400-9000, 400-10000, 420-440, 420-460, 420-480, 420-500, 420-520, 420-540, 420-560, 420-580, 420-600, 420-620, 420-640, 420-660, 420-680, 420-700, 420-800, 420-900, 420-1000, 420-1500, 420-2000, 420-3000, 420-3500, 420-4000, 420-4500, 420-5000, 420-5500, 420-6000, 420-6500, 420-7000, 420-8000, 420-9000, 420-10000, 440-460, 440-480, 440-500, 440-520, 440-540, 440-560, 440-580, 440-600, 440-620, 440-640, 440-660, 440-680, 440-700, 440-800, 440-900, 440-1000, 440-1500, 440-2000, 440-3000, 440-3500, 440-4000, 440-4500, 440-5000, 440-5500, 440-6000, 440-6500, 440-7000, 440-8000, 440-9000, 440-10000, 460-480, 460-500, 460-520, 460-540, 460-560, 460-580, 460-600, 460-620, 460-640, 460-660, 460-680, 460-700, 460-800, 460-900, 460-1000, 460-1500, 460-2000, 460-3000, 460-3500, 460-4000, 460-4500, 460-5000, 460-5500, 460-6000, 460-6500, 460-7000, 460-8000, 460-9000, 460-10000, 480-500, 480-520, 480-540, 480-560, 480-580, 480-600, 480-620, 480-640, 480-660, 480-680, 480-700, 480-800, 480-900, 480-1000, 480-1500, 480-2000, 480-3000, 480-3500, 480-4000, 480-4500, 480-5000, 480-5500, 480-6000, 480-6500, 480-7000, 480-8000, 480-9000, 480-10000, 500-520, 500-540, 500-560, 500-580, 500-600, 500-620, 500-640, 500-660, 500-680, 500-700, 500-800, 500-900, 500-1000, 500-1500, 500-2000, 500-3000, 500-3500, 500-4000, 500-4500, 500-5000, 500-5500, 500-6000, 500-6500, 500-7000, 500-8000, 500-9000, 500-10000, 520-540, 520-560, 520-580, 520-600, 520-620, 520-640, 520-660, 520-680, 520-700, 520-800, 520-900, 520-1000, 520-1500, 520-2000, 520-3000, 520-3500, 520-4000, 520-4500, 520-5000, 520-5500, 520-6000, 520-6500, 520-7000, 520-8000, 520-9000, 520-10000, 540-560, 540-580, 540-600, 540-620, 540-640, 540-660, 540-680, 540-700, 540-800, 540-900, 540-1000, 540-1500, 540-2000, 540-3000, 540-3500, 540-4000, 540-4500, 540-5000, 540-5500, 540-6000, 540-6500, 540-7000, 540-8000, 540-9000, 540-10000, 560-580, 560-600, 560-620, 560-640, 560-660, 560-680, 560-700, 560-800, 560-900, 560-1000, 560-1500, 560-2000, 560-3000, 560-3500, 560-4000, 560-4500, 560-5000, 560-5500, 560-6000, 560-6500, 560-7000, 560-8000, 560-9000, 560-10000, 580-600, 580-620, 580-640, 580-660, 580-680, 580-700, 580-800, 580-900, 580-1000, 580-1500, 580-2000, 580-3000, 580-3500, 580-4000, 580-4500, 580-5000, 580-5500, 580-6000, 580-6500, 580-7000, 580-8000, 580-9000, 580-10000, 600-620, 600-640, 600-660, 600-680, 600-700, 600-800, 600-900, 600-1000, 600-1500, 600-2000, 600-3000, 600-3500, 600-4000, 600-4500, 600-5000, 600-5500, 600-6000, 600-6500, 600-7000, 600-8000, 600-9000, 600-10000, 620-640, 620-660, 620-680, 620-700, 620-800, 620-900, 620-1000, 620-1500, 620-2000, 620-3000, 620-3500, 620-4000, 620-4500, 620-5000, 620-5500, 620-6000, 620-6500, 620-7000, 620-8000, 620-9000, 620-10000, 640-660, 640-680, 640-700, 640-800, 640-900, 640-1000, 640-1500, 640-2000, 640-3000, 640-3500, 640-4000, 640-4500, 640-5000, 640-5500, 640-6000, 640-6500, 640-7000, 640-8000, 640-9000, 640-10000, 660-680, 660-700, 660-800, 660-900, 660-1000, 660-1500, 660-2000, 660-3000, 660-3500, 660-4000, 660-4500, 660-5000, 660-5500, 660-6000, 660-6500, 660-7000, 660-8000, 660-9000, 660-10000, 680-700, 680-800, 680-900, 680-1000, 680-1500, 680-2000, 680-3000, 680-3500, 680-4000, 680-4500, 680-5000, 680-5500, 680-6000, 680-6500, 680-7000, 680-8000, 680-9000, 680-10000, 700-800, 700-900, 700-1000, 700-1500, 700-2000, 700-3000, 700-3500, 700-4000, 700-4500, 700-5000, 700-5500, 700-6000, 700-6500, 700-7000, 700-8000, 700-9000, 700-10000, 800-900, 800-1000, 800-1500, 800-2000, 800-3000, 800-3500, 800-4000, 800-4500, 800-5000, 800-5500, 800-6000, 800-6500, 800-7000, 800-8000, 800-9000, 800-10000, 900-1000, 900-1500, 900-2000, 900-3000, 900-3500, 900-4000, 900-4500, 900-5000, 900-5500, 900-6000, 900-6500, 900-7000, 900-8000, 900-9000, 900-10000, 1000-1500, 1000-2000, 1000-3000, 1000-3500, 1000-4000, 1000-4500, 1000-5000, 1000-5500, 1000-6000, 1000-6500, 1000-7000, 1000-8000, 1000-9000, 1000-10000, 1500-2000, 1500-3000, 1500-3500, 1500-4000, 1500-4500, 1500-5000, 1500-5500, 1500-6000, 1500-6500, 1500-7000, 1500-8000, 1500-9000, 1500-10000, 2000-3000, 2000-3500, 2000-4000, 2000-4500, 2000-5000, 2000-5500, 2000-6000, 2000-6500, 2000-7000, 2000-8000, 2000-9000, 2000-10000, 2500-3000, 2500-3500, 2500-4000, 2500-4500, 2500-5000, 2500-5500, 2500-6000, 2500-6500, 2500-7000, 2500-8000, 2500-9000, 2500-10000, 3000-3500, 3000-4000, 3000-4500, 3000-5000, 3000-5500, 3000-6000, 3000-6500, 3000-7000, 3000-8000, 3000-9000, 3000-10000, 3500-4000, 3500-4500, 3500-5000, 3500-5500, 3500-6000, 3500-6500, 3500-7000, 3500-8000, 3500-9000, 3500-10000, 4000-4500, 4000-5000, 4000-5500, 4000-6000, 4000-6500, 4000-7000, 4000-8000, 4000-9000, 4000-10000, 4500-5000, 4500-5500, 4500-6000, 4500-6500, 4500-7000, 4500-8000, 4500-9000, 4500-10000, 5000-5500, 5000-6000, 5000-6500, 5000-7000, 5000-8000, 5000-9000, 5000-10000, 5500-6000, 5500-6500, 5500-7000, 5500-8000, 5500-9000, 5500-10000, 6000-6500, 6000-7000, 6000-8000, 6000-9000, 6000-10000, 6500-7000, 6500-8000, 6500-9000, 6500-10000, 7000-8000, 7000-9000, 7000-10000, 8000-9000, 8000-10000, or 9000-10000 hr*ng/mL. In some cases, the $AUC_{Last}$ of the antiarrhythmic pharmaceutical agent administered via inhalation can be from about 200 to about 2000 hr*ng/mL. In some cases, the $AUC_{Last}$ of the antiarrhythmic pharmaceutical agent administered via inhalation can be from about 500 to about 800 hr*ng/mL. In some cases, the $AUC_{Last}$ of the antiarrhythmic pharmaceutical agent administered via inhalation can be from about 400 to about 600 hr*ng/mL. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $AUC_{Last}$ can be calculated as the area under the concentration-time curve up to the last measurable concentration. In some cases, the $AUC_{Last}$ can be calculated as the total drug exposure over time. In some cases, the $AUC_{Last}$ can be calculated from plasma concentration of the antiarrhythmic pharmaceutical agent measured in the left ventricular chamber. In some cases, the $AUC_{Last}$ can be calculated from plasma concentration of the antiarrhythmic pharmaceutical agent measured in the pulmonary artery. In some cases, the $AUC_{Last}$ can be calculated from plasma concentration of the antiarrhythmic pharmaceutical agent measured in the vein (e.g., femoral vein). In some cases, the $AUC_{Last}$ can be measured in a human PK/PD study.

In some cases, the distribution t of the antiarrhythmic pharmaceutical agent administered via inhalation can be from about 0.1 minute to about 15 minutes, such as from about 0.1-0.5, 0.1-1, 0.1-1.5, 0.1-2, 0.1-2.5, 0.1-2.6, 0.1-2.7, 0.1-2.8, 0.1-2.9, 0.1-3, 0.1-3.1, 0.1-3.2, 0.1-3.3, 0.1-3.4, 0.1-3.5, 0.1-3.6, 0.1-3.7, 0.1-3.8, 0.1-3.9, 0.1-4, 0.1-4.1, 0.1-4.2, 0.1-4.3, 0.1-4.4, 0.1-4.5, 0.1-5, 0.1-5.5, 0.1-6, 0.1-7, 0.1-8, 0.1-9, 0.1-10, 0.1-11, 0.1-12, 0.1-13, 0.1-14, 0.1-15, 0.5-1, 0.5-1.5, 0.5-2, 0.5-2.5, 0.5-2.6, 0.5-2.7, 0.5-2.8, 0.5-2.9, 0.5-3, 0.5-3.1, 0.5-3.2, 0.5-3.3, 0.5-3.4, 0.5-3.5, 0.5-3.6, 0.5-3.7, 0.5-3.8, 0.5-3.9, 0.5-4, 0.5-4.1, 0.5-4.2, 0.5-4.3, 0.5-4.4, 0.5-4.5, 0.5-5, 0.5-5.5, 0.5-6, 0.5-7, 0.5-8, 0.5-9, 0.5-10, 0.5-11, 0.5-12, 0.5-13, 0.5-14, 0.5-15, 1-1.5, 1-2, 1-2.5, 1-2.6, 1-2.7, 1-2.8, 1-2.9, 1-3, 1-3.1, 1-3.2, 1-3.3, 1-3.4, 1-3.5, 1-3.6, 1-3.7, 1-3.8, 1-3.9, 1-4, 1-4.1, 1-4.2, 1-4.3, 1-4.4, 1-4.5, 1-5, 1-5.5, 1-6, 1-7, 1-8, 1-9, 1-10, 1-11, 1-12, 1-13, 1-14, 1-15, 1.5-2, 1.5-2.5, 1.5-2.6, 1.5-2.7, 1.5-2.8, 1.5-2.9, 1.5-3, 1.5-3.1, 1.5-3.2, 1.5-3.3, 1.5-3.4, 1.5-3.5, 1.5-3.6, 1.5-3.7, 1.5-3.8, 1.5-3.9, 1.5-4, 1.5-4.1, 1.5-4.2, 1.5-4.3, 1.5-4.4, 1.5-4.5, 1.5-5, 1.5-5.5, 1.5-6, 1.5-7, 1.5-8, 1.5-9, 1.5-10, 1.5-11, 1.5-12, 1.5-13, 1.5-14, 1.5-15, 2-2.5, 2-2.6, 2-2.7, 2-2.8, 2-2.9, 2-3, 2-3.1, 2-3.2, 2-3.3, 2-3.4, 2-3.5, 2-3.6, 2-3.7, 2-3.8, 2-3.9, 2-4, 2-4.1, 2-4.2, 2-4.3, 2-4.4, 2-4.5, 2-5, 2-5.5, 2-6, 2-7, 2-8, 2-9, 2-10, 2-11, 2-12, 2-13, 2-14, 2-15, 2.5-2.6, 2.5-2.7, 2.5-2.8, 2.5-2.9, 2.5-3, 2.5-3.1, 2.5-3.2, 2.5-3.3, 2.5-3.4, 2.5-3.5, 2.5-3.6, 2.5-3.7, 2.5-3.8, 2.5-3.9, 2.5-4, 2.5-4.1, 2.5-4.2, 2.5-4.3, 2.5-4.4, 2.5-4.5, 2.5-5, 2.5-5.5, 2.5-6, 2.5-7, 2.5-8, 2.5-9, 2.5-10, 2.5-11, 2.5-12, 2.5-13, 2.5-14, 2.5-15, 2.6-2.7, 2.6-2.8, 2.6-2.9, 2.6-3, 2.6-3.1, 2.6-3.2, 2.6-3.3, 2.6-3.4, 2.6-3.5, 2.6-3.6, 2.6-3.7, 2.6-3.8, 2.6-3.9, 2.6-4, 2.6-4.1, 2.6-4.2, 2.6-4.3, 2.6-4.4, 2.6-4.5, 2.6-5, 2.6-5.5, 2.6-6, 2.6-7, 2.6-8, 2.6-9, 2.6-10, 2.6-11, 2.6-12, 2.6-13, 2.6-14, 2.6-15, 2.7-2.8, 2.7-2.9, 2.7-3, 2.7-3.1, 2.7-3.2, 2.7-3.3, 2.7-3.4, 2.7-3.5, 2.7-3.6, 2.7-3.7, 2.7-3.8, 2.7-3.9, 2.7-4, 2.7-4.1, 2.7-4.2, 2.7-4.3, 2.7-4.4, 2.7-4.5, 2.7-5, 2.7-5.5, 2.7-6, 2.7-7, 2.7-8, 2.7-9, 2.7-10, 2.7-11, 2.7-12, 2.7-13, 2.7-14, 2.7-15, 2.8-2.9, 2.8-3, 2.8-3.1, 2.8-3.2, 2.8-3.3, 2.8-3.4, 2.8-3.5, 2.8-3.6, 2.8-3.7, 2.8-3.8, 2.8-3.9, 2.8-4, 2.8-4.1, 2.8-4.2, 2.8-4.3, 2.8-4.4, 2.8-4.5, 2.8-5, 2.8-5.5, 2.8-6, 2.8-7, 2.8-8, 2.8-9, 2.8-10, 2.8-11, 2.8-12, 2.8-13, 2.8-14, 2.8-15, 2.9-3, 2.9-3.1, 2.9-3.2, 2.9-3.3, 2.9-3.4, 2.9-3.5, 2.9-3.6, 2.9-3.7, 2.9-3.8, 2.9-3.9, 2.9-4, 2.9-4.1, 2.9-4.2, 2.9-4.3, 2.9-4.4, 2.9-4.5, 2.9-5, 2.9-5.5, 2.9-6, 2.9-7, 2.9-8, 2.9-9, 2.9-10, 2.9-11, 2.9-12, 2.9-13, 2.9-14, 2.9-15, 3-3.1, 3-3.2, 3-3.3, 3-3.4, 3-3.5, 3-3.6, 3-3.7, 3-3.8, 3-3.9, 3-4, 3-4.1, 3-4.2, 3-4.3, 3-4.4, 3-4.5, 3-5, 3-5.5, 3-6, 3-7, 3-8, 3-9, 3-10, 3-11, 3-12, 3-13, 3-14, 3-15, 3.1-3.2, 3.1-3.3, 3.1-3.4, 3.1-3.5, 3.1-3.6, 3.1-3.7, 3.1-3.8, 3.1-3.9, 3.1-4, 3.1-4.1, 3.1-4.2, 3.1-4.3, 3.1-4.4, 3.1-4.5, 3.1-5, 3.1-5.5, 3.1-6, 3.1-7, 3.1-8, 3.1-9, 3.1-10, 3.1-11, 3.1-12, 3.1-13, 3.1-14, 3.1-15, 3.2-3.3, 3.2-3.4, 3.2-3.5, 3.2-3.6, 3.2-3.7, 3.2-3.8, 3.2-3.9, 3.2-4, 3.2-4.1, 3.2-4.2, 3.2-4.3, 3.2-4.4, 3.2-4.5, 3.2-5, 3.2-5.5, 3.2-6, 3.2-7, 3.2-8, 3.2-9, 3.2-10, 3.2-11, 3.2-12, 3.2-13, 3.2-14, 3.2-15, 3.3-3.4, 3.3-3.5, 3.3-3.6, 3.3-3.7, 3.3-3.8, 3.3-3.9, 3.3-4, 3.3-4.1, 3.3-4.2, 3.3-4.3, 3.3-4.4, 3.3-4.5, 3.3-5, 3.3-5.5, 3.3-6, 3.3-7, 3.3-8, 3.3-9, 3.3-10, 3.3-11, 3.3-12, 3.3-13, 3.3-14, 3.3-15, 3.4-3.5, 3.4-3.6, 3.4-3.7, 3.4-3.8, 3.4-3.9, 3.4-4, 3.4-4.1, 3.4-4.2, 3.4-4.3, 3.4-4.4, 3.4-4.5, 3.4-5, 3.4-5.5, 3.4-6, 3.4-7, 3.4-8, 3.4-9, 3.4-10, 3.4-11, 3.4-12, 3.4-13, 3.4-14, 3.4-15, 3.5-3.6, 3.5-3.7, 3.5-3.8, 3.5-3.9, 3.5-4, 3.5-4.1, 3.5-4.2, 3.5-4.3, 3.5-4.4, 3.5-4.5, 3.5-5, 3.5-5.5, 3.5-6, 3.5-7, 3.5-8, 3.5-9, 3.5-10, 3.5-11, 3.5-12, 3.5-13, 3.5-14, 3.5-15, 3.6-3.7, 3.6-3.8, 3.6-3.9, 3.6-4, 3.6-4.1, 3.6-4.2, 3.6-4.3, 3.6-4.4, 3.6-4.5, 3.6-5, 3.6-5.5, 3.6-6, 3.6-7, 3.6-8, 3.6-9, 3.6-10, 3.6-11, 3.6-12, 3.6-13, 3.6-14, 3.6-15, 3.7-3.8, 3.8-3.9, 3.8-4, 3.8-4.1, 3.8-4.2, 3.8-4.3, 3.8-4.4, 3.8-4.5, 3.8-5, 3.8-5.5, 3.8-6, 3.8-7, 3.8-8, 3.8-9, 3.8-10, 3.8-11, 3.8-12, 3.8-13, 3.8-14, 3.8-15, 3.9-4, 3.9-4.1, 3.9-4.2, 3.9-4.3, 3.9-4.4, 3.9-4.5, 3.9-5, 3.9-5.5, 3.9-6, 3.9-7, 3.9-8, 3.9-9, 3.9-10, 3.9-11, 3.9-12, 3.9-13, 3.9-14, 3.9-15, 4-4.1, 4-4.2, 4-4.3, 4-4.4, 4-4.5, 4-5, 4-5.5, 4-6, 4-7, 4-8, 4-9, 4-10, 4-11, 4-12, 4-13, 4-14, 4-15, 4.1-4.2, 4.1-4.3, 4.1-4.4, 4.1-4.5, 4.1-5, 4.1-5.5, 4.1-6, 4.1-7, 4.1-8, 4.1-9, 4.1-10, 4.1-11, 4.1-12, 4.1-13, 4.1-14, 4.1-15, 4.2-4.3, 4.2-4.4, 4.2-4.5, 4.2-5, 4.2-5.5, 4.2-6, 4.2-7, 4.2-8, 4.2-9, 4.2-10, 4.2-11, 4.2-12, 4.2-13, 4.2-14, 4.2-15, 4.3-4.4, 4.3-4.5, 4.3-5, 4.3-5.5, 4.3-6, 4.3-7, 4.3-8, 4.3-9, 4.3-10, 4.3-11, 4.3-12, 4.3-13, 4.3-14, 4.3-15, 4.4-4.5, 4.4-5, 4.4-5.5, 4.4-6, 4.4-7, 4.4-8, 4.4-9, 4.4-10, 4.4-11, 4.4-12, 4.4-13, 4.4-14, 4.4-15, 4.5-5, 4.5-5.5, 4.5-6, 4.5-7, 4.5-8, 4.5-9, 4.5-10, 4.5-11, 4.5-12, 4.5-13, 4.5-14, 4.5-15, 5-5.5, 5-6, 5-7, 5-8, 5-9, 5-10, 5-11, 5-12, 5-13, 5-14, 5-15, 5.5-6, 5.5-7, 5.5-8, 5.5-9, 5.5-10, 5.5-11, 5.5-12, 5.5-13, 5.5-14, 5.5-15, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 12-15, 13-14, 13-15, or 14-15 min. In some cases, the distribution $t_{1/2}$ of the antiarrhythmic pharmaceutical agent administered via inhalation can be from about 3 to about 5 minutes. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the distribution $t_{1/2}$ can be calculated as the time at which the antiarrhythmic pharmaceutical agent plasma levels decreased to half of what they were at equilibrium due to distribution to tissues throughout the body. In some cases, the distribution $t_{1/2}$ can be calculated as the time it takes for an antiarrhythmic pharmaceutical agent to lose half of its pharmacologic activity. In some cases, the distribution $t_{1/2}$ can be calculated from plasma concentration of the antiarrhythmic pharmaceutical agent measured in the left ventricular chamber. In some cases, the distribution $t_{1/2}$ can be calculated from plasma concentration of the antiarrhythmic pharmaceutical agent measured in the pulmonary artery. In some cases, the distribution $t_{1/2}$ can be calculated from plasma concentration of the antiarrhythmic pharmaceutical agent measured in the vein (e.g., femoral vein). In some cases, the distribution $t_{1/2}$ can be measured in a human PK/PD study.

In some cases, the elimination $t_{1/2}$ of the antiarrhythmic pharmaceutical agent administered via inhalation can be from about 1 hour to about 25 hours, such as from about 1-3, 1-5, 1-7, 1-7.5, 1-8, 1-8.5, 1-8.7, 1-8.9, 1-9.1, 1-9.3, 1-9.5, 1-9.7, 1-9.9, 1-10.1, 1-10.3, 1-10.5, 1-10.7, 1-10.9, 1-11.1, 1-11.3, 1-11.5, 1-11.7, 1-11.9, 1-12.1, 1-12.5, 1-13, 1-13.5, 1-14, 1-15, 1-16, 1-17, 1-18, 1-19, 1-20, 1-25, 3-5, 3-7, 3-7.5, 3-8, 3-8.5, 3-8.7, 3-8.9, 3-9.1, 3-9.3, 3-9.5, 3-9.7, 3-9.9, 3-10.1, 3-10.3, 3-10.5, 3-10.7, 3-10.9, 3-11.1, 3-11.3, 3-11.5, 3-11.7, 3-11.9, 3-12.1, 3-12.5, 3-13, 3-13.5, 3-14, 3-15, 3-16, 3-17, 3-18, 3-19, 3-20, 3-25, 5-7, 5-7.5, 5-8, 5-8.5, 5-8.7, 5-8.9, 5-9.1, 5-9.3, 5-9.5, 5-9.7, 5-9.9, 5-10.1, 5-10.3, 5-10.5, 5-10.7, 5-10.9, 5-11.1, 5-11.3, 5-11.5, 5-11.7, 5-11.9, 5-12.1, 5-12.5, 5-13, 5-13.5, 5-14, 5-15, 5-16, 5-17, 5-18, 5-19, 5-20, 5-25, 7-7.5, 7-8, 7-8.5, 7-8.7, 7-8.9, 7-9.1, 7-9.3, 7-9.5, 7-9.7, 7-9.9, 7-10.1, 7-10.3, 7-10.5, 7-10.7, 7-10.9, 7-11.1, 7-11.3, 7-11.5, 7-11.7, 7-11.9, 7-12.1, 7-12.5, 7-13, 7-13.5, 7-14, 7-15, 7-16, 7-17, 7-18, 7-19, 7-20, 7-25, 7.5-8, 7.5-8.5, 7.5-8.7, 7.5-8.9, 7.5-9.1, 7.5-9.3, 7.5-9.5, 7.5-9.7, 7.5-9.9, 7.5-10.1, 7.5-10.3, 7.5-10.5, 7.5-10.7, 7.5-10.9, 7.5-11.1, 7.5-11.3, 7.5-11.5, 7.5-11.7, 7.5-11.9, 7.5-12.1, 7.5-12.5, 7.5-13, 7.5-13.5, 7.5-14, 7.5-15, 7.5-16, 7.5-17, 7.5-18, 7.5-19, 7.5-20, 7.5-25, 8-8.5, 8-8.7, 8-8.9, 8-9.1, 8-9.3, 8-9.5, 8-9.7, 8-9.9, 8-10.1, 8-10.3, 8-10.5, 8-10.7, 8-10.9, 8-11.1, 8-11.3, 8-11.5, 8-11.7, 8-11.9, 8-12.1, 8-12.5, 8-13, 8-13.5, 8-14, 8-15, 8-16, 8-17, 8-18, 8-19, 8-20, 8-25, 8.5-8.7, 8.5-8.9, 8.5-9.1, 8.5-9.3, 8.5-9.5, 8.5-9.7, 8.5-9.9, 8.5-10.1, 8.5-10.3, 8.5-10.5, 8.5-10.7, 8.5-10.9, 8.5-11.1, 8.5-11.3, 8.5-11.5, 8.5-11.7, 8.5-11.9, 8.5-12.1, 8.5-12.5, 8.5-13, 8.5-13.5, 8.5-14, 8.5-15, 8.5-16, 8.5-17, 8.5-18, 8.5-19, 8.5-20, 8.5-25, 8.7-8.9, 8.7-9.1, 8.7-9.3, 8.7-9.5, 8.7-9.7, 8.7-9.9, 8.7-10.1, 8.7-10.3, 8.7-10.5, 8.7-10.7, 8.7-10.9, 8.7-11.1, 8.7-11.3, 8.7-11.5, 8.7-11.7, 8.7-11.9, 8.7-12.1, 8.7-12.5, 8.7-13, 8.7-13.5, 8.7-14, 8.7-15, 8.7-16, 8.7-17, 8.7-18, 8.7-19, 8.7-20, 8.7-25, 8.9-9.1, 8.9-9.3, 8.9-9.5, 8.9-9.7, 8.9-9.9, 8.9-10.1, 8.9-10.3, 8.9-10.5, 8.9-10.7, 8.9-10.9, 8.9-11.1, 8.9-11.3, 8.9-11.5, 8.9-11.7, 8.9-11.9, 8.9-12.1, 8.9-12.5, 8.9-13, 8.9-13.5, 8.9-14, 8.9-15, 8.9-16, 8.9-17, 8.9-18, 8.9-19, 8.9-20, 8.9-25, 9.1-9.3, 9.1-9.5, 9.1-9.7, 9.1-9.9, 9.1-10.1, 9.1-10.3, 9.1-10.5, 9.1-10.7, 9.1-10.9, 9.1-11.1, 9.1-11.3, 9.1-11.5, 9.1-11.7, 9.1-11.9, 9.1-12.1, 9.1-12.5, 9.1-13, 9.1-13.5, 9.1-14, 9.1-15, 9.1-16, 9.1-17, 9.1-18, 9.1-19, 9.1-20, 9.1-25, 9.3-9.5, 9.3-9.7, 9.3-9.9, 9.3-10.1, 9.3-10.3, 9.3-10.5, 9.3-10.7, 9.3-10.9, 9.3-11.1, 9.3-11.3, 9.3-11.5, 9.3-11.7, 9.3-11.9, 9.3-12.1, 9.3-12.5, 9.3-13, 9.3-13.5, 9.3-14, 9.3-15, 9.3-16, 9.3-17, 9.3-18, 9.3-19, 9.3-20, 9.3-25, 9.5-9.7, 9.5-9.9, 9.5-10.1, 9.5-10.3, 9.5-10.5, 9.5-10.7, 9.5-10.9, 9.5-11.1, 9.5-11.3, 9.5-11.5, 9.5-11.7, 9.5-11.9, 9.5-12.1, 9.5-12.5, 9.5-13, 9.5-13.5, 9.5-14, 9.5-15, 9.5-16, 9.5-17, 9.5-18, 9.5-19, 9.5-20, 9.5-25, 9.7-9.9, 9.7-10.1, 9.7-10.3, 9.7-10.5, 9.7-10.7, 9.7-10.9, 9.7-11.1, 9.7-11.3, 9.7-11.5, 9.7-11.7, 9.7-11.9, 9.7-12.1, 9.7-12.5, 9.7-13, 9.7-13.5, 9.7-14, 9.7-15, 9.7-16, 9.7-17, 9.7-18, 9.7-19, 9.7-20, 9.7-25, 9.9-10.1, 9.9-10.3, 9.9-10.5, 9.9-10.7, 9.9-10.9, 9.9-11.1, 9.9-11.3, 9.9-11.5, 9.9-11.7, 9.9-11.9, 9.9-12.1, 9.9-12.5, 9.9-13, 9.9-13.5, 9.9-14, 9.9-15, 9.9-16, 9.9-17, 9.9-18, 9.9-19, 9.9-20, 9.9-25, 10.1-10.3, 10.1-10.5, 10.1-10.7, 10.1-10.9, 10.1-11.1, 10.1-11.3, 10.1-11.5, 10.1-11.7, 10.1-11.9, 10.1-12.1, 10.1-12.5, 10.1-13, 10.1-13.5, 10.1-14, 10.1-15, 10.1-16, 10.1-17, 10.1-18, 10.1-19, 10.1-20, 10.1-25, 10.3-10.5, 10.3-10.7, 10.3-10.9, 10.3-11.1, 10.3-11.3, 10.3-11.5, 10.3-11.7, 10.3-11.9, 10.3-12.1, 10.3-12.5, 10.3-13, 10.3-13.5, 10.3-14, 10.3-15, 10.3-16, 10.3-17, 10.3-18, 10.3-19, 10.3-20, 10.3-25, 10.5-10.7, 10.5-10.9, 10.5-11.1, 10.5-11.3, 10.5-11.5, 10.5-11.7, 10.5-11.9, 10.5-12.1, 10.5-12.5, 10.5-13, 10.5-13.5, 10.5-14, 10.5-15, 10.5-16, 10.5-17, 10.5-18, 10.5-19, 10.5-20, 10.5-25, 10.7-10.9, 10.7-11.1, 10.7-11.3, 10.7-11.5, 10.7-11.7, 10.7-11.9, 10.7-12.1, 10.7-12.5, 10.7-13, 10.7-13.5, 10.7-14, 10.7-15, 10.7-16, 10.7-17, 10.7-18, 10.7-19, 10.7-20, 10.7-25, 10.9-11.1, 10.9-11.3, 10.9-11.5, 10.9-11.7, 10.9-11.9, 10.9-12.1, 10.9-12.5, 10.9-13, 10.9-13.5, 10.9-14, 10.9-15, 10.9-16, 10.9-17, 10.9-18, 10.9-19, 10.9-20, 10.9-25, 11.1-11.3, 11.1-11.5, 11.1-11.7, 11.1-11.9, 11.1-12.1, 11.1-12.5, 11.1-13, 11.1-13.5, 11.1-14, 11.1-15, 11.1-16, 11.1-17, 11.1-18, 11.1-19, 11.1-20, 11.1-25, 11.3-11.5, 11.3-11.7, 11.3-11.9, 11.3-12.1, 11.3-12.5, 11.3-13, 11.3-13.5, 11.3-14, 11.3-15, 11.3-16, 11.3-17, 11.3-18, 11.3-19, 11.3-20, 11.3-25, 11.5-11.7, 11.5-11.9, 11.5-12.1, 11.5-12.5, 11.5-13, 11.5-13.5, 11.5-14, 11.5-15, 11.5-16, 11.5-17, 11.5-18, 11.5-19, 11.5-20, 11.5-25, 11.7-11.9, 11.7-12.1, 11.7-12.5, 11.7-13, 11.7-13.5, 11.7-14, 11.7-15, 11.7-16, 11.7-17, 11.7-18, 11.7-19, 11.7-20, 11.7-25, 11.9-12.1, 11.9-12.5, 11.9-13, 11.9-13.5, 11.9-14, 11.9-15, 11.9-16, 11.9-17, 11.9-18, 11.9-19, 11.9-20, 11.9-25, 12.1-12.5, 12.1-13, 12.1-13.5, 12.1-14, 12.1-15, 12.1-16, 12.1-17, 12.1-18, 12.1-19, 12.1-20, 12.1-25, 12.5-13, 12.5-13.5, 12.5-14, 12.5-15, 12.5-16, 12.5-17, 12.5-18, 12.5-19, 12.5-20, 12.5-25, 13-13.5, 13-14, 13-15, 13-16, 13-17, 13-18, 13-19, 13-20, 13-25, 13.5-14, 13.5-15, 13.5-16, 13.5-17, 13.5-18, 13.5-19, 13.5-20, 13.5-25, 14-15, 14-16, 14-17, 14-18, 14-19, 14-20, 14-25, 15-16, 15-17, 15-18, 15-19, 15-20, 15-25, 16-17, 16-18, 16-19, 16-20, 16-25, 17-18, 17-19, 17-20, 17-25, 18-19, 18-20, 18-25, 19-20, 19-25, or 20-25 hours. In some cases, the elimination $t_{1/2}$ of the antiarrhythmic pharmaceutical agent administered via inhalation can be from about 8.5 to about 10.5 hours. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the elimination $t_{1/2}$ can be calculated as the time at which the antiarrhythmic pharmaceutical agent plasma levels decreased to half of what they were at equilibrium due to metabolism and elimination. In some cases, the elimination $t_{1/2}$ can be calculated from plasma concentration of the antiarrhythmic pharmaceutical agent measured in the left ventricular chamber. In some cases, the elimination $t_{1/2}$ can be calculated from plasma concentration of the antiarrhythmic pharmaceutical agent measured in the pulmonary artery. In some cases, the elimination $t_{1/2}$ can be calculated from plasma concentration of the antiarrhythmic pharmaceutical agent measured in the vein (e.g., femoral vein). In some cases, the elimination $t_{1/2}$ can be measured in a human PK/PD study.

In some cases, the maximum change in QRS interval duration (AQRS) following the antiarrhythmic pharmaceutical agent administered via inhalation can be from about 0.01 msec to about 100 msec, such as from about 0.01-0.1, 0.01-0.5, 0.01-1, 0.01-1.5, 0.01-2, 0.01-2.5, 0.01-3, 0.01-3.5, 0.01-4, 0.01-4.5, 0.01-5, 0.01-5.5, 0.01-6, 0.01-8, 0.01-10, 0.01-15, 0.01-20, 0.01-25, 0.01-30, 0.01-40, 0.01-50, 0.01-60, 0.01-70, 0.01-80, 0.01-90, 0.01-100, 0.1-0.5, 0.1-1, 0.1-1.5, 0.1-2, 0.1-2.5, 0.1-3, 0.1-3.5, 0.1-4, 0.1-4.5, 0.1-5, 0.1-5.5, 0.1-6, 0.1-8, 0.1-10, 0.1-15, 0.1-20, 0.1-25, 0.1-30, 0.1-40, 0.1-50, 0.1-60, 0.1-70, 0.1-80, 0.1-90, 0.1-100, 0.5-1, 0.5-1.5, 0.5-2, 0.5-2.5, 0.5-3, 0.5-3.5, 0.5-4, 0.5-4.5, 0.5-5, 0.5-5.5, 0.5-6, 0.5-8, 0.5-10, 0.5-15, 0.5-20, 0.5-25, 0.5-30, 0.5-40, 0.5-50, 0.5-60, 0.5-70, 0.5-80, 0.5-90, 0.5-100, 1-1.5, 1-2, 1-2.5, 1-3, 1-3.5, 1-4, 1-4.5, 1-5, 1-5.5, 1-6, 1-8, 1-10, 1-15, 1-20, 1-25, 1-30, 1-40, 1-50, 1-60, 1-70, 1-80, 1-90, 1-100, 1.5-2, 1.5-2.5, 1.5-3, 1.5-3.5, 1.5-4, 1.5-4.5, 1.5-5, 1.5-5.5, 1.5-6, 1.5-8, 1.5-10, 1.5-15, 1.5-20, 1.5-25, 1.5-30, 1.5-40, 1.5-50, 1.5-60, 1.5-70, 1.5-80, 1.5-90, 1.5-100, 2-2.5, 2-3, 2-3.5, 2-4, 2-4.5, 2-5, 2-5.5, 2-6, 2-8, 2-10, 2-15, 2-20, 2-25, 2-30, 2-40, 2-50, 2-60, 2-70, 2-80, 2-90, 2-100, 2.5-3, 2.5-3.5, 2.5-4, 2.5-4.5, 2.5-5, 2.5-5.5, 2.5-6, 2.5-8, 2.5-10, 2.5-15, 2.5-20, 2.5-25, 2.5-30, 2.5-40, 2.5-50, 2.5-60, 2.5-70, 2.5-80, 2.5-90, 2.5-100, 3-3.5, 3-4, 3-4.5, 3-5, 3-5.5, 3-6, 3-8, 3-10, 3-15, 3-20, 3-25, 3-30, 3-40, 3-50, 3-60, 3-70, 3-80, 3-90, 3-100, 3.5-4, 3.5-4.5, 3.5-5, 3.5-5.5, 3.5-6, 3.5-8, 3.5-10, 3.5-15, 3.5-3.20, 3.5-3.25, 3.5-3.30, 3.5-40, 3.5-50, 3.5-60, 3.5-70, 3.5-80, 3.5-90, 3.5-100, 4-4.5, 4-5, 4-5.5, 4-6, 4-8, 4-10, 4-15, 4-20, 4-25, 4-30, 4-40, 4-50, 4-60, 4-70, 4-80, 4-90, 4-100, 4.5-5, 4.5-5.5, 4.5-6, 4.5-8, 4.5-10, 4.5-15, 4.5-20, 4.5-25, 4.5-30, 4.5-4.50, 4.5-50, 4.5-60, 4.5-70, 4.5-80, 4.5-90, 4.5-100, 5-5.5, 5-6, 5-8, 5-10, 5-15, 5-20, 5-25, 5-30, 5-40, 5-50, 5-60, 5-70, 5-80, 5-90, 5-100, 5.5-6, 5.5-8, 5.5-10, 5.5-15, 5.5-20, 5.5-25, 5.5-30, 5.5-40, 5.5-50, 5.5-60, 5.5-70, 5.5-80, 5.5-90, 5.5-100, 6-8, 6-10, 6-15, 6-20, 6-25, 6-30, 6-40, 6-50, 6-60, 6-70, 6-80, 6-90, 6-100, 8-10, 8-15, 8-20, 8-25, 8-30, 8-40, 8-50, 8-60, 8-70, 8-80, 8-90, 8-100, 10-15, 10-20, 10-25, 10-30, 10-40, 10-50, 10-60, 10-70, 10-80, 10-90, 10-100, 15-20, 15-25, 15-30, 15-40, 15-50, 15-60, 15-70, 15-80, 15-90, 15-100, 20-25, 20-30, 20-40, 20-50, 20-60, 20-70, 20-80, 20-90, 20-100, 25-30, 25-40, 25-50, 25-60, 25-70, 25-80, 25-90, 25-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90, 60-100, 70-80, 70-90, 70-100, 80-90, 80-100, or 90-100 msec. In some cases, the maximum change in QRS interval duration (ΔQRS) following the antiarrhythmic pharmaceutical agent administered via inhalation can be from about 1 to about 10 msec. In some cases, the maximum change in QRS interval duration (ΔQRS) following the antiarrhythmic pharmaceutical agent administered via inhalation can be from about 5 to about 20 msec. In some cases, the ΔQRS can be measured in a human PK/PD study. In the present disclosure, the term "ΔQRS", if not referred to with reference to time post-administration of the antiarrhythmic agent, can be used interchangeably with the term "maximum ΔQRS", e.g. meaning the maximum change in QRS following administration of the antiarrhythmic agent as provided herein. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the time point at which the QRS interval is measured following the antiarrhythmic pharmaceutical agent administration via inhalation to determine the ΔQRS relative to pre-dose can be from about 0.1 minute to about 450 minutes, such as from about 0.1-1, 0.1-3, 0.1-5, 0.1-10, 0.1-15, 0.1-30, 0.1-45, 0.1-60, 0.1-90, 0.1-120, 0.1-150, 0.1-180, 0.1-210, 0.1-240, 0.1-270, 0.1-300, 0.1-330, 0.1-360, 0.1-390, 0.1-410, 0.1-450, 1-3, 1-5, 1-10, 1-15, 1-30, 1-45, 1-60, 1-90, 1-120, 1-150, 1-180, 1-210, 1-240, 1-270, 1-300, 1-330, 1-360, 1-390, 1-410, 1-450, 3-5, 3-10, 3-15, 3-30, 3-45, 3-60, 3-90, 3-120, 3-150, 3-180, 3-210, 3-240, 3-270, 3-300, 3-330, 3-360, 3-390, 3-410, 3-450, 5-10, 5-15, 5-30, 5-45, 5-60, 5-90, 5-120, 5-150, 5-180, 5-210, 5-240, 5-270, 5-300, 5-330, 5-360, 5-390, 5-410, 5-450, 10-15, 10-30, 10-45, 10-60, 10-90, 10-120, 10-150, 10-180, 10-210, 10-240, 10-270, 10-300, 10-330, 10-360, 10-390, 10-410, 10-450, 15-30, 15-45, 15-60, 15-90, 15-120, 15-150, 15-180, 15-210, 15-240, 15-270, 15-300, 15-330, 15-360, 15-390, 15-410, 15-450, 30-45, 30-60, 30-90, 30-120, 30-150, 30-180, 30-210, 30-240, 30-270, 30-300, 30-330, 30-360, 30-390, 30-410, 30-450, 45-60, 45-90, 45-120, 45-150, 45-180, 45-210, 45-240, 45-270, 45-300, 45-330, 45-360, 45-390, 45-410, 45-450, 60-90, 60-120, 60-150, 60-180, 60-210, 60-240, 60-270, 60-300, 60-330, 60-360, 60-390, 60-410, 60-450, 90-120, 90-150, 90-180, 90-210, 90-240, 90-270, 90-300, 90-330, 90-360, 90-390, 90-410, 90-450, 120-150, 120-180, 120-210, 120-240, 120-270, 120-300, 120-330, 120-360, 120-390, 120-410, 120-450, 150-180, 150-210, 150-240, 150-270, 150-300, 150-330, 150-360, 150-390, 150-410, 150-450, 180-210, 180-240, 180-270, 180-300, 180-330, 180-360, 180-390, 180-410, 180-450, 210-240, 210-270, 210-300, 210-330, 210-360, 210-390, 210-410, 210-450, 240-270, 240-300, 240-330, 240-360, 240-390, 240-410, 240-450, 270-300, 270-330, 270-360, 270-390, 270-410, 270-450, 300-330, 300-360, 300-390, 300-410, 300-450, 330-360, 330-390, 330-410, 330-450, 360-390, 360-410, 360-450, 390-410, 390-450, or 410-450 min.

The antiarrhythmic activity of pharmaceutical agent can be correlated with QRS interval duration. In some examples, the antiarrhythmic pharmaceutical agent administered via inhalation can have higher antiarrhythmic activity as compared to the antiarrhythmic pharmaceutical agent administered by intravenous delivery (e.g., intravenous infusion). In some cases, such a higher antiarrhythmic activity is reflected by a higher ratio of maximum ΔQRS to $C_{max}$. For example, given the same $C_{max}$, e.g., peak plasma concentration of the antiarrhythmic pharmaceutic agent, inhalation delivery of the antiarrhythmic agent as provided herein can have a higher maximum ΔQRS as compared to intravenous delivery of the same agent. In some cases, the comparison may not be made between corresponding doses via the two different administration routes, for example, inhalation of a first dose of the agent can have a first $C_{max}$ ($C_{max1}$) and a first maximum ΔQRS ($ΔQRS_{max1}$), and intravenous administration of a second dose of the agent can have a second $C_{max}$ ($C_{max}$ 2) and a second maximum ΔQRS ($ΔQRS_{max2}$). In some cases, $C_{max1}$ and $C_{max2}$ can be similar. In other case, $C_{max1}$ and $C_{max2}$ can be dissimilar. In some examples of the present disclosure, the ratio of $\Delta QRS_{max}$ versus $C_{max1}$ can be higher than $\Delta QRS_{max2}$ versus $C_{max2}$, i.e., $\Delta QRS_{max1}/C_{max1} > \Delta QRS_{max2}/C_{max2}$. In some cases, $\Delta QRS_{max1}/C_{max1}$ is at least 1.1 folds, at least 1.2 folds, at least 1.3 folds, at least 1.4 folds, at least 1.5 folds, at least 1.6 folds, at least 1.7 folds, at least 1.8 folds, at least 1.9 folds, at least 2.0 folds, at least 2.1 folds, at least 2.2 folds, at least 2.3 folds, at least 2.4 folds, at least 2.5 folds, at least 2.6 folds, at least 2.7 folds, at least 2.8 folds, at least 2.9 folds, at least 3.0 folds, at least 3.1 folds, at least 3.2 folds, at least 3.3 folds, at least 3.4 folds, at least 3.5 folds, at least 3.6 folds, at least 3.7 folds, at least 3.8 folds, at least 3.9 folds, at least 4.0 folds, at least 4.2 folds, at least 4.4 folds, at least 4.6 folds, at least 4.8 folds, at least 5.0 folds, at least 5.5 folds, at least 6 folds, at least 7 folds, at least 8 folds, at least 9 folds, at least 10 folds, at least 12 folds, at least 15 folds, at least 20 folds, at least 25 folds, or at least 50 folds greater than $\Delta QRS_{max2}/C_{max2}$. In some cases, $\Delta QRS_{max1}/C_{max1}$ is at least 2 folds greater than $\Delta QRS_{max2}/C_{max2}$. In one or more embodiments antiarrhythmic pharmaceutical agent is a class I, class II, class III, or class IV antiarrhythmic. In some embodiments, the antiarrhythmic pharmaceutical agent is a class Ic, anti-arrhythmic. In other embodiments, the antiarrhythmic pharmaceutical agent is flecainide or a pharmaceutically acceptable salt thereof.

Indications and Subjects

Examples of cardiac arrhythmias the methods, compositions, and kits provided herein can treat include, but are not limited to, tachycardia, supraventricular tachycardia (SVT), paroxysmal supraventricular tachycardia (PSVT), atrial fibrillation (AF), paroxysmal atrial fibrillation (PAF), persistent atrial fibrillation, permanent atrial fibrillation, atrial flutter, paroxysmal atrial flutter, and lone atrial fibrillation. In some cases, the methods, compositions, and kits provided herein find use in treating a subject suffering from atrial arrhythmia, e.g., atrial fibrillation.

Thus, the pharmaceutical compositions according to some examples of the present disclosure can be used to treat and/or provide prophylaxis for a broad range of patients. A suitable patient for, receiving treatment and/or prophylaxis as described herein is any mammalian patient in need thereof, preferably such mammal is a human. Examples of subjects include, but are not limited to, pediatric patients, adult patients, and geriatric patients. In some cases, the composition is intended only as a treatment for rapid resolution of symptoms and restoration of normal sinus rhythm, and is not taken as a preventative, e.g., when the patient is well, there is no need for drug—this can increase the benefit-risk ratio of the therapy and overall safety due to the sporadic or intermittent dosing, and the focus on reducing disabling symptoms and restoring sinus rhythm only when needed.

The dosage necessary and the frequency of dosing of the antiarrhythmic pharmaceutical agent depend on the composition and concentration of the antiarrhythmic pharmaceutical agent within the composition. In some cases, the dose is less than about 10%, 20%, 30%, 40%, 50%, 60%, 70%, 80%, 90%, or 95% of its normal intravenous dose. In some cases, the dose is about 5% to about 10%, is about 10% to about 20%, is about 20% to about 30%, is about 30% to about 40%, is about 50% to about 60%, is about 60% to about 70%, is about 70% to about 80%, is about 80% to about 90%, or is about 90% to about 95% of the intravenous dose.

Pharmaceutical compositions disclosed herein can be more effective in subjects that include or lack certain physiological or demographic factors, such as, for example, age at clinical presentation, certain hemodynamic criteria, electrophysiological features, and prior treatments. In some embodiments, a subject treated with a pharmaceutical composition of the disclosure suffers from an atrial fibrillation with an onset that occurred within 48 hours prior to the treating. In some embodiments, a subject treated with a pharmaceutical composition of the disclosure suffers from an atrial fibrillation with an onset that occurred from 1 hour to 48 hours prior to the treating. In some embodiments, a subject treated with a pharmaceutical composition of the disclosure suffers from recurrent atrial fibrillation. In some embodiments, a subject treated with a pharmaceutical composition of the disclosure has undergone cardiac ablation no less than 3 months prior to the treating. In some embodiments, a subject treated with a pharmaceutical composition of the disclosure has an ongoing prescription for an oral antiarrhythmic medication for atrial fibrillation. In some embodiments, the oral antiarrhythmic medication is flecainide, or a pharmaceutically acceptable salt thereof.

In some embodiments, a subject treated with a pharmaceutical composition of the disclosure is over 17 years in age. In some embodiments, a subject treated with a pharmaceutical composition of the disclosure is no more than 85 years in age. In some embodiments, a subject treated with a pharmaceutical composition of the disclosure is from 18 years old to 85 years old.

In some embodiments, a subject treated with a pharmaceutical composition of the disclosure has a systolic blood pressure that is below 180 mmHg, below 175 mmHg, below 170 mmHg, below 165 mmHg, below 160 mmHg, below 155 mmHg, or below 150 mmHg at the time of the treating. In some embodiments, a subject treated with a pharmaceutical composition of the disclosure has a systolic blood pressure that is greater than 70 mmHg, greater than 75 mmHg, greater than 80 mmHg, greater than 85 mmHg, greater than 90 mmHg, greater than 95 mmHg, greater than 100 mmHg, greater than 105 mmHg, greater than 110 mmHg, greater than 115 mmHg, or greater than 120 mmHg at the time of the treating.

In some embodiments, a subject treated with a pharmaceutical composition of the disclosure has a systolic blood pressure that is from about 60 mmHg to about 180 mmHg, from about 65 mmHg to about 180 mmHg, from about 70 mmHg to about 180 mmHg, from about 75 mmHg to about 180 mmHg, from about 80 mmHg to about 180 mmHg, from about 85 mmHg to about 180 mmHg, from about 90 mmHg to about 180 mmHg, from about 95 mmHg to about 180 mmHg, from about 100 mmHg to about 180 mmHg, from about 105 mmHg to about 180 mmHg, from about 110 mmHg to about 180 mmHg, from about 115 mmHg to about 180 mmHg, from about 120 mmHg to about 180 mmHg, from about 70 mmHg to about 175 mmHg, from about 70 mmHg to about 170 mmHg, from about 70 mmHg to about 165 mmHg, from about 70 mmHg to about 160 mmHg, from about 70 mmHg to about 155 mmHg, from about 70 mmHg to about 150 mmHg, from about 80 mmHg to about 165 mmHg, from about 90 mmHg to about 165 mmHg, from about 100 mmHg to about 165 mmHg, from about 70 mmHg to about 160 mmHg, from about 70 mmHg to about 160 mmHg, from about 75 mmHg to about 160 mmHg, from about 80 mmHg to about 160 mmHg, from about 85 mmHg to about 160 mmHg, from about 90 mmHg to about 160 mmHg, from about 95 mmHg to about 160 mmHg, from about 100 mmHg to about 160 mmHg, from about 70 mmHg to about 155 mmHg, from about 75 mmHg to about 155 mmHg, or from about 80 mmHg to about 155 mmHg.

In some embodiments, a subject treated with a pharmaceutical composition of the disclosure has a ventricular rate that is at least about 50 BPM, at least about 55 BPM, at least about 60 BPM, at least about 65 BPM, at least about 70 BPM, at least about 75 BPM, at least about 80 BPM, at least about 85 BPM, at least about 90 BPM, at least about 95 BPM, or at least about 100 BPM. In some embodiments, a subject treated with a pharmaceutical composition of the disclosure has a ventricular rate that is no greater than about 200 BPM, no greater than about 190 BPM, no greater than about 180 BPM, no greater than about 175 BPM, no greater than about 170 BPM, no greater than about 165 BPM, no greater than about 160 BPM, no greater than about 155 BPM, no greater than about 150 BPM, no greater than about 145 BPM, or no greater than about 140 BPM.

In some embodiments, a subject treated with a pharmaceutical composition of the disclosure has a ventricular rate that is from about 50 BPM to about 200 BPM, 50 BPM to about 180 BPM, from about 55 BPM to about 180 BPM, from about 60 BPM to about 180 BPM, from about 65 BPM to about 180 BPM, from about 70 BPM to about 180 BPM, from about 75 BPM to about 180 BPM, from about 80 BPM to about 180 BPM, about 85 BPM to about 180 BPM, about 95 BPM to about 180 BPM, about 100 BPM to about 180 BPM, from about 50 BPM to about 175 BPM, from about 50 BPM to about 170 BPM, from about 50 BPM to about 165 BPM, from about 50 BPM to about 160 BPM, from about 50 BPM to about 155 BPM, from about 70 BPM to about 175 BPM, about 70 BPM to about 170 BPM, about 70 BPM to about 165 BPM, about 70 BPM to about 160 BPM, about 70 BPM to about 155 BPM, about 75 BPM to about 180 BPM, about 75 BPM to about 175 BPM, about 75 BPM to about 170 BPM, about 75 BPM to about 165 BPM, about 75 BPM to about 160 BPM, about 75 BPM to about 155 BPM, about 80 BPM to about 175 BPM, about 80 BPM to about 170 BPM, about 80 BPM to about 165 BPM, about 80 BPM to about 160 BPM, about 80 BPM to about 155 BPM, about 80 BPM to about 150 BPM, about 80 BPM to about 145 BPM, about 85 BPM to about 155 BPM, about 90 BPM to about 155 BPM, about 95 BPM to about 155 BPM, or about 100 BPM to about 155 BPM.

In some embodiments, a subject treated with a pharmaceutical composition of the disclosure has not been treated with antiarrhythmic drugs or electrical cardioversion since onset of an episode of atrial arrhythmia for which the pharmaceutical composition is being administered. In some embodiments, a subject treated with a pharmaceutical composition of the disclosure does not exhibit acute decompensated heart failure. In some embodiments, a subject treated with a pharmaceutical composition of the disclosure does not exhibit, or has not exhibited heart failure with reduced ejection fraction. In some embodiments, a subject treated with a pharmaceutical composition of the disclosure does not exhibit, or has not exhibited myocardial ischemia. In some embodiments, a subject treated with a pharmaceutical composition of the disclosure does not exhibit, or has not exhibited myocardial infarction. In some embodiments, a subject treated with a pharmaceutical composition of the disclosure has not exhibited myocardial infarction (MI) within 3 months prior to administration of the pharmaceutical composition. In some embodiments, a subject treated with a pharmaceutical composition of the disclosure does not exhibit uncorrected severe aortic or mitral stenosis. In some embodiments, a subject treated with a pharmaceutical composition of the disclosure does not exhibit hypertrophic cardiomyopathy with outflow tract obstruction. In some embodiments, a subject treated with a pharmaceutical composition of the disclosure does not exhibit, or has not exhibited persistent atrial fibrillation. In some embodiments, a subject treated with a pharmaceutical composition of the disclosure does not exhibit atrial flutter. In some embodiments, a subject treated with a pharmaceutical composition of the disclosure has not exhibited an episode of atrial flutter within 6 months prior to the treating. In some embodiments, a subject treated with a pharmaceutical composition of the disclosure does not exhibit abnormal left ventricular ejection fraction. In some embodiments, a subject treated with a pharmaceutical composition of the disclosure does not exhibit heart failure that is class 2 or greater as according to New York Heart Association Functional Classification.

In some embodiments, a subject treated with a pharmaceutical composition of the disclosure is hemodynamically stable, has a systolic blood pressure that is greater than about 90 mmHg, has ventricular rate from about 70 BPM to about 170 BPM at the time of treating, and has does not exhibit, or has not exhibited myocardial infarction, myocardial ischemia, atrial stenosis, hypertrophic cardiomyopathy, and heart failure with reduced ejection fraction.

In some embodiments, a subject treated with a pharmaceutical composition of the disclosure does not exhibit, or has not exhibited a condition selected from the group consisting of: Long QT syndrome, Conduction disease (e.g. second- or third-degree heart block, bundle branch block), Sick sinus syndrome, Brugada Syndrome, and Torsades de pointed (TdP). In some embodiments, a subject treated with a pharmaceutical composition of the disclosure does not exhibit an ECG-related feature selected from the group consisting of: a QTc interval greater than 480 msec (estimated by the Fridericia's formula); a QRS duration greater than 105 ms; monomorphic or polymorphic ventricular tachycardias that are either sustained or not sustained; and excessive premature ventricular contractions, greater than 20 multi-focal PVC's per hour (ventricular extrasystoles); and a predominantly paced heart rhythm.

In some embodiments, a subject treated with a pharmaceutical composition of the disclosure does not exhibit severe renal impairment, wherein a eGFR of the subject is less than 30 mL/min/1.73 m2. In some embodiments, a subject treated with a pharmaceutical composition of the disclosure is not on dialysis. In some embodiments, a subject treated with a pharmaceutical composition of the disclosure does not exhibit abnormal liver function. In some embodiments, the abnormal liver function is hepatic disease or biochemical evidence of significant liver derangement. In some embodiments, a subject treated with a pharmaceutical composition of the disclosure does not exhibit uncorrected hypokalemia. In some embodiments, a subject treated with a pharmaceutical composition of the disclosure does not exhibit a serum potassium less than 3.6 mEq/L.

In some embodiments, a subject treated with a pharmaceutical composition of the disclosure does not exhibit an established pulmonary disease in need of inhalation medication. In some embodiments, a subject treated with a pharmaceutical composition of the disclosure does not exhibit, or has not exhibited a hypersensitivity to flecainide acetate or any of its active metabolites. In some embodiments, a subject treated with a pharmaceutical composition of the disclosure is not concomitantly administered a systemic drug that is an inhibitor of CYP 2D6. In some embodiments, the inhibitor of CYP 2D6 is an antidepressant, a neuroleptic, or an antihistamine. In some embodiments, the inhibitor of CYP 2D6 is propranolol or ritonavir. In some embodiments, a subject treated with a pharmaceutical composition of the disclosure is not concomitantly administered a systemic drug that is a CYP 2D6 inducer. In some embodiments, the CYP 2D6 inducer is phenytoin, phenobarbital, or carbamazepine.

In some embodiments, a subject treated with a pharmaceutical composition of the disclosure has not been treated with a Class I or a Class II antiarrhythmic drug within a week prior to administration of the pharmaceutical composition. In some embodiments, a subject treated with a pharmaceutical composition of the disclosure with an ongoing episode of atrial fibrillation has not been treated with a Class I or a Class III antiarrhythmic drug since onset of the ongoing episode. In some embodiments, a subject treated with a pharmaceutical composition of the disclosure is administered no more than 320 mg flecainide or a pharmaceutically acceptable salt thereof per day from any source. In some embodiments, a subject treated with a pharmaceutical composition of the disclosure with an ongoing episode of atrial fibrillation has not been treated with electrical cardioversion since onset of the ongoing episode. In some embodiments, a subject treated with a pharmaceutical composition of the disclosure has not been treated with amiodarone within 12 weeks prior to administration of the pharmaceutical composition. In some embodiments, a subject treated with a pharmaceutical composition of the disclosure has not been considered high risk for stroke based on screening coagulation panel. In some embodiments, a subject treated with a pharmaceutical composition of the disclosure does not exhibit a CHA2DS2-VASc score greater than 2.

In some embodiments, a subject treated with a pharmaceutical composition of the disclosure does not exhibit a congenital heart disease. In some embodiments, a subject treated with a pharmaceutical composition of the disclosure has not exhibited refractory atrial fibrillation that has been pharmacologically or electrically cardioverted. In some embodiments, a subject treated with a pharmaceutical composition of the disclosure does not exhibit atrial fibrillation that is secondary to electrolyte imbalance, thyroid disease, or a non-cardiovascular cause. In some embodiments, a subject treated with a pharmaceutical composition of the disclosure does not exhibit syncope.

In some embodiments, a subject treated with a pharmaceutical composition of the disclosure does not exhibit any serious or life threatening medical condition other than cardiac arrhythmia. In some embodiments, a subject treated with a pharmaceutical composition of the disclosure does not exhibit an acute pathogenic infection.

In some embodiments, a subject treated with a pharmaceutical composition of the disclosure has not exhibited a drug or alcohol dependence within 12 months prior to administration of the pharmaceutical composition. In some embodiments, a subject treated with a pharmaceutical composition of the disclosure does not exhibit a body mass index greater than 40 Kg/m$^2$.

In some embodiments, a subject treated with a pharmaceutical composition of the disclosure:
(i) suffers from an atrial fibrillation with an onset that occurred from 1 hour to 48 hours prior to the treating;
(ii) has undergone cardiac ablation no less than 3 months prior to the treating, has an ongoing prescription for oral flecainide or a pharmaceutically acceptable salt thereof, or suffers from recurrent atrial fibrillation;
(iii) is from 18 years old to 85 years old;
(iv) has a systolic blood pressure that is from about 100 mmHg to about 160 mmHg; and
(v) has a ventricular rate that is from about 80 BPM to about 155 BPM, wherein the subject does not exhibit:
(a) abnormal left ventricular ejection fraction within 6 months prior to the treating;
(b) heart failure that is class 2 or greater as classified by New York Heart Association Functional Classification within 6 months prior to the treating;
(c) myocardial infarction or a history thereof;
(d) hemodynamic or cardiac instability; and
(e) an episode of atrial flutter within 6 months prior to the treating, wherein the subject has not undergone cardiac surgery for any of the conditions of (a)-(e) within 6 months prior to the treating.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: Solubility of Flecainide Salts

This example illustrates that flecainide acetate, among the different flecainide salts that were tested, had the highest solubility in water. This example also illustrates that sodium chloride, which is suggested to be desirable to be added to inhalation formulation to reduce the incidence of cough, can render precipitation of flecainide free base when added into flecainide solution.

In this example, the solubility of flecainide citrate, flecainide phosphate, flecainide hydrochloride, and flecainide nitrate were all compared with that of flecainide acetate. As shown in TABLE 1, the solubility of flecainide acetate in water was at least an order of magnitude higher than the other salts formed. Moreover, the addition of sodium chloride (e.g. saline) to the formulation results in precipitation and loss of solubility of flecainide acetate from solution. X-ray powder diffraction (XRPD) analysis confirmed that there is form conversion when sodium chloride was added into the solution.

TABLE 1

Solubility comparison of different flecainide salts

| Media | | Concentration (mg/mL) | | |
|---|---|---|---|---|
| (0.1M) | pH | Freebase | Anion | Ksp |
| Acetic Acid | 4.6 | 64.01 | 16.04 | 4.20E−02 |
| Nitric Acid | 4.0 | 12.63 | 0.18 | 8.53E−05 |
| Sulfuric Acid | 1.5 | 0.94 | 3.69 | 1.97E−07 |
| Citric Acid | 3.2 | 21.90 | 11.95 | 3.30E−03 |
| Hydrochloric Acid | 5.0 | 5.34 | 0.49 | 1.78E−04 |

It is of note that formulating at a pH under 5.2 can risk undesirable organoleptic properties and toxicity issues. This example suggests that acetate salt of flecainide is more suitable for pharmaceutical formulation than some other salts of flecainide.

Example 2: Solubility of Flecainide Acetate in the Presence of Cyclodextrins

This example demonstrates the change in the water solubility of flecainide acetate in the presence of different cyclodextrins.

In this example, the solubility of flecainide acetate in water was shown to increase with increased concentration of various cyclodextrins. TABLE 2 summarizes the solubility of flecainide acetate as a function of cyclodextrin concentration along with 100 mM acetic acid buffer

TABLE 2

Solubility comparison of flecainide acetate in the presence of different cyclodextrins

| Cyclodextrin | Concentration (% w/v) | pH | Solubility (mg/mL) |
|---|---|---|---|
| α-cyclodextrin | 1 | 5.3 | 52.8 |
| | 2 | 5.4 | 52.8 |
| | 4 | 5.4 | 58.4 |
| | 8 | 5.4 | 71.5 |
| β-cyclodextrin | 1 | 5.3 | 55.0 |
| | 2 | 5.4 | 57.9 |
| γ-cyclodextrin | 1 | 5.4 | 56.2 |
| | 2 | 5.4 | 57.9 |
| | 4 | 5.4 | 61.1 |
| | 8 | 5.5 | 69.7 |
| | 10 | 5.5 | 71.1 |
| | 12 | 5.5 | 70.4 |
| hydroxypropyl-β-cyclodextrin | 1 | 5.3 | 56.0 |
| | 2 | 5.4 | 57.7 |
| | 4 | 5.4 | 60.4 |
| | 8 | 5.5 | 66.5 |
| methyl-β-cyclodextrin | 1 | 5.4 | 49.9 |
| | 2 | 5.4 | 53.0 |
| | 4 | 5.4 | 57.2 |
| | 8 | 5.5 | 61.4 |

Additionally, the solubility of flecainide acetate was measured in a constant cyclodextrin concentration (i.e. hydroxypropyl-β-cyclodextrin and β-cyclodextrin) with varying acetic acid buffer concentrations from 0 to 100 mM and there was very little difference observed in their solubility.

The solubility of the flecainide freebase was compared to flecainide acetate using the same buffer and cyclodextrin concentrations. The flecainide acetate concentration was found to be nearly 6 times greater than that of the freebase form.

Example 3: Solubility of Flecainide Acetate in the Presence of hydroxypropy-β-cyclodextrin (HPβCD)

This example demonstrates that solubility of flecainide acetate in water is increased as the concentration of HPβCD in the solution increases.

In this example, the solubility of flecainide acetate in HPβCD (Trappsol® hydroxypropyl-β-cyclodextrin; purchased from CTD Inc.) solutions of different concentrations was tested. The average molecular weight and degree of substitution of the tested HPβCD are 1495 and 6.2, respectively.

Flecainide acetate (dosing concentration: 100-150 mg/mL) was suspended in HPβCD solutions of different concentrations (0% to 180% w/v). The suspension was then magnetic stirred (1000 r/min) at RT for 24 hrs or 48 hrs. The suspension was then subject to centrifugation at 10000 rpm (3 min) and filtration by 0.45 μm membrane to obtain supernatant for HPLC solubility test, and the residual solids were analyzed by X-ray powder diffraction (XRPD) assay.

As shown in TABLE 3, flecainide acetate solubility at 48 hrs increased linearly with the HPβCD concentration in the range of 0%-40% (w/v), which suggests that the complexation may have occurred (FIG. 1). In one experiment, the solubility (48 hrs) of flecainide acetate in 40% (w/v) HPβCD solution reached 104.7 mg/mL (calculated as freebase). In another experiment, the solubility (48 hrs) of flecainide acetate in 40% (w/v) of HPβCD solution reached 108.6 mg/mL (calculated as freebase). It was also observed that flecainide acetate solubility in HPβCD solutions decreased from 60% to 140% (w/v) of HPβCD. The maximum solubility of 124.9 mg/mL (calculated as freebase) was observed in 180% (w/v) HPβCD solution at 24 hrs sampling time.

Within the range of 0%-40% (w/v) of HPβCD, the complexation stability constant ($K_{1:1}$) was determined as 5.75 by Phase Solubility Plot (Higuchi-Connors phase-solubility method).

TABLE 3

Solubility of flecainide acetate in HPBCD solution

| HP-β-CD Concentration | | 48 hrs Flecainide Acetate Solubility | |
|---|---|---|---|
| % w/v | mol/mL | mg/mL | mol/mL |
| 0 | 0 | 65.5 | 0.138 |
| 10 | 0.067 | 78.8 | 0.166 |
| 20 | 0.134 | 89.1 | 0.188 |
| 30 | 0.201 | 109.5 | 0.231 |
| 32 | 0.214 | 110.9 | 0.234 |
| 34 | 0.227 | 113.7 | 0.24 |
| 36 | 0.241 | 115.4 | 0.243 |
| 38 | 0.254 | 116.2 | 0.245 |
| 40 | 0.268 | 120.2 | 0.253 |

Example 4: Viscosity of Flecainide Acetate-HPβCD Solution

This example demonstrates the impact of HPβCD concentration on solution viscosity.

In this example and the following examples, the (HP)-β-cyclodextrin used is "Cavitron W7 HP7 PHARMA". The manufacturer (Ashland) specifies: <1.5% beta cyclodextrin (our batch had 1%) and molar substitution is between 0.86 and 1.14 (our batch had 1.05). From the manufacturer's brochure, the typical degree of substitution is 6.0 to 8.0 with an approximate average MW of 1520.

Higuchi-Connors phase-solubility experiments on solutions adjusted to a pH of 5.2 with NaOH confirmed that the complexation efficiency of HPβCD: flecainide acetate was 0.8, which means 80% of HPβCD molecules were complexed with flecainide acetate. As shown in Table 4, solution viscosity was increased with the addition of HPβCD. However, aerosol properties are not significantly affected up to at least about 22.5% HPβCD. Beyond this concentration, the aerosol output rate can diminish slightly.

TABLE 4

Viscosity of Flecainide Acetate HPβCD Solutions

| Formulation | Viscosity |
|---|---|
| 75 mg/mL FA (flecainide acetate), 90 mM AA (acetic acid), 10%w/v HPβCD, pH 5.2 | 1.8 cP |
| 88 mg/mL FA, 90 mM AA, 20% w/v HPβCD, pH 5.9 | 2.9 cP |
| 100 mg/mL FA, 90 mM AA, 30% w/v HPβCD, pH 5.9 | 4.9 cP |

Example 5: Pharmacokinetics and Pharmacodynamics Study in Pig Models

This example demonstrates the bioequivalence and pharmacodynamic equivalence of exemplary cyclodextrin-containing flecainide acetate formulations as compared to original flecainide acetate formulation.

IV Infusion.

Experiments were carried out in pigs to determine the pharmacokinetics (PK) at the same dose of flecainide delivered via IV infusion.

In these example, there solutions (original and new cyclodextrin-containing formulations) were prepared and compared in pig models of atrial fibrillation: (1) 75 mg/mL flecainide acetate, 10% sulfobutylether-β-cyclodextrin, 90 mM acetic acid, pH 5.2; (2) 75 mg/mL flecainide acetate, 10% hydroxypropyl-β-cyclodextrin, 90 mM acetic acid, pH 5.2; and (3) 35 mg/mL flecainide acetate, 90 mM acetate buffer, pH 5.2.

Each pig was given the same dose of flecainide using the three solutions in a cross-over design experiment with an intervening wash-out period of 2 hours.

Figure 2:
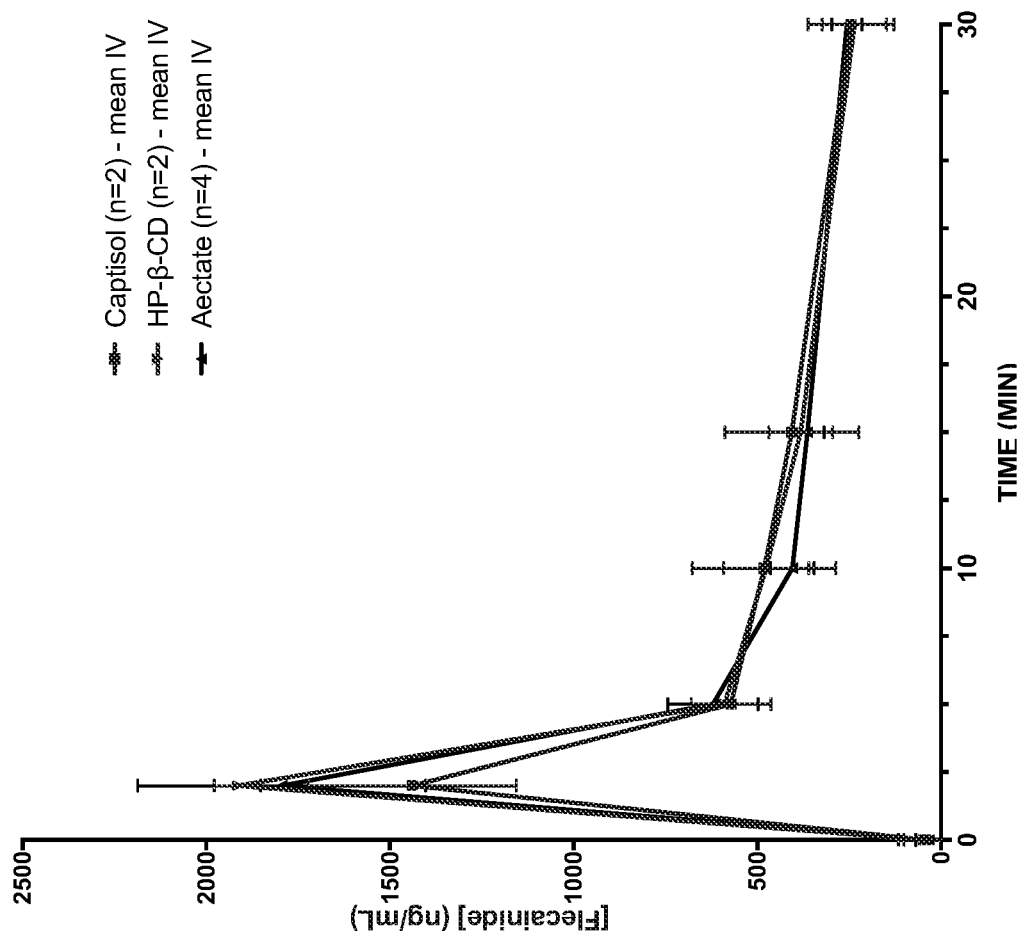
FIG. 2 is a chart summarizing pharmacokinetic profiles of three different flecainide formulations when delivered via intravenous infusion in pig model of atrial fibrillation.
Figure 3A:
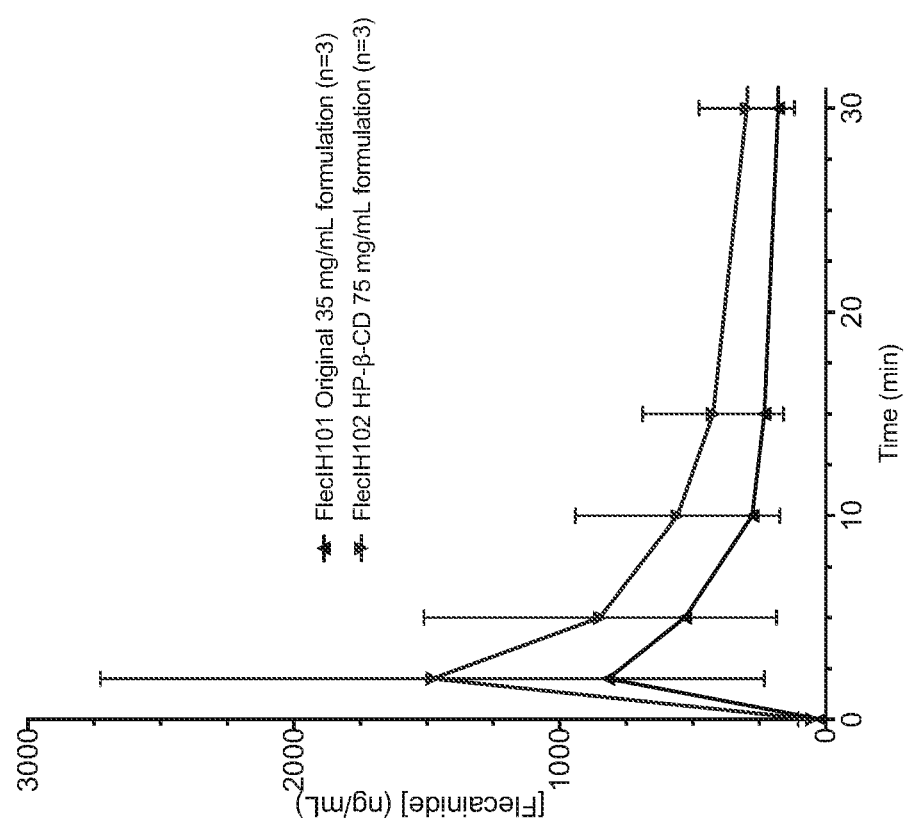
FIG. 3A is a chart summarizing pharmacokinetic profiles (plasma concentration of flecainide acetate) of two different flecainide formulations when delivered via intratracheal instillation at a dose of 0.75 mg/kg in pig model of atrial fibrillation.
Figure 3B:
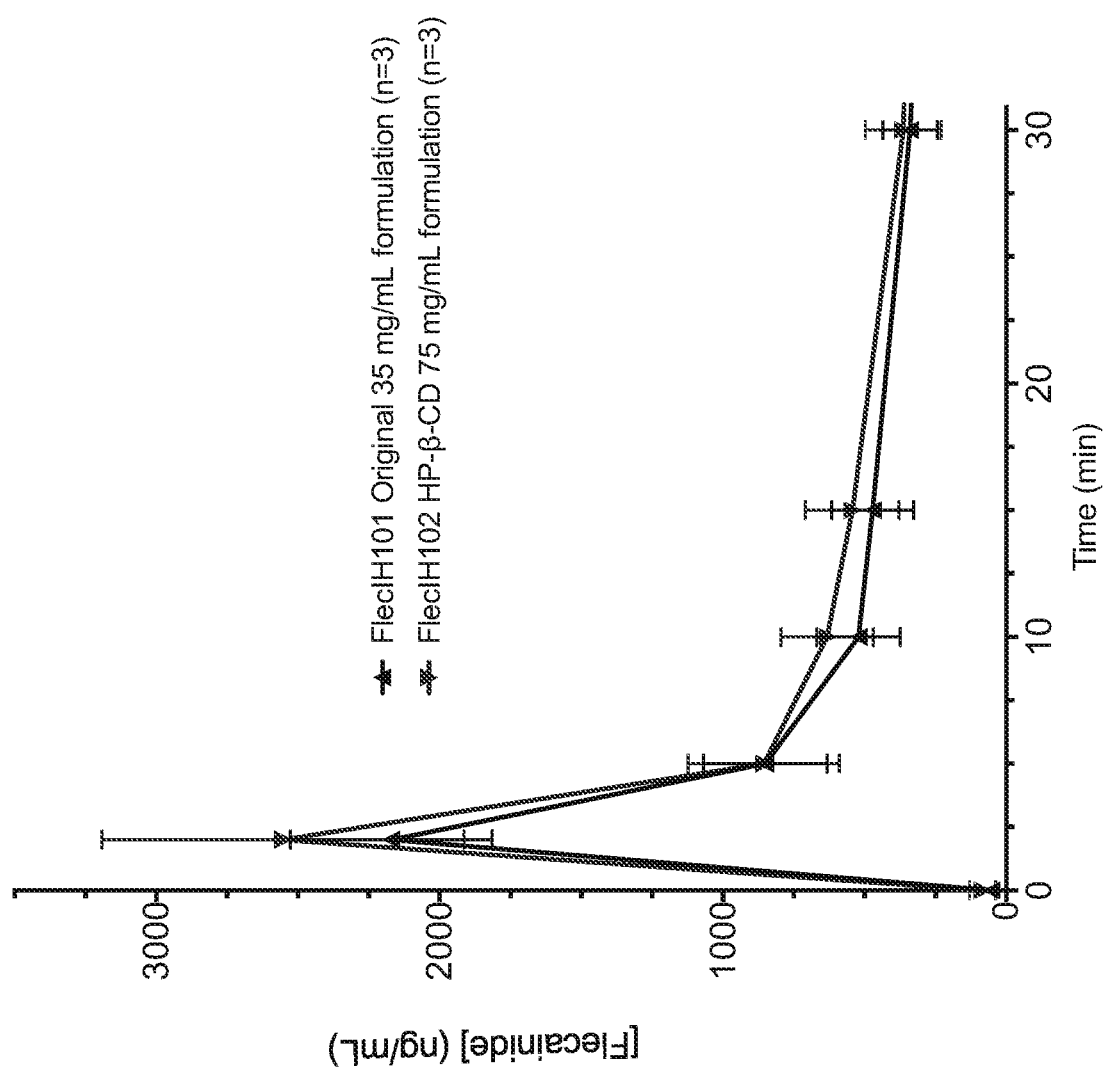
FIG. 3B is a chart summarizing pharmacokinetic profiles (plasma concentration of flecainide acetate) of two different flecainide formulations when delivered via intratracheal instillation at a dose of 1 mg/kg in pig model of atrial fibrillation.
Figure 4A:
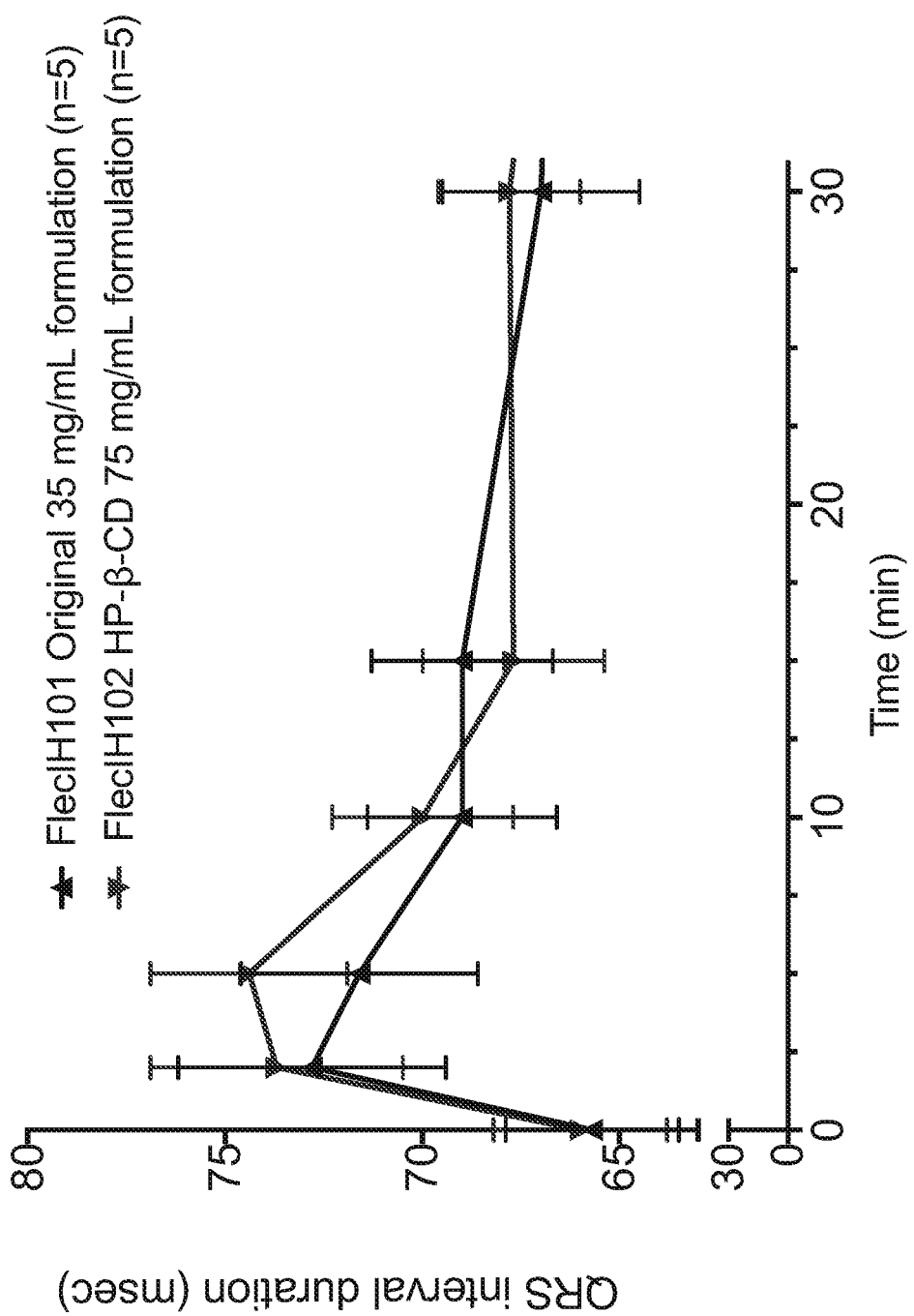
FIGS. 4A and 4B are charts summarizing pharmacodynamic profiles (QRS interval duration and atrial depolarization, respectively) of two different flecainide formulations when delivered via intratracheal instillation at a dose of 0.75 mg/kg in pig model of atrial fibrillation.
Figure 4B:
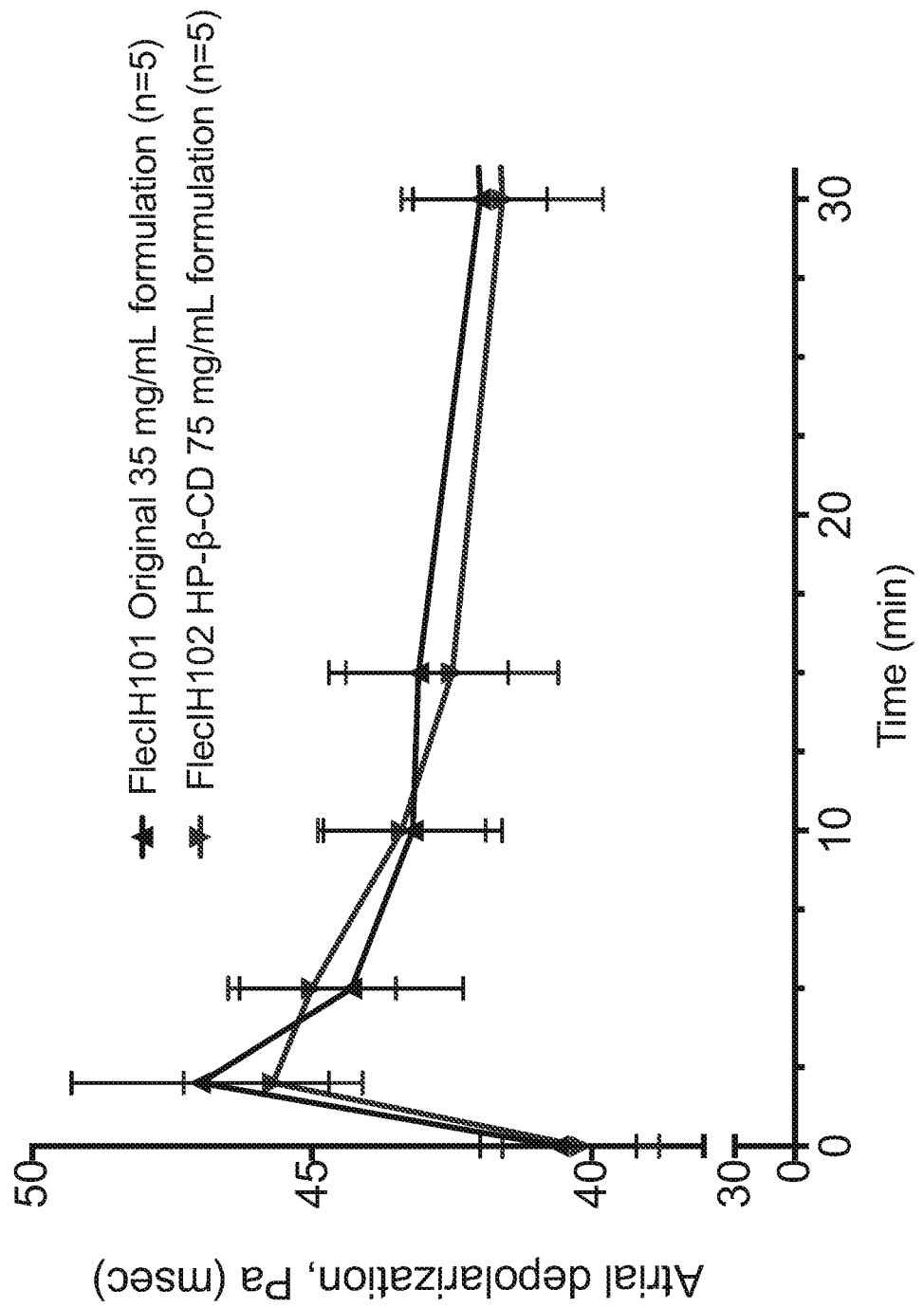
Figure 4C:
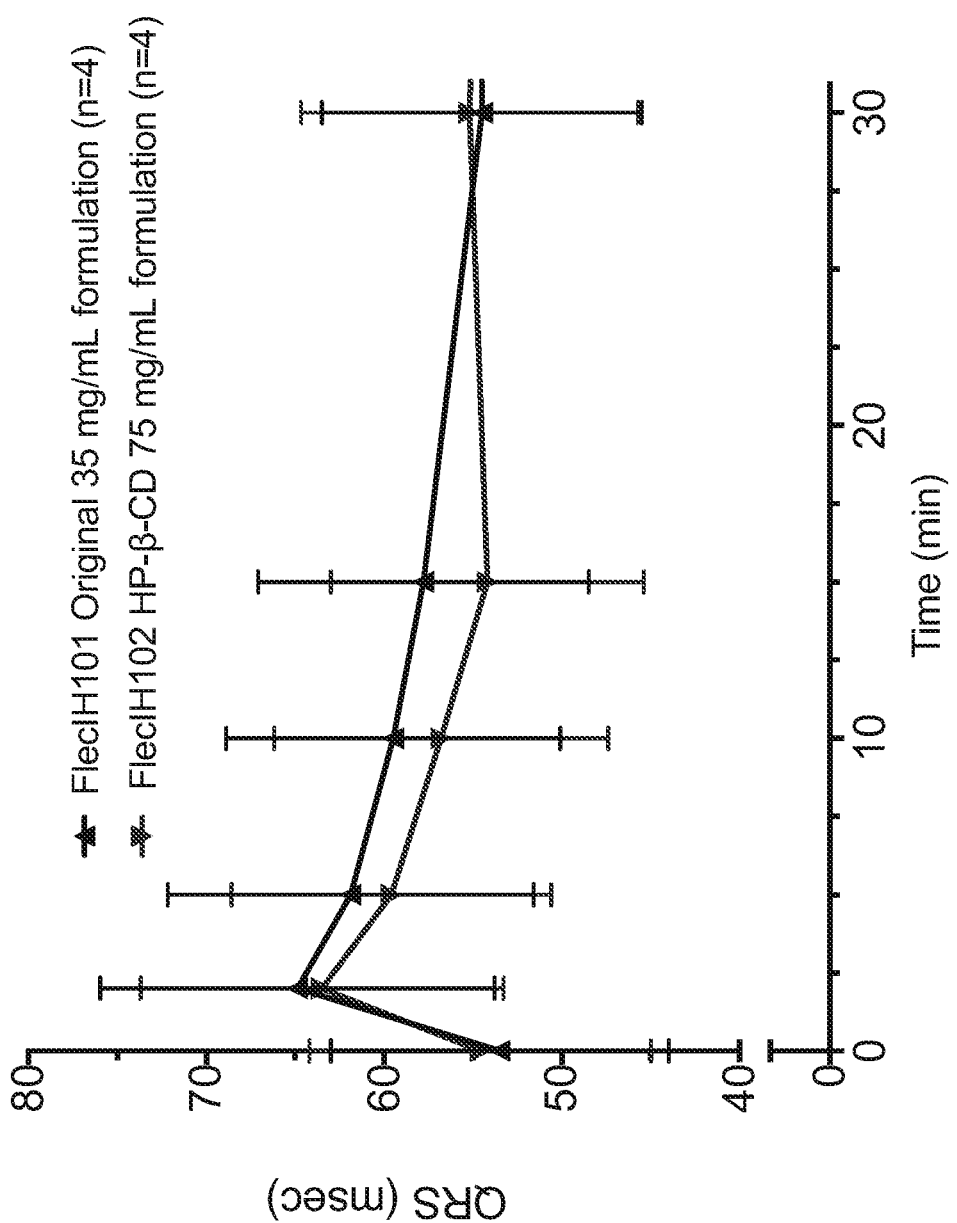
FIGS. 4C and 4D are charts summarizing pharmacodynamic profiles (QRS interval duration and atrial depolarization, respectively) of two different flecainide formulations when delivered via intratracheal instillation at a dose of 1 mg/kg in pig model of atrial fibrillation.
Figure 4D:
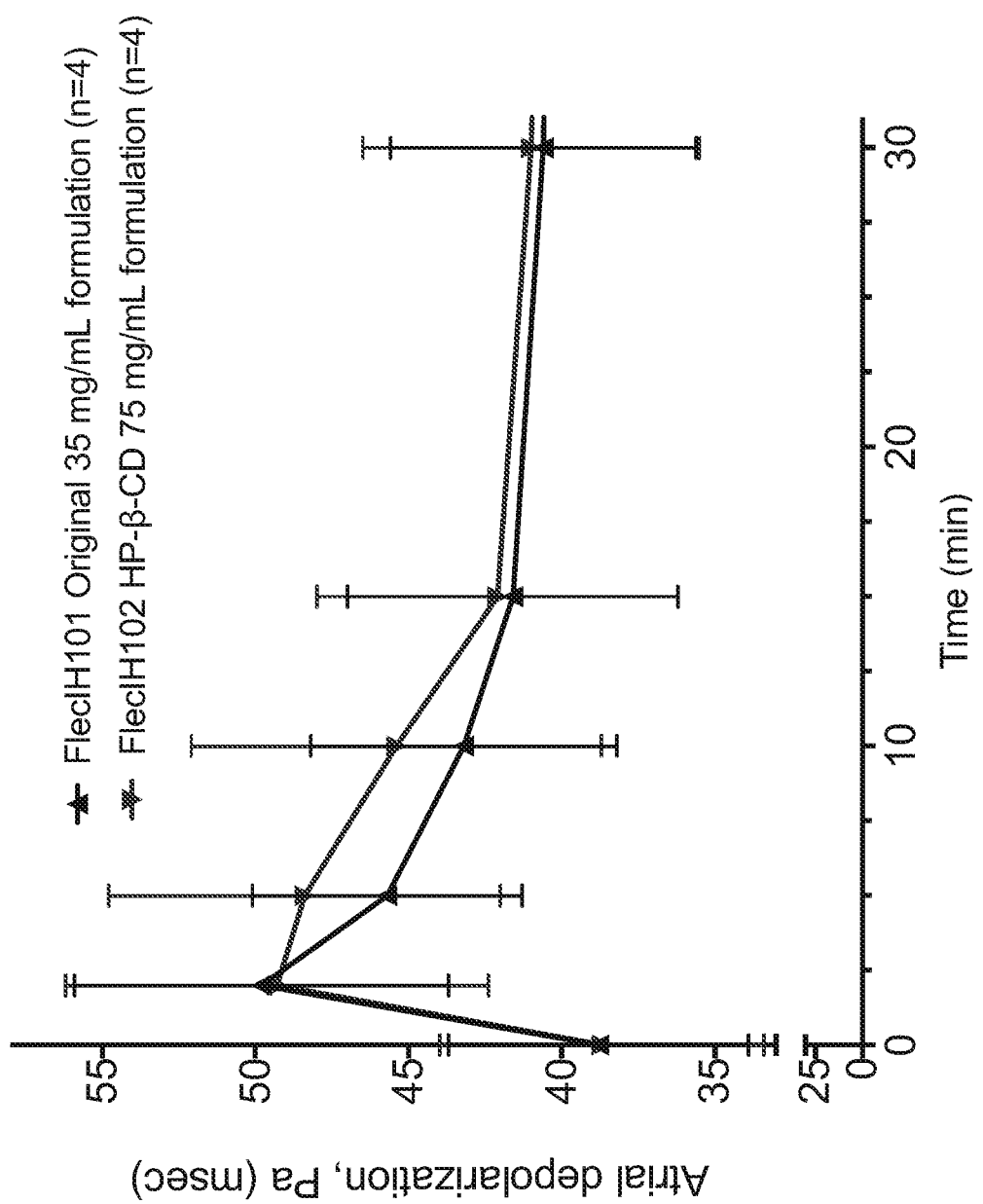
Figure 5:
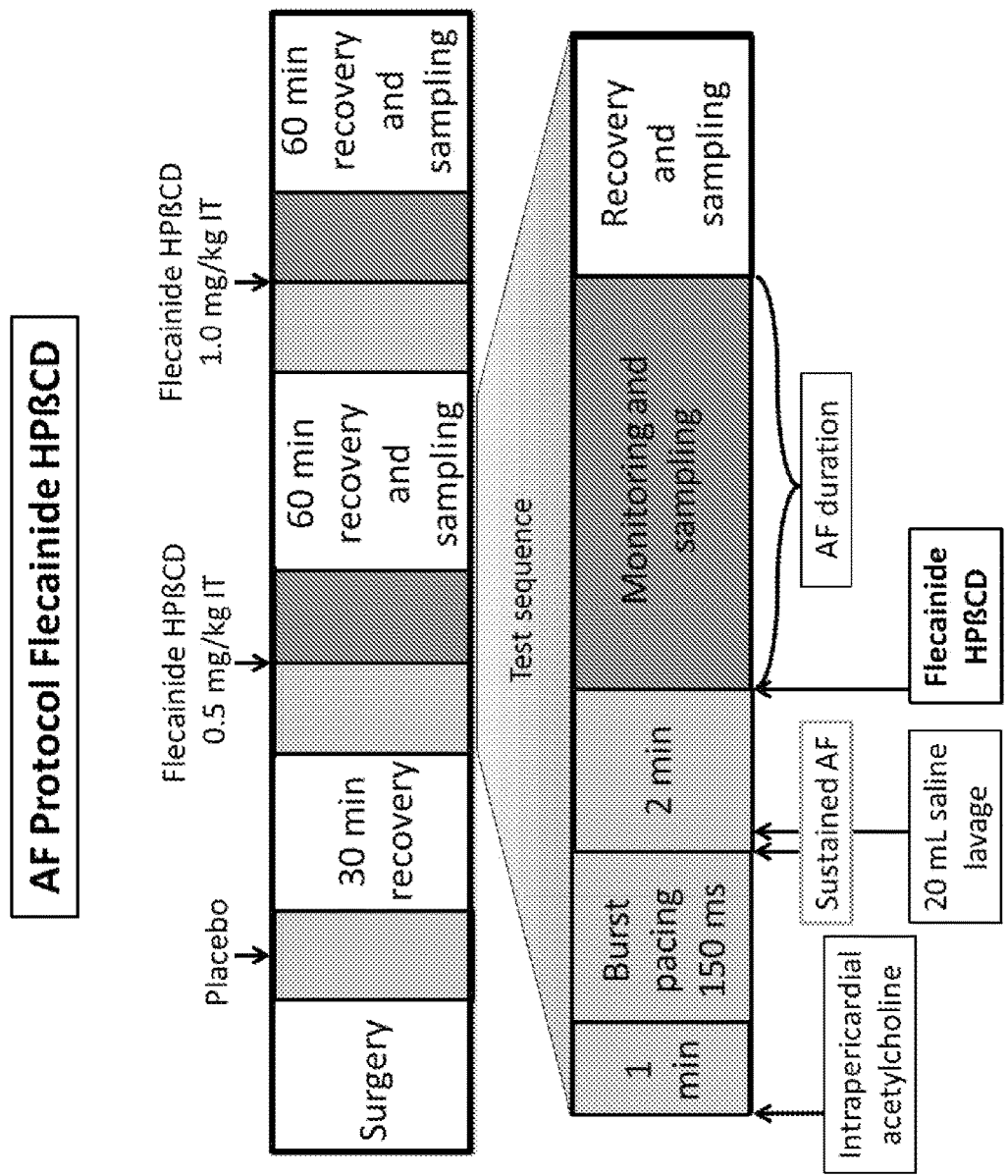
FIG. 5 is a schematic of experiment design in Example 9.

When adjusted for equivalent dose (1 mg/Kg body weight) and dose infusion rate (10 minutes), the three solutions appeared to result in near-equivalent PK profiles in the pig animal model, as shown in FIG. 2.

It was also observed that the $C_{max}$ attained with sulfobutylether-β-cyclodextrin was lower (about 20%) than that with hydroxypropyl-β-cyclodextrin and the original 35 mg/ml flecainide acetate formulations. The PK profile with hydroxypropyl-β-cyclodextrin was more similar to (7% higher in Cmax) that with the 35 mg/mL acetate buffer formulation. The Cmax, distribution and elimination phases were all near-identical between HPβCD and the original 35 mg/ml flecainide acetate formulation. This suggests that complexation between flecainide acetate and the cyclodextrins is loose and flecainide dissociates quickly once it is delivered into the systemic bloodstream.

IT Instillation.

Experiments were carried out in pigs to determine the pharmacokinetics (PK) and pharmacodynamics (PD; duration of QRS interval and atrial depolarization, Pa) at the same dose of flecainide delivered via IV infusion and intratracheal instillation, using two formulations.

In these examples, there solutions (original and new cyclodextrin-containing formulations) were prepared and compared in pig models of atrial fibrillation: (1) 75 mg/mL flecainide acetate, 10% hydroxypropyl-β-cyclodextrin, 90 mM acetic acid, pH 5.2; and (2) 35 mg/mL flecainide acetate, 90 mM acetate buffer 35 mg/mL, pH 5.2.

When adjusted for equivalent dose (0.75 mg Kg body weight and 1 mg/Kg body weight) and dose infusion rate (10 minutes), the two solutions appeared to result in near-equivalent PK and PD profiles in the pig animal model, as shown in FIGS. 3A-3B and 4A-4D.

Example 6: Safety Assessment of Inhalation Delivery of Flecainide Acetate Formulations Five Good Laboratory Practice (GLP) compliant 14-day repeat dose inhaled studies in rats and dogs were conducted to assess potential toxicology associated with FlecIH-101, FlecIH-102, and FlecIH-103 formulations (TABLE 5).

TABLE 5

| | Study Formulation* | Study Type** | Species | Study Description | NOAEL (mg/kg/day) |
|---|---|---|---|---|---|
| 1 | FlecIH-101 | 14-Day with recovery and TK | Rat | 14-Day nose only inhalation study with 14-day recovery | 28.7 |
| 2 | FlecIH-102 | 14-Day with recovery and TK | Rat | 14-Day nose only inhalation study with 14-day recovery; neurobehavioral assessments | 67.7 |
| 3 | FlecIH-103 | 14-Day with recovery and TK | Rat | 14-Day nose only inhalation study with 14-day recovery; neurobehavioral assessments | 30 |
| 4 | FlecIH-101 | 14-Day with recovery and TK | Dog | 14-Day face mask inhalation study with 14-day recovery; respiratory and cardiovascular safety pharmacology | 8.03 |
| 5 | FlecIH-102 | 14-Day with recovery and TK | Dog | 14-Day face mask inhalation study with 14-day recovery; respiratoryand cardiovascular safety pharmacology | 9.87 |

*See TABLE 19 for composition of each formulation.
**TK: Toxicokinetic
***No Observed Adverse Effect Level Results indicated that inhaled flecainide resulted in no new or unusual toxicology associated with inhalation of flecainide compared with the marketed IV and oral flecainide dosage forms. The No Observed Adverse Effect Levels (NOAELs) for the 14-day repeat dose rat and dog toxicology studies conducted with flecainide acetate in the acetic acid formulation (FlecIH-101) were 28.7 mg/kg/day (Study 1) and 8.03 mg/kg/day (Study 4), respectively; and the NOAELs for the 14-day repeat dose rat and dog toxicology studies conducted with flecainide acetate in the acetic acid formulation containing hydroxypropyl-β-cyclodextrin (Flec-IH-102) were 67.7 mg/kg/day (Study 2) and 9.87 mg/kg/day (Study 5), respectively. A bridging 14-day repeat dose rat study confirmed that 30 mg/kg/day flecainide acetate was the NOAEL in the acetic acid formulation containing hydroxypropyl-β-cyclodextrin and sodium saccharin (FlecIH-103, Study 3).

The critical effects identified were high dose respiratory tract findings in the rat inhalation toxicity study involving mild squamous cell metaplasia in the nose, minimal to mild squamous metaplasia in the larynx, and in the lung minimal to mild alveolar macrophage aggregates and neutrophilic infiltrates.

Overall, results indicate that nose-only exposure of rats to inhaled flecainide acetate at inhaled doses of 28.7-147.6 mg/kg resulted in few clinical signs, and no effects on body weight, neurobehavioral and clinical pathology parameters. Histopathological changes in the lungs, larynx and nasal turbinates during the dosing period were non-adverse changes at the lowest dose tested. Therefore, the NOAEL was 28.7 mg/kg flecainide by inhalation.

Inhalation toxicity studies were conducted in dogs. Overall, inhaled flecainide presented at doses up to 8.03 mg/kg in Study 4, and 9.87 mg/kg/day in Study 5 for 14 days (average for both genders) did not result in any adverse effects in clinical signs, body weights, clinical pathology parameters, pulmonary function parameters or histopathological changes. Electrocardiography showed changes of small magnitude in the PR intervals, QRS intervals, and HR. While possibly test-article related, these are non-adverse changes; therefore, the NOAEL was considered to be 9.87 mg/kg. Detailed study parameters and results for Study 5 are summarized below.

Study 5.

This example describes a 14-day repeated-dose toxicity study via face mask inhalation with 14 day recovery in dogs. The objective of this study was to evaluate the potential toxicity of aerosolized flecainide from the exemplary inhalation solution (75 mg/mL flecainide acetate/10% w/v HPβCD/90 mM acetic acid buffer formulation at pH 5.2) after face mask inhalation exposure for 14 consecutive days in Beagle dogs (4 dogs/sex/group), and to investigate whether the potential effects were reversible after a 14 day recovery period (2 dogs/sex/group); air and vehicle control groups were included. The study design is shown in TABLE 6.

TABLE 6

Study Design of Toxicity Assessment in Dogs

| Exposure | Exposure Duration (min) | Dose (mg/kg/day) M | F | Main Study M | F | Recovery M | F | TK Blood Collections | |
|---|---|---|---|---|---|---|---|---|---|
| Air | 60 | NA | NA | 4 | 4 | 2 | 2 | 6 | 6 |
| Vehicle | 60 | NA | NA | 4 | 4 | 2 | 2 | 6 | 6 |
| Low Dose | 10 | 1.68 | 2.04 | 4 | 4 | 2 | 2 | 4 | 4 |
| Mid Dose | 30 | 4.59 | 5.52 | 4 | 4 | 2 | 2 | 4 | 4 |
| High Dose | 60 | 9.75 | 9.98 | 4 | 4 | 2 | 2 | 6 | 6 |

In addition to the aerosol drug concentration, the aerosol particle size distribution was also characterized. The particle size average MMAD and GSD for the Low-, Mid-, and High-dose groups were 2.38 (1.79), 2.03 (1.87) and 2.08 (1.79) microns, respectively, and 1.74 (1.88) microns for vehicle control group. Average presented flecainide acetate doses were 1.86, 5.08, and 9.88 mg/kg in Low-, Mid- and High-dose groups respectively. Chamber oxygen levels were monitored throughout the exposures. Main study animals were sacrificed on Day 15. Recovery animals were sacrificed on Day 29 following a 14-day recovery period. Endpoints included clinical observations, body weights, ophthalmology, clinical pathology, urinalysis, gross pathology, histopathology, and bioanalytical and toxicokinetic analyses.

All study dogs survived to the scheduled euthanasia without instance of morbidity or mortality. Body weights showed no treatment related differences. The most common clinical observation was soft stool and occurred with similar incidence across genders and study groups periodically for the duration of the study; none of the clinical observations appeared related to flecainide or vehicle exposures. The only observation associated with flecainide exposure was labored respiration during or immediately post exposure; this occurred in several Mid- or High-dose animals on Day 1 or Day 7. In post-study ophthalmology examinations, new cataracts (less than 5% of lens) were observed in 5 dogs in the air control (2), Low-dose (1) and Mid-dose (2) groups, but not in any vehicle control or High-dose animals. Due to the small size, they may have been present but undetected on the pre-study exam. Respiratory parameters indicated no significant effect of exposure at any dose level or any time point. All ECGs were considered normal with no rhythm or waveform abnormalities. Small changes in heart rate, PR intervals and QRS intervals were possibly test-article related but were not considered adverse findings.

Statistically significant clinical chemistry, hematology and coagulation changes generally did not occur with consistency across genders or dose during the treatment or recovery periods points and were generally of small magnitude. Tissues were generally unremarkable upon gross examination. Necropsy findings of lung and thymus discoloration were observed in several vehicle and flecainide animals during treatment and in the recovery period. Other sporadic incidental gross observations occurred that were within normal limits or background level, and were not test article related. Minor, sporadic incidental histologic findings, as expected, occurred in this study. Such findings included cysts and minor infiltrates of various cell types. These were sporadic and/or occurred with a prevalence, character and severity that were indistinguishable from controls. There were no histopathologic changes attributable to treatment with the test article.

Overall, inhaled flecainide administered at doses up to 9.88 mg/kg/day for 14 days (average for both genders) did not cause any adverse effects in clinical signs, body weights, clinical pathology parameters, pulmonary function parameters or histopathological changes. Electrocardiography showed changes of small magnitude in the PR intervals, QRS intervals, and HR. While possibly test-article related these are non-adverse changes; therefore, the NOAEL was considered to be 9.88 mg/kg.

In summary, inhaled flecainide from the exemplary inhalation solution (75 mg/mL flecainide acetate/10% w/v HP-β-cyclodextrin/90 mM acetic acid buffer formulation at pH 5.2) using a face mask for 14 consecutive days in male and female Beagle dogs showed comparable results to those from the study conducted with the original inhalation solution (35 mg/mL flecainide acetate/90 mM acetic acid buffer formulation at pH 5.2).

Example 7: Exemplary Formulations with Reduced Acetic Acid Strength

This example demonstrates that in the presence of HPβCD, flecainide acetate solution can have less acetic acid buffer and can still maintain the solubility of flecainide acetate at concentrations higher than 125 mg/mL.

Although flecainide acetate shows high solubility at 0 mM acetic acid, freebase was observed to crash out in some instances. This was not observed at higher buffer strengths.

TABLE 7

Solubility of Flecainide Acetate at Different Acetic Acid Concentrations

| Cyclodextrin | Concentration (mM) | pH | Solubility (mg/mL) |
|---|---|---|---|
| hydroxypropyl-β-cyclodextrin (40% w/v) | 0 | 6.3 | 125 |
| | 25 | 5.5 | 131 |
| | 50 | 5.2 | 135 |
| | 75 | 5.1 | 135 |
| | 100 | 4.9 | 136 | w/v HPβCD/90 mM acetic acid buffer formulation at pH 5.2. The properties that the evaluation was based on were: sensation upon inhalation (burning/stinging/tingling or numbness); bitter taste/aftertaste in throat, cough, hoarseness of voice etc. Only 1 inhaled solution was tested per day per volunteer.

This evaluation was performed with in 3 consecutive iterations with different formulations to compare the various formulations in terms of their various concentrations of the active ingredient (flecainide acetate), pH of solution and other varying excipients.

Based on the observations made by the healthy volunteers, the most acceptable formulation as an inhalation solution in terms of the inhalation experience when compared to the control (75 mg/mL flecainide acetate/10% w/v HPβCD 90 mM acetic acid buffer formulation at pH 5.2) was the formulation with lower acetic acid concentration and higher pH (i.e. 75 mg/mL Flecainide acetate, 5 mM acetic acid, 20% w/v HPβCD in WFI, pH5.99).

Experiment #1

The set of solutions prepared for this experiment are shown in TABLE 8.

TABLE 8

Exemplary Formulations for Organoleptic Experiment #1

| S. No. | Exemplary Formulations | Features/Comments |
|---|---|---|
| 1. | 75 mg/mL Flecainide acetate, 90 mM acetic acid, 10% w/v hydroxypropyl-b-cyclodextrin in WFI, pH 5.2, 5% Mannitol | Control + 5% mannitol |
| 2. | 75 mg/mL Flecainide acetate, 25 mM acetic acid, 10% w/v hydroxypropyl-b-cyclodextrin in WFI, pH 5.2 | Control with lower (25 mM) acetic acid |
| 3. | 75 mg/mL Flecainide acetate, 90 mM acetic acid, 10% w/v hydroxypropyl-b-cyclodextrin in WFI, pH of 5.2 | Control |
| 4. | 75 mg/mL Flecainide acetate, 90 mM acetic acid, 10% w/v hydroxypropyl-b-cyclodextrin in WFI, pH of 5.5 | Control with higher pH (5.5) |
| 5. | 75 mg/mL Flecainide acetate, 90 mM acetic acid, 10% w/v hydroxypropyl-b-cyclodextrin in WFI, pH of 5.2, 10% Ethanol | Control + 10% ethanol |

The acceptability of various formulations of flecainide inhalation solution was evaluated in terms of their organoleptic properties (specifically, the smell/odor, sensation in the mouth and throat and taste) upon oral inhalation of the solution (administered as liquid aerosol).

Inhalation solutions were prepared to identify whether additives (such as mannitol or ethanol), lowering of acetic acid content, or raising the pH can improve their acceptability compared to the 75 mg/mL flecainide acetate/10%

Inhalation device: the inhalation device used for testing was AeroEclipse® II BAN, a hand-held nebulizer. It was run with compressed air from a portable compressor pump, (INVACARE Mobilaire) at 30 psi.

Inhalation procedure: 3 mL of the flecanide inhalation solution was placed in a newly opened package of the inhaler, for each solution tested (single use of inhaler). The subject was asked to relax, place the mouthpiece of the inhaler in the mouth and inhale the solution for about 2 seconds, hold their breath for seconds and release the breath in about 4 seconds for a total time of not greater than 1 minute. This inhalation pattern was roughly followed by all volunteers.

Volunteers: 3 healthy male volunteers, 1 healthy female volunteer. Age of volunteers: 40-68 years.

Observations are summarized in TABLE 9.

TABLE 9

Summary of observations from all 4 volunteers (experiment #1)

| S. No. | Exemplary Formulations | Cough | Burning/ Stinging Of throat | Numbness/ Tingling Of throat or lips | Bitter taste/ aftertaste | Voice turning hoarse | Comments |
|---|---|---|---|---|---|---|---|
| 1. | 75 mg/mL Flecainide acetate, 90 mM acetic acid, 10% w/v hydroxypropyl-b-cyclodextrin in WFI, pH 5.2, 5% Mannitol | high | Moderate | — | low | moderate | |
| 2. | 75 mg/mL Flecainide acetate, 25 mM acetic acid, 10% w/v hydroxypropyl-b-cyclodextrin in WFI, pH 5.2 | low | low | — | low | low | |
| 3. | 75 mg/mL Flecainide acetate, 90 mM acetic acid, 10% w/v hydroxypropyl-b-cyclodextrin in WFI, pH of 5.2 | moderate | moderate | moderate | moderate | Moderate-high | Tightness in throat |
| 4. | 75 mg/mL Flecainide acetate, 90 mM acetic acid, 10% w/v hydroxypropyl-b-cyclodextrin in WFI, pH of 5.5 | moderate | moderate | moderate | moderate | high | |
| 5. | 75 mg/mL Flecainide acetate, 90 mM acetic acid, 10% w/v hydroxypropyl-b-cyclodextrin in WFI, pH of 5.2, 10% Ethanol | high | high | — | moderate | high | Headache, lightheadedness for several hours |

Conclusions: Based on the observations made by the volunteers in the testing above, the most acceptable formulation as an inhalation solution in terms of the inhalation experience when compared to the control was the formulation with lower acetic acid concentration (i.e. 75 mg/mL Flecainide acetate, 25 mM acetic acid, 10% w/v hydroxypropyl-b-cyclodextrin in WFI, pH 5.2).

Experiment #2

The set of solutions prepared for this experiment are shown in TABLE 10.

TABLE 10

Exemplary Formulations for Organoleptic Experiment #2

| S. No. | Exemplary Formulations | Comments |
|---|---|---|
| 1. | 75 mg/mL Flecainide acetate, 90 mM acetic acid, 10% w/v hydroxypropyl-b-cyclodextrin in WFI, pH of 5.2 | Control |

TABLE 10-continued

Exemplary Formulations for Organoleptic Experiment #2

| S. No. | Exemplary Formulations | Comments |
|---|---|---|
| 2. | 75 mg/mL Flecainide acetate, 5 mM acetic acid, 20% w/v hydroxypropyl-b-cyclodextrin in WFI, pH 5.99 | Lower acetic acid, higher cyclodextrin, higher pH |
| 3. | 75 mg/mL Flecainide acetate, 5 mM acetic acid, 20% w/v hydroxypropyl-b-cyclodextrin in WFI, pH 5.99 (+2 drops of liquid Sweet N Low* to 3 mL of IH solution) | Formulation 2 + 2 drops of liquid sweetener |

*Other sweeteners that tried were liquid stevia, sweet n low powder, stevia powder, xylitol containing sprays and lozenges The inhalation device and procedure remained the same as for experiment #1. Number of volunteers was 3 (2 male volunteers+1 female volunteer). The solutions were tested for the same organoleptic properties as for experiment #1.

Observations from all 3 volunteers are summarized in TABLE 11.

TABLE 11

Summary of observations from all 3 volunteers (experiment #2)

| S. No. | Exemplary Formulations | Cough | Burning/ Stinging Of throat | Numbness/ Tingling Of throat or lips | Bitter taste/ aftertaste | Voice turning hoarse | Comments |
|---|---|---|---|---|---|---|---|
| 1. | 75 mg/mL Flecainide acetate, 90 mM acetic acid, 10% w/v hydroxypropyl-b-cyclodextrin in WFI, pH of 5.2 | moderate | moderate | moderate | moderate | Moderate-high | Tightness in throat |
| 2. | 75 mg/mL Flecainide acetate, 5 mM acetic acid, 20% w/v hydroxypropyl-b-cyclodextrin in WFI, pH 5.99 | v. low | low | — | low | low | |
| 3. | 75 mg/mL Flecainide acetate, 5 mM acetic acid, 20% w/v hydroxypropyl-b-cyclodextrin in WFI, pH 5.99 (+ 2 drops of liquid Sweet N Low* to 3 mL of IH solution) | v. low | v. low | — | v. low | low | Much smoother; easier to inhale; less stinging or burning sensation; almost no cough |

Conclusions: Based on the observations made by the volunteers in the testing above, the most acceptable formulation as an inhalation solution in terms of the inhalation experience when compared to the control (1 in table above) was the formulation with lower acetic acid concentration and higher pH (i.e. 75 mg/mL Flecainide acetate, 5 mM acetic acid, 20% w/v hydroxypropyl-b-cyclodextrin in WFI, pH5.99).

Adding 2 drops of liquid *Stevia* or liquid sweet n low (saccharin) to the solution were found to highly improve the inhalation experience. Liquid Sweet Low (containing saccharin; concentration unknown was found to be most effective.

IH flecanide solutions containing varying amounts of saccharin were prepared for testing as a next step.

Experiment 93

The set of solutions containing saccharin prepared for this experiment are shown in TABLE 12.

TABLE 12

Exemplary Formulations for Organoleptic Experiment #3

| S. No. | Composition of solution | Comments |
| --- | --- | --- |
| 1. | 75 mg/mL Flecainide acetate, 5 mM acetic acid, 20% w/v hydroxypropyl-b-cyclodextrin in WFI, pH 5.99 | Lower acetic acid, higher cyclodextrin, higher pH 0 µM sodium saccharin |
| 2. | 75 mg/mL Flecainide acetate, 5 mM acetic acid, 20% w/v hydroxypropyl-b-cyclodextrin in WFI, 250 µM sodium saccharin, pH 5.99 | 250 µM sodium saccharin |
| 3. | 75 mg/mL Flecainide acetate, 5 mM acetic acid, 20% w/v hydroxypropyl-b-cyclodextrin in WFI, 500 µM sodium saccharin, pH 5.99 | 500 µM sodium saccharin |
| 4. | 75 mg/mL Flecainide acetate, 5mM acetic acid, 20% w/v hydroxypropyl-b-cyclodextrin in WFI, 750 µM sodium saccharin, pH 5.99 | 750 µM sodium saccharin |
| 5. | 75 mg/mL Flecainide acetate, 5 mM acetic acid, 20% w/v hydroxypropyl-b-cyclodextrin in WFI, 1000 µM sodium saccharin, pH 5.99 | 1000 µM sodium saccharin |
| 6. | 75 mg/mL Flecainide acetate, 5 mM acetic acid, 20% w/v hydroxypropyl-b-cyclodextrin in WFI, 1250 µM sodium saccharin, pH 5.99 | 1250 µM sodium saccharin |

The inhalation device and procedure remained the same as for experiment #2. Number of volunteers was 3 (2 male volunteers+1 female volunteer). The solutions were tested for the same organoleptic properties as for experiments #1 and 2.

Observations from all 3 volunteers are summarized in TABLE 13.

TABLE 13

Summary of observations from all 3 volunteers (experiment #3)

| S. No. | Composition of solution | Cough | Burning/ Stinging Of throat | Numbness/ Tingling Of throat or lips | Bitter taste/ aftertaste | Voice turning hoarse | Comments |
| --- | --- | --- | --- | --- | --- | --- | --- |
| 1. | 75 mg/mL Flecainide acetate, 5 mM acetic acid, 20% w/v hydroxypropyl-b-cyclodextrin in WFI, pH 5.99 | v. low | low | — | low | low | Voice turned hoarse |
| 2. | 75 mg/mL Flecainide acetate, 5 mM acetic acid, 20% w/v hydroxypropyl-b-cyclodextrin in WFI, 250 µM sodium saccharin, pH 5.99 | Very low | Low | low | low | v. low | Localized burning in the throat |
| 3. | 75 mg/mL Flecainide acetate, 5 mM acetic acid, 20% w/v hydroxypropyl-b-cyclodextrin in WFI, 500 µM sodium saccharin, pH 5.99 | v. low | low | — | low | low | Burning or stinging at the back of throat |

TABLE 13-continued

Summary of observations from all 3 volunteers (experiment #3)

| S. No. | Composition of solution | Cough | Burning/ Stinging Of throat | Numbness/ Tingling Of throat or lips | Bitter taste/ aftertaste | Voice turning hoarse | Comments |
|---|---|---|---|---|---|---|---|
| 4. | 75 mg/mL Flecainide acetate, 5 mM acetic acid, 20% w/v hydroxypropyl-b-cyclodextrin in WFI, 750 µM sodium saccharin, pH 5.99 | v. low | v. low | none | v. low | none | Delayed and minor burning sensation of throat; minor cough reflex; overall the best inhalation experience of all solutions in this set. Easy to inhale. |
| 5. | 75 mg/mL Flecainide acetate, 5 mM acetic acid, 20% w/v hydroxypropyl-b-cyclodextrin in WFI, 1000 µM sodium saccharin, pH 5.99 | low | low | low | — | low | |
| 6. | 75 mg/mL Flecainide acetate, 5 mM acetic acid, 20% w/v hydroxypropyl-b-cyclodextrin in WFI, 1250 µM sodium saccharin, pH 5.99 | low | low | — | Low to moderate | Low to moderate | More burning of throat compared to 750 µM; lingering sensation in throat |

Conclusions: Based on the observations made by the volunteers in the testing above, the most acceptable formulation as an inhalation solution in terms of the inhalation experience when compared to the control (1 in table above) was the formulation the one containing 750 µM saccharin (i.e. 75 mg/mL Flecainide acetate, 5 mM acetic acid, 20% w/v hydroxypropyl-b-cyclodextrin in WFI, 750 µM sodium saccharin, pH 5.99).

Example 8. Further Improvement in Organoleptic Properties by Saccharin

This example demonstrates that organoleptic properties of the inhalation formulation can be further improved by addition of saccharin.

In this example, various products were tested to be used either prior to the inhalation procedure (prophylactic) or immediately following (treat) it with the goal to lessen the unpleasant sensory characteristics of the inhalation solution and thereby, improve the overall inhalation experience. A list of sweeteners that were tested is shown in TABLE 14.

Adding 2 drops of liquid *Stevia* or liquid Sweet-n-Low (saccharin) to the solution were found to highly improve the inhalation experience. Liquid Sweet-n-Low (containing saccharin; concentration unknown) was found to be most effective.

Various sugars (in powdered and liquid form) were used as additives to the flecainide acetate inhalation solution to improve the organoleptic properties, starting with the following FlecIH solution: 75 mg/nm Flecanide acetate, 5 mM acetic acid, 20% w/v hydroxypropyl-b-cyclodextrin in WFI, pH 5.9.

If the sugar was in a powder form, a few grains of it were added to 3 mL of FlecIH inhalation solution and stirred to dissolve. For solutions containing sugars (liquid form), 2 drops of each (exact/precise concentration unknown) were added to 3 mL of Flec IH inhalation solution. In both cases, the solution was "homogenized" by gently swirling the nebulizer while held upright, on the benchtop. Liquids were found to be easier/more convenient to work with than the powdered forms of sugars listed.

TABLE 14

List of Sweeteners Tested for Organoleptic Properties

| S. No. | Product | Country of origin | Results |
|---|---|---|---|
| 1. | Sweet n' low powder sweetener (saccharin) | USA | Lessens the bitter taste in mouth during and after inhalation; less stinging/burning of throat |

TABLE 14-continued

List of Sweeteners Tested for Organoleptic Properties

| S. No. | Product | Country of origin | Results |
|---|---|---|---|
| 2. | Truvia powder sweetener | USA | Lessens bitter taste in mouth during and after inhalation |
| 3. | Equal (aspartame) | USA | Lessens the bitter taste in mouth during and after inhalation |
| 4. | Stevia powder sachet | USA | Lessens the bitter taste in mouth during and after inhalation, less stinging/burning of throat |
| 5. | Aspen Naturals liquid stevia | USA | Much smoother mouthfeel; easier to inhale; less stinging or burning sensation; almost no cough |
| 6. | Now Better Stevia liquid sweetener | USA | Less bitter taste during/after inhalation; smoother mouthfeel |
| 7. | Sweet N' Low liquid sweetener (contains saccharin) | USA | Much smoother mouthfeel; easier to inhale; less stinging or burning sensation; almost no cough |
| 8 angiography catheter positioned in the endotracheal tube at the beginning of the inspiration phase. Sterile water (2 mL followed by 3 mL of air in a 5 mL syringe) was given as the placebo. AF duration was determined starting at the time of drug or placebo delivery until normal sinus rhythm was restored. A washout period of 60 min was allowed between doses. The effects on AF duration, mean arterial pressure (MAP), ventricular rate during AF, and dominant frequency were determined.

Plasma Samples.

Blood samples were drawn from a 7 Fr sheath placed in the jugular vein into sodium heparin tubes at the time when AF terminated and at 0, 2, 5, 10, 15, 30, 45, 60 min after bolus intratracheal flecainide HPβCD administration in the 60-min analysis protocol. All the samples were centrifuged and frozen at −80° C.

Statistical Analysis.

Data are reported as means SEM. Statistical analyses were performed using paired 2-tailed t tests. Statistical significance was assumed at p<0.05. Analysis of variance (ANOVA) with a post hoc Dunnett's test was performed when multiple comparisons were made.

Results.

Time course of plasma levels following intratracheal administration of Flecainide HPβCD.

Figure 6:
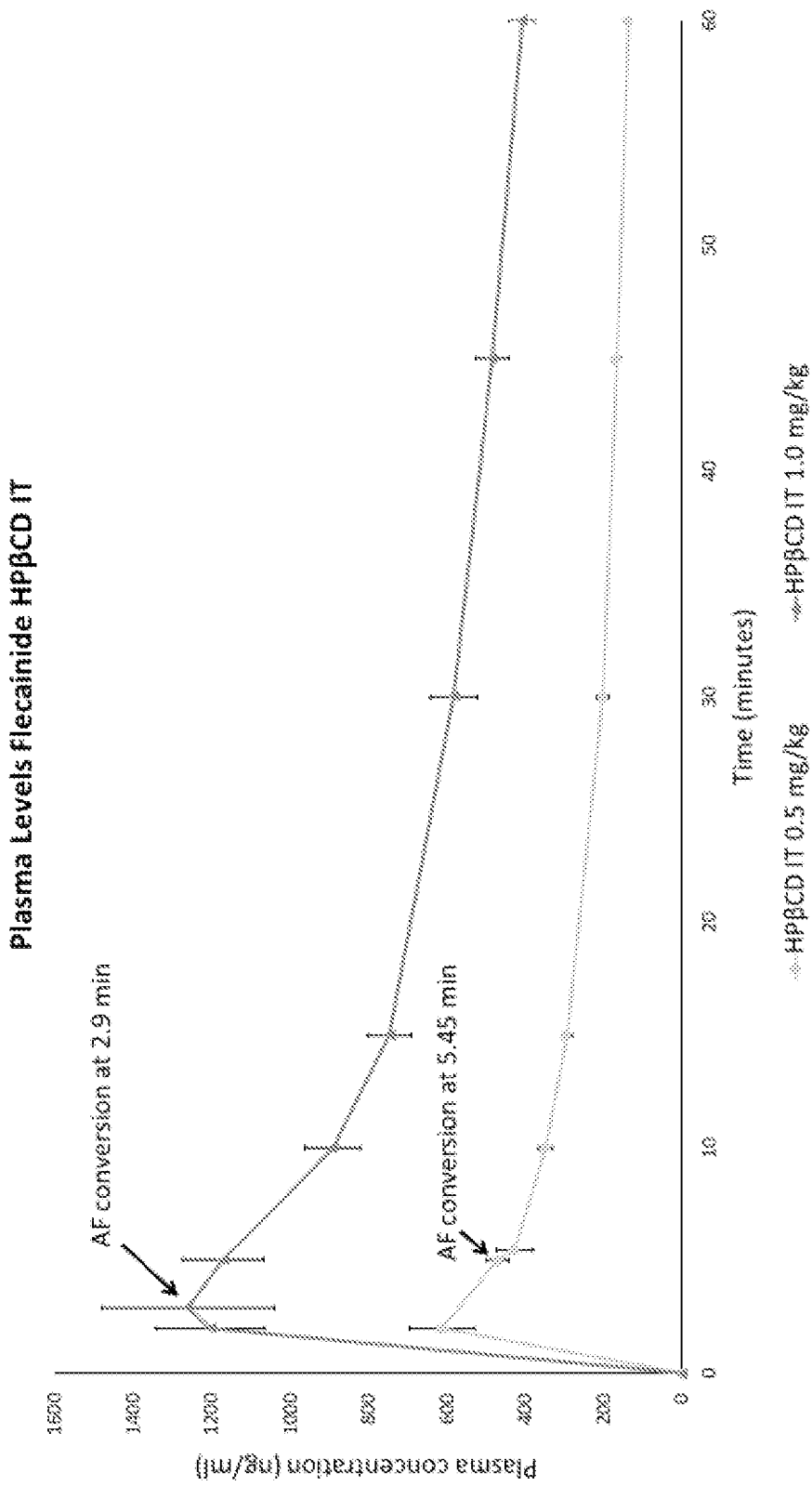
FIG. 6 is a chart summarizing plasma concentration of flecainide acetate when an exemplary HPβCD-flecainide formulation is delivered via intratracheal instillation at two different doses in pig model of atrial fibrillation.

Plasma levels of flecainide at both 0.5- and 1.0 mg/kg intratracheal doses exhibited a classical pharmacokinetic bio-exponential profile with peak levels ($C_{max}$) achieved at 2.0 or 2.8 minutes ($T_{max}$), respectively, after administration of the drug, and followed first by a rapid (distribution phase) and then later by a progressive decline (elimination phase) in plasma concentration of the drug (FIG. 6).

Effects on Atrial Fibrillation Duration.

Figure 7:
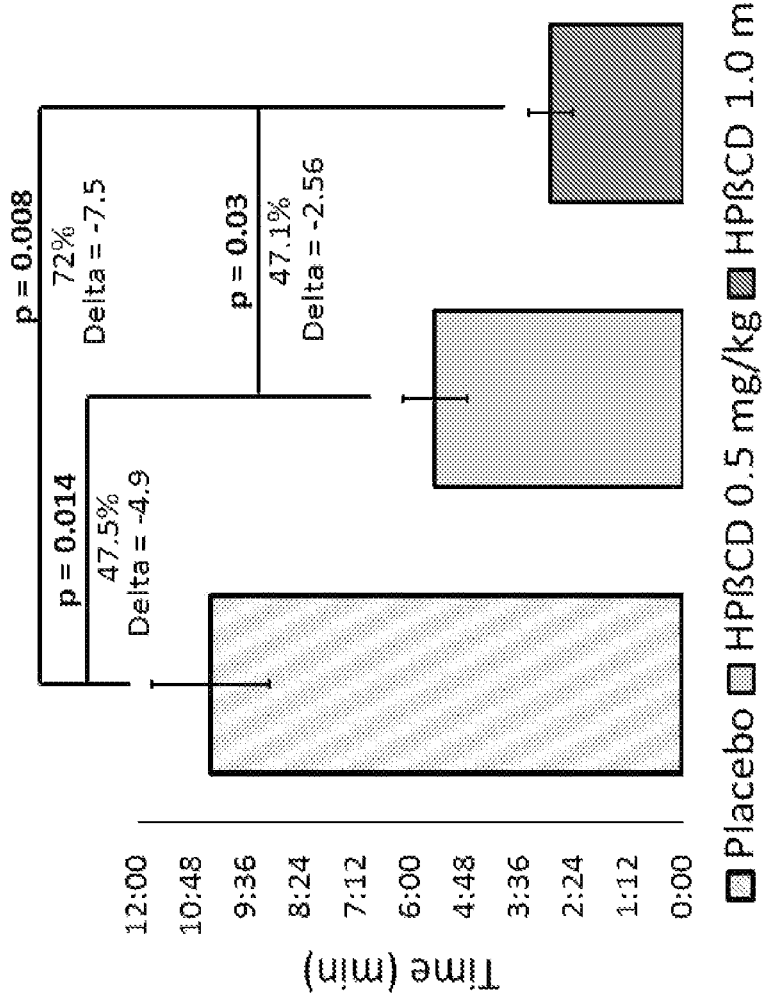
FIG. 7 summarizes atrial fibrillation duration in pig models in response to different treatments.
Figure 8:
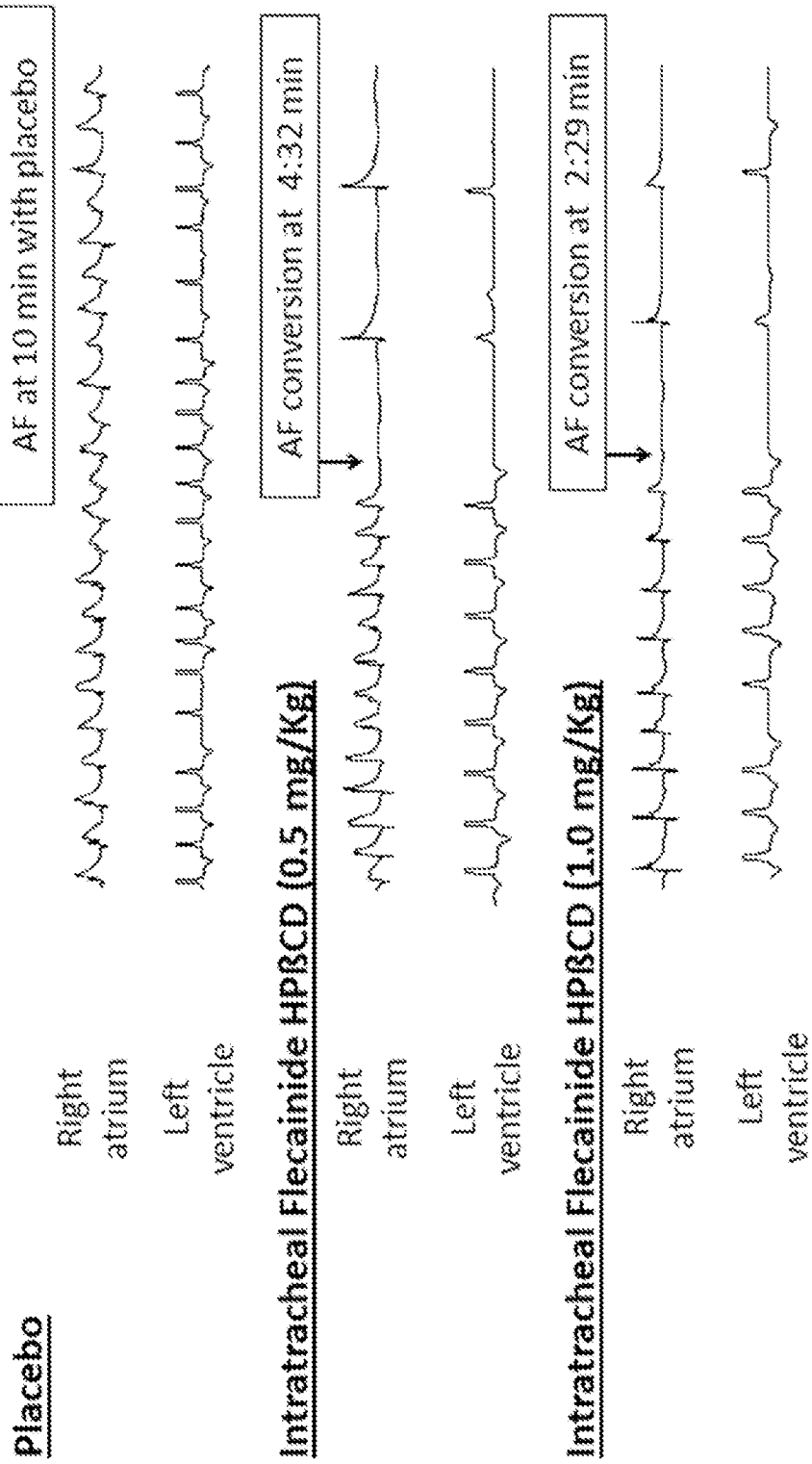
FIG. 8 shows illustrative example of conversion of AF in pig models in response to different treatments.

AF was successfully induced in all animals. Intratracheal instillation of flecainide HPβCD (0.5 mg/kg) decreased AF duration by 47% or 4.9 min in comparison to sterile water placebo (from 10.4±0.05 to 5.50.01 min, p=0.014). The intratracheal dose of 1.0 mg/kg flecainide HPβCD shortened the AF duration by 72% or 7.5 min (from 10.4±0.05 to 2.90.02 min, p=0.008) compared to sterile water placebo. The reduction in AF duration by the higher dose was 1.5-fold that of the lower dose (p=0.03). The summary data on AF duration and electrocardiograms from an illustrative example of conversion of AF are presented in FIGS. 7 and 8, respectively. Specifically, compared to placebo, the exemplary HPβCD-flecainide acetate formulation caused a dose-dependent shortening of AF duration by 48% (p=0.008) and 72% (p=0.03) for the 0.5- and 1.0-mg/kg doses, respectively (FIG. 7). Note in the ECG recordings the smooth transition to normal sinus rhythm. In the presence of the drug, there was one case of a brief 15-sec atrial flutter episode with a ventricular rate of 1340.5 bpm.

Effects on Dominant Frequency During AF.

Figure 9:
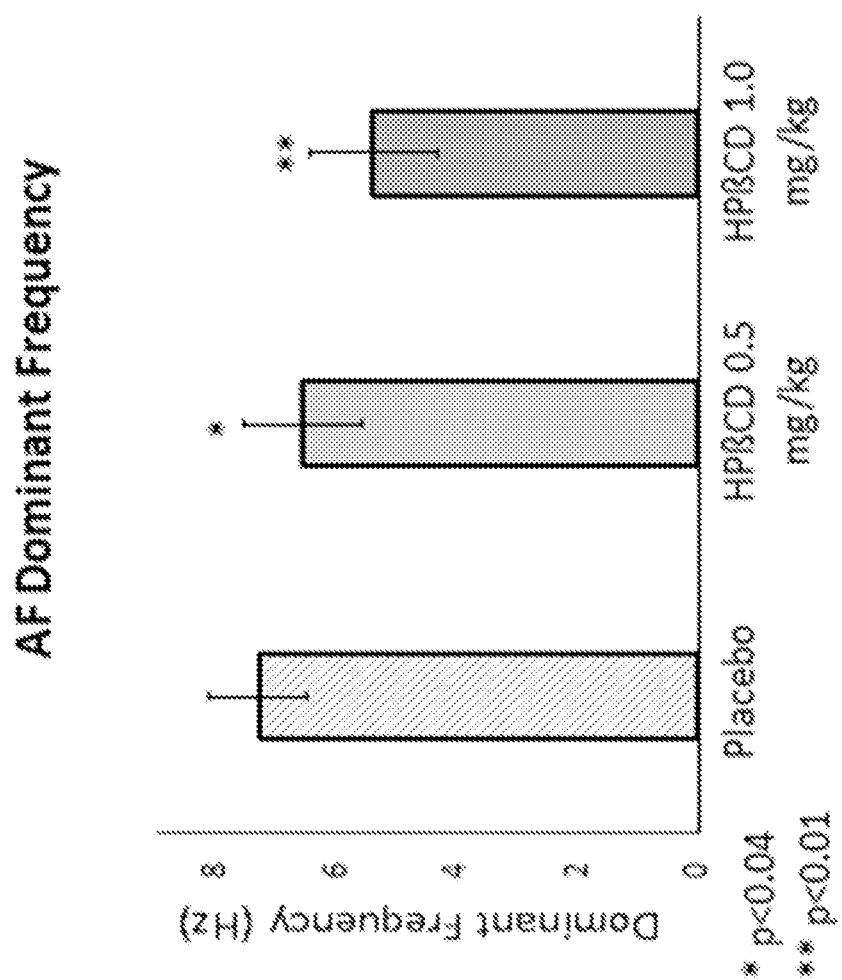
FIG. 9 is a chart summarizing dominant frequency during atrial fibrillation in pig model in response to different treatments.

Intratracheal delivery of flecainide HPβCD at both doses resulted in a significant reduction in dominant frequency during AF (FIG. 9), which can be an important measure associated with the organization of AF and of rotor dynamics, factors that can be responsible for initiation and maintenance of the arrhythmia. Compared to sterile water, the 0.5 mg/kg flecainide HPβCD reduced AF dominant frequency by 11% (from 7.3±0.8 to 6.5±1.0 Hz, p<0.04) and the 1.0 mg/kg dose reduced dominant frequency by 26% (from 7.3±0.8 to 5.4±1.0 Hz, p<0.01). The reduction in AF dominant frequency was associated with shortening of AF duration in a dose-response manner.

Effects on Ventricular Rate During AF

Figure 10:
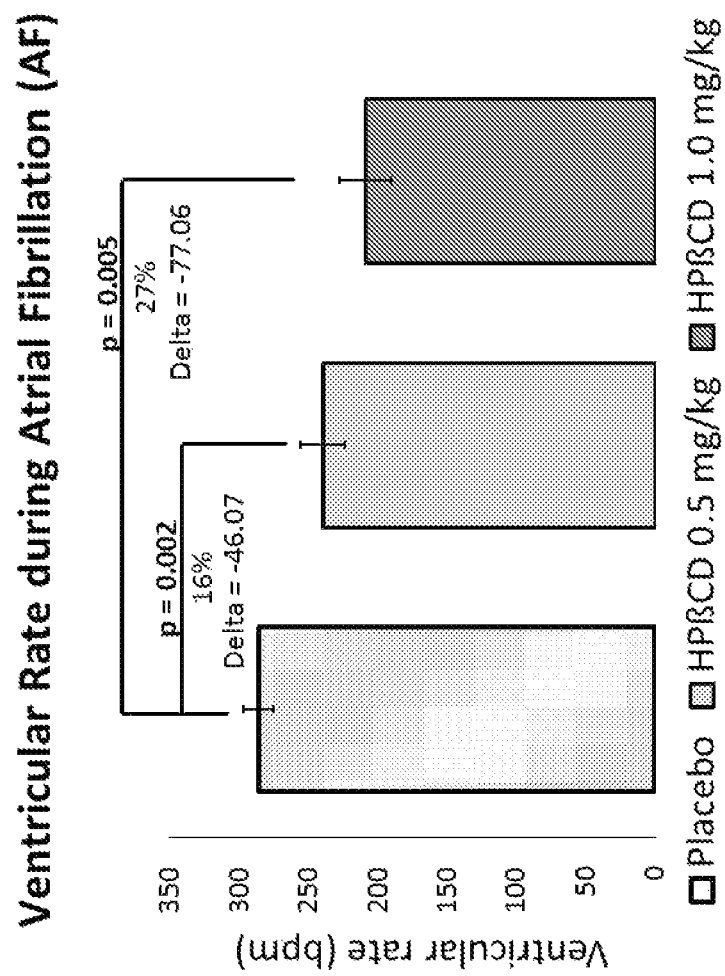
FIG. 10 is a chart summarizing ventricular rate in pig model in response to different treatments.

At both doses, flecainide HPβCD lowered ventricular rate during AF (FIG. 10). The lower dose reduced ventricular rate by 16% or 46 beats/min (from 286±10.7 to 24015.5 beats/min, p=0.002) and the higher dose reduced ventricular rate by 27% or 77 beats/min (from 286±10.7 to 209±18.8 beats/min, p=0.005), both compared to intratracheal delivery of sterile water placebo. After conversion, the ventricular rate for the placebo, 0.5 mg/kg and 1.0 mg/kg dose of flecainide HPβCD were 131±10.9, 99.6±3.5 and 1034.9 bpm, respectively.

Effects on Atrial Depolarization (P) and PR Interval.

Administration of flecainide HPβCD at both the 0.5- and 1.0-mg/kg intratracheal doses was accompanied by an increase in both atrial depolarization ($P_a$) and PR interval duration, which followed the plasma concentration profile. The increases in $P_a$ and PR interval duration were statistically significant at 2 and 5 min after drug administration. The increases in PR interval duration are indicative of a slowing of AV conduction, which is likely to be responsible for the observed decrease in ventricular rate during AF.

At 2 minutes after administration of intratracheal flecainide, $P_a$ duration was increased by 12% (from 431.6 to 48±2.2 ms; p=0.02) for the 0.5-mg/kg dose and by 17% (from 41±1.0 to 48±2.0 ms; p=0.009) for the 1.0-mg/kg dose, compared to pre-drug baseline. At 5 minutes, $P_a$ duration was increased by 12% (from 43±1.6 to 482.2 ms; p=0.007) and 20% (from 41±1.0 to 49±1.7 ms; p=0.005) for the lower and higher doses, respectively.

The 1.0-mg/kg intratracheal flecainide HPPCD dose significantly increased PR interval at both 2 (p=0.03) and 5 minutes (p=0.01) compared to pre-drug baseline (from 171±3.1 ms baseline to 186±6.7 ms and to 189±6.7 ms, increasing by 9% and 11%, respectively). The 0.5-mg/kg dose did not cause a significant change in PR interval at 2 minutes but provoked a significant 5% increase at 5 min (from 167±4.7 to 1755.6 ms; p=0.007).

Effects on Heart Rate and Mean Arterial Pressure.

Figure 11:
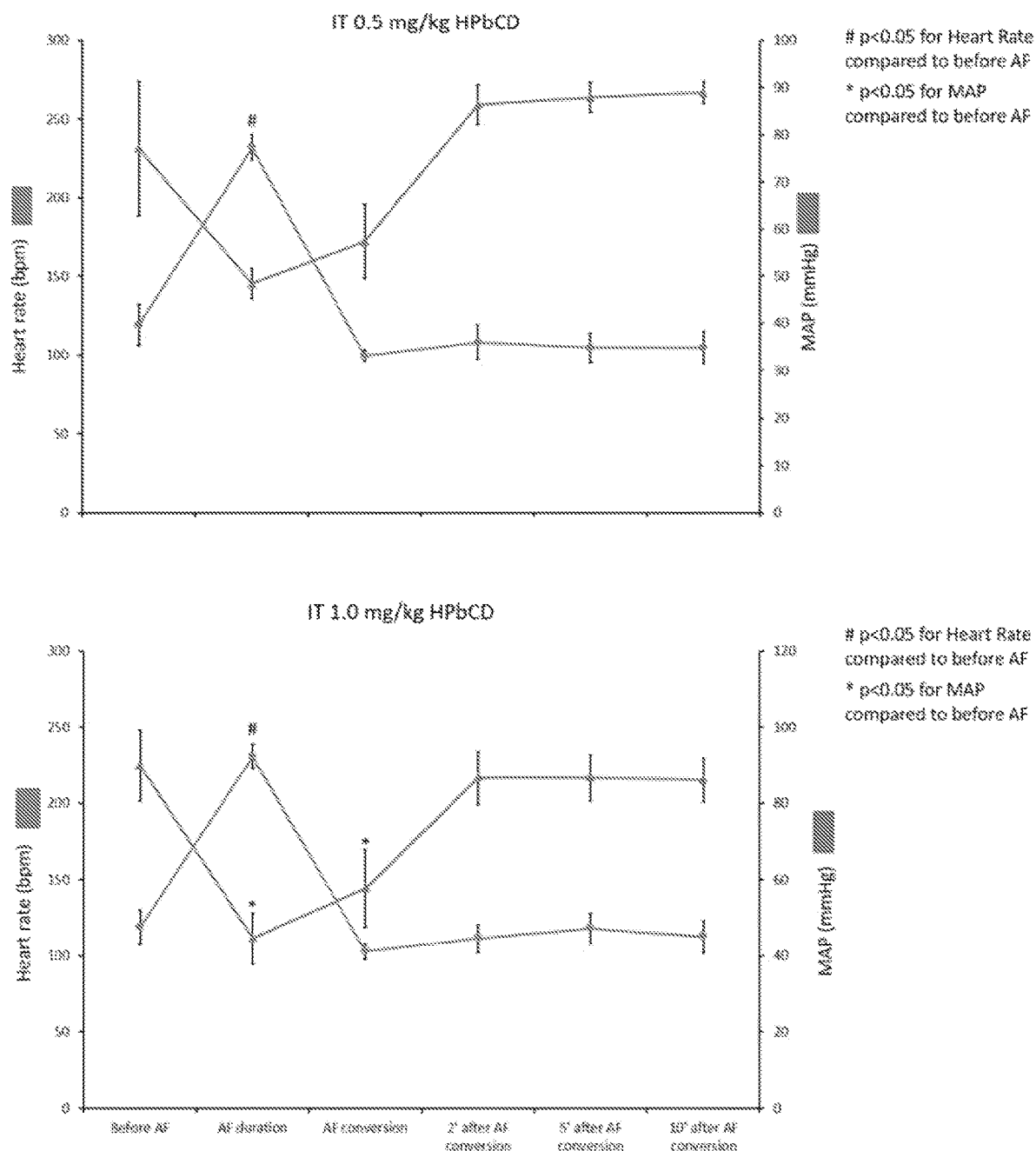
FIG. 11 show two charts summarizing heart rate in pig model of atrial fibrillation in response to intratracheal instillation of an exemplary flecainide formulation at doses of 0.5 mg/kg and 1.0 mg/kg, respectively.

The responses of heart rate and mean arterial pressure (MAP) to the induction and conversion of AF by intratracheal instillation of flecainide HPβCD doses of either 0.5 or 1.0 mg/kg are shown in FIG. 11. Induction of AF resulted in a marked increase in ventricular rate when compared to baseline pre-drug sinus rate (p<0.002 for both doses) and a corresponding reduction in MAP. With either dose, when AF was successfully terminated, both heart rate and MAP returned toward baseline levels within 2 minutes after conversion.

The multimodal actions of intratracheal delivery of the exemplary HPβCD-flecainide acetate formulation are likely to relate to the fact that this formulation inhibits both peak and late sodium currents. Inhibition of the fast sodium channel can contribute to an increase in atrial action potential duration reflected in the observed increase in $P_a$ duration and can also slow intra-atrial conduction, which is evident in the prolonged PR interval. In turn, the net effect of slowing atrial conduction can account for the demonstrated reduction in ventricular rate during AF. The inhibition of late $I_{Na}$ by the exemplary formulation has been found to suppress early and delayed after depolarizations in atrial and pulmonary veins, with a corresponding decrease in atrial ectopy. The net effect is likely to have contributed to a decrease in the firing rate of pulmonary vein foci during AF, which can lead to a decrease in AF dominant frequency, as found in the current study.

Example 10. Comparison of Cardioversions of Atrial Fibrillation Induced by Two Exemplary Formulations in Pigs This example compares the therapeutic effects of two exemplary HPβCD-flecainide acetate formulations via pulmonary delivery (intratracheal instillation).

In this example, two formulations were tested: (a) 75 mg/mL Flecainide acetate, 90 mM acetic acid, 10% w/v hydroxypropyl-b-cyclodextrin in WFI, pH 5.2 (the "High Acetate" formulation; the same exemplary formulation tested in Example 9); and (b) 75 mg/mL Flecainide acetate, 5 mM acetic acid, 20% w/v hydroxypropyl-b-cyclodextrin in WFI, pH 5.9 (the "Low Acetate" formulation). Experiments with "High Acetate" formulation are the same as the experiments described in Example 9, while experiments with "Low Acetate" formulation were conducted similarly to what is described in Example 9 except for the use of "Low Acetate" formulation instead of the "High Acetate" formulation. Briefly, Yorkshire pigs were administered with an intrapericardial injection of acetylcholine and burst pacing to induce AFIB (atrial fibrillation). They were then dosed by intratracheal instillation with a cyclodextrin-based formulation (HPβCD) 2 min after AFIB initiation. After AFIB conversion, AFIB reinduction was attempted 30 minutes after dosing and 60 minutes after dosing, and the duration of AFIB was measured.

Figure 12:
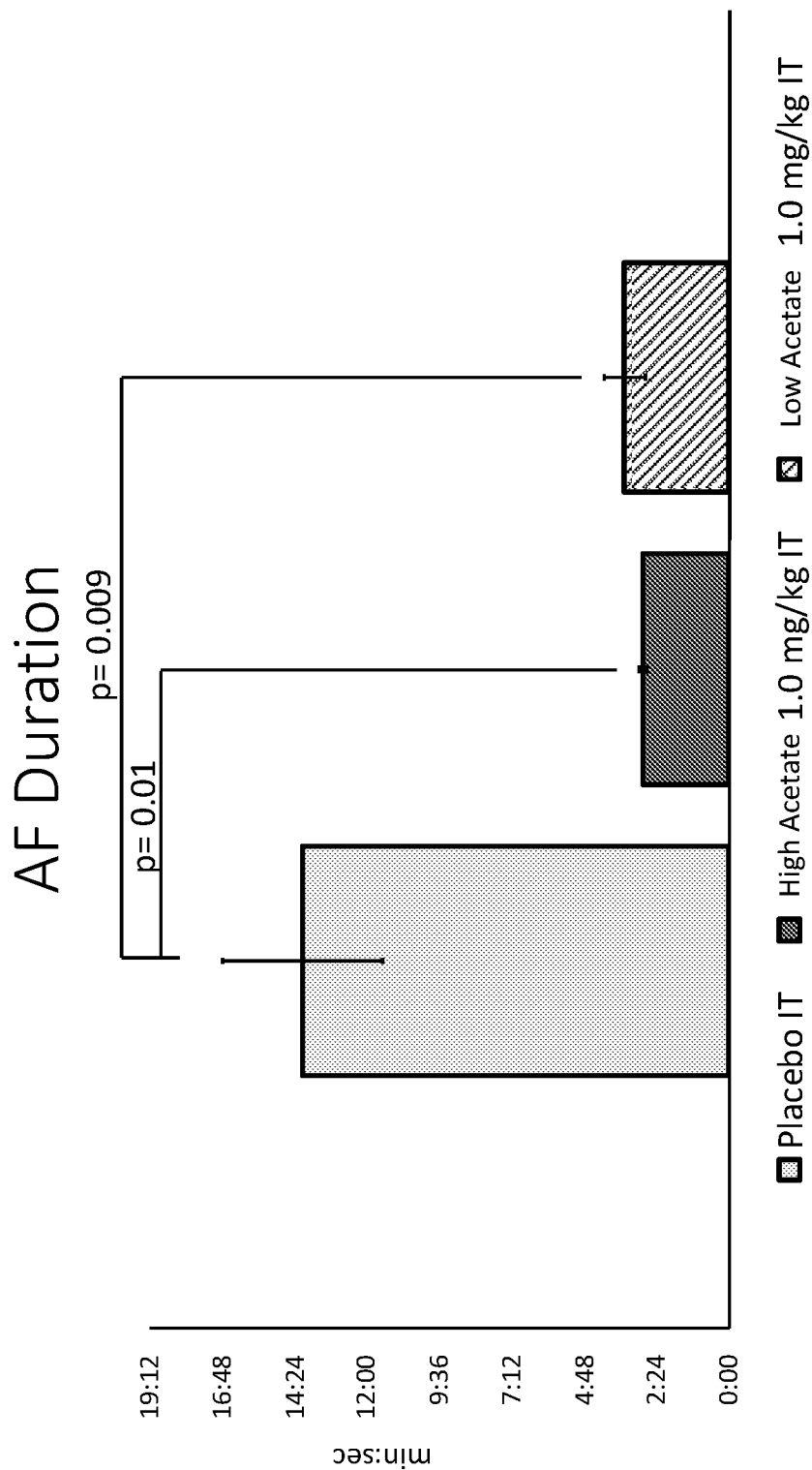
FIG. 12 is a chart summarizing atrial fibrillation duration in pig model in response to different treatments.
Figure 16:
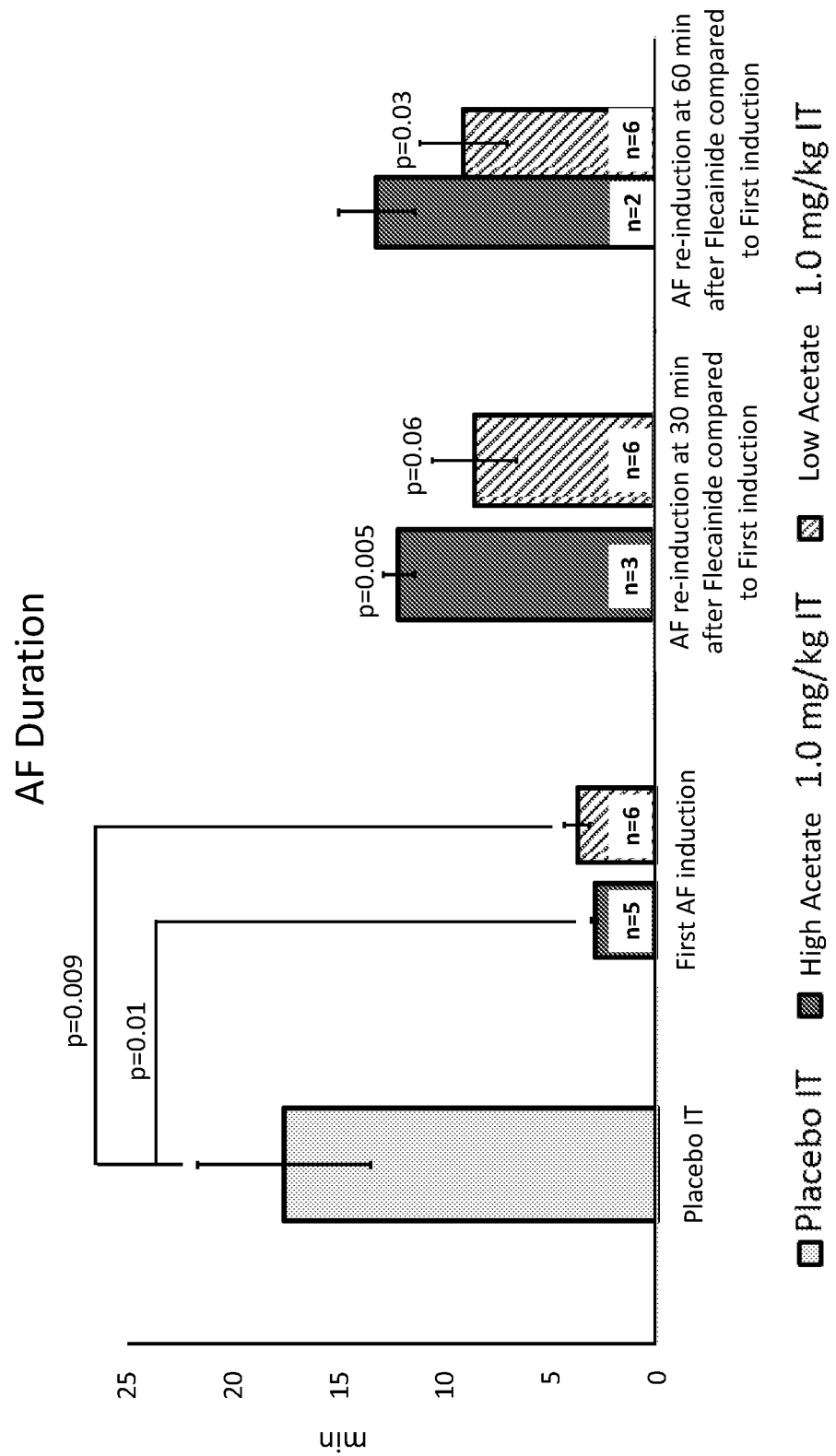
FIG. 16 is a chart summarizing atrial fibrillation duration when the atrial fibrillation is re-induced in pig model in response to different treatments.

The following observations were made:

(1) The "Low Acetate" and "High Acetate" HPβCD formulations had equivalent efficacy in accelerating conversion of AFIB to normal sinus rhythm, as demonstrated in FIGS. 12 and 16.

Figure 13:
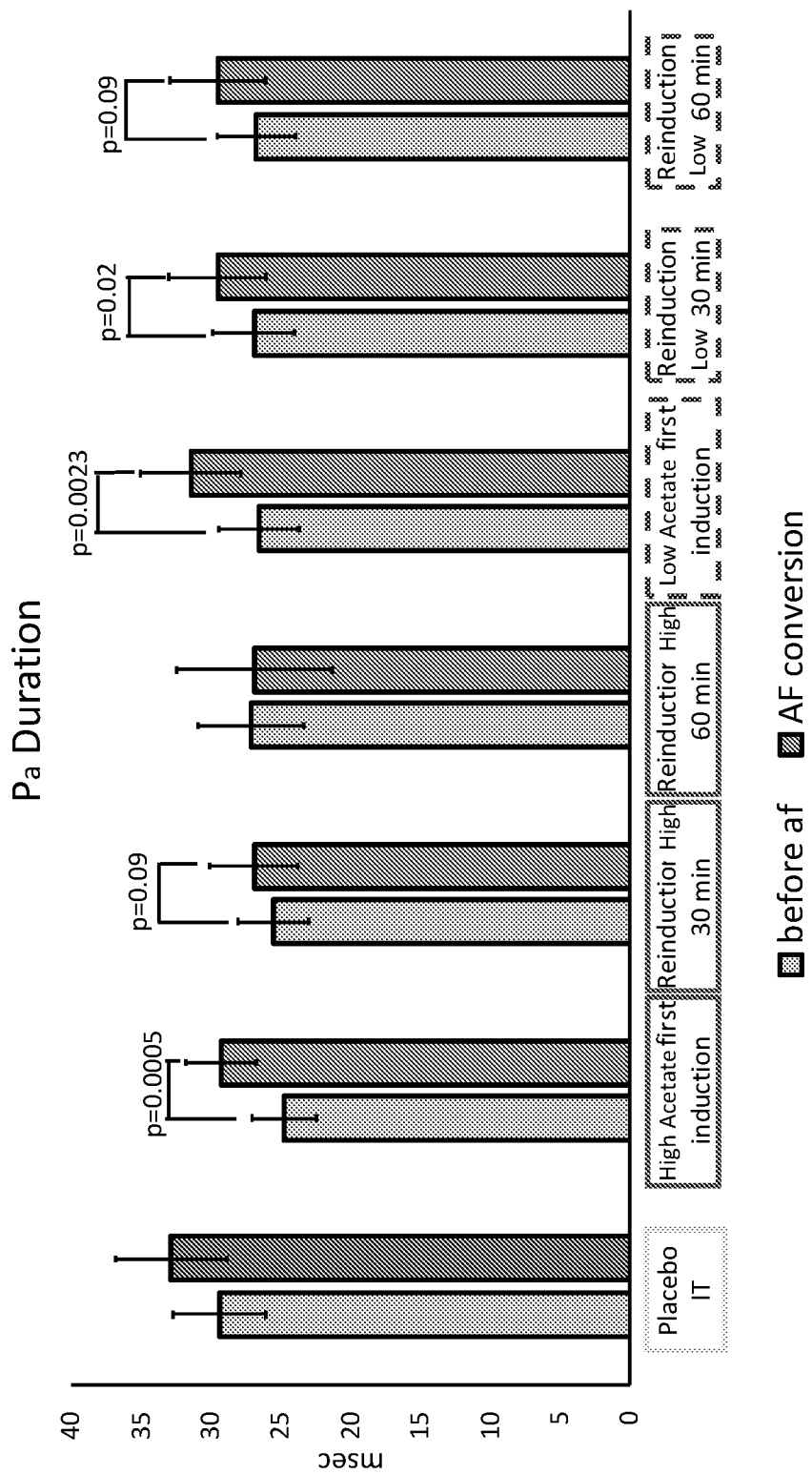
FIG. 13 is a chart summarizing atrial depolarization in pig model in response to different treatments.
Figure 14:
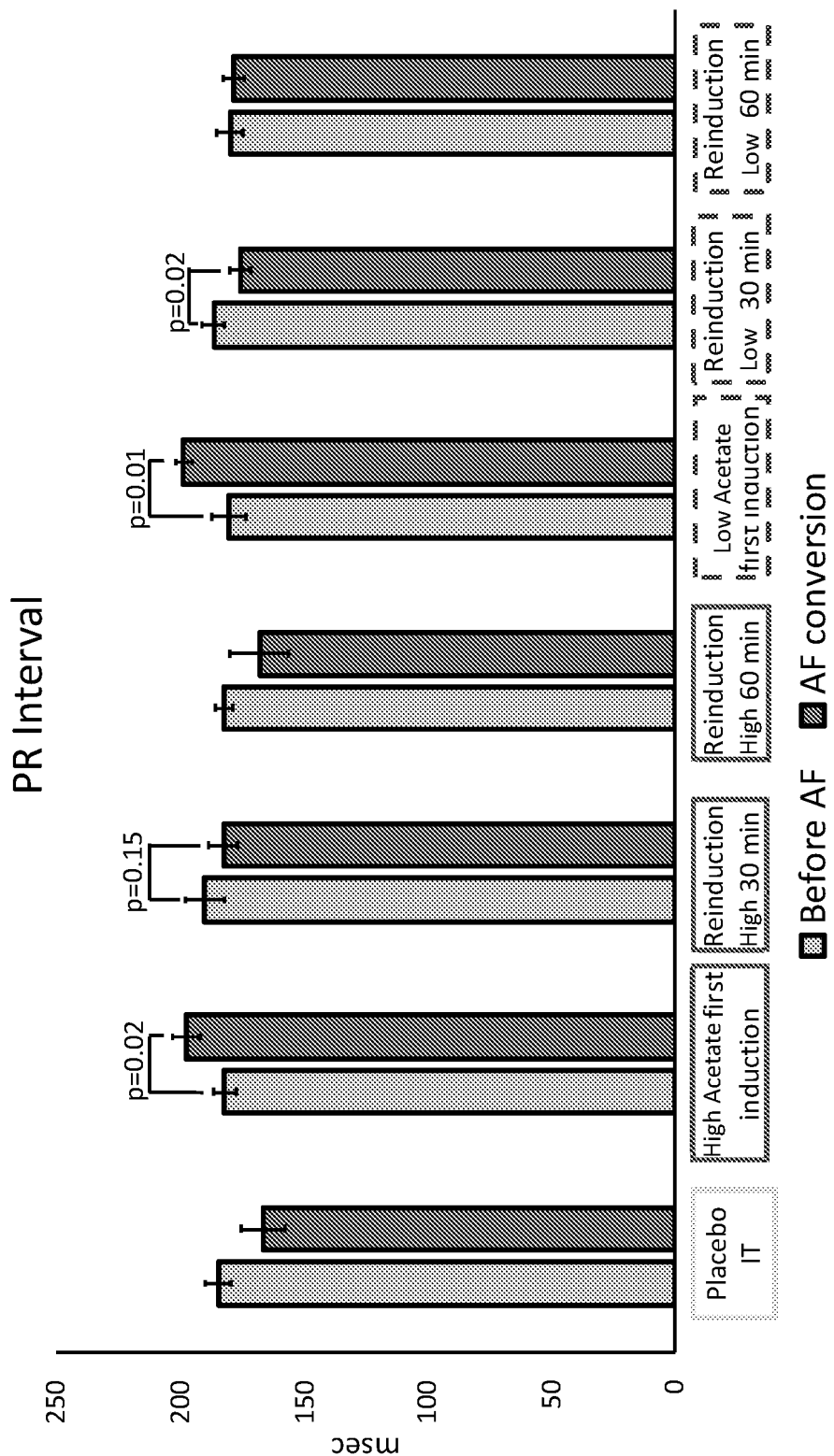
FIG. 14 is a chart summarizing PR interval in pig model in response to different treatments.
Figure 15:
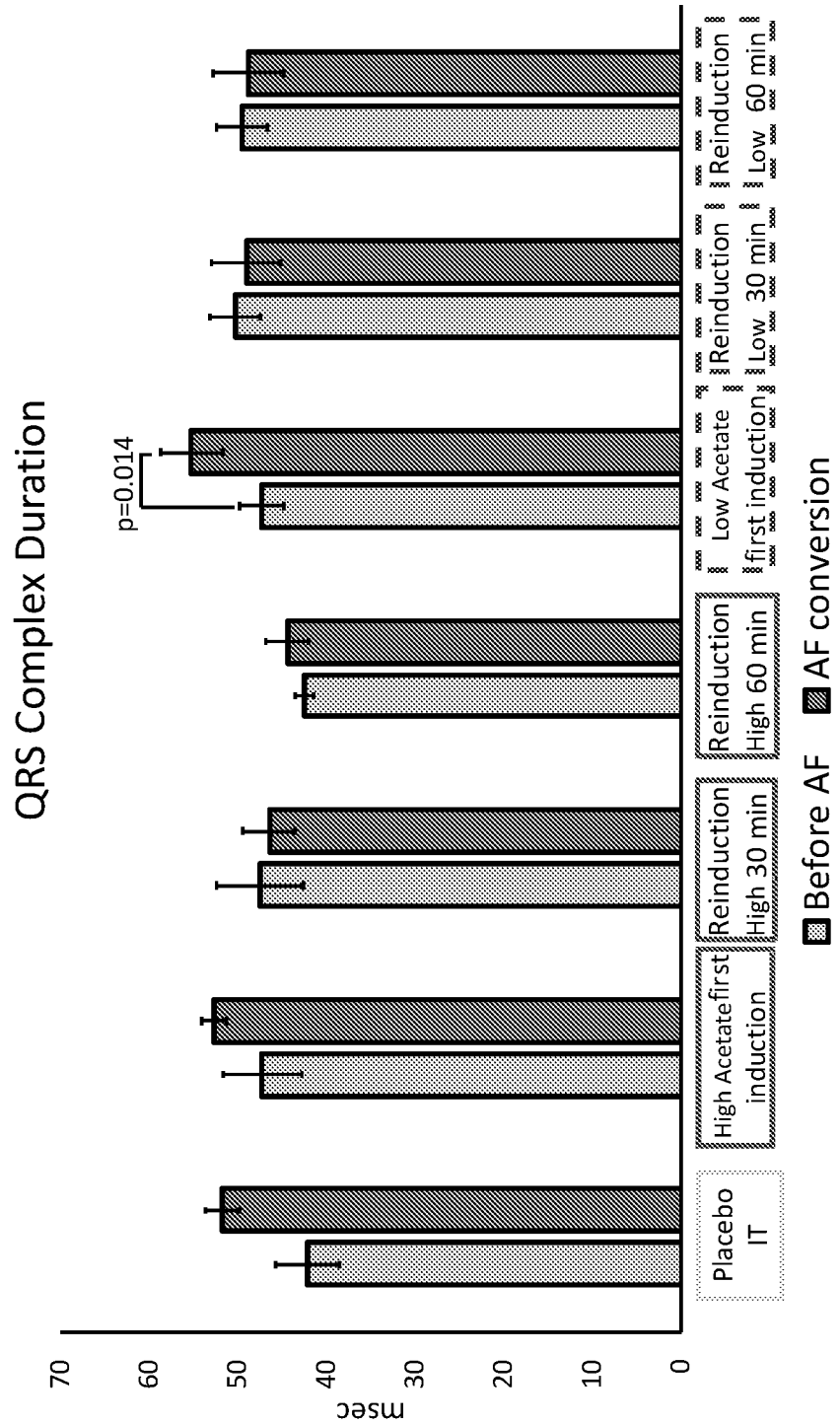
FIG. 15 is a chart summarizing QRS duration in pig model in response to different treatments.

(2) As shown in FIGS. 13 and 16, the "Low Acetate" solution appeared to have a persistent effect on both prolonging atrial depolarization (Pa) and suppressing AFIB re-induction. AFIB durations after re-induction in the "Low Acetate" group were approximate half of that in the placebo group, even an hour after dosing.

Figure 17:
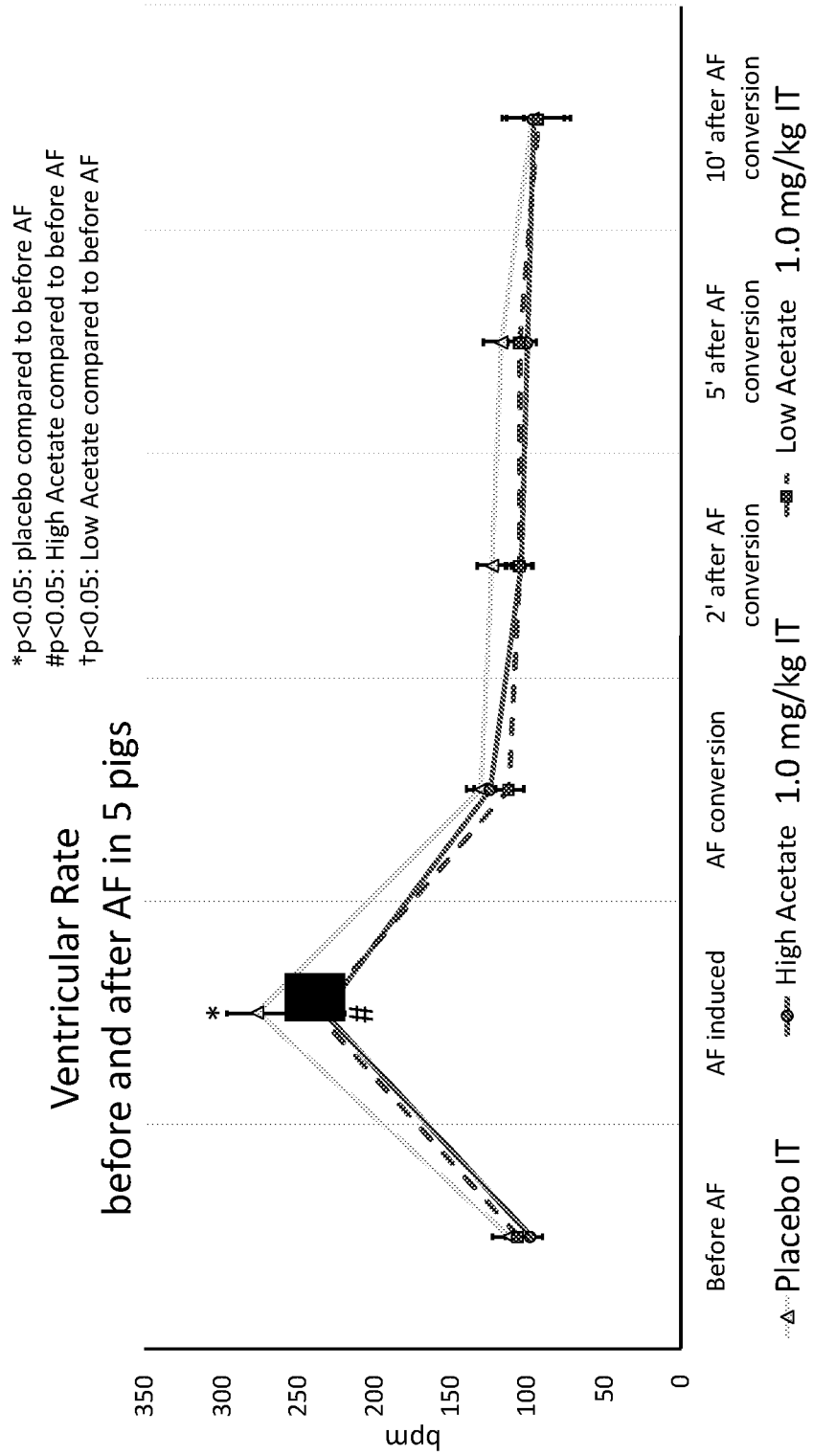
FIG. 17 is a chart summarizing ventricular rate in pig model in response to different treatments.
Figure 18:
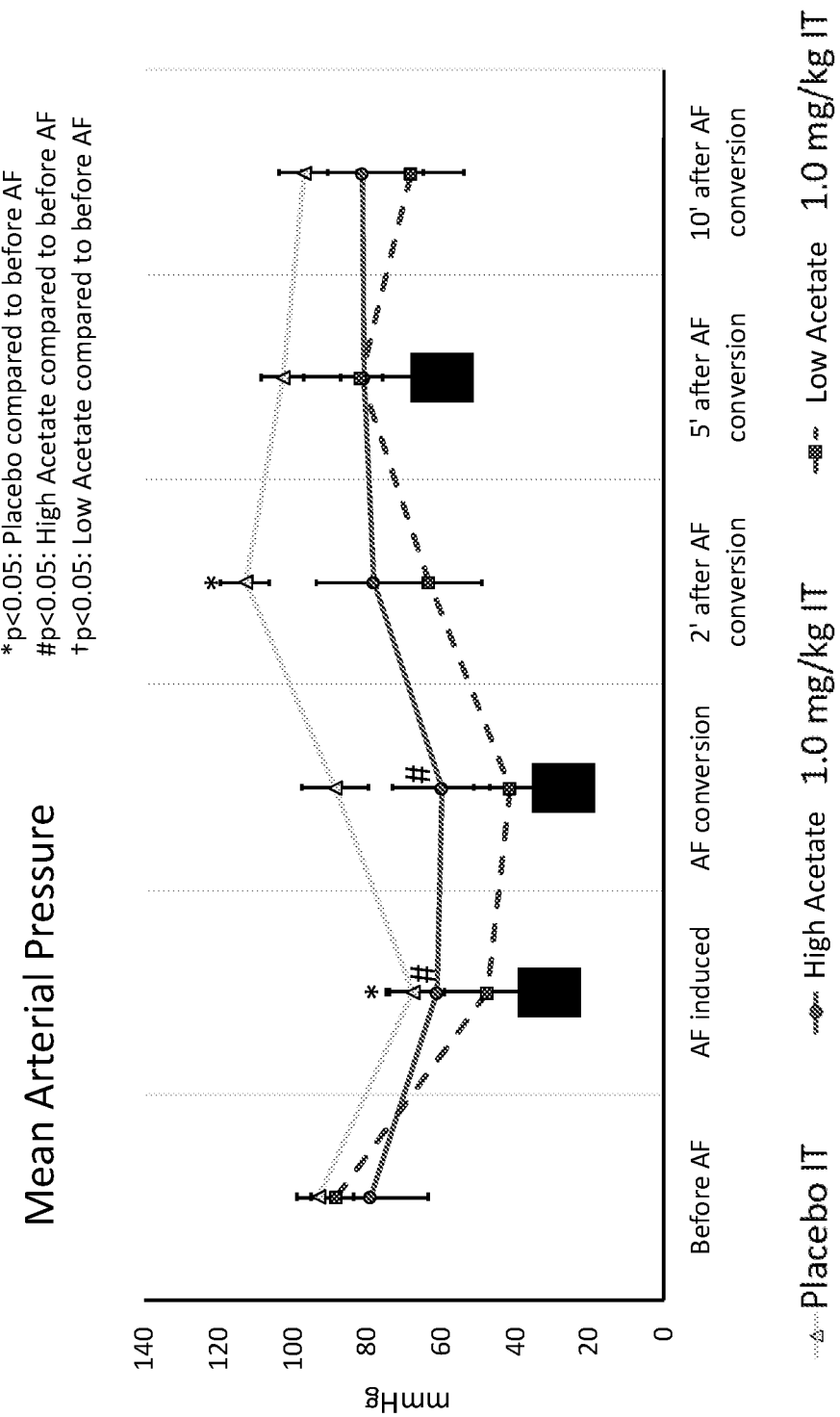
FIG. 18 is a chart summarizing mean arterial pressure in pig model in response to different treatments.
Figure 19:
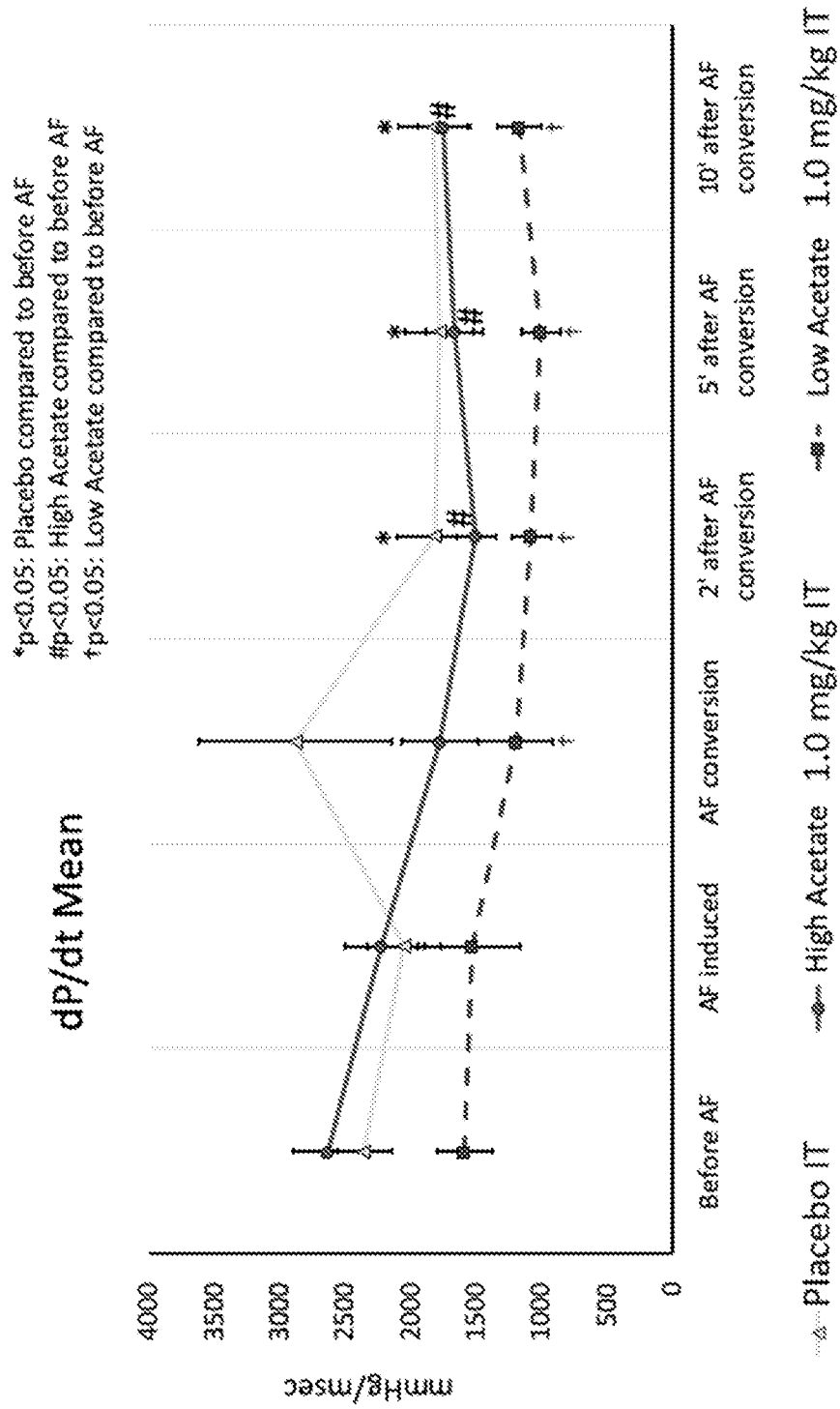
FIG. 19 is a chart summarizing left ventricular contractility in pig model in response to different treatments.

(3) The hemodynamic effects on heart rate, arterial blood pressure, and left ventricular contractility were comparable between the two solutions (FIGS. 17-19).

Figure 20:
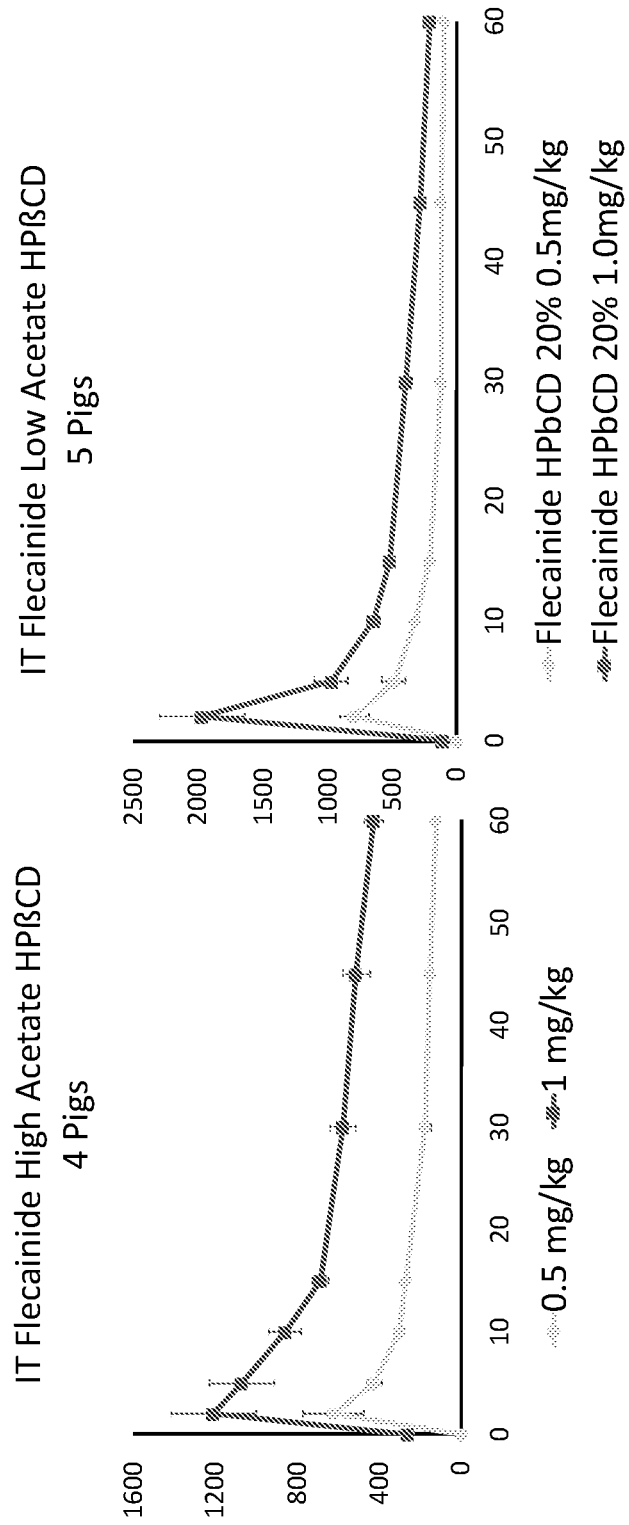
FIG. 20 is a chart summarizing plasma concentration of flecainide acetate in pig model in response to different treatments.

(4) As shown in FIG. 20, the "Low Acetate" solution resulted in a greater increase in $C_{max}$ than the "High Acetate" solution. Without wishing to be bound by a particular theory, there could be greater tissue penetration of the "Low Acetate" solution in the alveoli, and enhanced tissue penetration by the "Low Acetate" solution can help explain the persistent effect on atrial depolarization (Pa) duration and suppression of AFIB.

In addition to the above, it was also observed "High Acetate" formulations produced a "gag response" in the pigs (a contraction of the back of the throat triggered by the delivery of the formulation.) In contrast, the "Low Acetate" solution appeared to induce minimal or no gag response in the pigs to IT administration.

Example 11. Exemplary Mixed Acid Flecainide Formulations

This example demonstrates several exemplary formulations of flecainide in which flecainide acetate is dissolved in a mixture of different acids. This example also demonstrates that by mixing with a variety of acids, the solubility of flecainide acetate can be increased.

In this example, solubility of flecainide acetate was measured in total 38 different acid mixture (binary/temary/quatemary-mixtureofaceticacid/nitricacid/sulfuricacid/citricacid), as listed in TABLES 15-17. In this example, flecainide acetate (dosing concentration: –90 mg/mL) were suspended in the corresponding medium with different binary, temary, or quaternary acid systems. The suspensions were magnetic stirred (1000 r/min) at 25° C. for 24 hrs and 48 hrs. Centrifugation of the suspension solutions was performed at 10000 rpm (3 min) and then filtration conducted with 0.45 μm membrane to obtain supermatant for HPLC solubility test and pH test, and residual solids for XRPD test. The max solubility of flecanide acetate (82.4 mg/mL) was observed, which was in a mixture of 50 mM acetic acid, 0.5 mM nitric acid, and 0.00375 mM sulfuric acid, with no form conversion.

TABLE 15

Solubility of Flecainide Acetate in Binary Acid Mixture

| | Medium in | Solubility (mg/mL) | | | | | | Form | |
| | | Freebase | | Acetate base | | pH | | Conversion | |
| No. | Exemplary Formulation | 24 hr | 48 hr | 24 hr | 48 hr | 24 hr | 48 hr | 24 hr | 48 hr |
|---|---|---|---|---|---|---|---|---|---|
| 18-A1 | 50 mM HOAc + 0.5 mM HNO3 | 64.0 | 69.5 | 73.3 | 79.6 | 4.6 | 4.7 | N | N |
| 18-A2 | 50 mM HOAc + 0.25 mM HNO3 | 64.7 | 66.7 | 74.1 | 76.4 | 4.5 | 4.8 | N | N |
| 18-A3 | 50 mM HOAc + 0.0075 mM H2SO4 | 67.1 | 67.1 | 76.8 | 76.9 | 4.6 | 5.0 | N | N |
| 18-A4 | 50 mM HOAc + 0.00375 mM H2SO4 | 65.8 | 65.4 | 75.4 | 74.9 | 5.1 | 4.9 | N | N |
| 31-A25 | 50 mM HOA + 6 mM Citric acid | 65.8 | 68.2 | 75.3 | 78.1 | 4.7 | 4.9 | Y | Y |
| 31-A26 | 50 mM HOAc + 3 mM Citric acid | 68.6 | 71.4 | 78.6 | 81.4 | 4.7 | 4.9 | N | N |
| 18-A7 | 25 mM HOAc + 0.5 mM HNO3 | 66.0 | 63.6 | 75.5 | 72.9 | 5.6 | 5.6 | N | N |
| 18-A8 | 25 mM HOAc + 0.25 mM HNO3 | 65.5 | 64.4 | 75.0 | 73.7 | 5.7 | 5.3 | N | N |

TABLE 15-continued

Solubility of Flecainide Acetate in Binary Acid Mixture

| No. | Medium in Exemplary Formulation | Solubility (mg/mL) Freebase 24 hr | 48 hr | Acetate base 24 hr | 48 hr | pH 24 hr | 48 hr | Form Conversion 24 hr | 48 hr |
|---|---|---|---|---|---|---|---|---|---|
| 18-A9 | 25 mM HOAc + 0.0075 mM H2SO4 | 64.2 | 63.5 | 73.5 | 72.7 | 5.5 | 5.4 | N | N |
| 18-A10 | 25 mM HOAc + 0.00375 mM H2SO4 | 65.1 | 65.1 | 74.6 | 74.5 | 5.2 | 5.4 | N | N |
| 31-A27 | 25 mM HOAc + 6 mM Citric acid | 65.8 | 64.1 | 75.4 | 73.4 | 4.9 | 5.0 | Y | Y |
| 31-A28 | 25 mM HOAc + 3 mM Citric acid | 64.6 | 67.1 | 73.9 | 76.8 | 5.0 | 5.2 | Y | Y |

TABLE 16

Solubility of Flecainide Acetate in Ternary Acid Mixture

| No. | Medium in Exemplary Formulation | Solubility (mg/mL) Freebase 24 hr | 48 hr | Acetate base 24 hr | 48 hr | pH 24 hr | 48 hr | Form Conversion 24 hr | 48 hr |
|---|---|---|---|---|---|---|---|---|---|
| 31-A1 | 50 mM HAc + 0.5 mM HNO3 + 0.0075 mM H2SO4 | 68.2 | 66.4 | 78.1 | 76.0 | 4.9 | 5.0 | N | N |
| 31-A2 | 50 mM HAc + 0.5 mM HNO3 + 0.00375 mM H2SO4 | 67.4 | 72.0 | 77.2 | 82.4 | 4.9 | 5.0 | N | N |
| 31-A3 | 50 mM HAc + 0.5 mM HNO3 + 6 mM Citric acid | 63.9 | 65.3 | 73.1 | 74.7 | 4.8 | 5.0 | Y | Y |
| 31-A4 | 50 mM HAc + 0.5 mM HNO3 + 3 mM Citric acid | 65.9 | 68.9 | 75.5 | 78.9 | 4.9 | 5.0 | N | N |
| 31-A5 | 50 mM HAc + 0.25 mM HNO3 + 0.0075 mM H2SO4 | 65.9 | 67.0 | 75.5 | 76.7 | 5.0 | 5.1 | N | N |
| 31-A6 | 50 mM HAc + 0.25 mM HNO3 + 0.00375 mM H2SO4 | 65.4 | 67.7 | 74.9 | 77.6 | 5.0 | 5.2 | N | N |
| 31-A7 | 50 mM HAc + 0.25 mM HNO3 + 6 mM Citric acid | 62.2 | 66.1 | 71.3 | 75.7 | 4.8 | 5.0 | Y | Y |
| 31-A8 | 50 mM HAc + 0.25 mM HNO3 +3 mM Citric acid | 64.2 | 71.3 | 73.5 | 81.6 | 4.9 | 5.1 | Y | Y |
| 31-A9 | 50 mM HAc + 0.0075 mM H2SO4 + 6 mM Citric acid | 62.6 | 69.6 | 71.7 | 79.7 | 4.8 | 5.0 | Y | Y |
| 31-A10 | 50 mM HAc + 0.0075 mM H2SO4 +3 mM Citric acid | 64.5 | 66.3 | 73.9 | 75.9 | 4.9 | 5.0 | Y | Y |
| 31-A11 | 50 mM HAc + 0.00375 mM H2SO4 + 6 mM Citric acid | 62.6 | 63.7 | 71.7 | 73.0 | 4.8 | 5.0 | Y | Y |
| 31-A12 | 50 mM HAc + 0.00375 mM H2SO4 +3 mM Citric acid | 63.4 | 64.5 | 72.5 | 73.8 | 4.9 | 5.2 | Y | Y |

TABLE 16-continued

Solubility of Flecainide Acetate in Ternary Acid Mixture

| No. | Medium in Exemplary Formulation | Solubility (mg/mL) Freebase 24 hr | 48 hr | Acetate base 24 hr | 48 hr | pH 24 hr | 48 hr | Form Conversion 24 hr | 48 hr |
|---|---|---|---|---|---|---|---|---|---|
| 31-A13 | 25 mM HAc + 0.5 mM HNO3 + 0.0075 mM H2SO4 | 64.1 | 64.6 | 73.3 | 73.9 | 5.3 | 5.6 | N | N |
| 31-A14 | 25 mM HAc + 0.5 mM HNO3 + 0.00375 mM H2SO4 | 64.0 | 67.5 | 73.3 | 77.2 | 5.3 | 5.6 | N | N |
| 31-A15 | 25 mM HAc + 0.5 mM HNO3 + 6 mM Citric acid | 62.3 | 63.0 | 71.4 | 72.1 | 5.0 | 5.3 | Y | Y |
| 31-A16 | 25 mM HAc + 0.5 mM HNO3 + 3 mM Citric acid | 62.5 | 66.6 | 71.6 | 76.3 | 5.1 | 5.1 | Y | Y |
| 31-A17 | 25 mM HAc + 0.25 mM HNO3 0.0075 mM | 62.7 | 69.0 | 71.8 | 79.0 | 5.3 | 5.3 | N | N |
| 31-A18 | 25 mM HAc + 0.25 mM HNO3 + 0.00375 mM H2SO4 | 64.5 | 66.5 | 73.8 | 76.2 | 5.3 | 5.3 | N | N |
| 31-A19 | 25 mM HAc + 0.25 mM HNO3 + 6 mM Citric | 61.8 | 64.4 | 70.8 | 73.7 | 5.0 | 5.0 | Y | Y |
| 31-A20 | 25 mM HAc + 0.25 mM HNO3 +3 mM Citric | 61.8 | 63.1 | 70.8 | 72.3 | 5.2 | 5.2 | Y | Y |
| 31-A21 | 25 mM HAc + 0.0075 mM H2SO4 + 6 mM | 61.6 | 63.6 | 70.5 | 72.8 | 5.0 | 5.1 | Y | Y |
| 31-A22 | 25 mM HAc + 0.0075 mM H2SO4 + 3 mM | 62.4 | 64.6 | 71.4 | 74.0 | 5.1 | 5.2 | Y | Y |
| 31-A23 | 25 mM HAc + 0.00375 mM H2SO4 + 6 mM Citric acid | 62.1 | 62.5 | 71.1 | 71.6 | 5.0 | 5.2 | Y | Y |
| 31-A24 | 25 mM HAc + 0.00375 mM H2SO4 +3 mM Citric acid | 62.8 | 63.8 | 71.9 | 73.1 | 5.1 | 5.4 | Y | Y |

TABLE 17

Solubility of Flecainide Acetate in Quaternary Acid Mixture

| No. | Medium in Exemplary Formulation | Solubility (mg/mL) Freebase 24 hr | 48 hr | Acetate base 24 hr | 48 hr | pH 24 hr | 48 hr | Form Conversion 24 hr | 48 hr |
|---|---|---|---|---|---|---|---|---|---|
| A29 | 50 mM HAc + 0.5 mM HNO$_3$ + 0.0075 mM H2SO4 + 6 mM Citric acid | 70.9 | 71.4 | 81.1 | 81.7 | 4.4 | 4.5 | N | N |
| A30 | 25 mM HAc + 0.25 mM HNO$_3$ + 0.00375 mM H$_2$SO$_4$ + 3 mM Citric acid | 67.4 | 69.0 | 77.2 | 78.9 | 4.7 | 4.8 | N | N |

Example 12. Clinical Performance of Exemplary Flecainide Formulations

This example describes an ongoing Phase 2 clinical study conducted with exemplary flecainide formulations as described herein. The FL-002 (INSTANT) study is a Phase 2, prospective, multi-center study of flecainide acetate oral inhalation solution ("IH Flec") for acute cardioversion to sinus rhythm (SR) in patients with recent onset of symptomatic paroxysmal atial fibrillation (AF).

Patient eligibility. Patient eligibility for this study is generally consistent with eligibility for IV flecainide. 18 years and older, both male and female sexes are eligible for this study. Inclusion and exclusion criteria are summarized in TABLE 18A and TABLE 18B, respectively.

TABLE 18A

Patient Inclusion Criteria for Clinical Study

| Inclusion | Phase 2a | Phase 2b/3 |
| --- | --- | --- |
| Clinical Presentation | Recent-onset, symptomatic AF >1 or <48 hours | Same |
| Pre-Study Inclusion | Current PIP users, post-3 months ablation, recurrent AF | Same |

TABLE 18B

Patient Exclusion Criteria for Clinical Study

| Exclusion | Phase 2a | Phase 2b/3 |
| --- | --- | --- |
| Clinical Presentation | <18 years of age | <18 or >85 years of age |
| Hemodynamic Criteria | Hemodynamic Instability<br>SBP < 90 mmHg<br>Ventricular HR <70 or 170 bpm<br>History of acute decompensated HF<br>Any history or HF with reduced Ejection Fraction<br>Other relevant structural heart disease (prior MI, signs/symptoms of myocardial ischemia, stenosis, cardiomyopathy) | Hemodynamic and/or cardiac instability<br>SBP <100 or >160 mmHg<br>Ventricular HR <80 or >155 upon screening<br>Same<br>Abnormal LVEF or Class 2+ HF (NYHA) within 6 months prior to screening<br>Prior MI OR Signs of prior MI |
| Arrhythmia Criteria | Persistent AF<br>Atrial flutter at presentation<br>History of rhythm abnormalities: LQTS, conduction disease, sick sinus, Brugada, Torsades de pointes<br>ECG-related features: QTc interval >480 ms, QRS duration ≥120 ms or history of wide QRS, predominately paced heart rhythm, sustained or non-sustained VT, excessive PVC's. | One or more episodes of atrial flutter within 6 months prior to screening |
| Treatment | Current AF episode treated with Class 1 or 3 AAD, or ECV<br>Previous non-responder to flecainide | Cardiac Surgery for any exclusionary conditions within 6 months prior to screening |

Study Design. The study consists of 2 parts: Part A and Part B. Part A (dose finding) evaluates the feasibility of administration of IH Flec. Part B will confirm the dose and will include a pilot sub-study to simulate a patient led scenario with medical supervision.

Part A study. Dosing regimen includes: 30, 60, 90 and 120 mg of IH Flec (inhaled flecainide, e.g., eTLD) and the concentration of flecainide in the inhalation solutions tested includes 35, 45 and 75 mg/mL. IH Flec formulations tested in this study include the ones listed in TABLE 19 (*, "CD" denotes a cyclodextrin-based formulation including 10% (w/v) hydroxy propyl β-cyclodextrin, 90 mM acetic acid buffer, and having a pH of 5.2; *, "iCD-SAC" denotes a cyclodextrin-based formulation including 20% (w/v) hydroxypropyl 3-cyclodextrin, 5 mM acetic acid, and 750 M saccharin, and having a pH of 5.9.).

TABLE 19

Exemplary flecainide formulations tested in the clinical study

| | Inhalation solution [concentration (mg/mL)] | | | |
|---|---|---|---|---|
| | 30 [35] | | 120 [75] | |
| | Formulation | | | |
| | 60 [35] | 90 [45] | CD* | iCD-SAC** |
| | Flec IH-101 | | (Flec IH-102) | (Flec IH-103) |
| Flecainide Dose (eTLD) | 30 mg | 60 mg | 90 mg | 120 mg |
| Concentration of flecainide acetate (mg/mL) | 35 | 35 | 45 | 75 |
| Other components: | | | | |
| Acetic acid buffer | | 90 mM | 90 mM | 5 mM |
| Hydroxypropyl β-cyclodextrin (w/v) | | 0 | 10% | 20% |
| pH* | | 5.2 | 5.2 | 5.9 |
| Estimated Duration of Inhalation Regimen (min) | 4.5 | 10 | 10 | 8 |
| Dosing pattern$^a$ | A | B | B | C |
| Approximate Rate of Dose Delivery (mg/min) | 6.7 | 6.0 | 9.0 | 15.0 |
| Inhalation Regimen | Dose/inhale to completion | | Dose/inhale to conversion | |

$^a$A: 4.5 minutes inhalation (no breaks); B: 4.5 minutes inhalation, followed by 1 minute break, followed by 4.5 minutes inhalation; C: 3 minutes inhalation, followed by 1 minute break, followed by 3 minutes inhalation
'Dose/inhale to completion' = inhale until the full dose is administered
'Dose/inhale to conversion' = Inhale until the time of conversion of AF to SR, or continue to inhale until the full dose is administered, whichever occurs first
*NaOH is added as necessary to achieve specified pH In this study, for inhalation delivery of flecainide, the estimated total lung doses (eTLDs) were calculated to account for losses of flecainide in the inhalation device and losses of flecainide in subjects' mouth and throat. eTLD was thereby used to denote the dose that actually reached the lungs of the subjects. By design, in all nebulizers there can be a residual volume or mass of drug solution that stays in the nebulizer, and there can also be a percentage of the aerosol caught by subject's throat and mouth. For instance, in this study, it was estimated that 30% of the aerosol was lost in subject's throat and mouth. Therefore the eTLD would be:

eTLD=(100−30)%*amount of aerosolized drug that left nebulizer=70%*(amount of drug placed in nebulizer−amount of drug staying in nebulizer).

Part B study. The effective dose in Part A will be confirmed in Part B study. Part B is an open-label, multicenter study in the same patient population as Part A (i.e., recent onset, symptomatic PAF, without known structural heart disease) to confirm the safety (including tolerability) and efficacy of the optimal inhaled flecainide dose determined in Part A. A total of up to 85 patients will be enrolled to evaluate safety and tolerability of the 120 mg eTLD, and to more accurately determine the AF conversion rate for the 120 mg dose. Part B also includes optional sub-studies that are open to consenting patients: 1) to evaluate the feasibility of using a hand-held echocardiograph device during screening, and 2) to evaluate independent self-administration of inhaled flecainide in the hospital setting for a recurrent episode of recent-onset AF, but only for patients whose recent-onset AF was converted to SR with inhaled flecainide with the initial treatment.

Data Collection

In both parts of the study, after written informed consent has been obtained, the patient is connected to cardiac telemetry monitoring and study ECG devices to evaluate the stability of AF during the next hour. Vital signs, triplicate 12-lead ECGs, and blood samples for PK analysis are collected at multiple serial time points just before, during, and after the inhalation regimen, and at the time of conversion to SR. Ambulatory ECG (12-lead Holter) data are collected from the time of informed consent until 90 minutes postdose in order to identify the time of conversion to SR and to monitor safety. Discharge is at the discretion of the treating physician but may not be scheduled prior to 90 minutes postdose. If conversion to SR does not occur within a certain time period postdose, the Investigator may offer another appropriate therapy, as per the clinical site's standard-of-care, except for IV ibutilide or sotalol which are not allowed. All patients have a Day 2 and a Day 5 (±1 day) telephone assessment.

Nebulizer Configuration.

The AeroEclipse®II BAN inhaler was used for nebulization and inhalation of the exemplary flecainide formulations. It is available as an approved device in several countries across the world including European countries, USA, and Canada. The inhaler is a hand-held, breath actuated, jet nebulizer which operates through a source of compressed air available as medical air in the hospital ER. The AeroEclipse®BAN delivers a high respirable dose and an optimal particle size to reach the deeper lung regions to enable faster drug absorption. Flecainide acetate inhalation solution or placebo inhalation solution is transferred from the vial into the reservoir of the AeroEclipse®II BAN at a volume corresponding to the required dose to the lung (TABLE 20), in accordance with the specific instructions provided for each study protocol.

TABLE 20

| Study Drug | Nominal Dose Level (eTLD) (mg) | Nominal Volume per Dose (mL) | Number of Nebulizers Required | Total Volume Filled into each Nebulizer (mL)* |
|---|---|---|---|---|
| FlecIH-101 | 30 | 2.7 | 1 | 2.7† |
| | 60 | 5.4 | 2 | 2.7† |
| | 90 | 6.6 | 2 | 3.3‡ |

TABLE 20-continued

| Study Drug | Nominal Dose Level (eTLD) (mg) | Nominal Volume per Dose (mL) | Number of Nebulizers Required | Total Volume Filled into each Nebulizer (mL)* |
|---|---|---|---|---|
| FlecIH-102 | 120 | 4.2 | 1 | 4.2‡ |
|  | 90 | 3.5 | 1 | 3.5‡ |
| FlecIH-103 | 120 | 4.2 | 1 | 4.2‡ |
|  | 90 | 3.5 | 1 | 3.5‡ |

*The total volume to be filled in each dosing cup are based on the following calcuations:
1. †Assumes a 70% lung deposition; ‡Assumes a 70% lung deposition and in addition, 12.5% loss due to fugitive aerosol based on in-vitro experiments.
2. Accounts for device retention of approximately 1.5 mL.

Inhalation Guidelines.

Participants in the study were administered the study medications according to the following guidelines:

- Subject self-administers inhalation using the AeroEclipse® II BAN
- Subject is seated upright in a comfortable chair or adjustable bed with table that has adjustable height in front (e.g. overbed table on casters) where the subject can rest his/her arms (e.g. overbed table on casters) from approximately 30 minutes prior to the start of inhalation up to at least 15 minutes after the last inhalation is completed.
- The setting at the site allows for subject to remain in this upright sitting position while linked to cardiac monitoring systems, while blood samples are being collected and while self-administering the inhalation solution which is linked to compressed air.
- The subject receives clear instructions from trained study personnel on how to self-administer the treatment in accordance with the instructions for use.
- A topical oral anesthetic spray (e.g., containing lidocaine [e.g., Medica] or phenol [e.g., Chloraseptic]) or lozenge [e.g., Trachitol or Cepacol] may be applied to the back of the subject's throat prophylactically if not contraindicated, to improve the tolerability of the inhalation procedure.
- A sugar-containing spray or lozenge (e.g., for dry mouth) may be applied or used prophylactically if not contraindicated, to improve the tolerability of the inhalation procedure.
- The subject may practice the inhalation procedure (without flecainide and for approximately 1 minute, for example) prior to study drug administration.
- Once the inhalation pattern is established, the subject should not remove inhaler device from the mouth for the required inhalation time. If the subject removes the nebulizer for any reason (e.g., cough, excessive saliva, etc.) for >30 seconds, then the inhalation time for that inhalation should be extended by the length of the interruption. Subjects can elect to terminate inhalation of study medication at any time, for any reason.

Part A: Study Enrollment, Demographics, and Medical History by Inhaled Flecainide Dose Cohort Enrollment status for completed Part A of the study is shown in TABLE 21.

TABLE 21

Number of Patients Enrolled in the Study

| Flecainide Dose (eTLD) | 30 mg | 60 mg | 90 mg | 120 mg | | |
|---|---|---|---|---|---|---|
| Inhalation Solution & Formulation | 35 mg/mL FlecIH-101 (N) | 45 mg/mL FlecIH-101 (N) | 75 mg/mL FlecIH-102 (N) | 75 mg/mL FlecIH-103 (N) | | Total (N) |
| Enrolled & Completed | 10 | 22 | 21 | 19 | 29 | 101 |
| Efficacy Evaluable | 10 | 20[a] | 21 | 17[b] | 27[c] | 95 |

Abbreviations:
N = number of patients in a given group
[a] 2 patients were not in AF at the time of inhaled flecainide administration
[b] 2 patients: 1 was not in AF at the time of inhaled flecainide administration and 1 did not complete the inhalation (dosing was interrupted)
[c] 2 patients: 1 was not in AF at the time Selected demographic and medical history information of the patients enrolled in Part A is provided in TABLE 22.

TABLE 22

Demographic and Medical History of Enrolled Patients

| | | | | 120 mg | |
|---|---|---|---|---|---|
| Characteristic | 30 mg (N = 10) | 60 mg (N = 22) | 90 mg (N = 21) | FlecIH-102 (N = 19) | FlecIH-103 (N = 27) |
| Age | | | | | |
| mean ± SD | 59.3 ± 6.5 | 62.0 ± 13.4 | 58.9 ± 9.3 | 63.4 ± 8.6 | 62.9 ± 12.8 |
| median | 60.0 | 63.0 | 59.0 | 62.0 | 61.0 |
| Min-Max | 48.0-66.0 | 33.0-89.0 | 39.0-76.0 | 53.0-82.0 | 39.0-84.0 |
| Gender: Male | 90.0% | 77.3% | 66.7% | 42.1% | 70.4% |
| Duration of presenting AF period | | | | | |
| ≥1 h up to ≤24 h | 60.0% | 63.6% | 85.7% | 94.7% | 88.9% |
| >24 h up to ≤48 h | 40.0% | 36.4% | 14.3% | 5.3% | 11.1% |

TABLE 22-continued

Demographic and Medical History of Enrolled Patients

| Characteristic | 30 mg (N = 10) | 60 mg (N = 22) | 90 mg (N = 21) | 120 mg FlecIH-102 (N = 19) | 120 mg FlecIH-103 (N = 27) |
|---|---|---|---|---|---|
| Body Mass Index | | | | | |
| mean ± SD | 26.9 ± 3.9 | 26.3 ± 3.1 | 27.3 ± 3.9 | 28.2 ± 5.4 | 26.6 ± 3.8 |
| median | 25.75 | 26.05 | 26.40 | 26.60 | 26.30 |
| Min-Max | 23.1-36.3 | 21.5-31.6 | 20.6-34.1 | 20.9-38.8 | 29.6-36.2 |
| CHA2DS2VASc score | | | | | |
| mean ± SD | 1.1 ± 0.9 | 1.6 ± 1.5 | 1.3 ± 1.3 | 1.7 ± 1.4 | 1.5 ± 1.5 |
| median | 1.00 | 1.50 | 1.00 | 1.00 | 1.00 |
| Min-Max | 0.0-2.0 | 0.0-6.0 | 0.0-4.0 | 0.0-4.0 | 0.0-4.0 |
| NYHA Class | | | | | |
| No heart failure | 90.0% | 100.0% | 100.0% | 100.0% | 92.6% |
| Class I | 10.0% | 0.0% | 0.0% | 0.0% | 7.4% |
| AF Episode is: | | | | | |
| First AF episode | 60.0% | 50.0% | 38.1% | 47.4% | 40.7% |
| Recurrent episode of PAF | 40.0% | 40.0% | 47.6% | 47.4% | 55.6% |
| Episode post-cardiac ablation for PAF | 0.0% | 10.0% | 14.3% | 5.3% | 3.7% |

Abbreviations:
N = number of patients in a given group;
PAF = paroxysmal atrial fibrillation;
SD = standard deviation;
h = hour
Source: February 2020 DSMB Report, 17 Feb. 2020

Part A: Pharmacodynamic (QRS Interval) Results

The 12-lead ECG recordings for the patients enrolled in Part A of the study have been analyzed to summarize the maximal QRS interval and change from baseline QRS (L QRS) interval durations following inhaled flecainide (TABLE 23). The QRS interval was found to transiently increase soon after the end of dose inhalation and quickly return toward pre-dose levels. The mean maximal QRS interval durations following inhaled flecainide at the 30, 60, 90 and 120 mg eTLDs were similar (93 to 99 msec). The mean L QRSmax increases above baseline (i.e., prior to dosing) for the 30, 60, 90 and 120 mg (FecIH-102 and FlecIH-103) eTLD cohorts were 1.6, 4.2, 4.1, 9.0 and 9.5 msec, respectively.

TABLE 23

Summary of Maximal QRS Intervals

| Parameter | 30 mg (N = 9) | 60 mg (N = 20) | 90 mg (N = 20) | 120 mg FlecIH-102 (N = 15) | 120 mg FlecIH-103 (N = 21) |
|---|---|---|---|---|---|
| QRSmax | | | | | |
| mean ± SD | 99.1 ± 20.0 | 95.9 ± 7.6 | 92.7 ± 9.4 | 94.7 ± 12 | 98.5 ± 6.5 |
| Min-Max | 79.1-109.1 | 83-115.5 | 83.3-113 | 86.3-136 | 91-106.3 |
| ΔQRSmax | | | | | |
| mean ± SD | 1.6 ± 1.7 | 4.2 ± 4.6 | 4.1 ± 3.2 | 9.0 ± 7.5 | 9.5 ± 4.1 |
| Min-Max | 0-5.3 | −3.0-13.1 | 0.3-9.7 | 0.3-30.5 | 5.8-20.3 |

Figure 21:
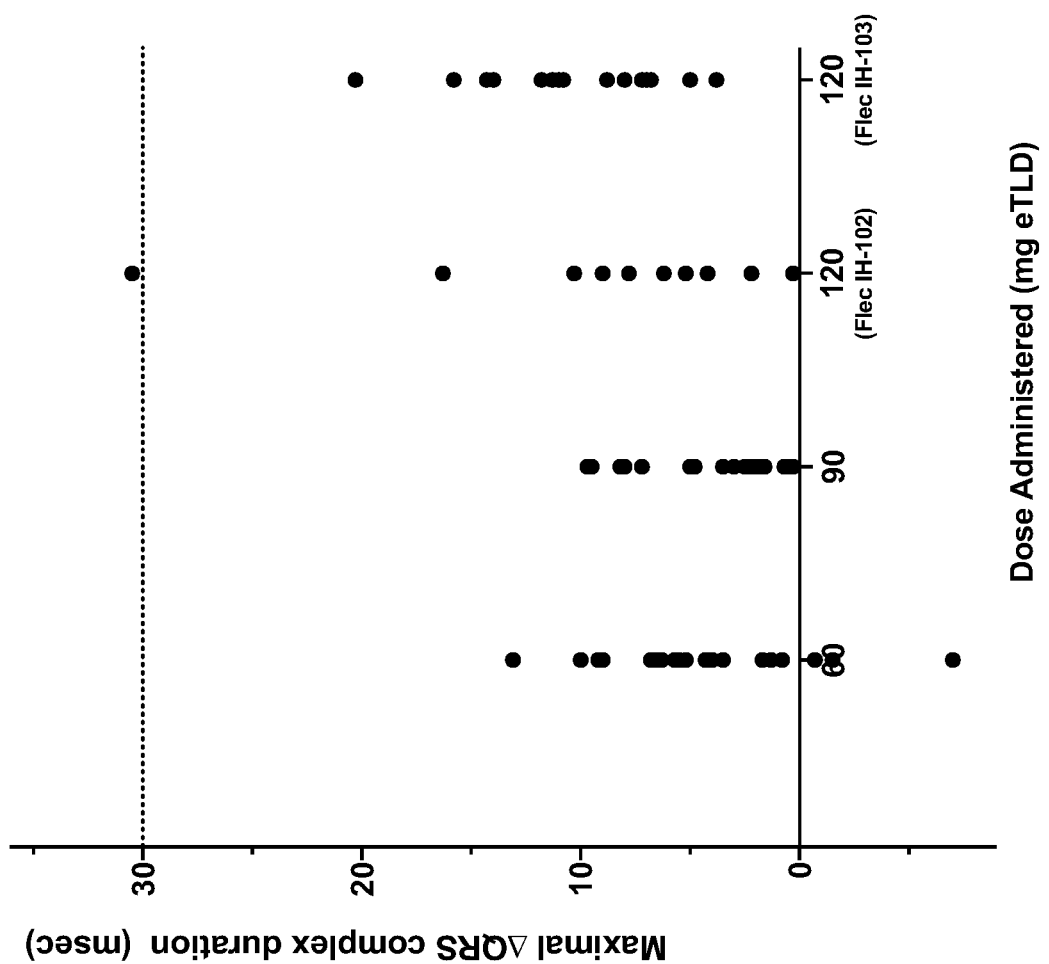
FIG. 21 is a chart summarizing the magnitude of the prolongations of the QRS interval duration ($AQRS_{max}$) in individual human subjects after inhalation of the formulations of flecainide described in TABLE 19.
Figure 22A:
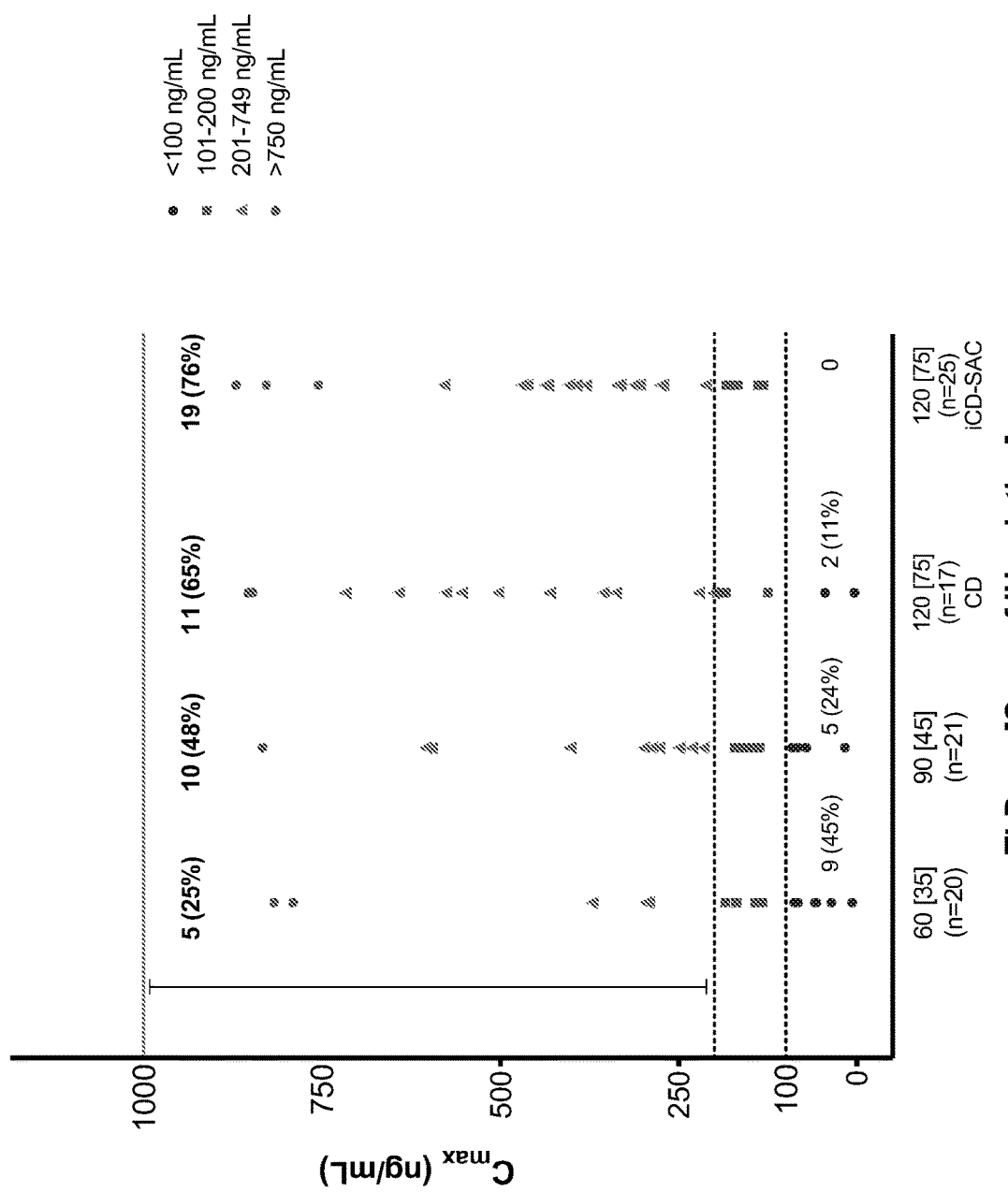
FIG. 22A is a chart summarizing peak plasma concentration of flecainide ($C_{max}$) in individual human subjects after inhaling flecainide formulations described in TABLE 19. Coefficient of variance (% CV) in $C_{max}$ values were 111, 83, 67, and 55 for 60 [65], 90 [45], 120 [75] CD, and 120 [75] iCD-SAC dose cohorts, respectively.
Figure 22B:
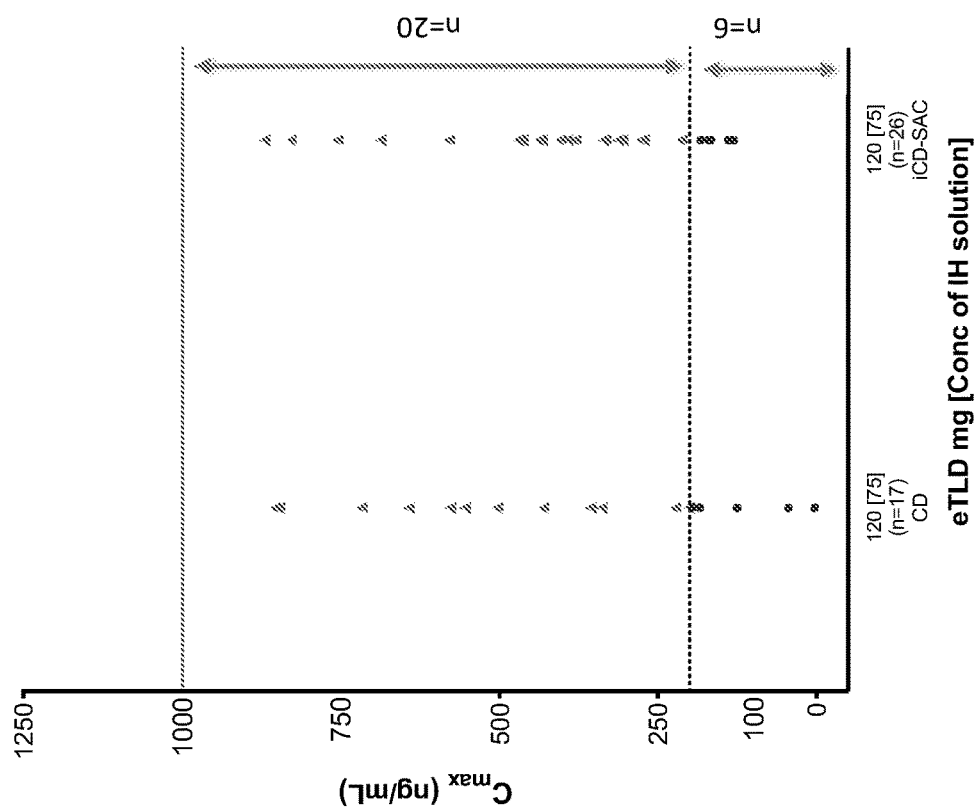
FIG. 22B is a chart summarizing peak plasma concentration of flecainide ($C_{max}$) in individual human subjects after inhaling CD and iCD flecainide formulations described in TABLE 19.
Figure 22C:
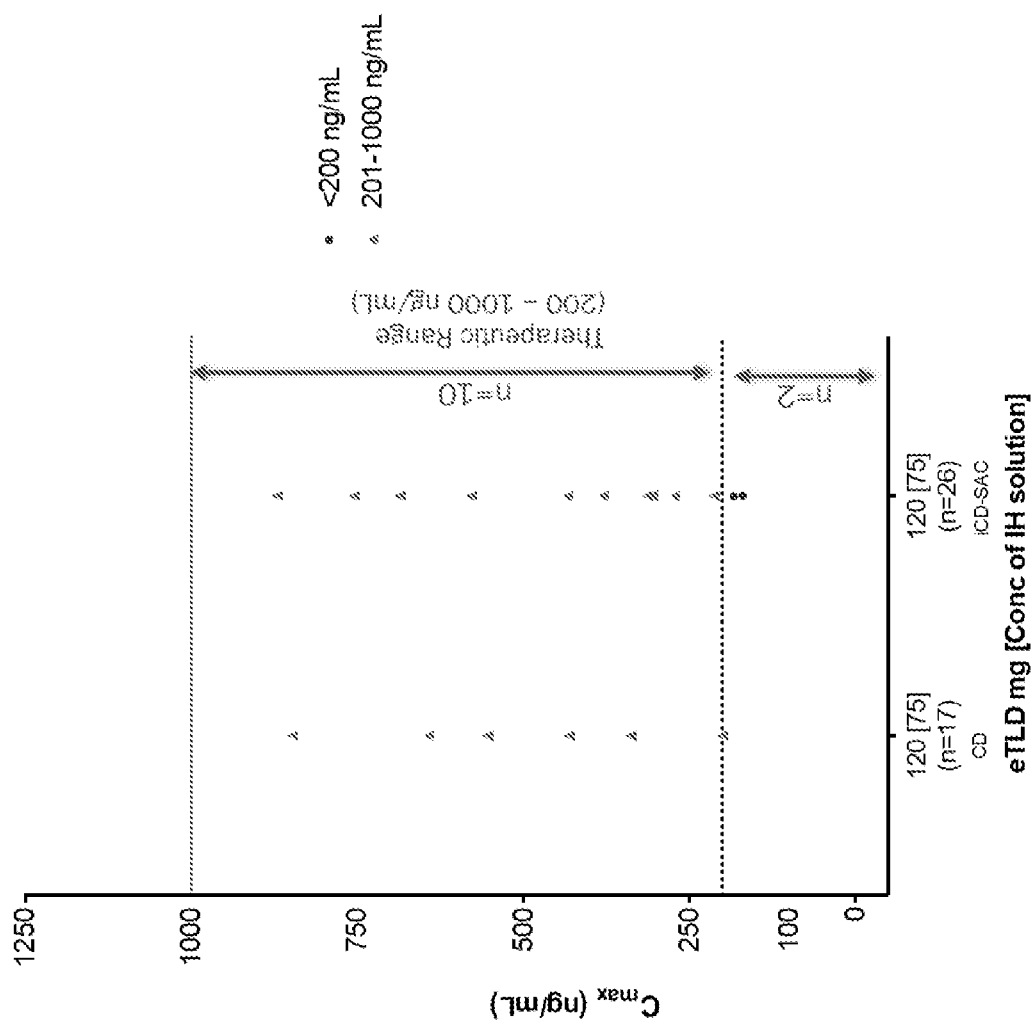
FIG. 22C is a chart summarizing peak plasma concentration of flecainide ($C_{max}$) in individual human subjects that underwent cardioversion after inhaling CD and iCD flecainide formulations described in TABLE 19.

The magnitude of the prolongations of the QRS interval duration (Δ QRSmax) for the individual patients in Part A of the study (60, 90 and 120 mg eTLDs) are graphically presented in FIG. 21. There was only one patient who had a Δ QRS of ≥30 msec following inhaled flecainide; this patient (120 mg FlecIH-102) with a baseline pre-dose QRS interval duration of 106 msec had a maximum QRS duration of 136 msec (Δ QRSmax of 30.5 msec). The ECG was consistent with left anterior fascicular block, and no treatment was required.

Part A: Adverse Events

Adverse event data for 99 patients dosed at the different dose levels with inhaled flecainide is summarized in TABLE 24. Treatment-emergent adverse events (TEAEs) were reported by 80/99 patients (81%) and were considered related to study drug in 74/99 (75%) patients. Treatment-emergent serious adverse events (TESAEs) were reported by 7 patients. Three patients in the 60 mg group experienced an SAE that was considered to be unrelated to study drug. SAEs considered study drug-related were reported for 1/21 patients in the 90 mg group (5%) and 3/46 patients (6.5%) in the 120 mg group. All study drug-related SAEs were transient and resolved without treatment or clinical sequelae. No deaths have been reported in patients enrolled in the study.

be less in patients treated at the 120 mg eTLD with the FlecIH-103 inhalation solution. The majority of patients had events that were considered mild (64/99; 65%); 33/99 (33%) patients had events that were moderate in intensity. Only 2 (2%) patients had severe TEAEs, and in both cases, it was a worsening of a pre-existing condition; both events were considered SAEs. In general, the incidence of TEAEs that were considered related to study drug did not an increase with an increase in dose.

TABLE 24

Summary of Number of Adverse Events

| | Flecainide Dose (eTLD) | | | | | |
|---|---|---|---|---|---|---|
| | 30 mg | 60 mg | 90 mg | 120 mg | | Total |
| | | FlecIH-101 | | FlecIH-102 | FlecIH-103 | |
| | (N = 10) n (%) | (N = 22) n (%) | (N = 21) n (%) | (N = 19) n (%) | (N = 27) n (%) | (N = 99) n (%) |
| Patients with at least one: | | | | | | |
| TEAE | 9 (90) | 16 (73) | 18 (86) | 16 (84) | 21 (78) | 80 (81) |
| Study-drug Related$^{a,b}$ | 8 (80) | 14 (64) | 17 (81) | 16 (84) | 19 (70) | 74 (75) |
| Moderate or Severe$^c$ | 1 (10) | 6 (27) | 6 (29) | 11 (58) | 11 (41) | 35 (35) |
| Severe$^c$ | 0 | 1 (5) | 0 | 0 | 1 (4) | 2 (2) |
| TESAE$^d$ | 0 | 3 (14) | 1 (5) | 1 (5) | 2 (7) | 7 (7) |
| Study-drug Related$^{a,b}$ | 0 | 0 | 1 (5) | 1 (5) | 2 (7) | 4 (4) |
| Moderate or Severe$^c$ | 0 | 2 (9) | 1 (5) | 1 (5) | 2 (7) | 6 (6) |
| Severe$^c$ | 0 | 1 (5) | 0 | 0 | 1 (4) | 2 (2) |

Abbreviations:
N = number of patients in a given group;
n = number of patients with a given event;
TEAE = treatment-emergent adverse event;
TESAE = treatment-emergent serious adverse event
$^a$Study-drug related = Investigator assessment of probably or possibly related to Study Drug
$^b$Patients reporting more than one event were counted only once using the strongest study-drug relationship category
$^c$Patients reporting more than one event were counted only once using the highest severity grade
$^d$TESAE tally based on manual review of SAEs reported The most commonly reported (≥5 patients [5%] overall) TEAEs in decreasing order of frequency were (TABLE 25): cough (52%), oropharyngeal pain (14%), throat irritation (12%), dysphagia (9%), salivary hypersecretion (8%), hypotension (7%), dyspnea (6%) and dizziness (5%). In general, the incidence of AEs by preferred term did not increase with an increase in dose. The incidence of AEs associated with the inhalation (e.g., cough, throat irritation, etc.) appeared to

TABLE 25

Summary of Adverse Events

| | Flecainide Dose Group (eTLD) | | | | | |
|---|---|---|---|---|---|---|
| | 30 mg | 60 mg | 90 mg | 120 mg | | |
| | | FlecIH-101 | | FlecIH-102 | FlecIH-103 | Total |
| System Organ Class, Preferred Term$^a$ | (N = 10) n (%) | (N = 22) n (%) | (N = 21) n (%) | (N = 19) n (%) | (N = 27) n (%) | (N = 99) n (%) |
| Gastrointestinal disorders | 0 | 5 (23) | 8 (38) | 3 (16) | 7 (26) | 23 (23) |
| Dysphagia | 0 | 2 (9) | 3 (14) | 2 (11) | 2 (7) | 9 (9) |
| Salivary hypersecretion | 0 | 1 (5) | 4 (19) | 1 (5) | 2 (7) | 8 (8) |
| Nervous system disorders | 2 (20) | 2 (9) | 0 | 1 (5) | 2 (7) | 7 (7) |
| Dizziness | 2 (20) | 1 (5) | 0 | 0 | 2 (7) | 5 (5) |
| Respiratory, thoracic and mediastinal disorders | 8 (80) | 14 (64) | 12 (57) | 14 (74) | 12 (44) | 60 (61) |
| Cough | 8 (80) | 9 (41) | 11 (52) | 13 (68) | 10 (37) | 51 (52) |
| Oropharyngeal pain | 0 | 3 (14) | 4 (19) | 4 (21) | 3 (11) | 14 (14) |
| Dyspnea | 0 | 1 (5) | 1 (5) | 3 (16) | 1 (4) | 6 (6) |
| Throat irritation | 1 (10) | 6 (27) | 1 (5) | 3 (16) | 1 (4) | 12 (12) |

TABLE 25-continued

Summary of Adverse Events

| | Flecainide Dose Group (eTLD) | | | | | |
|---|---|---|---|---|---|---|
| | 30 mg | 60 mg | 90 mg | 120 mg | | |
| | FlecIH-101 | | | FlecIH-102 | FlecIH-103 | Total |
| Vascular disorders | 1 (30) | 2 (9) | 1 (5) | 2 (11) | 3 (11) | 10 (10) |
| Hypotension | 1 (10) | 1 (5) | 1 (5) | 2 (11) | 2 (7) | 7 (7) |

Abbreviations:
N = number of patients in a given group;
n = number of patients with a given event;
TEAE = treatment-emergent adverse events
Note:
If a patient had more than one event coded to the same MedDRA term, the patient was counted only once
<sup>a</sup>8 patients had their AF terminated on the study day (either by study drug or other means [or they did not have AF at presentation]), and had a recurrence of AF in the days following the study day; these events of AF ('atrial fibrillation') were categorized as TEAEs, and none were considered related to study drug.

Adverse events of special interest (AESIs) for the study include the following:
1. AEs related to the AeroEclipse® BAN inhalation device
2. Elevation of liver enzyme laboratory findings (combined elevations of aminotransferases and bilirubin) considered to signal possible liver injury
3. Pregnancy in a female study participant or in a female partner of a study participant while participating in the study
4. Cardiac AEs known to be related to other formulations of flecainide (i.e., IV and oral): hypotension, ventricular tachycardia, bradycardia, sinus pauses post conversion of AF to SR, and atrial flutter with 1:1 conduction with fast ventricular response (ventricular heart rate ≥200 bpm).

These events are closely monitored in the trial in order to rapidly detect any trends indicative of a safety concern. The cardiac AESIs are monitored by frequent review of AEs, vital sign and ECG listings.

No AESIs related to the inhalation device, liver enzymes or pregnancies have been reported. Cardiac AESIs have been reported as follows:

Hypotension: 7 patients (3 mild and 1 moderate, related; 3 moderate, not related). All hypotension cases were transient, none were considered to be serious, and none required treatment with vasopressors or positive chronotropic/inotropic agents.

Bradycardia: 4 patients (2 mild, 1 related [post-conversion to SR] and 1 not related; 1 moderate, related [post-conversion to SR]; 1 SAE, related. All bradycardia events resolved without treatment.

Sinus pause post-conversion of AF to SR: 2 patients (2 SAEs, related. Both sinus pause events resolved quickly without treatment.

Atrial flutter with 1:1 conduction and rapid ventricular response: 1 patient (1 SAE, related. Event resolved quickly without treatment.

4 patients experienced SAEs (TABLE 26) that were considered study-drug related: sinus pause/ventricular asystole associated with conversion to SR (2 patients), bradycardia (1 patient), and atrial flutter with 1:1 conduction and a fast ventricular response (1 patient).

TABLE 26

Summary of Adverse Events of Special Interest

| Patient ID | Dose Cohort (mg eTLD) | SAE | $C_{max}$ (ng/mL) |
|---|---|---|---|
| NL020-1013 | 90 | Sinus Pause post conversion | 833.8 |
| NL033-1008 | 120 | Sinus Pause post conversion | 430.8 |
| NL030-1008 | 120 | Severe Bradycardia | 332.4 |
| NL038-1001 | 120 | Atrial flutter rapid VR | 204.6 |

Three additional patients (60 mg dose cohort) had SAEs reported, none of which were considered to be related to study-drug treatment.

Part A; Pharmacokinetics and Conversion Rate

Plasma levels of flecainide are used to monitor drug delivery of flecainide into the systemic circulation following oral inhalation of the drug. Peak plasma levels ($C_{max}$) of flecainide achieved following the inhalation have been shown to occur within 3 minutes of completion of the inhalation. The $C_{max}$ values for the 30, 60, 90 and 120 mg dose cohorts are provided in TABLE 27, along with the rate of AF conversion to SR (within 60 minutes of dosing) for each dose cohort. There was a dose-related increase in mean $C_{max}$ values.

TABLE 27

| | Flecainide Dose (eTLD) | | | | |
|---|---|---|---|---|---|
| | | | | 120 mg | |
| Parameter | 30 mg | 60 mg | 90 mg | FlecIH-102 | FlecIH-103 |
| Number of patients treated | 10 | 20 | 21 | 19 | 27 |

TABLE 27-continued

| | Flecainide Dose (eTLD) | | | | |
|---|---|---|---|---|---|
| | | | | 120 mg | |
| Parameter | 30 mg | 60 mg | 90 mg | FlecIH-102 | FlecIH-103 |
| Number of evaluable patients (by PK) | 10 | 20 | 21 | 17 | 27 |
| $C_{max}$ (mean ± SD, ng/mL) | 127 ± 99.5 | 199 ± 222 | 248 ± 207 | 400 ± 269 | 385 ± 209 (n = 26) |
| Range (ng/mL) | 5.8-369 | 6.6-817 | 17-834 | 3.6-854 | 131-871 |
| | 78% | 111% | 83% | 67% | |
| Conversion Rate (AF to SR) | 1/10 (10%) | 7/20 (35%) | 7/21 (33%) | 6/17 (35%) | 12/27 (44%) |
| $\Delta QRS_{max}$ (msec, (SEM)) (number of patients) | 5.5 ± 13.1 (4.1) (10) | 4.2 ± 4.6 (1.0) (20) | 4.1 ± 3.2 (0.7) (20) | 9.0 ± 7.5 (1.9) (15) | 9.5 ± 4.1 (0.9) (21) |

Figure 23A:
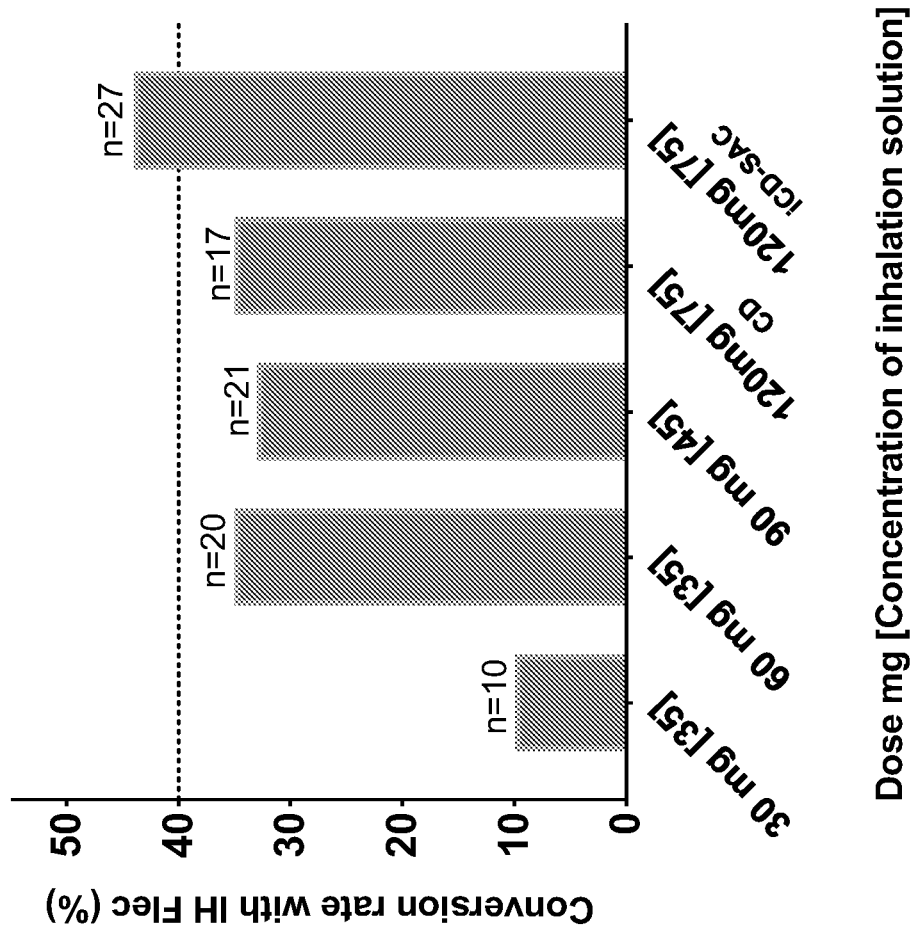
FIG. 23A is a chart summarizing the cardioversion rate inhuman subjects as categorized according to the administered formulation as described in TABLE 19.
Figure 23B:
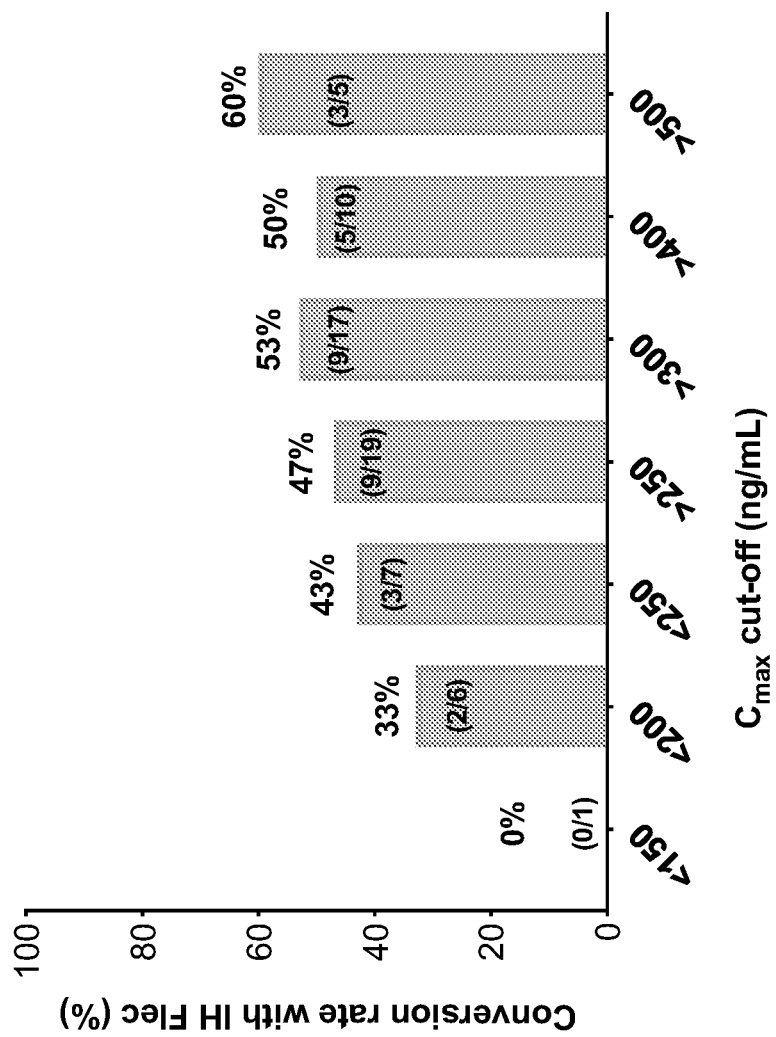
FIG. 23B is a chart summarizing the cardioversion rate in human subjects as categorized according to the $C_{max}$ of flecainide measured after inhalation of flecainide formulations described in TABLE 19.
Figure 23C:
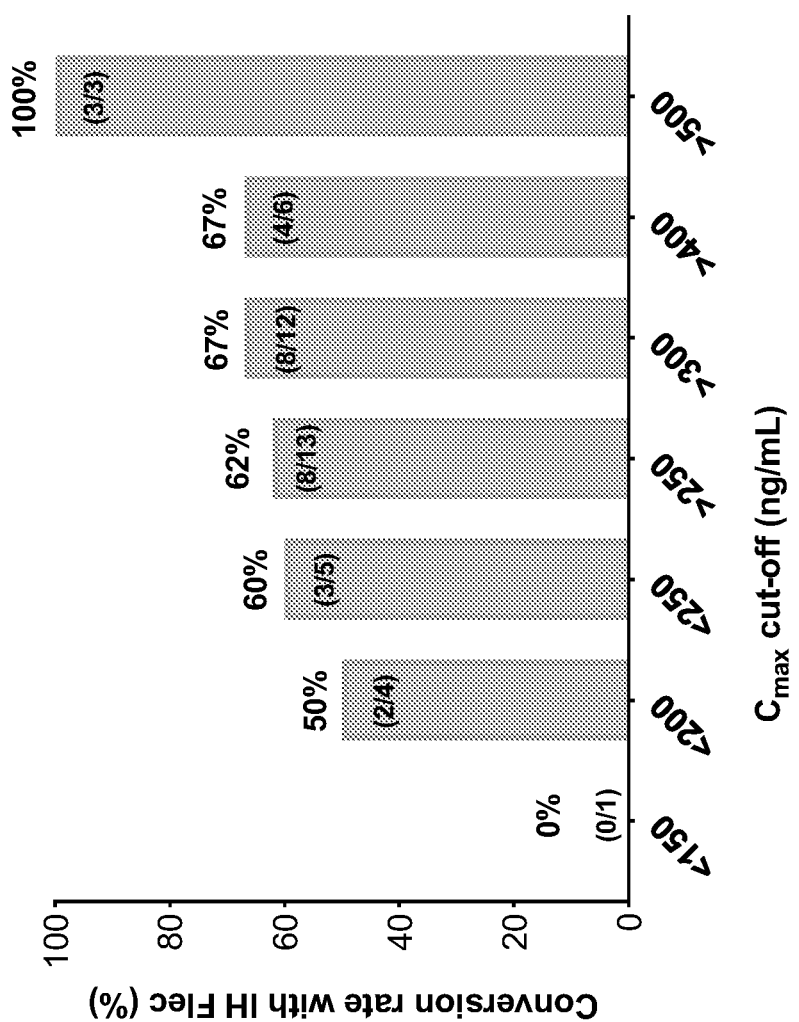
FIG. 23C is a chart summarizing the cardioversion rate inhuman subjects who had a ventricular rate of ≥80 and <155 bpm at screening, as categorized according to the $C_{max}$ of flecainide measured after inhalation of flecainide formulations described in TABLE 19.
Figure 23D:
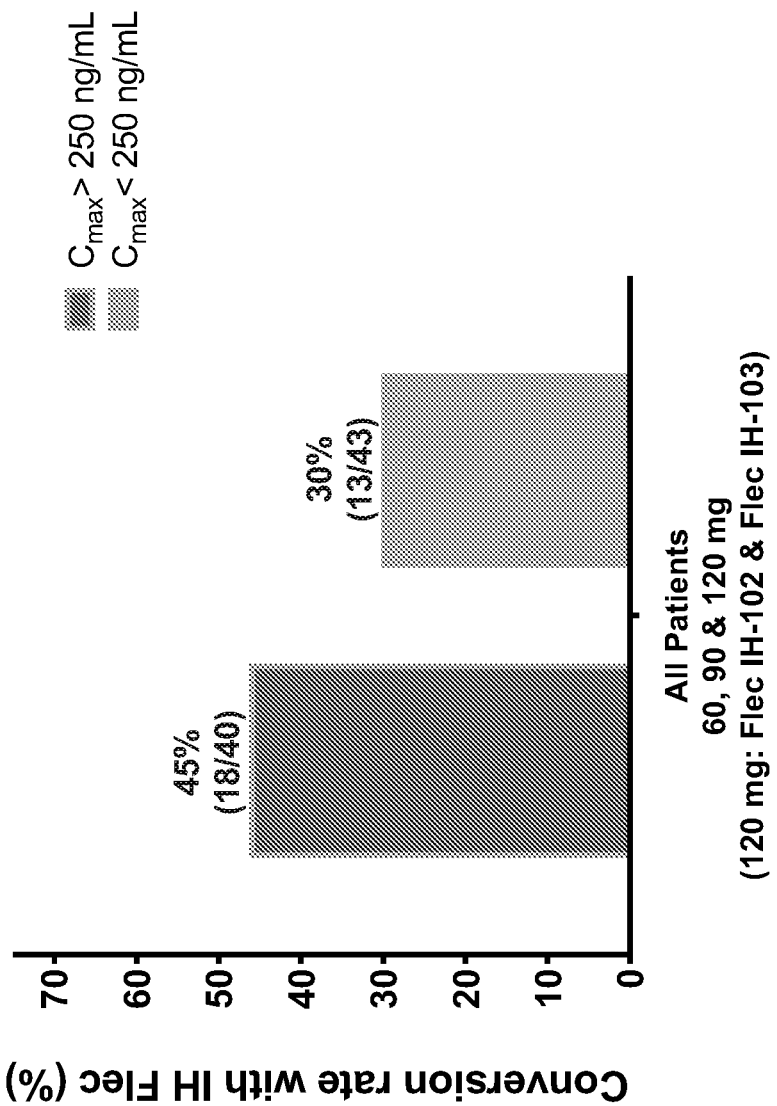
FIG. 23D is a chart summarizing the cardioversion rate in human subjects as categorized by observed $C_{max}$ (<250 ng/mL or >250 ng/mL) across all dose cohorts.

Note:
Evaluable patients include those who were in AF at the time of treatment and completed inhalation of the flecainide dose The rate of conversion of AF to SR by dose level is depicted in the bar graph in FIG. 23A; although the conversion rate increased from 10 to 35% between the 30 and 60 mg eTLD cohorts, the conversion rate remained in the mid-30% range for the 90 and 120 mg (FecIH-102) eTLDs. With implementation of the FlecIH-103 inhalation solution, the conversion rate for the 120 mg (FlecIH-103) cohort increased to 44%. The therapeutic plasma range for oral and IV flecainide is generally considered to be 200-1000 ng/mL (Conard et al., 1984a and 1984b; Flecainide Acetate Tablets US Prescribing Information, 2017). For patients in AF who were treated with inhaled flecainide doses of 60, 90 or 120 mg dose, a categorical analysis was performed using a $C_{max}$ cut-off of 250 ng/mL; patients achieving a $C_{max}$ higher than 250 ng/mL had a conversion rate of 45%, whereas patients with $C_{max}$ less than 250 ng/mL had a conversion rate of 30% (FIG. 23D). As would be expected, these data suggest that the probability of conversion of AF to SR is greater in patients who reach a plasma concentration in the therapeutic range following inhalation of flecainide.

Figure 24:
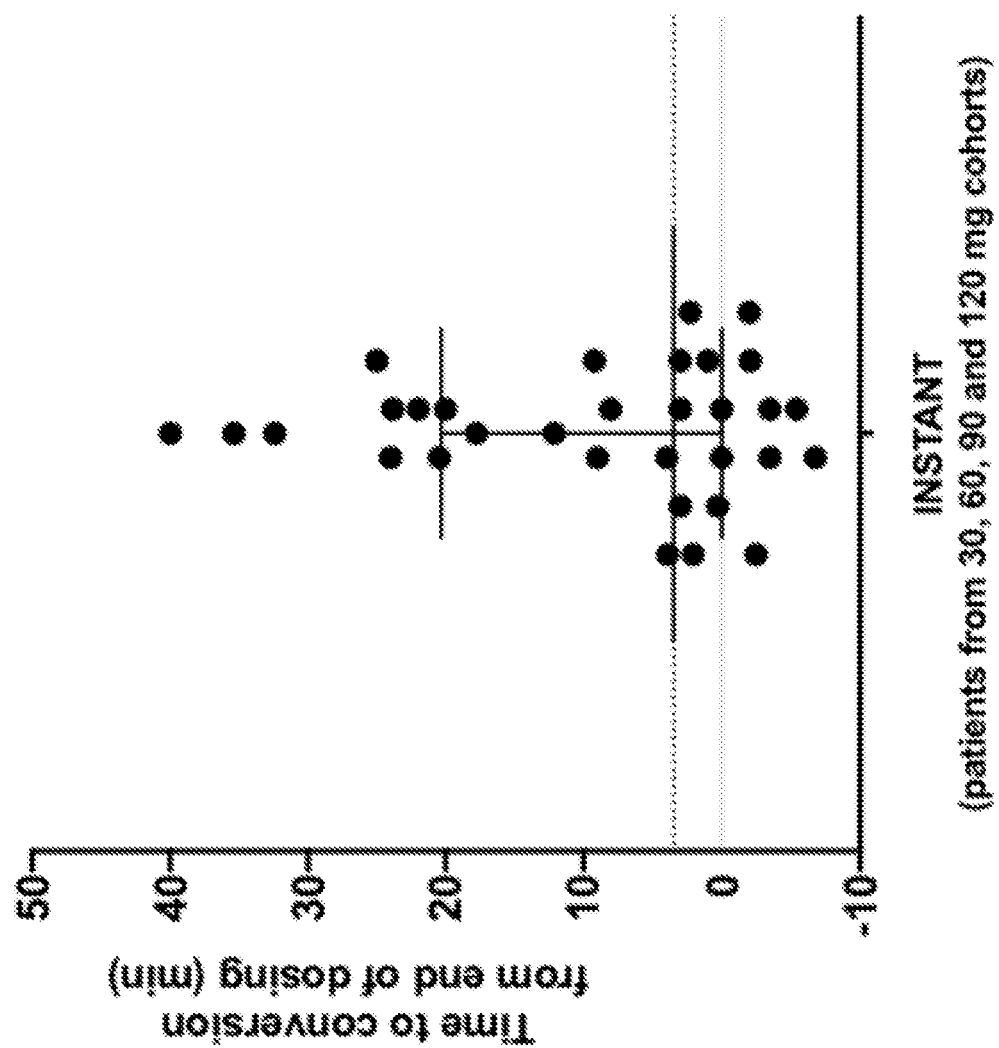
FIG. 24 is a chart summarizing the time to conversion of atrial fibrillation to normal sinus rhythm from the end of flecainide inhalation in human subjects administered the formulations described in TABLE 19.

For the 32 patients across all dose groups (30, 60, 90 and 120 mg) whose AF converted to SR within 60 minutes of completing the inhalation, the median time to conversion was very rapid, that is, 3.5 minutes from the end of the inhalation (FIG. 24), with the time of conversion ranging from −7 to 40 minutes from the end of the inhalation. The time to conversion was ≤3 minutes for 50% of those who converted and was ≤4 minutes for 56% of those who converted to SR.

Figure 25:
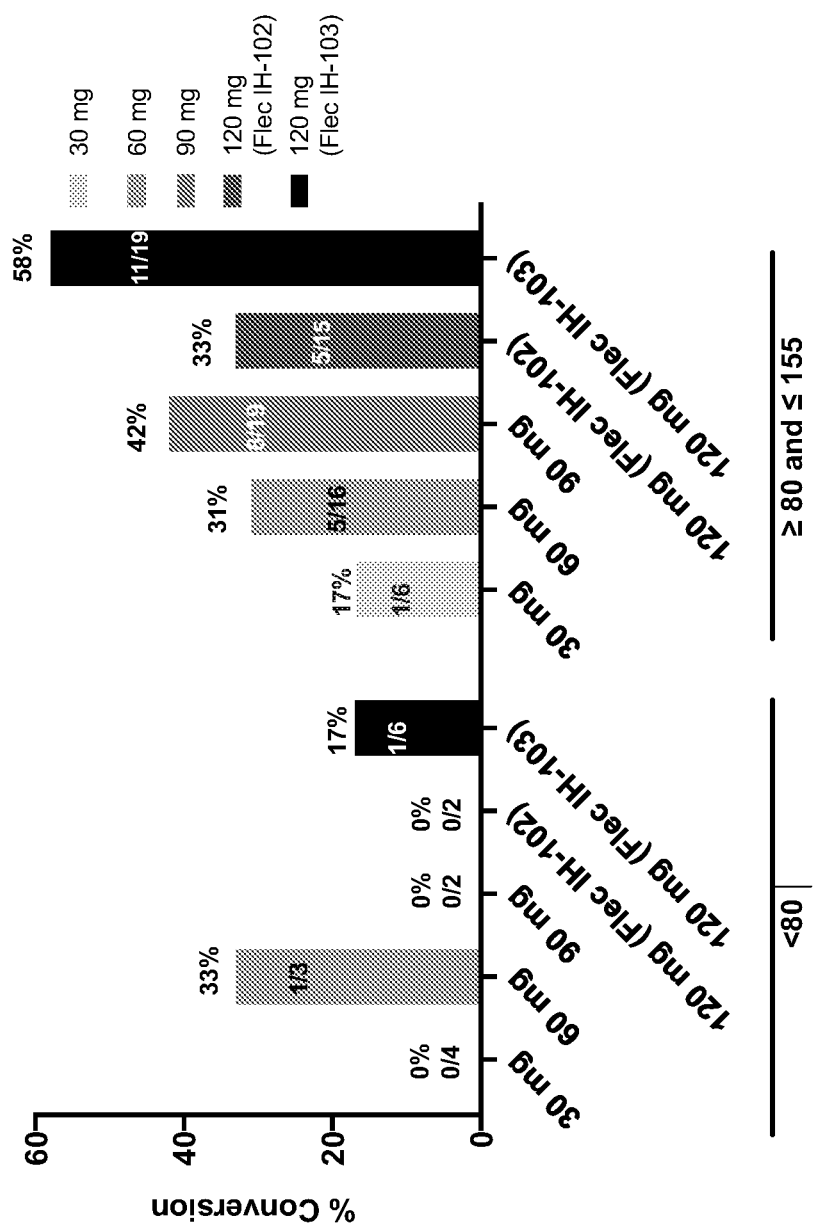
FIG. 25 is a chart summarizing the cardioversion rate in human subjects categorized by subjects who had a ventricular rate of <80 PM at screening and those who had a ventricular rate of ≥80 and ≤155 bpm at screening, and further categorized according to administered formulation (as described in TABLE 19).

Eligibility for enrollment in Part A of the study included a requirement that the baseline ventricular rate be ≥70 bpm and ≤170 bpm. In a post-doc analysis, it was observed that patients having a slow ventricular rate (<80 bpm) responded less favorably to conversion of their AF to SR by inhaled flecainide. The conversion rate for the pooled dose groups of patients (eTLDs of 60, 90 and 120 mg) with a baseline ventricular rate <80 bpm was 15%, whereas those having a baseline ventricular rate of ≥80 bpm and ≤155 bpm had a higher conversion rate of 42% (FIG. 25). For the 120 mg cohort (FecIH-103), the conversion rate for patients with a baseline ventricular rate ≥80 bpm and ≤155 bpm was 58% (11/19), whereas for those with a baseline rate <80 bpm, it was only 17% (1/6).

Patients in AF with slower ventricular rates can still have a very rapid atrial rate due to AF. The slower ventricular rate in patients with AF can be indicative of high vagal tone. The high vagal tone can lead to slower AV nodal conduction and shorter atrial refractory period. The slower AV nodal conduction can be the cause of the slower ventricular rate and the shorter atrial refractory period can render flecainide less effective to convert AF to SR. Without wishing to be bound by aby particular theory, the latter is a plausible explanation to for the lower effectiveness of flecainide to convert AF to SR when the heart rate is <80 bpm.

Part A: Summary 101 patients have been treated with inhaled flecainide (30 mg, n=10; 60 mg, n=22; 90 mg, n=21; 120 mg [FlecIH-102], n=19; and 120 mg [FecIH-103], n=29) in the INSTANT (FLE-002) Study. Inhaled flecainide in this dose range has been shown to be safe. Dose-related increases in $C_{max}$ were observed (127, 199, 248, 400 and 385 ng/mL, respectively) with conversion rates of AF to SR (10%, 35%, 33%, 35% and 44%, respectively). In patients whose AF converted to SR with inhaled flecainide, the median time to conversion was 3.5 minutes after completion of the inhalation. Conversion of AF to SR was shown to be greater in patients who achieved $C_{max}$ in the therapeutic range for flecainide (>250 ng/mL), and in patients with a ventricular rate >80 bpm while in AF.

Prolongation of the QRS interval in patients receiving inhaled flecainide was in a range considered to be safe. There was only one patient (120 mg eTLD) who had a ΔQRSmax of ≥30 msec following inhaled flecainide; the patient had a transient increase in QRS duration to 136 msec from a baseline of 106 msec (ΔQRSmax of 30.5 msec). The ECG was consistent with left anterior fascicular block, and no treatment was required.

The majority of patients had AEs that were mild in severity and the most commonly reported AEs were associated with the inhalation route of administration, e.g., cough and throat irritation. Among all patients treated in Part A, 4 patients experienced SAEs considered related to inhaled flecainide that are consistent with the known effects of IV flecainide used for the same indication: sinus pause/arrest post-conversion of AF to SR (2 patients), bradycardia (1 patient), and atrial flutter with 1:1 conduction and rapid ventricular response (1 patient). All SAEs resolved rapidly without treatment.

Patients treated with the FlecIH-103 inhalation solution with improved organoleptic properties appeared to have a lower incidence of AEs related to the inhalation and a higher conversion rate.

Example 13. Sensory Property Evaluation of Exemplary Formulations

This example describes sensory property evaluations of some exemplary formulations according to the present disclosure.

One example formulation that was tested contains 75 mg/mL flecainide acetate in 20% HPPCD, 5 mM ascorbic acid, and 0.75 mM saccharin. The pH of the solution is 5.9. This formulation has less odor as compared to acetic acid-based formulations. Subjects inhaling this formulation did not cough and reported it caused stinging feeling in the throat, but such feeling went away in minutes. Its overall sensory property is much improved as compared to FlecIH-103 formulation (75 mg/mL flecainide acetate in 20% HPPCD, 5 mM acetic acid, 0.75 mM saccharin).

Another example formulation contains 75 mg/mL flecainide acetate in 20% HPPCD, 5 mM DL-lactic acid, 0.75 mM saccharin. The pH of the solution is 5.9. This formulation also has less odor as compared to acetic acid-based formulations. Subjects inhaling this formulation reported there was no stinging feeling in the throat and its overall feeling was even better as compared to the above ascorbic acid-based formulation.

A third example formulation contains 75 mg/mL flecainide acetate in 20% HPβCD, 5 mM citric acid, 0.75 mM saccharin. The pH of the solution is 5.7. This formulation also has no vinegary odor. Subjects inhaling this formulation reported there was minimal throat discomfort or the discomfort would disappear in minutes. No cough was observed.

Example 14. Solubility of Flecainide in D/L-Lactic Acid Media

The solubility of flecainide was measured in both D-lactic acid and L-lactic acid aqueous solutions after resting for 24 hours and 48 hours.

Flecainide feebase was suspended in pure water or 20% w/v HPβCD at 100 mg flecainide per milliliter of solution. D-lactic acid, L-lactic acid, or DL-lactic acid was slowly added portionwise to the suspension while stirring. The system was left to equilibrate for 30 minutes, and the pH was determined. The pH was then adjusted to 5.2-6 with NaOH if necessary. After addition of NaOH, the system was again left to equilibrate for 30 minutes before pH was measured. After the desired pH was achieved, the suspension was stirred (1000 rpm) at ambient temperature for 48 hours. At 24 hours and 48 hours of stirring, samples of each solution were centrifuged at 10000 rpm for 2 minutes and filtered with a 0.45 μm membrane to obtain supernatant for pH determination and HPLC analysis. Solids from each sample were also characterized by X-ray powder diffraction (XRPD) analysis. The results are summarized in TABLE 28.

TABLE 28

| Media | | Solubility (mg/mL) | | pH | | | Form Change | |
|---|---|---|---|---|---|---|---|---|
| Excipient | Acid | 24 h | 48 h | initial | 24 h | 48 h | 24 h | 48 h |
| none | DL-lactic acid | 76.3 | 73.4 | 5.3 | 6.1 | 6 | Y | Y |
|  | D-lactic acid | 90.1 | 91 | 5.2 | 5.1 | 5.4 | * | * |
|  | L-lactic acid | 96.6 | 97.8 | 5.3 | 5.6 | 5.1 | * | * |
| 20% w/v HPβCD | DL-lactic acid | 72.4 | 71.3 | 5.3 | 6.5 | 6.4 | Y | Y |
|  | D-lactic acid | 84.8 | 88.4 | 5.2 | 5.8 | 5.5 | * | * |
|  | L-lactic acid | 87.6 | 89.3 | 5.7 | 6.3 | 6 | * | * |

* No XPRD characterization was performed because residual solid was observed other than slight cloudiness after 24 h and 48 h.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A pharmaceutical composition, comprising:
   (1) a therapeutically effective amount of a salt of flecainide,
   (2) a cyclodextrin, and
   (3) an acid,
   wherein said pharmaceutical composition is in the form of a liquid solution that has said salt of flecainide at a concentration above 60 mg/mL, said cyclodextrin at a concentration of from about 5% (w/v) to about 50% (w/v) of said liquid solution, said acid at a concentration of 2 mM to 10 mM, and a pH above 5.5 when measured at room temperature.

2. The pharmaceutical composition of claim 1, wherein said concentration of said cyclodextrin is from about 15% (w/v) to about 25% (w/v) of said liquid solution.

3. The pharmaceutical composition of claim 1, wherein said concentration of said cyclodextrin is about 20% (w/v) of said liquid solution.

4. The pharmaceutical composition of claim 1, wherein said cyclodextrin is selected from the group consisting of: α-cyclodextrin, β-cyclodextrin, γ-cyclodextrin, hydroxypropyl-β-cyclodextrin, hydroxyethyl-β-cyclodextrin, hydroxypropyl-γ-cyclodextrin, hydroxyethyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, succinyl-β-cyclodextrin, 6A-amino-6A-deoxy-N-(3-hydroxypropyl)-β-cyclodextrin, sulfobutylether-β-cyclodextrin, sulfobutylether-γ-cyclodextrin, sulfoalkylether-β-cyclodextrins, and sulfoalkylether-γ-cyclodextrins.

5. The pharmaceutical composition of claim 1, wherein said cyclodextrin comprises hydroxypropyl-β-cyclodextrin.

6. The pharmaceutical composition of claim 1, wherein said concentration of said salt of flecainide is up to 200 mg/mL.

7. The pharmaceutical composition of claim 1, wherein said concentration of said salt of flecainide is from about 65 mg/mL to about 95 mg/mL.

8. The pharmaceutical composition of claim 1, wherein said concentration of said salt of flecainide is about 75 mg/mL.

9. The pharmaceutical composition of claim 1, wherein said salt of flecainide is selected from the group consisting of: flecainide acetate, flecainide hydrochloride, flecainide citrate, flecainide phosphate, and flecainide nitrate.

10. The pharmaceutical composition of claim 1, wherein said salt of flecainide comprises flecainide acetate.

11. The pharmaceutical composition of claim 1, wherein said acid is selected from the group consisting of: acetic acid, citric acid, nitric acid, hydrochloric acid, sulfuric acid, maleic acid, tartaric acid, phosphoric acid, aconitic acid, adipic acid, ascorbic acid, benzoic acid, caprylic acid, cholic acid, formic acid, glutamic acid, lactic acid, propionic acid, sorbic acid, stearic acid, and succinic acid.

12. The pharmaceutical composition of claim 1, wherein said acid comprises acetic acid.

13. The pharmaceutical composition of claim 1, wherein said acid comprises citric acid.

14. The pharmaceutical composition of claim 1, wherein said concentration of said acid is about 5 mM.

15. The kit of claim 1, wherein said pH of said liquid solution is about 5.9 when measured at room temperature.

16. The pharmaceutical composition of claim 1, wherein said pharmaceutical composition further comprises a sweetener.

17. The pharmaceutical composition of claim 16, wherein said sweetener is selected from the group consisting of acesulfame potassium, aspartame, cyclamate, mogrosides, saccharin, *stevia*, sucralose, neotame, mannitol, sorbitol, xylitol, lactitol, isomalt, maltitol, and pharmaceutically acceptable salts thereof.

18. The pharmaceutical composition of claim 1, wherein said pharmaceutical composition is formulated for administration via inhalation.

19. A unit dose of a pharmaceutical composition that comprises: a salt of flecainide, a cyclodextrin, and an acid, wherein said pharmaceutical composition is in the form of a liquid solution that has said salt of flecainide at a concentration above 60 mg/mL, said cyclodextrin at a concentration of from about 5% (w/v) to about 50% (w/v) of said liquid solution, said acid at a concentration of 2 mM to 10 mM, and a pH above 5.5 when measured at room temperature, and wherein said unit dose comprises from about 50 mg to about 350 mg of said salt of flecainide.

20. The unit dose of claim 19, comprising from about 250 mg to about 350 mg of said salt of flecainide.

21. The unit dose of claim 19, comprising from about 100 mg to about 250 mg of said salt of flecainide.

22. The unit dose of claim 20, wherein:
(i) said salt of flecainide comprises flecainide acetate, and said concentration of said salt of flecainide is about 75 mg/mL;
(ii) said acid comprises acetic acid; and
(iii) said cyclodextrin comprises hydroxypropyl-β-cyclodextrin, and said concentration of said cyclodextrin is about 20% (w/v) of said liquid solution.

23. The unit dose of claim 21, wherein:
(i) said salt of flecainide comprises flecainide acetate, and said concentration of said salt of flecainide is about 75 mg/mL;
(ii) said acid comprises acetic acid; and
(iii) said cyclodextrin comprises hydroxypropyl-β-cyclodextrin, and said concentration of said cyclodextrin is about 20% (w/v) of said liquid solution.

24. The unit dose of claim 19, wherein said concentration of salt of flecainide is from about 65 mg/mL to about 95 mg/mL.

25. The unit dose of claim 24, wherein said salt of flecainide comprises flecainide acetate.

26. The unit dose of claim 25, wherein said cyclodextrin comprises hydroxypropyl-β-cyclodextrin, and said concentration of said cyclodextrin is from about 15% (w/v) to about 25% (w/v) of said liquid solution.

27. The unit dose of claim 26, wherein said pH is about 5.8 to about 6.2 when measured at room temperature.

28. The composition of claim 1, wherein:
(a) said salt of flecainide comprises flecainide acetate, and said concentration of said salt of flecainide is about 75 mg/mL;
(b) said acid comprises acetic acid; and
(c) said cyclodextrin comprises hydroxypropyl-β-cyclodextrin, and said concentration of said cyclodextrin is about 20% (w/v) of said liquid solution.

* * * * *

UNITED STATES PATENT AND TRADEMARK OFFICE
CERTIFICATE OF CORRECTION

PATENT NO. : 11,020,384 B2
APPLICATION NO. : 16/901941
DATED : June 1, 2021
INVENTOR(S) : Michael Laird Hurrey et al.

It is certified that error appears in the above-identified patent and that said Letters Patent is hereby corrected as shown below:

In the Claims

Column 99, Claim 15, Line 20:
Replace "kit" with –pharmaceutical composition–

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*